US005582979A

United States Patent [19]

Weber

[11] Patent Number: 5,582,979
[45] Date of Patent: *Dec. 10, 1996

[54] LENGTH POLYMORPHISMS IN (DC-DA)$_N$·(DG-DT)$_N$ SEQUENCES AND METHOD OF USING THE SAME

[75] Inventor: James L. Weber, Marshfield, Wis.

[73] Assignee: Marshfield Clinic, Marshfield, Wis.

[*] Notice: The term of this patent shall not extend beyond the expiration date of Pat. No. 5,075,217.

[21] Appl. No.: 222,177

[22] Filed: Apr. 4, 1994

Related U.S. Application Data

[63] Continuation of Ser. No. 754,351, Sep. 5, 1991, abandoned, which is a continuation-in-part of Ser. No. 341,562, Apr. 21, 1991, Pat. No. 5,075,217.

[51] Int. Cl.$^6$ .............................. C12Q 1/68; C12P 19/34; C07H 21/04
[52] U.S. Cl. ........................... 435/6; 435/91.2; 536/23.1; 536/24.3; 536/24.31
[58] Field of Search ............................... 536/23.1, 24.31, 536/24.33; 435/6, 91.2

[56] References Cited

U.S. PATENT DOCUMENTS 4,683,195  7/1987  Mullis et al. ................................. 435/6
4,683,202  7/1987  Mullis et al. ............................ 435/91.2

FOREIGN PATENT DOCUMENTS 238329  9/1987  European Pat. Off. ..

OTHER PUBLICATIONS

Nathans et al "Isolation and Nucleotide Sequence of the Gene Encoding . . . ," PNAS 81: 4851–5, Aug. 1984.
Litt and Luty "A Hypervariable Microsatellite Revealed by in vitro Amplification . . . ," Mar. 1989 Am. J. Hum. Genet. 44:397–401.
Litt et al "A Highly Polymorphic (TG)n Microsatellite at the D11S35 Locus" Mar. 29, 1989 J Cell Biochem Supp. 13D, p. 32 abstract #K219.
Hamada et al "Characterization of Genomic Polyd2T–dG)·Poly (dC–dA) Sequences . . . ," 1984. Mol. Cell. Biol. 4:2610–21.
Aldridge et al., 1984, "A Strategy to Reveal High–Frequency RFLPs Along the Human X Chromosome." Am. J. Hum. Genet. 36:546–564.
Benton and Davis, 1977, "Screening λgt Recombinant Clones by Hybridization to Single Plaques In Situ." Science 196:180–182.
Biggin et al., 1983, "Buffer Gradient Gels and $^{35}$S Label as an Aid to Rapid DNA Sequence Determination." Proc. Natl. Acad. Sci. USA 80:3963–3965.
Bostein et al., 1980, "Construction of a Genetic Linkage Map in Man Using Restriction Fragment Length Polymorphisms." Am. J. Hum. Genet. 32:314–331.
Clark, 1988, "Novel Non–Templated Nucleotide Addition Reactions Catalyzed by Procaryotic and Eucaryotic DNA Polymerases." Nucleic Acids Res. 16:9677–9686.

Das et al., 1987, "The Human Apolipoprotein C–II Gene Sequence Contains a Novel Chromosome 19–Specific Minisatellite in Its Third Intron." J. Biol. Chem. 262:4787–4793.
Donis–Keller et al., 1987, "A Genetic Linkage Map of the Human Genome." Cell 51:319–337.
Elbrecht, A., 1987, "Lab Hints: Irish Cream Liqueur as a Blocking Agent for DNA Dot Blots." B.M. Biochemica, 4:12–13.
Floyd–Smith, G., Whitehead, A. S., Colten, H. R., and Francke, U., 1986, "The Human C–Reactive Protein Gene (CRP) and Serum Amyloid P Component Gene (APCS) are Located on the Proximal Long Arm of Chromosome I." Immunogenetics 24:171–176.
Griffin et al., 1988, "Synthesis of Hexokinase 1 (HK1) cDNA Probes by Mixed Oligonucleotide Primed Amplification of cDNA (MOPAC) Using Primer Mixtures of High Complexity". Am. J. Hum. Genet. 43 (Suppl.):A185.
Gross and Garrard, 1986, "The Ubiquitous Potential Z–Forming Sequence of Eucaryotes, (dT–dG)$_n$·(dC–dA)$_n$, is not Detectable in the Genomes of Eubacteria, Archaebacteria, or Mitochondria." Mol. Cell. Biol. 6:3010–3013.
Gusella, J. F., 1986, "DNA Polymorphism and Human Disease," Ann. Rev. Biochem. 55:831–854.
Hamada, H., Petrino, M. G. and Kakunaga, T., 1982, "A Novel Repeated Element with Z–DNA–Forming Potential is Widely Found in Evolutionarily Diverse Eukaryotic Genomes," Proc. Nat. Acad. Sci. U.S.A. 79:6465–6469.
Hamada and Kakunaga, 1982, "Potential Z–DNA Forming Sequences are Highly Dispersed in the Human Genome." Nature 298:396–398.
Jeffreys et al., 1985, "Hypervariable 'Minisatellite' Regions in Human DNA." Nature 314:67–73.
Jeffreys et al., 1988, "Spontaneous Mutation Rates to New Length Alleles at Tandem–Repetitive Hypervariable Loci in Human DNA." Nature 332:278–281.
Ledbetter, D. H., Rich, D. C., O'Connell, P., Leppert, M., and Carey, J. C., 1989, "Precise Localization of NFI to 17q11.2 by Balanced Translocation." Am. J. Hum. Genet. 44:20–24.
Ledbetter, S. A., Schwartz, C. E., Davies, K. E. and Ledbetter D. H., 1991, "New Somatic Cell Hybrids for Physical Mapping in Distal Xq and the Fragine X Region." Am. J. Med. Genet. 38:418–420.

(List continued on next page.)

Primary Examiner—John L. Leguyader
Assistant Examiner—Thomas G. Larson
Attorney, Agent, or Firm—DeWitt Ross & Stevens

[57] ABSTRACT

Abundant interspersed repetitive DNA sequences of the form (dC-dA)$_n$·(dG-dT)$_n$ have been shown to exhibit length polymorphisms. The polymorphisms can be used to identify individuals as in paternity and forensic testing, and can be used to map genes which are involved in genetic diseases or in other economically important traits. The polynucleotide provided consists of a DNA fragment, preferably ≦300 base pairs in length containing one or more blocks of tandem dinucleotide repeats (dC-dA)$_n$·(dG-dT)$_n$ wherein n≧6 and preferably ≧10.

10 Claims, 8 Drawing Sheets

OTHER PUBLICATIONS

Litt, M., Buroker, N. E., Kondoleon, S., Douglass, J., Liston, D., Sheehy, R., and Magenis, R. E., 1988, "Chromosomal Localization of the Human Proenkephalin and Prodynorphin Genes." *Am. J. Hum. Genet.* 42:327–334.

Luty, J. A., Guo, Z., Willard, H. F., Ledbetter, D. H., Ledbetter, S. and Litt, M., 1990, "Five Polymorphic Microsatellite VNTRs on the Human X Chromosome." *Am. J. Hum. Genet.* 46:776–783.

Matthews and Kricka, 1988, "Analytical Strategies for the Use of DNA Probes." *Anal. Biochem.* 169:1–25.

Miesfeld et al., 1981, "A Member of a New Repeated Sequence Family Which is Conserved Throughout Eucaryotic Evolution is Found Between the Human $\delta$ and $\beta$ Globin Genes." *Nucleic Acids Res.* 9:5931–5947.

Mullis and Faloona, 1987, "Specific Synthesis of DNA in Vitro via a Polymerase–Catalyzed Chain Reaction." *Method Enzymol.* 155:335–350.

Nakamura et al., 1987, "Variable Number of Tandem Repeat VNTR Markers for Human Gene Mapping." *Science* 235:1616–1622.

Nicklas et al., 1987, "Molecular Analyses of in Vivo hprt Mutations in Human T–Lymphocytes: I. Studies of How Frequency 'Spontaneous' Mutants by Southern Blots." *Mutagenesis* 2:341–347.

Overhauser et al., 1987, "Identification of 28 DNA Fragments that Detect RFLP's in 13 Distinct Physical Regions of the Short Arm of Chromosome 5." *Nucleic Acids Res.* 15:4617–4627.

Saiki et al., 1985, "Enzymatic Amplification of $\beta$–Globin Genomic Sequences and Restriction Site Analysis for Diagnosis of Sickle Cell Anemia." *Science* 230:1350–1354.

Saiki et al., 1988, "Primer–Directed Enzymatic Amplification of DNA with a Thermostable DNA Polymerase." *Science* 239:487–491.

Schumm et al., 1988, "Identification of More than 500 RFLPs by Screening Random Genomic Clones." *Am. J. Hum. Genet.* 42:143–159.

Shen and Rutter, 1984, "Sequence of the Human Somatostatin I Gene," *Science* 224:168–171.

Slightom et al., 1980, "Human Fetal $^G\gamma$ and $^A\gamma$ Globin Genes: Complete Nucleotide Sequences Suggest that DNA can be Exchanged Between These Duplicated Genes." *Cell* 21:627–638.

Tautz and Renz, 1984, "Simple Sequences are Ubiquitous Repetitive Components of Eukaryotic Genomes." *Nucleic Acids Res.* 12:4127–4138.

vanTuinen, P., Rich, D. C. Summers, K. M., and Ledbetter, D. H., 1987, "Regional Mapping Panel for Human Chromosome 17: Application to Neurofibromatosis Type 1." *Genomics* 1:374–381.

vanTuinen, P., Dobyns, W. B., Rich, D. C., Summers, K. M., Robinson, T. J., Nakamura, Y., and Ledbetter, D. H., 1988, "Molecular Detection of Microscopic and Submicroscopic Deletions Associated with Miller–Dieker Syndrome." *Am. J. Hum. Genet.* 43:587–596.

Weber and May, 1988, "An Abundant New Class of Human DNA Polymorphisms." *Am. J. Hum. Genet.* 43:A161 Abstract.

Weber et al., 1988, "Primary Structure of a *Plasmodium falciparum* Malaria Antigen Located at the Merozoite Surface and Within the Parasitophorous Vacuole." *J. Biol. Chem.* 263:11421–11425.

Weber, J. L. and May, P. E., 1989, "Abundant Class of Human DNA Polymorphisms Which Can Be Typed Using the Polymerase Chain Reaction." *Am. J. Hum. Genet.* 44:388–396.

White and Lalouel, 1988, "Sets of Linked Genetic Markers for Human Chromosomes." *Annu. Rev. Genet.*, 22:259–279.

Zoghbi, H. Y., McCall, A. E., LeBorgne–Demarquoy, F., 1990, "The Use of Radiation Hybrids and Interspersed Repetitive Sequence (IRS) PCR for the Rapid Isolation of 23 DNA Fragments Near the Spinocerebellar Ataxia (SCA1) Locus." *Am. J. Hum. Genet.* 47:A206.

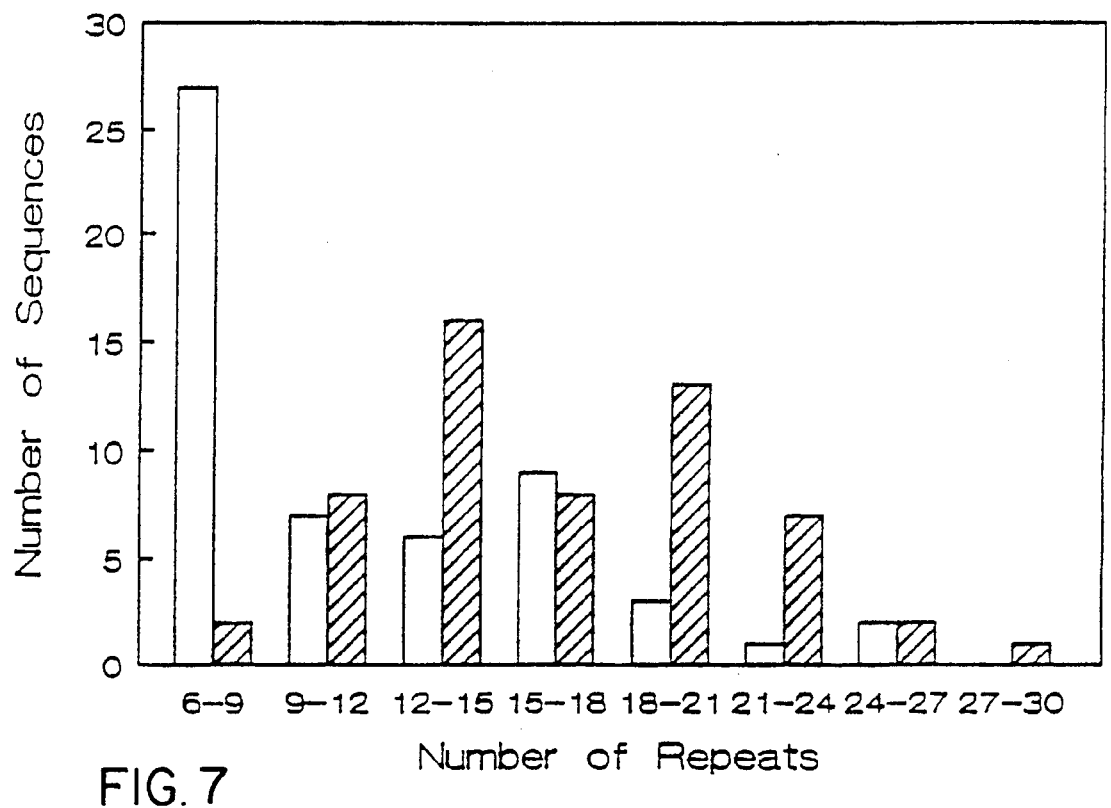
FIG. 7
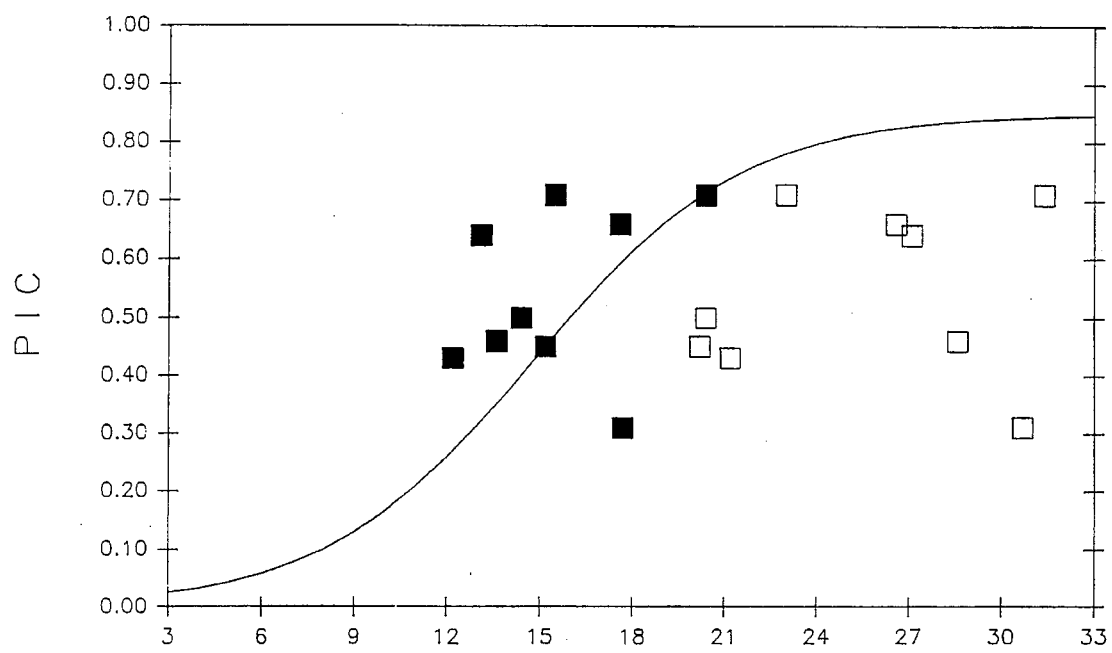
FIG. 9  Weighted Average Number of Repeats

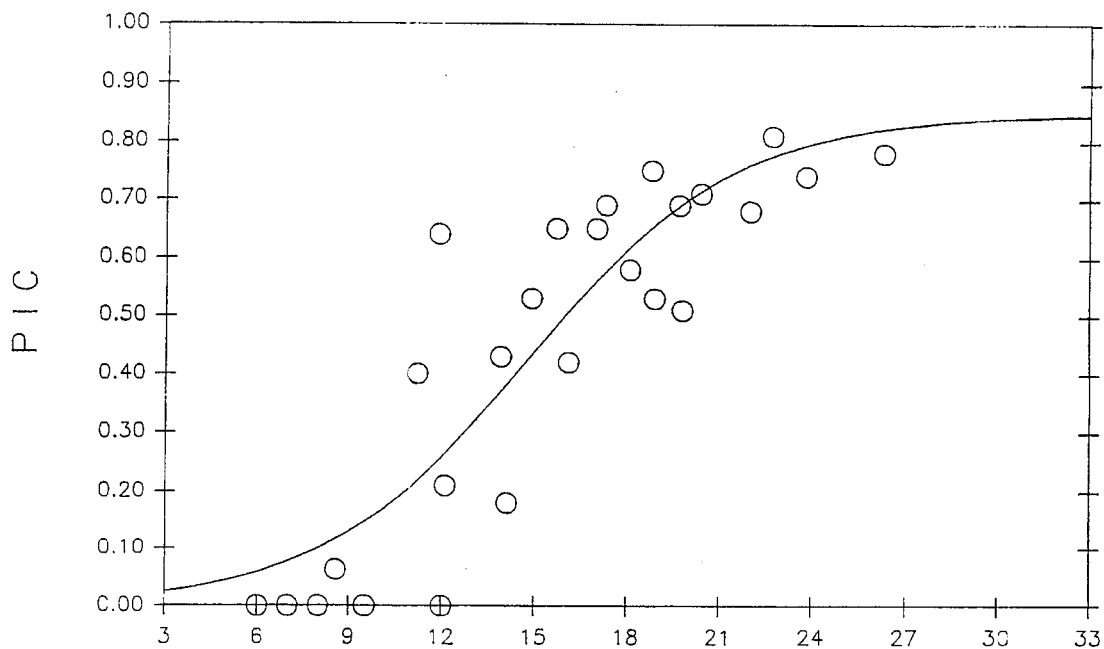
FIG. 8A  Weighted Average Number of Repeats
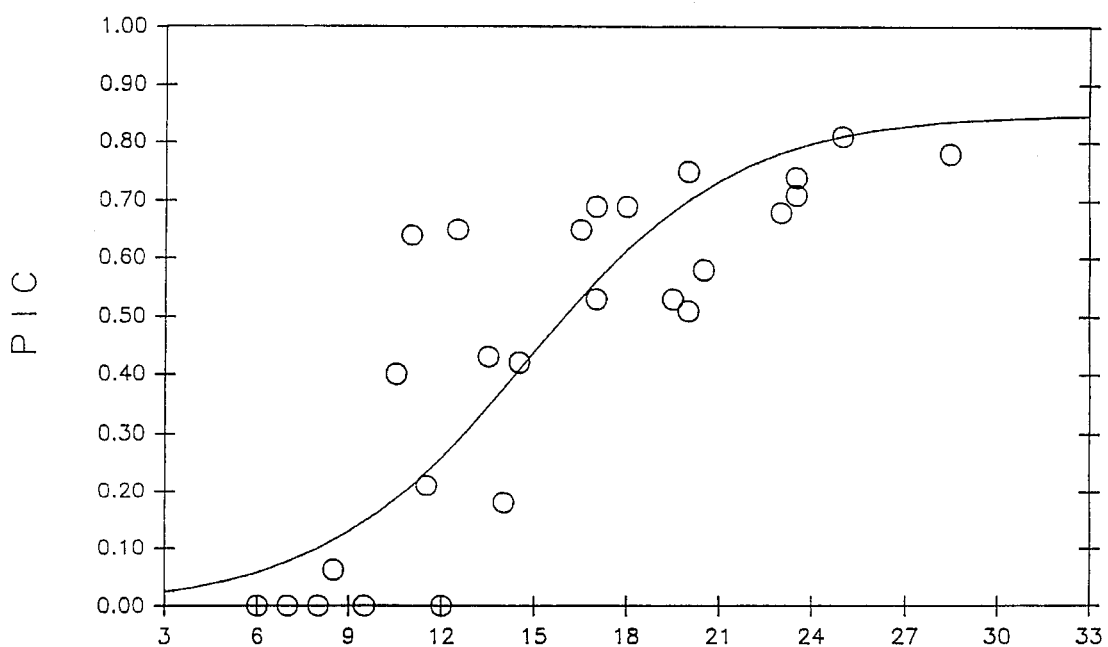
FIG. 8B  Number of Repeats

LENGTH POLYMORPHISMS IN $(DC-DA)_N \cdot (DG-DT)_N$ SEQUENCES AND METHOD OF USING THE SAME This invention was made with United States Government support awarded by NIH Grant GM41773. The United States Government has certain rights in this invention.

REFERENCE TO RELATED APPLICATION

This is a continuation of application Ser. No. 07/754,351 filed on Sep. 5, 1991 now abandoned, which is continuation-in-part of U.S. patent application Ser. No. 07/341,562, filed Apr. 21, 1989 to James L. Weber, now U.S. Pat. No. 5,075,217.

FIELD OF THE INVENTION

The present invention relates to polynucleotides which comprise an abundant new class of DNA polymorphisms and to methods for analyzing and using these polymorphisms. The polymorphisms can be used to identify individuals such as in paternity and forensic testing cases, and can also be used to map genes which are involved in genetic diseases or in other economically important traits.

BACKGROUND OF THE INVENTION

The vast majority of DNA in higher organisms is identical in sequence among different individuals (or more accurately among the chromosomes of those individuals). A small fraction of DNA, however, is variable or polymorphic in sequence among individuals, with the formal definition of polymorphism being that the most frequent variant (or allele) has a population frequency which does not exceed 99% (Gusella, J. F. (1986), *Ann. Rev. Biochem.* 55:831–854). In the past, polymorphisms were usually detected as variations in gene products or phenotypes such as human blood types. Currently, almost all polymorphisms are detected directly as variations in genomic DNA.

Analysis of DNA polymorphisms has relied on variations in the lengths of DNA fragments produced by restriction enzyme digestion. Most of these restriction fragment length polymorphisms (RFLPs) involve sequence variations in one of the recognition sites for the specific restriction enzyme used. This type of RFLP contains only two alleles, and hence is relatively uninformative.

A second type of RFLP is more informative and involves variable numbers of tandemly repeated DNA sequences between the restriction enzyme sites. These polymorphisms called minisatellites or VNTRs (for variable numbers of tandem repeats) were developed first by Jeffreys (Jeffreys et al. (1985), *Nature* 314:67–73). Jeffreys has filed two European patent applications, 186,271 and 238,329, dealing with the minisatellites. The first Jeffreys' application ('271) identified the existence of DNA regions containing hypervariable tandem repeats of DNA. Although the tandem repeat sequences generally varied between minisatellite regions, Jeffreys noted that many minisatellites had repeats which contain core regions of highly similar sequences. Jeffreys isolated or cloned, from genomic DNA, polynucleotide probes comprised essentially of this core sequence (i.e., wherein the probe had at least 70% homology with one of his defined cores). These probes were found to hybridize with multiple minisatellite regions (or loci). The probes were found to be useful in forensic or paternity testing by the identification of unique or characteristic minisatellite profiles. The later Jeffreys' European patent application proposed the use of probes which were specific for individual minisatellites located at specific loci in the genome. One problem with the Jeffreys' approach is that some of the most highly variable and hence useful minisatellites are susceptible to significant frequencies of random mutation (Jeffreys et al., 1988, *Nature* 332:278–281).

Other tandemly repeated DNA families, different in sequence from the Jeffreys minisatellites, are known to exist. In particular, $(dC\text{-}dA)_n \cdot (dG\text{-}dT)_n$ sequences have been found in all eukaryotes that have been examined. In humans there are 50,000–100,000 blocks of $(dC\text{-}dA)_n \cdot (dG\text{-}dT)_n$ sequences, with n ranging from about 15–30 (Miesfeld et al. (1981), *Nucleic Acids Res.* 9:5931–5947; Hamada and Kakunaga (1982), *Nature* 298:396–398; Tautz and Renz (1984), *Nucleic Acids Res.* 12:4127–4138).

Prior to the work of this invention, a number of different human blocks of $(dC\text{-}dA)_n \cdot (dG\text{-}dT)_n$ repeats had been cloned and sequenced, mostly unintentionally along with other sequences of interest. Several of these characterized sequences were analyzed independently from two or more alleles. In arriving at this invention, sequences from these different alleles were compared. Variations in the number of repeats per block of repeats were found in several cases (Weber and May, 1989, *Am. J. Hum. Genet.* 44:388–396, incorporated herein by reference in its entirety).

Although three isolated research groups produced published notations of site specific differences in sequence length (Das et al., 1987, *J. Biol Chem.* 262:4787–4793; Slightom et al., 1980, *Cell* 21:627–638; Shen and Rutter, 1984, *Science* 244:168–171), none of the groups recognized nor appreciated the extent of this variability or its usefulness and none generalized the observation. The other groups also did not consider the use of $(dC\text{-}dA)_n \cdot (dG\text{-}dT)_n$ sequences as genetic markers and did not offer a method by which such polymorphisms might be analyzed.

SUMMARY OF THE INVENTION

It has been discovered that $(dC\text{-}dA)_n \cdot (dG\text{-}dT)_n$ sequences exhibit length polymorphisms and therefore serve as an abundant pool of potential genetic markers (Weber and May, 1988, *Am. J. Hum. Genet.* 43:A161 Abstract); Weber and May, 1989, *Am J. Hum. Genet.* 44:388–396) (both incorporated herein by reference). Accordingly, as a first feature of the present invention, polynucleotides are provided consisting of a DNA fragment, preferably $\leq 300$ base pairs (bp) in length, containing one or more blocks of tandem dinucleotide repeats $(dC\text{-}dA)_n \cdot (dG\text{-}dT)_n$ where n is preferably $\geq 6$, and more preferably $\geq 10$.

A further aspect of the invention is the provision of a method for analyzing one or more specific $(dC\text{-}dA)_n \cdot (dG\text{-}dT)_n$ polymorphisms individually or in combination, which involves amplification of a small segment(s) of DNA containing the block of repeats and some non-repeated flanking DNA, starting with a DNA template using the polymerase chain reaction, and sizing the resulting amplified DNA, preferably by electrophoresis on polyacrylamide gels.

In a preferred embodiment, the amplified DNA is labeled during the amplification reactions by incorporation of radioactive nucleotides or nucleotides modified with a non-radioactive reporter group.

A further aspect of the invention is the provision of primers for the amplification of the polymorphic tandemly repeated fragments. The primers are cloned, genomic or preferably synthesized, and contain at least a portion of the non-repeated, non-polymorphic flanking region sequence.

A further aspect of the invention is the provision of a method for determining the sequence information necessary for primer production through the isolation of DNA fragments, preferably as clones, containing the $(dC-dA)_n.(dG-dT)_n$ repeats, by hybridization of a synthetic, cloned, amplified or genomic probe, which contains a sequence that is substantially homologous to the tandemly repeated sequence $(dC-dA)_n.(dG-dT)_n$, to the DNA fragment. In a preferred embodiment the probe would be labeled, e.g., end labeling, internal labeling or nick translation.

A further aspect of this invention is to define the sequence in terms of numbers of repeats and repeat sequence. Using a set of precise classification rules, the sequences were divided into three categories: perfect repeat sequences without interruptions in the runs of CA or GT dinucleotides, imperfect repeat sequences with one or more interruptions in the run of repeats, and compound repeat sequences with adjacent tandem simple repeats of a different sequence. Informativeness of $(dC-dA)_n.(dG-dT)_n$ markers in the perfect sequence category was found to increase with increasing average numbers of repeats.

The present invention is also directed to a method for detecting the presence in genomic DNA of a specific trait in a subject, such as a human or other animal. The method includes isolating the genomic DNA from the subject and analyzing the genomic DNA with a polymorphic amplified DNA marker containing one or more sequences in the form $(dC-dA)_n.(dG-dT)_n$, wherein n is $\geq 6$. The analysis comprises amplification using the polymerase chain reaction of one or more short DNA fragments containing the tandem repeats followed by measurement of the sizes of the amplified fragments using gel electrophoresis. This method has specific use for disease traits such as Huntington's disease and cystic fibrosis.

The present invention is also directed to a method for determining the paternity of an individual comprising amplification of polymorphic DNA fragments from the mother of the individual, the suspected father of the individual and the individual, analyzing the sizes of the fragments by gel electrophoresis, and comparing the electrophoretic patterns to determine correspondence between the individual's pattern and the mother's pattern and thereby determining whether the suspected father is the actual father of the individual.

The present invention is also directed to a kit for the rapid analysis of one or more specific DNA polymorphisms of the type described in this application which through proximity to a DNA abnormality causing a genetic disease permit determination of the presence or absence of the abnormality. The kit includes oligodeoxynucleotide primers for the amplification of fragments containing one or more sequences of the form $(dC-dA)_n.(dG-dT)_n$, where $n \geq 6$.

In addition to the inherent useful properties of the $(dC-dA)_n.(dG-dT)_n$ markers, the use of the polymerase chain reaction (PCR) to analyze the markers offers substantial advantages over the conventional blotting and hybridization used to type RFLPs. One of these advantages is sensitivity. Whereas microgram amounts of DNA are generally used to type RFLPs, nanogram amounts of genomic DNA are sufficient for routine genotyping of the block markers, and the polymerase chain reaction has recently been described as capable of amplifying DNA from a single template molecule (Saiki et al., 1988), *Science* 239:487–491). Enough DNA can be isolated from a single modest blood sample to type tens of thousands of $(dC-dA)_n.(dG-dT)_n$ block markers.

Another advantage of the polymerase chain reaction is that the technique can be partially automated. For example, several commercial heating blocks are available which can automatically complete the temperature cycles used for the polymerase reaction. Automatic amplification reactions and the capability to analyze hundreds of markers on each polyacrylamide gel mean that the $(dC-dA)_n.(dG-dT)_n$ markers can be analyzed faster than RFLPs and are more readily usable in practical applications such as identity testing.

Specific applications for the present invention include the identification of individuals such as in paternity and maternity testing, immigration and inheritance disputes, zygosity testing in twins, tests for inbreeding in man, evaluation of the success of bone marrow transplantation, quality control of human cultured cells, identification of human and animal remains, and testing of semen samples, blood stains, and other material in forensic medicine. In this application, the ability to run numerous markers in a single amplification reaction and gel lane gives this procedure the possibility of extreme efficiency and high throughput.

Another specific application is in human genetic analysis, particularly in the mapping through linkage analysis of genetic disease genes and genes affecting other human traits, and in the diagnosis of genetic disease through coinheritance of the disease gene with one or more of the polymorphic $(dC-dA)_n.(dG-dT)_n$ markers.

A third specific application contemplated for the present invention is in commercial animal breeding and pedigree analysis. All mammals tested for $(dC-dA)_n.(dG-dT)_n$ sequences have been found to contain them (Gross and Garrard, 1986, *Mol. Cell. Biol.* 6:3010–3013). Also, as a byproduct of efforts to develop $(dC-dA)_n.(dG-dT)_n$ markers specific for human chromosome 19 from a library development from a hamster-human somatic cell hybrid, several hamster $(dC-dA)_n.(dG-dT)_n$ markers have been developed (Weber and May, 1988, *Am. J. Hum. Genet.* 44(3):388–396).

A fourth specific application is in commercial plant breeding. Traits of major economic importance in plant crops can be identified through linkage analysis using polymorphic DNA markers. The present invention offers an efficient new approach to developing such markers for various plant species.

It is also contemplated that the present invention and method of characterization could be easily extended to include other tandemly repeated simple sequences which may be polymorphic. Examples include $(dG-dA)_n.(dC-dT)_n$, $(dT-dA)_n.(dA-dT)_n$, and even $(dA)_n.(dT)_n$.

BRIEF DESCRIPTION OF THE FIGURES

FIG. 7 is a graph illustrating the length distributions of $(dC-dA)_n.(dG-dT)_n$ sequences. Abscissa values were taken as the number of repeats within the longest run of uninterrupted repeats, even for imperfect and compound repeat sequences. Repeats were counted beginning with either purines or pyrimidines, and half repeats were counted. Numbers of repeats were not averages but were rather taken from individual sequences. The open bars depict results for the GenBank sequences and the hatched bars results for the cloned sequences.

FIG. 8A illustrates a plot showing the informativeness of perfect repeat sequence $(dC-dA)_n.(dG-dT)_n$ polymorphisms as a function of repeat length. FIG. 8A was obtained using weighted average numbers of repeats for each polymorphism.

FIG. 8B illustrates a plot showing the informativeness of perfect repeat sequence $(dC-dA)_n.(dG-dT)_n$ polymorphisms as a function of repeat length similar to FIG. 8A. FIG. 8A was obtained using the number of repeats found within the original sequences used for PCR primer synthesis. The curves in the plots of FIGS. 8A and 8B are identical.

FIG. 9 is a chart illustrating the informativeness of imperfect repeat sequence $(dC-dA)_n.(dG-dT)_n$ polymorphisms as a function of repeat length. Data for the open squares were obtained by counting the number of repeats within the entire imperfect repeat sequence. Data for the filled squares were obtained by counting only the repeats within the longest run of uninterrupted repeats. All variation in numbers of repeats for each marker was assumed to be confined to the longest run of uninterrupted repeats. The curve is identical to the one shown in FIG. 8.

Figure 1:
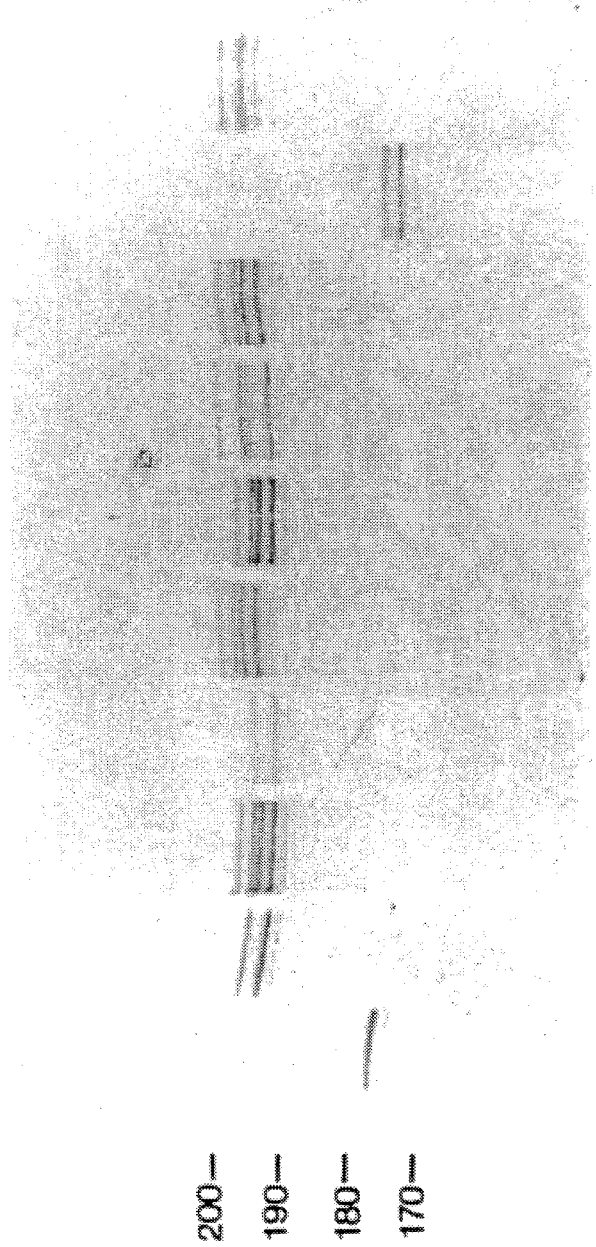
FIG. 1 is an example of a human $(dC-dA)_n.(dG-dT)_n$ polymorphism showing the sequence of the amplified DNA, the primers used in the amplification, and an autoradiograph of a polyacrylamide gel loaded with amplified DNA from this marker.

DETAILED DESCRIPTION OF THE PREFERRED EMBODIMENTS Definitions:

All of the terms used herein should be known to one skilled in the art. However, the following definitions are provided to assist in providing a clear and consistent understanding scope and detail of the terms:

$(CA)_n$:

The subscript "$n$" refers to the number of repeats of the nucleotides in the parentheses immediately preceding the number. For example, $(CA)_{10}$ is a shorthand version of "CACACACACACACACACACA." (i.e., nucleotides 1–20 of SEQ. ID NO:59)

Heterozygosity:

The fraction of individuals that have different alleles at a particular locus (as opposed to two copies of the same allele). Heterozygosity is usually expressed in percent. Heterozygosity values range from 0 to 100%.

Hybridization:

The process in which a strand of nucleic acid joins with a complementary strand through base pairing.

Informativeness:

The informativeness of a human DNA polymorphism is a measure of the utility of the polymorphism. In general, higher informativeness means greater utility. Informativeness is usually defined in terms of either heterozygosity or Polymorphism Information Content (PIC).

Polymorphism information content (PIC): Because matings between two individuals who are both heterozygous but have identical genotypes are often not useful in genetic analysis, PIC was defined to more accurately reflect true informativeness (Botstein, D., et al., 1980, *Am. J. Hum. Genet.*, 32, 314–331). PIC values range from to 1.0, and are smaller in value than heterozygosities. For markers that are highly informative (heterozygosities exceeding about 70%), the difference between heterozygosity and PIC is slight.

Polymorphism:

A condition in DNA in which the most frequent variant (or allele) has a population frequency which does not exceed 99%.

Primers: A substrate that is required for a polymerization reaction and that is structurally similar to the product of the reaction.

Development of Polymorphic DNA Marker.

Development of a polymorphic DNA marker based on length variations in blocks of $(dC-dA)_n.(dG-dT)_n$ repeats involves a series of steps.

First, the sequence of a segment of DNA containing the $(dC-dA)_n.(dG-dT)_n$ repeats must be determined. This is accomplished most commonly by selecting a genomic DNA clone through hybridization to synthetic poly(dC-dA).poly(dG-dT) and then subsequently sequencing that clone. This same step can also be accomplished simply by selecting a suitable sequence from the literature or from one of the DNA sequence databases such as GenBank. The latter approach is severely limited by the relatively small number of $(dC-dA)_n.(dG-dT)_n$ sequences that have been published.

Second, once the sequence to be used is in hand, a pair of appropriate primers can be synthesized which are at least partially complementary to non-repeated, non-polymorphic sequences which flank the block of dinucleotide repeats on either side.

Third, these primer pairs are used in conjunction with a genomic DNA (or occasionally cloned DNA) template to amplify a small segment of DNA containing the repeats using the polymerase chain reaction (Saiki et al., 1985, *Science* 230:1350–1354 and U.S. Pat. No. 4,683,202 to Mullis et al, the substance of which is incorporated herein in its entirety). The process of polymerase chain reaction (PCR) uses an exponential process of replication. PCR permits a target sequence of DNA to be multiplied as quickly as a millionfold within hours. In PCR, a target sequence of double-stranded DNA is denatured into single-stranded form by a process of heating. Two small pieces of synthetic DNA, each complementing a sequence at one end of the target sequence, serve as primers and bind with their complementary sequences on the single strand. Polymerases start at each primer, copying the sequence of that strand and ultimately producing exact replicas of the target sequence. The product of each cycle then serves as a template for succeeding cycles, resulting in an exponential process of replication. After repeated cycles, the pool of pieces of DNA with the target sequence has been greatly multiplied. This amplified genetic material is then available for further analysis and use. The DNA is preferably labeled during the amplification process by incorporating radioactive nucleotides.

Fourth, the amplified DNA is resolved by polyacrylamide gel electrophoresis in order to determine the sizes of these fragments and hence the genotypes of the genomic DNA donor.

In a more particular aspect of the present invention, some or all of the polynucleotide primers are $^{32}P$ or $^{35}P$ labeled in any conventional manner, such as end labeling, interior labeling, or post reaction labeling. Alternative methods of labeling are fully within the contemplation of the invention such as biotin labeling or enzyme labeling (Matthews and Kricka 1988, *Anal. Biochem.* 169:1–25).

The practical outer limits of the length of the amplified DNA fragment is generally limited only by the resolving power of the particular separation system employed. The thin denaturing gels used in the work leading to this application are capable of resolving fragments differing by as little as 2 bases up to a total fragment length of about 300 bp. Use of longer gels and longer electrophoresis times could extend the resolving power up to perhaps 600 bp or even more. However the longer the fragment the lower the proportion of its length will be made up of the $(dC-dA)_n.(dG-dT)_n$ sequences, and hence the more difficult the resolution.

Categorizing the Sequences.

Examination of over 100 human $(dC-dA)_n.(dG-dT)_n$ sequences both from direct sequencing of clones selected by hybridization to poly(dC-dA).poly(dG-dT) and from computer searches of GenBank, show that the sequences differ from each other in two major respects. First, they contain different total numbers of repeats, and second, they contain variable numbers of sequence imperfections and or tandem repeats of other simple sequence families.

Using a set of precise classification rules, the sequences can be divided into three categories. The rules for categorizing the $(dC-dA)_n.(dG-dT)_n$ sequences follow:

1. Perfect repeat sequences are defined as alternating, tandem CA repeats, i.e., CACACA..., without interruption and without adjacent repeats of another sequence.

2. Imperfect repeat sequences are defined as two or more runs of uninterrupted CA repeats separated by no more than 3 consecutive non-repeat bases. Terminal runs of uninterrupted CA repeats (outside of non-repeat bases) must each be at least 3 full repeats in length. The sequence $(CA)_{22}GACACAC$ (nucleotides 109–160 of SEQ. ID. NO:8) would therefore be classified as an imperfect repeat sequence with 25.5 total repeats, while the sequence $(CA)_{22}GACACA$ (nucleotides 109–159 of SEQ. ID NO:8) would be classified as a perfect repeat sequence with 22 repeats. Internal runs of uninterrupted CA repeats must be at least 1.5 repeats in length. The sequence $(AC)_{12}GTACATAA(AC)_{10}$ (SEQ. ID. NO:457) would be scored as a single imperfect repeat sequence, but the sequence $A(CA)_{15}TACG(CA)_6$ (SEQ. ID. NO:458) would be scored as two separate perfect repeat sequences.

3. Compound repeat sequences are defined as runs of CA repeats separated by no more than 3 consecutive non-repeat bases from a run of $\geq 5$ uninterrupted dinucleotide or longer repeat length repeats of a sequence other than $(dC-dA)_n.(dG-dT)_n$ or from $\geq 10$ uninterrupted mononucleotides. Compound repeats are subclassified as perfect or imperfect depending on the status of the $(dC-dA)_n.(dG-dT)_n$ block, perfect repeat sequences without interruptions in the runs of CA or GT dinucleotides (64% of total), imperfect repeat sequences with one or more interruptions in the run of repeats (25%), and compound repeat sequences with adjacent tandem simple repeats of a different sequence (11%).

The rules are written for the $(CA)_n$ strands, but apply equally well to the $(GT)_n$ strands.

Informativeness of the $(dC-dA)_n.(dG-dT)_n$ Repeats.

To exemplify the informativeness of the $(dC-dA)_n.(dG-dT)_n$ repeats, sequences from over 100 different polymorphic markers of the type which can be used within the present invention are listed in Table 1 and in Table 40. Each sequence represents only one allele at each specific locus. The first five sequences in Table 1 were taken from a computer search of GenBank; the remaining sequences were determined in the laboratory (see Example I). As can be seen in this compilation, the sequences exhibit substantial variation in the form of the tandem repeats. Some sequences, for example markers Mfd3, Mfd17 and Mfd23, contain only CA-GT repeats with no imperfections. Other sequences, for example Mfd2, Mfd7, and Mfd19 contain in addition to long runs of perfect CA-GT repeats, one or more imperfections in the run of repeats. These imperfections can be additional bases as in Mfd2 or more frequently GA-TC, AT-TA or CG-GC dinucleotide repeats as in Mfd7, Mfd13 and Mfd19. Homogenous runs of other dinucleotide repeats are often found in association with the CA-GT repeats like for example in Mfd5 and Mfd21. All of these repeat sequences can be used in this application.

Every human $(dC-dA)_n.(dG-dT)_n$ sequence with 11 or more repeats that has been tested by the invention has been found to be polymorphic (over 100 sequences to date). Since there are an estimated 50,000–100,000 $(dC-dA)_n.(dG-dT)_n$ blocks in the human genome, blocks are separated by an average spacing of 30,000–60,000 bp which is extremely tight in genetic terms. Two polymorphic markers spaced so that there is only 1% recombination between them are generally thought to be about $10^6$ bp apart; markers spaced only 50,000 bp apart on the average would be coinherited 99.95% of the time. This means that $(dC-dA)_n.(dG-dT)_n$ markers should find significant usage in the genetic mapping and clinical diagnosis of human genetic diseases, much as RFLPs have been used in the mapping and diagnosis of diseases such as cystic fibrosis (White and Lalouel, 1988, *Ann. Rev. Genet.* 22:259–279).

The correspondence between polymorphisms which are relatively rare in the genome and the $(dC-dA)_n.(dG-dT)_n$ sequences is very strong evidence that the repeats are mainly, if not entirely, responsible for the sequence length variations. Further evidence comes from the fact that amplified polymorphic fragments containing the $(dC-dA)_n.(dG-dT)_n$ sequences always differ in size by multiples of 2 bp. Direct sequencing (see Example VI below) of allelic DNA also confirms this interpretation.

The informativeness of the $(dC-dA)_n.(dG-dT)_n$ polymorphisms is good to very good, with heterozygosities ranging from 34–91%. Most of the $(dC-dA)_n.(dG-dT)_n$ markers are therefore more informative than the two-allele RFLPs (Donis-Keller et al. (1987), *Cell* 51:319–339; Schumm et al. (1988), *Am. J. Hum. Genet.* 42:143–159). The number of alleles counted for the $(dC-dA)_n.(dG-dT)_n$ markers tested to date has ranged from 4–11. Relatively high numbers of alleles also improve the usefulness of these markers. Alleles tend to differ by relatively few numbers of repeats, with the result that all alleles for a single marker may span a range in size of 20 bp or less. This means that amplified fragments from several different markers can be analyzed simultaneously on the same polyacrylamide gel lanes, greatly improving the efficiency of the amplification process and the ability to identify individuals using the test.

As of the date of this application, over 100 polymorphic repeat sequences have been discovered by the inventor. A summary of these repeat sequences is presented on Table 1. Tables 2–39 describe some of the repeat sequences in more detail, including the name of the locus, the source, the primer sequences, the frequency, the chromosomal location, and the Mendelian inheritance, and other identifying comments. Table 40 lists the complete nucleic acid sequence of some of the claimed polymorphic repeat sequences.

TABLE 1

| Marker | Repeat Sequence | Primer Sequence |
|---|---|---|
| Mfd1 | CATA(CA)$_{19}$ (SEQ. ID. NO: 53) | GCTAGCCAGCTGGTGTATT (SEQ. ID. NO: 54) |
| | | ACCACTCTGGGAGAAGGGTA (SEQ. ID. NO: 55) |
| Mfd2 | (AC)$_{13}$A(AC)$_{17}$A (SEQ. ID. NO: 56) | CATTAGGATGCATTCTTCTG (SEQ. ID. NO: 57) |
| | | GTCAGGATTGAACTGGAAC (SEQ. ID. NO: 58) |
| Mfd3 | (CA)$_{16}$C (SEQ. ID. NO: 59) | GGTCTGGAAGTACTGAGAAA (SEQ. ID. NO: 60) |
| | | GATTCACTGCTGTGGACCCA (SEQ. ID. NO: 61) |
| Mfd4 | (AC)$_{12}$GCACAA(AC)$_{13}$A (SEQ. ID. NO: 62) | GCTCAAATGTTTCTGCAACC (SEQ. ID. NO: 63) |
| | | CTTTGTAGCTCGTGATGTGA (SEQ. ID. NO: 64) |
| Mfd5 | (CT)$_7$(CA)$_{23}$ (SEQ. ID. NO: 65) | CATAGCGAGACTCCATTCTC (SEQ. ID. NO: 66) |
| | | GGGAGAGCGGCAAAGATCGAT (SEQ. ID. NO: 67) |
| Mfd6 | (CA)$_5$AA(CA)$_{13}$ (SEQ. ID. NO: 68) | TCCTACCTTAATTTCTTCGCT (SEQ. ID. NO: 69) |
| | | GCAGGTTGTTTAATTTCGGC (SEQ. ID. NO: 70) |
| Mfd7 | (CA)$_{20}$TA(CA)$_2$ (SEQ. ID. NO: 71) | GTTAGCATAATGCCCTCAAG (SEQ. ID. NO: 72) |
| | | CGATGGAGTTTATGTTGAGA (SEQ. ID. NO: 73) |
| Mfd8 | (AC)$_{20}$A (SEQ. ID. NO: 74) | CGAAAGTTCAGAGATTTGCA (SEQ. ID. NO: 75) |
| | | ACAATTAGGATTAGCTGTGA (SEQ. ID. NO: 76) |
| Mfd9 | (AC)$_{17}$G (SEQ. ID. NO: 77) | ATGTCTCCTTGGTAAGTTA (SEQ. ID. NO: 78) |
| | | AATACCTAGGAAGGGGAGGG (SEQ. ID. NO: 79) |
| Mfd10 | (AC)$_{14}$A (SEQ. ID. NO: 80) | CATGCCTGGCCTTACTTGC (SEQ. ID. NO: 81) |
| | | AGTTTGAGACCAGCCTGCG (SEQ. ID. NO: 82) |
| Mfd11 | (AC)$_{23}$A (SEQ. ID. NO: 83) | ACTCATGAAGGTGACAGTTC (SEQ. ID. NO: 84) |
| | | GTGTTGTTGACCTATTGCAT (SEQ. ID. NO: 85) |
| Mfd12 | (AC)$_{11}$AT(AC)$_8$A (SEQ. ID. NO: 86) | GGTTGAGATGCTGACATGC (SEQ. ID. NO: 87) |
| | | CAGGGTGGCTGCTGTTATAATG (SEQ. ID. NO: 88) |
| Mfd13 | (CA)$_4$CGCG(CA)$_{19}$C (SEQ. ID. NO: 89) | TCCCTTGCTCCCCAAACG (SEQ. ID. NO: 90) |
| | | ATTAATCCATCTAAAAGCGAA (SEQ. ID. NO: 91) |
| Mfd14 | (AC)$_{23}$A (SEQ. ID. NO: 92) | AAGGATATTGTCCTGAGGA (SEQ. ID. NO: 93) |
| | | TTCTGATATCAAAACCTGGC (SEQ. ID. NO: 94) |
| Mfd15 | (AC)$_{25}$ (SEQ. ID. NO: 95) | GGAAGAATCAAATAGACAAT (SEQ. ID. NO: 96) |
| | | GCTGGCCATATATATATTTAAACC (SEQ. ID. NO: 97) |
| Mfd16 | G(CG)$_4$(CA)$_5$TA(CA)$_3$(TA)$_2$(CA)$_6$CCAA(CA)$_{21}$ (SEQ. ID. NO: 98) | AGAGATTAAAGGCTAAATTC (SEQ. ID. NO: 99) |
| | | TTCGTAGTTGGTTAAAATTG (SEQ. ID. NO: 100) |
| Mfd17 | (AC)$_{23}$ (SEQ. ID. NO: 101) | TTTCCACTGGGAACATGGT (SEQ. ID. NO: 102) |
| | | ACTCTTTGTTGAATTCCCAT (SEQ. ID. NO: 103) |
| Mfd18 | (AC)$_{18}$ (SEQ. ID. NO: 104) | AGCTATCATCACCCTATAAAAT (SEQ. ID. NO: 105) |
| | | AGTTTAACCATGTCTCTCCCG (SEQ. ID. NO: 106) |
| Mfd19 | (AC)$_8$AG(AC)$_3$AG(AC)$_{24}$TCAC(TC)$_6$T (SEQ. ID. NO: 107) | TCTAACCCTTTGGCCATTTG (SEQ. ID. NO: 108) |
| | | GCTGTTACATTGTTGCTTC (SEQ. ID. NO: 109) |
| Mfd20 | (AC)$_{17}$ (SEQ. ID. NO: 110) | TTTGAGTAGGTGGCATCTCA (SEQ. ID. NO: 111) |
| | | TTAAAATGTTGAAGGCATCTTC (SEQ. ID. NO: 112) |
| Mfd21 | (TA)$_6$TT(TA)$_2$TC(TA)$_5$TT(TA)$_3$CA(TA)$_7$(CA)$_8$TACATG(TA)$_3$ (SEQ. ID. NO: 113) | GCTCAGGAGTTCGAGATCA (SEQ. ID. NO: 114) |
| | | CACCACCCGACATTTTA (SEQ. ID. NO: 115) |
| Mfd22 | (AC)$_{20}$AG(AGAC)$_5$AGA (SEQ. ID. NO: 116) | TGGGTAAAGAGTGAGGCTG (SEQ. ID. NO: 117) |
| | | GGTCCAGTAAGAGAGACAGT (SEQ. ID. NO: 118) |
| Mfd23 | (AC)$_{20}$ (SEQ. ID. NO: 119) | AGTCCTCTGTGCACTTTGT (SEQ. ID. NO: 120) |
| | | CCAGACATGGCAGTCCTA (SEQ. ID. NO: 121) |
| Mfd24 | (AC)$_7$AGAG(AC)$_{14}$A (SEQ. ID. NO: 122) | AAGCTTGTATCTTTCTCAGG (SEQ. ID. NO: 123) |
| | | ATCTACCTTGGCTGTCATTG (SEQ. ID. NO: 124) |
| Mfd25 | (AC)$_{11}$ (SEQ. ID. NO: 125) | TTTATGCGAGCGTATGGATA (SEQ. ID. NO: 126) |
| | | CACCACCATTGATCTGGAAG (SEQ. ID. NO: 127) |
| Mfd26 | (AC)$_{28}$A (SEQ. ID. NO: 128) | CAGAAAATTCTCTCTGGCTA (SEQ. ID. NO: 129) |
| | | CTCATGTTCCTGGCAAGAAT (SEQ. ID. NO: 130) |
| Mfd27 | (CA)$_9$AA(CA)$_{19}$(GA)$_7$ (SEQ. ID. NO: 131) | GATCCACTTTAACCCAAATAC (SEQ. ID. NO: 132) |
| | | GGCATCAACTTGAACAGCAT (SEQ. ID. NO: 133) |
| Mfd28 | (AC)$_{10}$AG(AC)$_{21}$A (SEQ. ID. NO: 134) | AACACTAGTAGACATATTTTCA (SEQ. ID. NO: 135) |
| | | AGCTAGGCCTGAAGGCTTCT (SEQ. ID. NO: 136) |
| Mfd29 | (AC)$_{19.5}$ (SEQ. ID. NO: 137) | AGTCCCTCGAGATGCACT (SEQ. ID. NO: 138) |
| | | TTCTTTGTCTTTACATGTGGC (SEQ. ID. NO: 139) |
| Mfd30 | (AC)$_{18.5}$ (SEQ. ID. NO: 140) | CCATGTCCCATATCCTACA (SEQ. ID. NO: 141) |
| | | TGAAATCACTGATGACAATG (SEQ. ID. NO: 142) |
| Mfd31 | (AC)$_{13}$A (SEQ. ID. NO: 143) | TAATAAAGGAGCCAGCTATG (SEQ. ID. NO: 144) |
| | | ACATCTGATGTAAATGCAAGT (SEQ. ID. NO: 145) |
| Mfd32 | (AC)$_{12}$A (SEQ. ID. NO: 146) | AGCGATATTTTTACTTCTCTG (SEQ. ID. NO: 147) |
| | | CTGGTTGTACATGCCTGAC (SEQ. ID. NO: 148) |
| Mfd33 | (AC)$_{14}$AT(AC)$_{13}$ (SEQ. ID. NO: 149) | AGCCTGGGAGTCAGAGTGA (SEQ. ID. NO: 150) |
| | | AGCTCCAAATCAAAGACGT (SEQ. ID. NO: 151) |
| Mfd34 | (AC)$_{14}$AT(AC)$_{15}$ (SEQ. ID. NO: 152) | GGTTCTTTTTCTAGTTCTTC (SEQ. ID. NO: 153) |
| | | TCATATAGCCTTTGTTTGCA (SEQ. ID. NO: 154) |
| Mfd35 | In preparation | GTGGAGAGTAAGACTCTGTC (SEQ. ID. NO: 155) |
| | | TGATGCAACACAGGAGACCT (SEQ. ID. NO: 156) |
| Mfd36 | (AC)$_{15}$AT(AC)$_6$A (SEQ. ID. NO: 157) | AGCTATAATGCATCATGCA (SEQ. ID. NO: 158) |
| | | TGGTCTATAACTGGTCTATG (SEQ. ID. NO: 159) |
| Mfd37 | (AC)$_{10}$A (SEQ. ID. NO: 160) | AAAAGTTGTTCCCTCCCCGTT (SEQ. ID. NO: 161) |
| | | ACAAGGTGACAAGGTGCCTA (SEQ. ID. NO: 162) |
| Mfd38 | (AT)$_{14}$(AC)$_{14.5}$ (SEQ. ID. NO: 163) | ATCTCTGTTCCCTCCCCGTT (SEQ. ID. NO: 164) |
| | | CTTATTGGCCTGAAGGTAG (SEQ. ID. NO: 165) |
| Mfd39 | (TC)$_{12.5}$GTT(TC)$_{11.5}$(CA)$_{14}$A(AC)$_{3.5}$ (SEQ. ID. NO: 166) | GGGTTGGTTGTAAATTAAAAC (SEQ. ID. NO: 167) |
| | | TGTCAAATACTTAAGCACAG (SEQ. ID. NO: 168) |
| Mfd40 | (CA)$_{13}$C(CA)$_6$T(AC)$_5$ (SEQ. ID. NO: 169) | GGCATCATTTTAGAAGGAAAT (SEQ. ID. NO: 170) |
| | | ACATTTGTTCAGGACCAAG (SEQ. ID. NO: 171) |
| Mfd41 | (AC)$_{17}$ (SEQ. ID. NO: 172) | CAGGTTCTGTCATAGGACTA (SEQ. ID. NO: 173) |
| | | TTCTGGAAACCTACTCCTGA (SEQ. ID. NO: 174) |
| Mfd42 | (CA)$_{16}$T(AC)$_{3.5}$ (SEQ. ID. NO: 175) | GGCCTCAAAGAATCCTACAG (SEQ. ID. NO: 176) |
| | | GACACGTAGTTGCTTATTAC (SEQ. ID. NO: 177) |
| Mfd43 | In preparation | TTGGAAGCCTTAGGAAGTGC (SEQ. ID. NO: 178) |
| | | AAGAATTCTAGTTTCAATACCG (SEQ. ID. NO: 179) |
| Mfd44 | (CA)$_{17}$ (SEQ. ID. NO: 180) | GTATTTTGGTATGCTTTGC (SEQ. ID. NO: 181) |
| | | CTATTTTGGAATATATGTGCCT (SEQ. ID. NO: 182) |
| Mfd45 | (CA)$_{20.5}$ (SEQ. ID. NO: 183) | TCCAGCAGAGAAAGGGTTAT (SEQ. ID. NO: 184) |
| | | GGCAAAGAGAACTCATCAGA (SEQ. ID. NO: 185) |
| Mfd46 | (AC)$_{25}$ (SEQ. ID. NO: 186) | AAAAGGAAGAATCAAATAGAC (SEQ. ID. NO: 187) |
| | | ATATATTTAAACCATTTGAAAG (SEQ. ID. NO: 188) |
| Mfd47 | (AC)$_{17.5}$ (SEQ. ID. NO: 189) | ACAGAGTGAGACCGTGTAAC (SEQ. ID. NO: 190) |
| | | AGAGAAGCATCTCACTTAGT (SEQ. ID. NO: 191) |

TABLE 1-continued

| Marker | Repeat Sequence | Primer Sequence |
|---|---|---|
| Mfd48 | (AC)$_{17}$ (SEQ. ID. NO: 192) | TGTCTCCTGCTGAGAATAG (SEQ. ID. NO: 193) | TAATATCCAAACCACAAAGT (SEQ. ID. NO: 194) |
| Mfd49 | (CA)$_{22}$ (SEQ. ID. NO: 195) | GATAAATGCCAAACATGTTGT (SEQ. ID. NO: 196) | TGCTCTCAGGATTTCCTCCA (SEQ. ID. NO: 197) |
| Mfd50 | (CA)$_{19}$ (SEQ. ID. NO: 198) | ACATTCTAAGACTTTCCCAAT (SEQ. ID. NO: 199) | AGAGCATGCACCCTGAATTG (SEQ. ID. NP: 200) |
| Mfd51 | In preparation | AGCTGATACACCACTTCTGA (SEQ. ID. NO: 201) | GACAGAAATATTCCTTCCCAT (SEQ. ID. NO: 202) |
| Mfd52 | (AC)$_{18}$TTG(CA)$_3$ (SEQ. ID. NO: 203) | AAATCAGACAAGTACAGGTG (SEQ. ID. NO: 204) | ATGAACTTGTTCTGGGAGGA (SEQ. ID. NO: 205) |
| Mfd53 | In preparation | TGCCCTGCCACTCTAGCCT (SEQ. ID. NO: 206) | GCTATCAACAAGCTTTAGGT (SEQ. ID. NO: 207) |
| Mfd54 | (AC)$_{16}$ (SEQ. ID. NO: 210) | CTGACAGGTTGAGGCTGCA (SEQ. ID. NO: 208) | CAGTTTGTATGTATGTTTGGA (SEQ. ID. NO: 209) |
| Mfd55 | (AC)$_{16}$ (SEQ. ID. NO: 210) | GTCAACATAGTGAGACCCCA (SEQ. ID. NO: 211) | ATCCAGCCTGTAACACATTC (SEQ. ID. NO: 212) |
| Mfd56 | In preparation | CTGGTGAATTCAAACAACCT (SEQ. ID. NO: 213) | TTTTCTCTGACACCTCAACT (SEQ. ID. NO: 214) |
| Mfd57 | (CA)$_{15.5}$ (SEQ. ID. NO: 215) | GATCTATCCCTCACTTACG (SEQ. ID. NO: 216) | TATGAACAGACAAGTGGAGC (SEQ. ID. NO: 217) |
| Mfd58 | (CA)$_{16.5}$ (SEQ. ID. NO: 218) | CTCATTTGAAGACTGCAGCA (SEQ. ID. NO: 219) | AGGGCTTCCTCCTGCCATCTA (SEQ. ID. NO: 220) |
| Mfd59 | (AC)$_{23.5}$ (SEQ. ID. NO: 221) | AAGAACCATGCGATACGACT (SEQ. ID. NO: 222) | CATTCCTAGATGGGTAAAGC (SEQ. ID. NO: 223) |
| Mfd60 | In preparation | GCCCTATAAAATCCTAATTAAC (SEQ. ID. NO: 224) | CAAGAGCGAAAGTCCGTCTC (SEQ. ID. NO: 225) |
| Mfd61 | (CA)$_{23}$ (SEQ. ID. NO: 226) | GCCCTATAAAATCCTAATTAAC (SEQ. ID. NO: 227) | GAAGGAGAATTGTAATTCCG (SEQ. ID. NO: 228) |
| Mfd62 | (AC)$_{21}$ (SEQ. ID. NO: 229) | AGCTTTACAGATGAGACCAG (SEQ. ID. NO: 230) | CAGCCAAATTTCTTGAGTCCG (SEQ. ID. NO: 231) |
| Mfd63 | (CA)$_{20.5}$ (SEQ. ID. NO: 232) | CAAAACCAAAAAACCAAAGGC (SEQ. ID. NO: 233) | CAATCTGTGACAGTTTCTCA (SEQ. ID. NO: 234) |
| Mfd64 | (AC)$_{15.5}$ (SEQ. ID. NO: 235) | ACGAACATTCTACAAGTTAC (SEQ. ID. NO: 236) | TTTTACTTCCTTTGCCTCAG (SEQ. ID. NO: 237) |
| Mfd65 | (CA)$_{14.5}$ (SEQ. ID. NO: 238) | GCAAACCACAATGGAATGCA (SEQ. ID. NO: 239) | CTTTACTTCCTTTGCCTCAG (SEQ. ID. NO: 240) |
| Mfd66 | (AC)$_{22}$ (SEQ. ID. NO: 241) | GCCCCTACCTTGCTAGTTA (SEQ. ID. NO: 242) | AACCTCAGCTTATACCCAAG (SEQ. ID. NO: 243) |
| Mfd67 | (TC)$_{12}$(AC)$_{18}$ (SEQ. ID. NO: 244) | ATCGCCCTTATGGAGTGC (SEQ. ID. NO: 245) | CCCACTCCTCTGTCATTGTA (SEQ. ID. NO: 246) |
| Mfd68 | In preparation | ATGTATAGAATTCCATTCCTG (SEQ. ID. NO: 247) | TAAAATCAAGTGTGATGTAG (SEQ. ID. NO: 248) |
| Mfd69 | (AC)$_{18.5}$A(AC)$_3$ (SEQ. ID. NO: 249) | TAGCTGGTGCATAAGCTCAC (SEQ. ID. NO: 250) | GTTAGTGGAAGAGCAGAGC (SEQ. ID. NO: 251) |
| Mfd70 | In preparation | AACATAGTGAAACCCCATCT (SEQ. ID. NO: 252) | GTGCCACTACATGCAGCTA (SEQ. ID. NO: 253) |
| Mfd71 | In preparation | CCAAACTACAATACCCAGCTA (SEQ. ID. NO: 254) | CTGATTTGAGTATAACCAATA (SEQ. ID. NO: 255) |
| Mfd72 | (AC)$_{17}$G(GA)$_8$ (SEQ. ID. NO: 256) | AGAAGACATAAGGATACTGC (SEQ. ID. NO: 257) | GATCCCAACTATTTCTTCT (SEQ. ID. NO: 258) |
| Mfd73 | In preparation | CCTGGAAAAATGGCTCACC (SEQ. ID. NO: 259) | GGAAAATCAGTCCTCTAGTTG (SEQ. ID. NO: 260) |
| Mfd74 | In preparation | TTTCACCTCCTTGGCTTTGT (SEQ. ID. NO: 261) | ATCCCTTTTACAACAACTGC (SEQ. ID. NO: 262) |
| Mfd75 | In preparation | CTCACTCATGCTTGTTTGA (SEQ. ID. NO: 263) | GATCACGTCAGACTGGGCT (SEQ. ID. NO: 264) |
| Mfd76 | In preparation | CCTGTGAGACAAAGCAAGAC (SEQ. ID. NO: 265) | GACATTAGGCACAGGGCTAA (SEQ. ID. NO: 266) |
| Mfd77 | In preparation | ATAGACTTCCAGACAGATAG (SEQ. ID. NO: 267) | CCCTCTCCATTCCTGGTACT (SEQ. ID. NO: 268) |
| Mfd78 | In preparation | GAATCCATAGCTGTACTCCA (SEQ. ID. NO: 269) | AATTGTCTATGGTCCCAGCA (SEQ. ID. NO: 270) |
| Mfd79 | (AC)$_{15.5}$ (SEQ. ID. NO: 271) | GATAAAACTGCATAGAAATGCG (SEQ. ID. NO: 272) | CAACTGGGATATTGACATTG (SEQ. ID. NO: 273) |
| Mfd80 | In preparation | TTGAGGCTGCGAAGTGAGCTAT (SEQ. ID. NO: 274) | ATGTTGTGTTTCACAGCAG (SEQ. ID. NO: 275) |
| Mfd81 | In preparation | GCAACTCATGTCACCAATTCT (SEQ. ID. NO: 276) | ATAGTCAATGGTTAATGCTC (SEQ. ID. NO: 277) |
| Mfd82 | In preparation | AGCTTGGGTGCAAGAAGAG (SEQ. ID. NO: 278) | GATCCCATTATTTAAAAGTGTA (SEQ. ID. NO: 279) |
| Mfd83 | In preparation | GATCTCATGTGCTCAGTTTA (SEQ. ID. NO: 280) | CCAAAAAGTGCAAATTTAGAGT (SEQ. ID. NO: 281) |
| Mfd84 | (AC)$_5$AT(AC)$_2$AGATT(AC)$_2$GG(AC)$_{17}$ (SEQ. ID. NO: 282) | AATGTCCTTGTACTTTAGGAT (SEQ. ID. NO: 283) | CACTTAATATCTCAATGTATAC (SEQ. ID. NO: 284) |
| Mfd85 | In preparation | GATCTTTCCATCTTCTGAC (SEQ. ID. NO: 285) | GAGGGACGGAGCAACTGAT (SEQ. ID. NO: 286) |
| Mfd86 | In preparation | CAACATAGCAAGACCCTGTC (SEQ. ID. NO: 287) | GCACATGCCAAGAGACAAG (SEQ. ID. NO: 288) |
| Mfd87 | In preparation | TCAAAAGCTGTAATTGGAG (SEQ. ID. NO: 289) | TGCAATCTGTAAGCATTCCT (SEQ. ID. NO: 290) |
| Mfd88 | In preparation | ACCTGAGTTGTTCATCAATAC (SEQ. ID. NO: 291) | GCTATGAATCATCCATGTTGT (SEQ. ID. NO: 292) |
| Mfd89 | In preparation | GTCTGTTTGCTTGGCTCCA (SEQ. ID. NO: 293) | AGCTATGAAGTGGGAGTTCA (SEQ. ID. NO: 294) |
| Mfd90 | In preparation | ATTTGGATGAGCAAGCCT (SEQ. ID. NO: 295) | ATCTGTATATATGTGTACCTG (SEQ. ID. NO: 296) |
| Mfd91 | In preparation | CTACATATTTCTAAATACATGC (SEQ. ID. NO: 297) | ACTTAGTAGTTTTAAGCAGGA (SEQ. ID. NO: 298) |
| Mfd92 | In preparation | ATTTCCACCCACTTCTGT (SEQ. ID. NO: 299) | GATGGTGTTGAGAATTAGGC (SEQ. ID. NO: 300) |
| Mfd93 | (AAAT)$_6$TT(TA)$_7$(CA)$_{13}$ (SEQ. ID. NO: 301) | GACAGAGTTGAGACTCCATCT (SEQ. ID. NO: 302) | CTTCCCATTTTCAATCCCTAG (SEQ. ID. NO: 303) |
| Mfd94 | AAACGCACAG(AC)$_{21.5}$ (SEQ. ID. NO: 304) | AGTCTTTCTCTGTTTGCT (SEQ. ID. NO: 305) | CCCTAAGGACAGAACAAGTG (SEQ. ID. NO: 306) |
| Mfd95 | GGAGATTTGG(AC)$_{23}$ (SEQ. ID. NO: 307) | TAGGCCCTACTGCAATAATG (SEQ. ID. NO: 308) | CTTTATCTTCACACAGCTTC (SEQ. ID. NO: 309) |
| Mfd96 | In preparation | TCAACAATGGCCGAGGTTA (SEQ. ID. NO: 310) | AACCTGACACCATGCTCCT (SEQ. ID. NO: 311) |
| Mfd97 | CTCTCTCTCT(CA)$_{11.5}$ (SEQ. IS. NO: 312) | TTCTATTTCTGAAGGTGAACTA (SEQ. ID. NO: 313) | ATAGTTACCATCAGTCACTG (SEQ. ID. NO: 314) |

TABLE 1-continued

| Marker | Repeat Sequence | Primer Sequence |
|---|---|---|
| Mfd98 | In preparation | TCTGGAGACCACTAACTGTA (SEQ. ID. NO: 315) |
| | | ACTCTCCATGAGTCCTGATG (SEQ. ID. NO: 316) |
| Mfd99 | TCTCTATCTT(CA)$_{20.5}$ (SEQ. ID. NO: 317) | ATGAGCTAATTCTCTATCTTC (SEQ. ID. NO: 318) |
| | | TAGCCTACATAAAGGAGGGT (SEQ. ID. NO: 319) |
| Mfd100 | In preparation | GGAGCCAAATACTAAATTCT (SEQ. ID. NO: 320) |
| | | TTAGGCACTTTAATCAGGCT (SEQ. ID. NO: 321) |
| Mfd101 | (AC)$_{17}$ (SEQ. ID. NO: 322) | CATAAAAGGCTTATTGGTTTG (SEQ. ID. NO: 323) |
| | | CAAAACAGAGAACAGAGTAG (SEQ. ID. NO: 324) |
| Mfd102 | (AC)$_{19}$AA(AC)$_{3}$A (SEQ. ID. NO: 325) | AGGAGAGCTAGAGCTTCTAT (SEQ. ID. NO: 326) |
| | | GTTTCAACATGAGTTTCAGA (SEQ. ID. NO: 327) |
| Mfd103 | GCAGTAAAAG(CA)$_{20}$ (SEQ. ID. NO: 328) | CAGATAAACTAATACAAGCAG (SEQ. ID. NO: 329) |
| | | CTCTGCCTCCCAAAGTGCT (SEQ. ID. NO: 330) |
| Mfd104 | TTATATATAT(AC)$_{14.5}$ (SEQ. ID. NO: 331) | GATCATGTGAGTTAATACTTAAT (SEQ. ID. NO: 332) |
| | | TCAGCTGCCTGTATTACTTCA (SEQ. ID. NO: 333) |
| Mfd105 | TCAAACACAA(AC)$_{16}$ (SEQ. ID. NO: 334) | GATCCTGTCTCAAACACAAAC (SEQ. ID. NO: 335) |
| | | AAGTCTTCAGCTTTATCAAC (SEQ. ID. NO: 336) |
| Mfd106 | TCTTCCCCCA(AC)$_{20.5}$ (SEQ. ID. NO: 337) | GATCTGTCTCTCCCCCAAC (SEQ. ID. NO: 338) |
| | | TTTCATGTTGCAGTCAGAGC (SEQ. ID. NO: 339) |
| Mfd107 | TGCCCGGCCT(AC)$_{16}$ (SEQ. ID. NO: 340) | CCCAAAGTACTGGGATTACA (SEQ. ID. NO: 341) |
| | | TTCAAGTGTTACTGTACTGC (SEQ. ID. NO: 342) |
| Mfd108 | GTGGCTAAAT(AC)$_{16}$ (SEQ. ID. NO: 343) | GCCCTGAAGTGGCTAAATA (SEQ. ID. NO: 344) |
| | | CCCCTCACCACATCACTTG (SEQ. ID. NO: 345) |
| Mfd109 | GGGAAATAGG(CA)$_{18}$ (SEQ. ID. NO: 346) | GACACAGAGAAGGGAAATAG (SEQ. ID. NO: 347) |
| | | TCCCATATCCTATGTAGAAG (SEQ. ID. NO: 348) |
| Mfd110 | (ATTT)$_{11}$AT (SEQ. ID. NO: 349) | GCTAGAGGGAGGTTTAATTG (SEQ. ID. NO: 350) |
| | | AATTAGCCAGGTGTTGTTGGT (SEQ. ID. NO: 351) |
| Mfd111 | TGAGACCCTG(AC)$_{15.5}$ (SEQ. ID. NO: 352) | AACCAAGATTGTGCCACTG (SEQ. ID. NO: 353) |
| | | GATCATGACTCTTTTGTG (SEQ. ID. NO: 354) |
| Mfd112 | CCACCCCAG(CA)$_{24.5}$ (SEQ. ID. NO: 355) | GATCCATGCCACCCCCCA (SEQ. ID. NO: 356) |
| | | CCTCTCAGACTCATCCCAC (SEQ. ID. NO: 357) |
| Mfd113 | (AC)$_{18}$ (SEQ. ID. NO: 358) | CTGCTGACTTTGACTCAGTA (SEQ. ID. NO: 359) |
| | | GGTCCTGAGCAGGTCTCTTC (SEQ. ID. NO: 360) |
| Mfd114 | GTTATCCATT(AC)$_{19.5}$ (SEQ. ID. NO: 361) | TGGCATCTCTAATCATACTG (SEQ. ID. NO: 362) |
| | | GACTAAAACATTGCAGAATAC (SEQ. ID. NO: 363) |
| Mfd115 | ATAGAGAAGG(AC)$_{17.5}$ (SEQ. ID. NO: 364) | AGAAAATAAGAATAGAGAAGG (SEQ. ID. NO: 365) |
| | | CAAGAACTATGTTATTGGGA (SEQ. ID. NO: 366) |
| Mfd116 | CCCCACCCA(AC)$_{20}$ (SEQ. ID. NO: 367) | CTGCACTAGAAAGGCAGAGT (SEQ. ID. NO: 368) |
| | | TGCAGCACCAAACACCAAGT (SEQ. ID. NO: 369) |
| Mfd117 | GCAGCAACAT(AC)$_{16.5}$ (SEQ. ID. NO: 370) | ACAAGAGCACATTTAGTCAG (SEQ. ID. NO: 371) |
| | | AGCTTCATTTTCCCTCTAG (SEQ. ID. NO: 372) |
| Mfd118 | (AC)$_{15}$ (SEQ. ID. NO: 373) | CTTTCTTATAGTTAAGGTTAGC (SEQ. ID. NO: 374) |
| | | TAGCATCAGAAGACCTGGC (SEQ. ID. NO: 375) |
| Mfd119 | (AC)$_{16}$ (SEQ. ID. NO: 376) | GAATCTTAAGTAGTTATCCCTC (SEQ. ID. NO: 377) |
| | | CTACAAAAAGTCAGATACCT (SEQ. ID. NO: 378) |
| Mfd120 | (TC)$_5$(AC)$_{20}$ (SEQ. ID. NO: 379) | CAATGACTTAAGCACACTAAG (SEQ. ID. NO: 380) |
| | | TCAGAGGTTGAGGCTGAAG (SEQ. ID. NO: 381) |
| Mfd121 | (TC)$_5$(CA)$_{23.5}$ (SEQ. ID. NO: 382) | GATCTGGGTATGTCTTTCTG (SEQ. ID. NO: 383) |
| | | ACTGGGACTCTAACTAATGT (SEQ. ID. NO: 384) |
| Mfd122 | TTTACAGTAG(CA)$_{17}$ (SEQ. ID. NO: 385) | ATGCAGAATCTACAAGGACC (SEQ. ID. NO: 386) |
| | | CTTTAACATCCTTTAACAGC (SEQ. ID. NO: 387) |
| Mfd123 | (AC)$_{21.5}$ (SEQ. ID. NO: 388) | AGCAGCTATTATGGAATTGC (SEQ. ID. NO: 389) |
| | | CAACATATGCAAGGTGCCTA (SEQ. ID. NO: 390) |
| Mfd124 | ATTAGCATA(AC)$_{20.5}$ (SEQ. ID. NO: 391) | TGCTTAAACAGAAAAGTAGC (SEQ. ID. NO: 392) |
| | | TAAAACGTACCCAGTACCT (SEQ. ID. NO: 393) |
| Mfd125 | CTGAAACAAA(AC)$_{23}$(POST ALU) (SEQ. ID. NO: 394) | TGAGACCCTGTCTCTGAAAC (SEQ. ID. NO: 395) |
| | | TGTATGGGCTCTGAAATTG (SEQ. ID. NO: 396) |

TABLE 2

Dinucleotide Repeat Polymorphism Mfd11 at the D19S49 Locus

SOURCE/DESCRIPTION: A genomic Sau3A I fragment from a large insert human chromosome 19-specific phage library (LL19NL01) was cloned into mp18 and selected by hybridization to poly(dC-dA).poly(dG-dT). The cloned fragment was designated Mfd11. Sequencing of Mfd11 provided the information necessary for polymerase chain reaction primer synthesis. The clone length was 265 bp, and the predicted length of the amplified fragment was 121 bp.
PRIMER SEQUENCES: ACTCATGAAGGTGACAGTTC (CA strand) (SEQ ID NO: 84);
GTGTTGTTGACCTATTGCAT (GT strand) (SEQ ID NO: 85)
FREQUENCY: Estimated from 152 chromosomes of unrelated CEPH family parents (Caucasians). PIC = 0.71.

| Allele (bp) | Frequency | Allele (bp) | Frequency |
|---|---|---|---|
| 122 | 0.07 | 114 | 0.05 |
| 120 | 0.16 | 110 | 0.01 |
| 118 | 0.17 | 108 | 0.43 |
| 116 | 0.10 | 106 | 0.01 |

CHROMOSOMAL LOCALIZATION: Assignment to chromosome 19 was verified using DNA templates isolated from panels of somatic cell hybrids. P. deJong supplied the chromosome 19-specific phage library.
MENDELIAN INHERITANCE: Co-dominant segregation was observed in 40 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the CA and GT strand bands. The dinucleotide repeat sequence in Mfd11 was of the form $(AC)_{23}A$ (SEQ ID NO: 83). The sequence of Mfd11 has been submitted to GenBank.

REFERENCES: Weber, J. L. and May, P. E. (1989) Am. J. Hum. Genet. 44:388–396.

TABLE 3

$(dC-dA)_n.(dG-dT)_n$ Polymorphism Mfd12 On Chromosome 16 (D16S250)

SOURCE/DESCRIPTION: A human genomic Sau3A I fragment of 318 bp was cloned into mp18 and selected by hybridization to poly(dC-dA).poly(dG-dT). Sequencing of the cloned fragment provided the information necessary for polymerase chain reaction primer synthesis.
Amplification was expected to produce a fragment of 234 bp.
PRIMER SEQUENCES: GGTTGAGATGCTGACATGC (CA strand) (SEQ ID NO: 87); CAGGGTGGCTGTTATAATG (GT strand) (SEQ ID NO: 88)
FREQUENCY: Estimated from 152 chromosomes of unrelated CEPH family grandparents (Caucasians). PIC = 0.43.

| Allele (bp) | Frequency | Allele (bp) | Frequency |
|---|---|---|---|
| 240 | 0.01 | 236 | 0.58 |
| 238 | 0.05 | 234 | 0.37 |

CHROMOSOMAL LOCALIZATION: Mfd12 was assigned to chromosome 16 using DNA templates isolated from panels of somatic cell hybrids.
MENDELIAN INHERITANCE: Co-dominant segregation of Mfd12 was observed in 15 two generation families.
OTHER COMMENTS: Sizes of the alleles were determined by comparison to mp8 DNA sequencing ladders and were the averages of the sizes of the CA and GT strand bands. The sequence of Mfd12 in the form $(AC)_{11}AT(AC)_8A$ (SEQ ID

TABLE 3-continued $(dC-dA)_n.(dG-dT)_n$ Polymorphism Mfd12 On Chromosome 16 (D16S250)

NO: 86) and has been submitted to GenBank.

REFERENCES: Weber, J. L. and May, P. E. (1989) Am. J. Hum. Genet. 44:388–396.

TABLE 4

Dinucleotide Repeat Polymorphism Mfd13 at the D19S75 Locus

SOURCE/DESCRIPTION: A genomic Sau3A I fragment from a large insert human chromosome 19-specific phage library (LL19NL01) was cloned into mp18 and selected by hybridization to poly(dC-dA).poly(dG-dT). The cloned fragment was designated Mfd13. Sequencing of Mfd13 provided the information necessary for polymerase chain reaction primer synthesis. The clone length was 242 bp, and the predicted length of the amplified fragment was 143 bp.
PRIMER SEQUENCES: ATTAATCCATCTAAAAGCGAA (CA strand) (SEQ ID NO: 91); TTCCCTTTGCTCCCCAAACG (GT strand) (SEQ ID NO: 90)
FREQUENCY: Estimated from 100 chromosomes of unrelated CEPH family grandparents (Caucasians). PIC = 0.61.

| Allele (bp) | Frequency | Allele (bp) | Frequency |
|---|---|---|---|
| 152 | 0.01 | 144 | 0.12 |
| 150 | 0.11 | 142 | 0.02 |
| 148 | 0.56 | 136 | 0.05 |
| 146 | 0.13 | | |

CHROMOSOMAL LOCALIZATION: Assignment to chromosome 19 was verified using DNA templates isolated from a panel of somatic cell hybrids.
MENDELIAN INHERITANCE: Co-dominant segregation was observed in 14 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd13 was of the form $(CA)_4CGCG(CA)_{19}C$ (SEQ ID NO: 89). The sequence of Mfd13 has been submitted to GenBank.

REFERENCES: Weber, J. L. and May, P. E. (1989) Am. J. Hum. Genet. 44:388–396.

TABLE 5

Dinucleotide Repeat Polymorphism Mfd14 at the D9S43 Locus

SOURCE/DESCRIPTION: A human genomic Alu I fragment was cloned into mp10 and selected by hybridization to poly(dC-dA).poly(dG-dT). The cloned fragment was designated Mfd14. Sequencing of Mfd14 provided the information necessary for polymerase chain reaction primer synthesis. The clone length was 175 bp, and the predicted length of the amplified fragment was 93 bp.
PRIMER SEQUENCES: TTCTGATATCAAAACCTGGC (CA strand) (SEQ ID NO: 94); AAGGATATTGTCCTGAGGA (GT strand) (SEQ ID NO: 93)
FREQUENCY: Estimated from 106 chromosomes of unrelated CEPH family grandparents (Caucasians). PIC = 0.74.

| Allele (bp) | Frequency | Allele (bp) | Frequency |
|---|---|---|---|
| 102 | 0.01 | 92 | 0.19 |
| 100 | 0.01 | 90 | 0.05 |
| 98 | 0.21 | 86 | 0.01 |
| 96 | 0.33 | 80 | 0.02 |

TABLE 5-continued

Dinucleotide Repeat Polymorphism Mfd14 at the D9S43 Locus

| | |
|---|---|
| 94 | 0.18 |

CHROMOSOMAL LOCALIZATION: Assigned to chromosome 9 using DNA templates isolated from panels of somatic cell hybrids. MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd14 was of the form $(AC)_{23}A$ (SEQ ID NO: 92). The sequence of Mfd14 has been submitted to GenBank.

REFERENCES: Weber, J. L. and May, P. E. (1989) Am. J. Hum. Genet. 44:388–396.

TABLE 6

Dinucleotide Repeat Polymorphisms Mfd15 and Mfd41 at the D17S250 and D17S261 Loci SOURCE/DESCRIPTION: Human genomic DNA fragments were cloned into m13 and selected by hybridization to poly(dC-dA).poly(dG-dT). Sequencing of the clones provided the information necessary for polymerase chain reaction primer synthesis.
Locus: D17S250
Clone Designation: Mfd15
Clone Length: 261 bp
Predicted Length of Amplified Fragment: 162 bp
Primer Sequences:   GGAAGAATCAAATAGACAAT (CA strand) (SEQ ID NO: 96)
GCTGGCCATATATATATTTAAACC (GT strand) (SEQ ID NO: 97)
Locus: D17S261
Clone Designation: Mfd41
Clone Length: >293 bp
Predicted Length of Amplified Fragment: 159 bp
Primer Sequences:   CAGGTTCTGTCATAGGACTA (CA strand) (SEQ ID NO: 173)
TTCTGGAAACCTACTCCTGA (GT strand) (SEQ ID NO: 174)
FREQUENCY: Mfd15: Estimated from 112 chromosomes of unrelated CEPH family grandparents (Caucasians). PIC = 0.81. 0.81.

| Allele (bp) | Frequency | Allele (bp) | Frequency |
|---|---|---|---|
| 169 | 0.01 | 159 | 0.08 |
| 167 | 0.05 | 157 | 0.16 |
| 165 | 0.05 | 155 | 0.12 |
| 163 | 0.05 | 153 | 0.32 |
| 161 | 0.04 | 151 | 0.12 |

Mfd41: Estimated from 116 chromosomes of unrelated CEPH family grandparents (Caucasians). PIC = 0.44.

| Allele (bp) | Frequency | Allele (bp) | Frequency |
|---|---|---|---|
| 171 | 0.01 | 161 | 0.10 |
| 165 | 0.01 | 159 | 0.71 |
| 163 | 0.04 | 157 | 0.13 |

CHROMOSOMAL LOCALIZATION: Mfd15 was assigned to 17q11.2-q12 and Mfd41 assigned to 17p12-p11.1 using DNA templates isolated from panels of chromosomal and subchromosomal somatic cell hybrids (1–3). S. Naylor and S. Diehl provided DNA from chromosome 17-specific somatic cell hybrids.
MENDELIAN INHERITANCE: Co-dominant segregation of Mfd15 and Mfd41 was observed in 18 and 15 two or three generation families respectively.
OTHER COMMENTS: Conditions for the amplification reactions were as described (4) except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands for Mfd15, and the sizes of the most intense bands for Mfd41. The dinucleotide repeat sequence in Mfd15 was of the form $(AC)_{25}$ (SEQ ID NO: 95), and in Mfd41 of the form $(AC)_{17}$ (SEQ ID NO: 172). The sequences of Mfd15 and Mfd41 have been submitted to GenBank.

REFERENCES:
1. vanTuinen, P., Rich, D. C., Summers, K. M., and Ledbetter, D. H. (1987) Genomics 1:374–381.
2. vanTuinen, P., Dobyns, W. B., Rich, D. C., Summers, K. M., Robinson, T. J., Nakamura, Y., and Ledbetter, D. H. (1988) Am. J. Hum. Genet. 43:587–596.
3. Ledbetter, D. H., Rich, D. C., O'Connell, P., Leppert, M., and Carey, J. C. (1989) Am. J. Hum. Genet. 44:20–24.
4. Weber, J. L. and May, P. E. (1989) Am. J. Hum. Genet. 44:388–396.

TABLE 7

Dinucleotide Repeat Polymorphism Mfd17 at the D3S196 Locus

SOURCE/DESCRIPTION: A human genomic Alu I fragment was cloned into mp10 and selected by hybridization to poly(dC-dA).poly(dG-dT). The cloned fragment was designated Mfd17. Sequencing of Mfd17 provided the information necessary for polymerase chain reaction primer synthesis. The clone length was 180 bp, and the predicted length of the amplified fragment was 94 bp.
PRIMER SEQUENCES: ACTCTTTGTTGAATTCCCAT (CA-strand) (SEQ ID NO: 103);
TTTCCACTGGGGAACATGGT (GT-strand) (SEQ ID NO: 102)
FREQUENCY: Estimated from 104 chromosomes of unrelated CEPH family grandparents (Caucasians). PIC = 0.68.

| Allele (bp) | Frequency | Allele (bp) | Frequency |
|---|---|---|---|
| 98 | 0.06 | 90 | 0.04 |
| 96 | 0.16 | 88 | 0.37 |
| 94 | 0.32 | 86 | 0.02 |
| 92 | 0.03 | | |

CHROMOSOMAL LOCALIZATION: Assigned to chromosome 3 using DNA templates isolated from panels of somatic cell hybrids. S. Naylor provided DNA from a chromosome 3-specific somatic cell hybrid.
MENDELIAN INHERITANCE: Co-dominant segregation of Mfd17 was observed in 43 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd17 was of the form $(AC)_{23}$ (SEQ ID NO: 101). The sequence of Mfd17 has been submitted to GenBank.

REFERENCES: Weber, J. L. and May, P. E. (1989) Am. J. Hum. Genet. 44:388–396.

TABLE 8

Dinucleotide Repeat Polymorphisms Mfd18, Mfd39 and Mfd45 at the D8S85, D8S87, and D8S88 Loci SOURCE/DESCRIPTION: Human genomic DNA fragments were cloned into m13 and selected by hybridization to poly(dC-dA).poly(dG-dT). Sequencing of the clones provided the information necessary for polymerase chain reaction primer synthesis.
Locus: D8S85
Clone Designation: Mfd18
Clone Length: 203 bp
Predicted Length of Amplified Fragment: 80 bp
Primer Sequences:   AGCTATCATCACCCTATAAAAT (CA strand) (SEQ ID NO: 105)
AGTTTAACCATGTCTCTCCCG (GT strand) (SEQ ID NO: 106)
Locus: D8S87
Clone Designation: Mfd39
Clone Length: 266 bp
Predicted Length of Amplified Fragment: 150 bp
Primer sequences:   GGGTTGGTTGTAAATTAAAAC (CA strand) (SEQ ID NO: 167)
TGTCAAATACTTAAGCACAG (GT strand) (SEQ ID NO: 168)
Locus: D8S88
Clone Designation: Mfd45
Clone Length: >285 bp
Predicted Length of Amplified Fragment: 87 bp
Primer sequences:   TCCAGCAGAGAAAGGGTTAT (CA strand) (SEQ ID NO: 184)
GGCAAAGAGAACTCATCAGA (GT strand) (SEQ ID NO: 185)
FREQUENCY: Mfd18: Estimated from 116 chromosomes of unrelated CEPH family grandparents (Caucasians). PIC = 0.69.

| Allele (bp) | Frequency | Allele (bp) | Frequency |
|---|---|---|---|
| 84 | 0.01 | 76 | 0.22 |
| 82 | 0.36 | 74 | 0.22 |
| 80 | 0.19 | | |

Mfd39: Estimated from 96 chromosomes of unrelated CEPH family grandparents (Caucasians). PIC = 0.65.

| Allele (bp) | Frequency | Allele (bp) | Frequency |
|---|---|---|---|
| 157 | 0.02 | 149 | 0.14 |
| 155 | 0.18 | 147 | 0.04 |
| 153 | 0.06 | 145 | 0.05 |
| 151 | 0.51 | | |

Mfd45: Estimated from 120 chromosomes of unrelated CEPH family grandparents (Caucasians). PIC = 0.82.

| Allele (bp) | Frequency | Allele (bp) | Frequency |
|---|---|---|---|
| 100 | 0.02 | 88 | 0.15 |
| 98 | 0.04 | 86 | 0.25 |
| 96 | 0.10 | 84 | 0.12 |
| 92 | 0.04 | 82 | 0.03 |
| 90 | 0.21 | 76 | 0.03 |

CHROMOSOMAL LOCALIZATION: The three markers were assigned to chromosome 8 using DNA templates isolated from panels of somatic cell hybrids.
MENDELIAN INHERITANCE: Co-dominant segregation of Mfd18, Mfd39, and Mfd45 were observed in 15–19 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands for Mfd18 and Mfd39, and the sizes of the most intense bands for Mfd45. The dinucleotide repeat sequence in Mfd18 was of the form $(AC)_{18}$ (SEQ ID NO: 104), in Mfd39 $(TC)_{12.5}GTT(TC)_{11.5}(CA)_{14}A(CA)_{5.5}$ (SEQ ID NO: 166), and in

TABLE 8-continued

Dinucleotide Repeat Polymorphisms Mfd18, Mfd39 and Mfd45 at the D8S85, D8S87, and D8S88 Loci Mfd45 $(CA)_{20.5}$ (SEQ ID NO: 183). Sequences of all three clones have been submitted to GenBank.

REFERENCES:
Weber, J. L. and May, P. E. (1989) Am. J. Hum. Genet. 44:388–396.

TABLE 9

Dinucleotide Repeat Polymorphism Mfd19 at the D2S71 Locus

SOURCE/DESCRIPTION: A human genomic Alu I fragment was cloned into mp10 and selected by hybridization to poly(dC-dA).poly(dG-dT). The cloned fragment was designated Mfd19. Sequencing of Mfd19 provided the information necessary for polymerase chain reaction primer synthesis. The clone length was 200 bp, and the predicted length of the amplified fragment was 147 bp.
PRIMER SEQUENCES: GCTTGTTACATTGTTGCTTC (CA strand) (SEQ ID NO: 109); TCTAACCCTTTGGCCATTTG (GT strand) (SEQ ID NO: 108)
FREQUENCY: Estimated from 102 chromosomes of unrelated CEPH family grandparents (Caucasians). PIC = 0.57.

| Allele (bp) | Frequency | Allele (bp) | Frequency |
|---|---|---|---|
| 154 | 0.01 | 144 | 0.02 |
| 152 | 0.61 | 142 | 0.01 |
| 150 | 0.04 | 140 | 0.06 |
| 148 | 0.09 | 138 | 0.15 |
| 146 | 0.02 | | |

CHROMOSOMAL LOCALIZATION: Assigned to chromosome 2 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd19 was of the form $(AC)_8AG(AC)_3AG(AC)_{24}TCA(CT)_7$ (SEQ ID NO: 107). The sequence of Mfd19 has been submitted to GenBank.

REFERENCES: Weber, J. L. and May, P. E. (1989) Am. J. Hum. Genet. 44:388–396.

TABLE 10

Dinucleotide Repeat Polymorphisms Mfd20 and Mfd50 at the D7S435 and D7S440 Loci

SOURCE/DESCRIPTION: Human genomic DNA fragments were cloned into m13 and selected by hybridization to poly(dC-dA).poly(dG-dT). Sequencing of the clones provided the information necessary for polymerase chain reaction primer synthesis.
Locus: D7S435
Clone Designation: Mfd20
Clone Length: 282 bp
Predicted Length of Amplified Fragment: 132 bp
Primer Sequences:   TTAAAATGTTGAAGGCATCTTC (CA strand) (SEQ ID NO: 112)
TTTGAGTAGGTGGCATCTCA (GT strand) (SEQ ID NO: 111)
Locus: D7S440
Clone Designation: Mfd50
Clone Length: 317 bp
Predicted Length of Amplified Fragment: 175 bp
Primer Sequences:   ACATTCTAAGACTTTCCCAAT (CA strand) (SEQ ID NO: 199)
AGAGCATGCACCCTGAATTG (GT

TABLE 10-continued

Dinucleotide Repeat Polymorphisms Mfd20 and Mfd50 at the D7S435 and D7S440 Loci strand) (SEQ ID NO: 200)
FREQUENCY: Mfd20: Estimated from 112 chromosomes of unrelated CEPH family grandparents (Caucasians). PIC = 0.53.

| Allele (bp) | Frequency | Allele (bp) | Frequency |
|---|---|---|---|
| 134 | 0.01 | 126 | 0.57 |
| 132 | 0.27 | 122 | 0.03 |
| 128 | 0.12 | | |

Mfd50: Estimated from 112 chromosomes of unrelated CEPH family grandparents (Caucasians). PIC = 0.70.

| Allele (bp) | Frequency | Allele (bp) | Frequency |
|---|---|---|---|
| 191 | 0.02 | 181 | 0.02 |
| 189 | 0.13 | 179 | 0.04 |
| 187 | 0.23 | 177 | 0.04 |
| 185 | 0.04 | 175 | 0.44 |
| 183 | 0.03 | 169 | 0.01 |

CHROMOSOMAL LOCALIZATION: Mfd20 and Mfd50 were assigned to chromosome 7 by using DNA templates isolated from panels of somatic cell hybrids. S. Naylor kindly provided DNA from a chromosome 7-specific somatic cell hybrid.
MENDELIAN INHERITANCE: Co-dominant segregation of Mfd20 and Mfd50 was observed in 18 and 15 two or three generation families respectively.
OTHER COMMENTS: Conditions for the amplification reactions were as described in the reference except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands for Mfd20, and the sizes of the most intense bands for Mfd50. The dinucleotide repeat sequence in Mfd20 was of the form $(AC)_{17}$ (SEQ ID NO: 110), and in Mfd50 of the form $(CA)_{19}$ (SEQ ID NO: 198). Sequences of both clones have been submitted to GenBank.

REFERENCES: Weber, J. L. and May, P. E. (1989) Am. J. Hum. Genet. 44:388–396.

TABLE 11

Dinucleotide Repeat Polymorphism Mfd22 at the D4S171 Locus

SOURCE/DESCRIPTION: A human genomic Alu I fragment was cloned into mp10 and selected by hybridization to poly(dC-dA).poly(dG-dT). The cloned fragment was designated Mfd22. Sequencing of Mfd22 provided the information necessary for polymerase chain reaction primer synthesis. The clone length was 264 bp, and the predicted length of the amplified fragment was 150 bp.
PRIMER SEQUENCES: TGGGTAAAGAGTGAGGCTG (CA strand) (SEQ ID NO: 117); GGTCCAGTAAGAGGACAGT (GT strand) (SEQ ID NO: 118)
FREQUENCY: Estimated from 96 chromosomes of unrelated CEPH family grandparents (Caucasians). PIC = 0.67.

| Allele (bp) | Frequency | Allele (bp) | Frequency |
|---|---|---|---|
| 161 | 0.01 | 149 | 0.04 |
| 157 | 0.02 | 147 | 0.09 |
| 155 | 0.08 | 145 | 0.01 |
| 153 | 0.39 | 143 | 0.01 |
| 151 | 0.34 | | |

CHROMOSOMAL LOCALIZATION: Assigned to chromosome 4 using DNA templates isolated from panels of somatic cell hybrids. S. Naylor provided DNA from a chromosome 4-specific somatic cell hybrid.

TABLE 11-continued

Dinucleotide Repeat Polymorphism Mfd22 at the D4S171 Locus

MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd22 was of the form $(AC)_{20}AG(AGAC)_5AGA$ (SEQ ID NO: 116). The sequence of Mfd22 has been submitted to GenBank.

REFERENCES: Weber, J. L. and May, P. E. (1989) Am. J. Hum. Genet. 44:388–396.

TABLE 12

Dinucleotide Repeat Polymorphisms Mfd12, Mfd23, Mfd24, Mfd62 and Mfd65 at the D16S260, D16S261, D16S265, D16S266, and D16S267 Loci SOURCE/DESCRIPTION: Human genomic DNA fragments were cloned into m13 and selected by hybridization to poly(dC-dA).poly(dG-dT). Sequencing of the clones provided the information necessary for polymerase chain reaction primer synthesis.
Locus: D16S260
Clone Designation: Mfd12
Clone Length: 318 bp
Predicted Length of Amplified Fragment: 234 bp
Primer Sequences:   GGTTGAGATGCTGACATGC (CA strand) (SEQ ID NO: 87)
CAGGGTGGCTGTTATAATG (GT strand) (SEQ ID NO: 88)
Locus: D16S265
Clone Designation: Mfd23
Clone Length: 178 bp
Predicted Length of Amplified Fragment: 100 bp
Primer Sequences:   CCAGACATGGCAGTCTCTA (CA strand) (SEQ ID NO: 121)
AGTCCTCTGTGCACTTTGT (GT strand) (SEQ ID NO: 120)
Locus: D16S261
Clone Designation: Mfd24
Clone Length: >185 bp
Predicted Length of Amplified Fragment: 89 bp
Primer Sequences:   AAGCTTGTATCTTTCTCAGG (CA strand) (SEQ ID NO: 123)
ATCTACCTTGGCTGTCATTG (GT strand) (SEQ ID NO: 124)
Locus: D16S266
Clone Designation: Mfd62
Clone Length: 202 bp
Predicted Length of Amplified Fragment: 101 bp
Primer Sequences:   AGCTTTACAGATGAGACCAG (CA strand) (SEQ ID NO: 230)
CAGCCAATTTCTTGAGTCCG (GT strand) (SEQ ID NO: 231)
Locus: D16S267
Clone Designation: Mfd65
Clone Length: 220 bp
Predicted Length of Amplified Fragment: 153 bp
Primer Sequences:   GCAAACCACAATGGAATGCA (CA strand) (SEQ ID NO: 239)
CTTTACTTCCTTTGCCTCAG (GT strand) (SEQ ID NO: 240)
FREQUENCY: Mfd12: Estimated from 152 chromosomes of unrelated CEPH family parents (Caucasians). PIC = 0.43.

| Allele (bp) | Frequency | Allele (bp) | Frequency |
|---|---|---|---|
| 240 | 0.01 | 236 | 0.58 |
| 238 | 0.04 | 234 | 0.37 |

TABLE 12-continued

Dinucleotide Repeat Polymorphisms Mfd12, Mfd23, Mfd24, Mfd62 and Mfd65 at the D16S260, D16S261, D16S265, D16S266, and D16S267 Loci Mfd23: Estimated from 104 chromosomes of unrelated CEPH family grandparents (Caucasians). PIC = 0.75.

| Allele (bp) | Frequency | Allele (bp) | Frequency |
|---|---|---|---|
| 117 | 0.01 | 105 | 0.01 |
| 115 | 0.01 | 103 | 0.18 |
| 113 | 0.03 | 101 | 0.05 |
| 111 | 0.05 | 99 | 0.07 |
| 109 | 0.11 | 95 | 0.01 |
| 107 | 0.07 | 89 | 0.41 |

Mfd24: Estimated from 122 chromosomes of unrelated CEPH family grandparents (Caucasians). PIC = 0.66.

| Allele (bp) | Frequency | Allele (bp) | Frequency |
|---|---|---|---|
| 100 | 0.01 | 94 | 0.40 |
| 98 | 0.07 | 92 | 0.25 |
| 96 | 0.25 | 88 | 0.02 |

Mfd62: Estimated from 118 chromosomes of unrelated CEPH family grandparents (Caucasians). PIC = 0.54.

| Allele (bp) | Frequency | Allele (bp) | Frequency |
|---|---|---|---|
| 104 | 0.02 | 98 | 0.08 |
| 102 | 0.06 | 96 | 0.57 |
| 100 | 0.26 | 94 | 0.01 |

Mfd65: Estimated from 120 chromosomes of unrelated CEPH family grandparents (Caucasians). PIC = 0.45.

| Allele (bp) | Frequency | Allele (bp) | Frequency |
|---|---|---|---|
| 170 | 0.01 | 166 | 0.21 |
| 168 | 0.12 | 154 | 0.67 |

CHROMOSOMAL LOCALIZATION: All five markers were assigned to 16 using DNA templates isolated from panels of somatic cell hybrids. C. Jones kindly provided DNA from a chromosome 16-specific hybrid.
MENDELIAN INHERITANCE: Segregation of Mfd12 was not tested. Co-dominant segregation of Mfd23–Mfd65 was observed in 15–18 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands for Mfd12, Mfd23 and Mfd24, and the sizes of the most intense bands for Mfd62 and Mfd65. The dinucleotide repeat sequence in Mfd12 was of the form $(AC)_{11}AT(AC)_8A$ (SEQ ID NO: 86), in Mfd23 $(AC)_{20}$ (SEQ ID NO: 119), in Mfd24 $(AC)_7AGAG(AC)_{14}A$ (SEQ ID NO: 122), in Mfd62 $(AC)_{21}$ (SEQ ID NO: 229), and in Mfd65 $(CA)_{14.5}$ (SEQ ID NO: 238). Sequences of the five clones have been submitted to GenBank.

REFERENCES: Weber, J. L. and May, P. E. (1989) Am. J. Hum. Genet. 44:388–396.

TABLE 13

$(dC-dA)_n.(dG-dT)_n$ Polymorphism Mfd24 on Chromosome 16 (D16S261)

SOURCE/DESCRIPTION: A human genomic Alu I fragment of 190 bp was cloned into mp10 and selected by hybridization to poly(dC-dA).poly(dG-dT). Sequencing of the cloned fragment provided the information necessary for polymerase chain reaction primer synthesis. Amplification was expected to produce a fragment of 89 bp.
PRIMER SEQUENCES: AAGCTTGTATCTTTCTCAGG (CA strand) (SEQ ID NO: 123); ATCTACCTTGGCTGTCATTG (GT strand) (SEQ ID NO: 124)
FREQUENCY: Estimated from 61 CEPH family grandparents (Caucasians). PIC = 0.66.

| Allele (bp) | Frequency | Allele (bp) | Frequency |
|---|---|---|---|
| 100 | 0.01 | 94 | 0.40 |
| 98 | 0.07 | 92 | 0.25 |
| 96 | 0.25 | 88 | 0.02 |

CHROMOSOMAL LOCALIZATION: Provisionally assigned to chromosome 16 by using DNA templates isolated from panels of somatic cell hybrids, including a panel from BIOS Corp., New Haven, CT, USA. C. Jones provided DNA from a chromosome 16-specific somatic cell hybrid.
MENDELIAN INHERITANCE: Co-dominant segregation of Mfd24 was observed in 18 two or three generation families.
OTHER COMMENTS: Sizes of the alleles were determined by comparison to mp8 DNA sequencing ladders and were the averages of the sizes of the GT-strand and CA-strand bands. The sequence of Mfd24 is $(AC)_7AGAG(AC)_{14}A$ (SEQ. ID. NO: 122) has been submitted to GenBank.

REFERENCES: Weber, J. L. and May, P. E. (1989) Am. J. Hum. Genet. 43:388–396.

TABLE 14

Dinucleotide Repeat Polymorphism Mfd25 at the D20S27 Locus

SOURCE/DESCRIPTION: A human genomic Alu I fragment was cloned into mp10 and selected by hybridization to poly(dC-dA).poly(dG-dT). The cloned fragment was designated Mfd25. Sequencing of Mfd25 provided the information necessary for polymerase chain reaction primer synthesis. The clone length was 190 bp, and the predicted length of the amplified fragment was 130 bp.
PRIMER SEQUENCES: TTTATGCGAGCGTATGGATA (CA strand) (SEQ ID NO: 126); CACCACCATTGATCTGGAAG (GT strand) (SEQ ID NO: 127)
FREQUENCY: Estimated from 110 chromosomes of unrelated CEPH family grandparents (Caucasians). PIC = 0.64.

| Allele (bp) | Frequency | Allele (bp) | Frequency |
|---|---|---|---|
| 138 | 0.11 | 132 | 0.35 |
| 136 | 0.15 | 128 | 0.01 |
| 134 | 0.38 | | |

CHROMOSOMAL LOCALIZATION: Assigned to chromosome 20 using DNA templates isolated from panels of somatic cell hybrids.
MENDELIAN INHERITANCE: Co-dominant segregation was observed in 40 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd25 was of the form $(AC)_{11}$ (SEQ ID NO: 125). The sequence of Mfd25 has been submitted to GenBank.

REFERENCES: Weber, J. L. and May, P. E. (1989) Am. J. Hum. Genet. 44:388–396.

TABLE 15

Dinucleotide Repeat Polymorphism Mfd26 at the D18S34 Locus

SOURCE/DESCRIPTION: A human genomic Alu I fragment was cloned into mp10 and selected by hybridization to poly(dC-dA).poly(dG-dT). The cloned fragment was designated Mfd26. Sequencing of Mfd26 provided the information necessary for polymerase chain reaction primer synthesis. The clone length was 223 bp, and the predicted length of the amplified fragment was 115 bp.
PRIMER SEQUENCES: CAGAAAATTCTCTCTGGCTA (CA strand) (SEQ ID NO: 129); CTCATGTTCCTGGCAAGAAT (GT strand) (SEQ ID NO: 130)
FREQUENCY: Estimated from 108 chromosomes of unrelated CEPH family grandparents (Caucasians). PIC = 0.78.

| Allele (bp) | Frequency | Allele (bp) | Frequency |
|---|---|---|---|
| 119 | 0.01 | 109 | 0.20 |
| 117 | 0.03 | 107 | 0.06 |
| 115 | 0.07 | 105 | 0.11 |
| 113 | 0.28 | 103 | 0.01 |
| 111 | 0.22 | | |

CHROMOSOMAL LOCALIZATION: Assigned to chromosome 18 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein the reference except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd26 was of the form $(AC)_{28}A$ (SEQ ID NO: 128). The sequence of Mfd26 has been submitted to GenBank.

REFERENCES: Weber, J. L. and May, P. E. (1989) Am. J. Hum. Genet. 44:388–396.

TABLE 16

Dinucleotide Repeat Polymorphisms Mfd27, Mfd34, Mfd40, Mfd48 and Mfd63 at the D5S107, D5S108, D5S111, D5S117 and D5S118 Loci SOURCE/DESCRIPTION: Human genomic DNA fragments were cloned into m13 and selected by hybridization to poly(dC-dA).poly(dG-dT). Sequencing of the clones provided the information necessary for polymerase chain reaction primer synthesis.
Locus: D5S107
Clone Designation: Mfd27
Clone Length: 194 bp
Predicted Length of Amplified Fragment: 145 bp
Primer Sequences: GATCCACTTTAACCCAAATAC (CA strand) (SEQ ID NO: 132)
GGCATCAACTTGAACAGCAT (GT strand) (SEQ ID NO: 133)
Locus: D5S108
Clone Designation: Mfd34
Clone Length: 183 bp
Predicted Length of Amplified Fragment: 88 bp
Primer Sequences: GGTTTCTTTTTTCTAGTTCTTC (CA strand) (SEQ ID NO: 153)
TCATATAGCCTTTTGTTTGCA (GT strand) (SEQ ID NO: 154)
Locus: D5S111
Clone Designation: Mfd40
Clone Length: 259 bp
Predicted Length of Amplified Fragment: 169 bp
Primer Sequences: GGCATCATTTTAGAAGGAAAT (CA strand) (SEQ ID NO: 170)
ACATTTGTTCAGGACCAAAG (GT strand) (SEQ ID NO: 171)
Locus: D5S117
Clone Designation: Mfd48
Clone Length: 323 bp
Predicted Length of Amplified Fragment: 151 bp
Primer Sequences: TGTCTCCTGCTGAGAATAG (CA strand) (SEQ ID NO: 193)
TAATATCCAAACCACAAAGGT (GT strand) (SEQ ID NO: 194)
Locus: D5S118
Clone Designation: Mfd63
Clone Length: 305 bp
Predicted Length of Amplified Fragment: 89 bp
Primer Sequences: CAAAACCAAAAAACCAAAGGC (CA strand) (SEQ ID NO: 233)
CAATCTGTGACAGTTTCTCA (GT strand) (SEQ ID NO: 234)

FREQUENCY: Mfd27: Estimated from 120 chromosomes of unrelated CEPH family grandparents (Caucasians). PIC = 0.78.

| Allele (bp) | Frequency | Allele (bp) | Frequency |
|---|---|---|---|
| 155 | 0.01 | 143 | 0.10 |
| 153 | 0.07 | 141 | 0.04 |
| 151 | 0.12 | 139 | 0.02 |
| 149 | 0.31 | 135 | 0.01 |
| 147 | 0.25 | 133 | 0.07 |

Mfd34: Estimated from 122 chromosomes of unrelated CEPH family grandparents (Caucasians). PIC = 0.45.

| Allele (bp) | Frequency | Allele (bp) | Frequency |
|---|---|---|---|
| 93 | 0.01 | 87 | 0.02 |
| 91 | 0.34 | 83 | 0.04 |
| 89 | 0.59 | | |

Mfd40: Estimated from 102 chromosomes of unrelated CEPH family grandparents (Caucasians). PIC = 0.51.

| Allele (bp) | Frequency | Allele (bp) | Frequency |
|---|---|---|---|
| 171 | 0.59 | 167 | 0.22 |
| 169 | 0.20 | | |

Mfd48: Estimated from 112 chromosomes of unrelated CEPH family grandparents (Caucasians). PIC = 0.62

| Allele (bp) | Frequency | Allele (bp) | Frequency |
|---|---|---|---|
| 163 | 0.05 | 155 | 0.05 |
| 161 | 0.01 | 153 | 0.33 |
| 159 | 0.08 | 151 | 0.02 |
| 157 | 0.45 | 147 | 0.01 |

Mfd 63: Estimated from 122 chromosomes of unrelated CEPH family grandparents (Caucasians). PIC = 0.48

| Allele (bp) | Frequency | Allele (bp) | Frequency |
|---|---|---|---|
| 92 | 0.02 | 84 | 0.02 |
| 90 | 0.08 | 82 | 0.01 |
| 88 | 0.05 | 80 | 0.04 |
| 86 | 0.70 | 78 | 0.08 |

CHROMOSOMAL LOCALIZATION: The five markers were assigned to 5 using DNA templates isolated from panels of somatic cell hybrids. C. Jones kindly provided DNA from a chromosome 5-specific hybrid.
MENDELIAN INHERITANCE: Co-dominant segregation of Mfd27, Mfd34, Mfd40, Mfd48, and Mfd63 was observed in 15–18 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA

TABLE 16-continued

Dinucleotide Repeat Polymorphisms Mfd27, Mfd34, Mfd40, Mfd48 and Mfd63 at the D5S107, D5S108, D5S111, D5S117 and D5S118 Loci sequencing ladders and were the averages of the sizes of the GT-strand and CA-strand bands for Mfd27, Mfd34, and Mfd40, and the sizes of the most intense bands for Mfd48 and Mfd63. The dinucleotide repeat sequence in Mfd27 was of the form $(CA)_9AA(CA)_{19}(GA)_7$ (SEQ ID NO: 131), in Mfd34 $(AC)_4AT(AC)_{15}$ (SEQ ID NO: 152), in Mfd40 $(CA)_{13}C(CA)_6T(AC)_5$ (SEQ ID NO: 169), in Mfd48 $(AC)_{17}$ (SEQ ID NO: 192), and in Mfd63 $(CA)_{20}C$ (SEQ ID NO: 232). Sequences of all five clones have been submitted to GenBank.

REFERENCES: Weber, J. L. and May, P. E. (1989) Am. J. Hum. Genet. 44:388–396.

TABLE 17

Dinucleotide Repeat Polymorphism Mfd28 at the D10S89 Locus

SOURCE/DESCRIPTION: A human genomic Alu I fragment was cloned into mp10 and selected by hybridization to poly(dC-dA) · poly(dG-dT). The cloned fragment was designated Mfd28. Sequencing of Mfd28 provided the information necessary for polymerase chain reaction primer synthesis. The clone length was 229 bp, and the predicted length of the amplified fragment was 150 bp.
PRIMER SEQUENCES: AACACTAGTGACATTATTTTCA (CA strand) (SEQ ID NO:135);
AGCTAGGCCTGAAGGCTTCT (GT strand)
(SEQ ID NO:136)
FREQUENCY: Estimated from 120 chromosomes of unrelated CEPH family grandparents (Caucasians). PIC = 0.71.

| Allele (bp) | Frequency | Allele (bp) | Frequency |
|---|---|---|---|
| 156 | 0.02 | 148 | 0.08 |
| 154 | 0.04 | 146 | 0.03 |
| 152 | 0.15 | 144 | 0.38 |
| 150 | 0.28 | 142 | 0.02 |

CHROMOSOMAL LOCALIZATION: Assigned to chromosome 10 using DNA templates isolated from panels of somatic cell hybrids. C. Jones provided DNA from a chromosome 10-specific hybrid.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd28 was of the form $(AC)_{10}AG(AC)_{21}A$ (SEQ ID NO:134). The sequence of Mfd28 has been submitted to GenBank.
REFERENCES: Weber, J. L. and May, P. E. (1989) Am. J. Hum. Genet. 44:388–396.

TABLE 18

Dinucleotide Repeat Polymorphism Mfd30 at the D3S240 Locus

SOURCE/DESCRIPTION: A human genomic Alu I fragment was cloned into mp10 and selected by hybridization to poly(dC-dA) · poly(dG-dT). The cloned fragment was designated Mfd30. Sequencing of Mfd30 provided the information necessary for polymerase chain reaction primer synthesis. The clone length was 221 bp, and the predicted length of the amplified fragment was 92 bp.
PRIMER SEQUENCES: CCATGTCCCATATCTCTACA (CA strand) (SEQ ID NO:141);
TGAAATCACTGATGACAATG (GT strand)
(SEQ ID NO:142)
FREQUENCY: Estimated from 122 chromosomes of unrelated CEPH family grandparents (Caucasians). PIC = 0.30.

TABLE 18-continued

| Allele (bp) | Frequency | Allele (bp) | Frequency |
|---|---|---|---|
| 99 | 0.01 | 91 | 0.02 |
| 97 | 0.08 | 89 | 0.01 |
| 95 | 0.01 | 87 | 0.82 |
| 93 | 0.01 | 83 | 0.04 |

CHROMOSOMAL LOCALIZATION: Assigned to chromosome 3 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd30 was of the form $(AC)_{18}A$ (SEQ ID NO:140). The sequence of Mfd30 has been submitted to GenBank.
REFERENCES: Weber, J. L. and May, P. E. (1989) Am. J. Hum. Genet. 44:388–396.

TABLE 19

Dinucleotide Repeat Polymorphism Mfd31 at the PENK Locus
SOURCE/DESCRIPTION: A $(dC-dA)_n \cdot (dG-dT)_n$ sequence was found within an intron of the human proenkephalin gene by computer search of GenBank (Accession number K00489). Polymerase chain reaction primers were selected from the sequence to give an amplified fragment with predicted length of 79 bp. The pair of primers was designated Mfd31.
PRIMER SEQUENCES: TAATAAAGGAGCCAGCTATG (CA strand) (SEQ ID NO:144);
ACATCTGATGTAAATGCAAGT (GT strand)
(SEQ ID NO:145)
FREQUENCY: Estimated from 106 chromosomes of unrelated CEPH family grandparents (Caucasians). PIC = 0.43.

| Allele (bp) | Frequency | Allele (bp) | Frequency |
|---|---|---|---|
| 83 | 0.01 | 77 | 0.02 |
| 81 | 0.42 | 75 | 0.01 |
| 79 | 0.54 | | |

CHROMOSOMAL LOCALIZATION: Litt et al. mapped PENK to chromosome 8. This assignment was confirmed using DNA templates isolated from a panel of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence at PENK was of the form $(AC)_{13}A$ (SEQ ID NO:143).
REFERENCES: Weber, J. L. and May, P. E. (1989) Am. J. Hum. Genet. 44:388–396. Litt, M., Buroker, N. E., Kondoleon, S., Douglass, J., Liston, D., Sheehy, R., and Magenis, R. E. (1988) Am. J. Hum. Genet. 42:327–334.

TABLE 20

Dinucleotide Repeat Polymorphism Mfd32 at the D18S35 Locus
SOURCE/DESCRIPTION: A human genomic Alu I fragment was cloned into mp10 and selected by hybridization to poly(dC-dA) · poly(dG-dT). The cloned fragment was designated Mfd32. Sequencing of Mfd32 provided the information necessary for polymerase chain reaction primer synthesis. The clone length was 143 bp, and the predicted length of the amplified fragment was 104 bp.
PRIMER SEQUENCES: AGCTAGATTTTACTTCTCTG

TABLE 20-continued (CA strand) (SEQ ID NO:147);
CTGGTTGTACATGCCTGAC (GT strand)
(SEQ ID NO:148)
FREQUENCY: Estimated from 106 chromosomes of unrelated
CEPH family grandparents (Caucasians). PIC = 0.65.

| Allele (bp) | Frequency | Allele (bp) | Frequency |
|---|---|---|---|
| 124 | 0.04 | 108 | 0.09 |
| 122 | 0.26 | 106 | 0.13 |
| 118 | 0.02 | 104 | 0.45 |

CHROMOSOMAL LOCALIZATION: Assigned to chromosome
18 using DNA templates isolated from panels of somatic cell
hybrids.
MENDELIAN INHERITANCE: Co-dominant segregation was
observed in 15 two generation families.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders and were the averages of the sizes of
the GT-strand and CA-strand bands. The dinucleotide
repeat sequence in Mfd32 was of the form $(AC)_{12}A$ (SEQ ID
NO:146). The sequence of Mfd32 has been submitted to
GenBank.
REFERENCES: Weber, J. L. and May, P. E. (1989) Am. J. Hum.
Genet. 44:388–396.

TABLE 21

Dinucleotide Repeat Polymorphism Mfd33
at the D22S156 Locus

SOURCE/DESCRIPTION: A human genomic Alu I fragment
was cloned into mp10 and selected by hybridization to
poly(dC-dA) · poly(dG-dT). The cloned fragment was
designated Mfd33. Sequencing of Mfd33 provided the
information necessary for polymerase chain reaction
primer synthesis. The clone length was 155 bp, and the
predicted length of the amplified fragment was 106 bp.
PRIMER SEQUENCES: AGCCTGGGAGTCAGAGTGA
(CA strand) (SEQ ID NO:150);
AGCTCCAAATCCAAAGACGT (GT strand)
(SEQ ID NO:151)
FREQUENCY: Estimated from 116 chromosomes of unrelated
CEPH family grandparents (Caucasians). PIC = 0.64.

| Allele (bp) | Frequency | Allele (bp) | Frequency |
|---|---|---|---|
| 110 | 0.01 | 102 | 0.24 |
| 108 | 0.04 | 98 | 0.01 |
| 106 | 0.27 | 96 | 0.01 |
| 104 | 0.42 | | |

CHROMOSOMAL LOCALIZATION: Assigned to chromosome
22 using DNA templates isolated from panels of somatic cell
hybrids. Sue Naylor kindly provided DNA from chromosome
22-specific hybrids.
MENDELIAN INHERITANCE: Co-dominant segregation was
observed in 15 two generation families.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders and were the averages of the sizes of
the GT-strand and CA-strand bands. The dinucleotide
repeat sequence in Mfd33 was of the form $(AC)_{14}AT(AC)_{13}$
(SEQ ID NO:149). The sequence of Mfd33 has been
submitted to GenBank.
REFERENCES: Weber, J. L. and May, P. E. (1989) Am. J. Hum.
Genet. 44:388–396.

TABLE 22

$(dC-dA)_n \cdot (dG-dT)_n$ Polymorphism Mfd34
on Chromosome 5 (D5S108)

SOURCE/DESCRIPTION: A human genomic Alu I fragment of
183 bp was cloned into mp10 and selected by hybridization
to poly(dC-dA) · poly(dG-dT). Sequencing of the cloned
fragment provided the information necessary for
polymerase chain reaction primer synthesis.
Amplification was expected to produce a fragment of 88 bp.
PRIMER SEQUENCES: GGTTTCTTTTTTCTAGTTCTTC
(CA strand) (SEQ ID NO:153);
TCATATAGCCTTTTGTTTGCA (GT strand)
(SEQ ID NO:154)
FREQUENCY: Estimated from 61 CEPH family grandparents
(Caucasians). PIC = 0.45.

| Allele (bp) | Frequency | Allele (bp) | Frequency |
|---|---|---|---|
| 93 | 0.01 | 87 | 0.02 |
| 91 | 0.34 | 83 | 0.04 |
| 89 | 0.59 | | |

CHROMOSOMAL LOCALIZATION: Provisionally assigned to
chromosome 5 by using DNA templates isolated from panels
of somatic cell hybrids, including a panel from BIOS,
Corp., New Haven, CT, USA. C. Jones provided DNA from a
chromosome 5-specific somatic cell hybrid.
MENDELIAN INHERITANCE: Co-dominant segregation of
Mfd34 was observed in 18 two or three generation families.
OTHER COMMENTS: Sizes of the alleles were determined by
comparison to mp8 DNA sequencing ladders and were the
averages of the sizes of the GT-strand and CA-strand
bands. The sequence of Mfd34 is $(AC)_4AT(AC)_{15}$ (SEQ ID
NO:152) and has been submitted to GenBank.
REFERENCES: Weber, J. L. and May, P. E. (1989) Am. J. Hum.
Genet. 43:388–396.

TABLE 23

Dinucleotide Repeat Polymorphism Mfd36 at the D2S72 Locus

SOURCE/DESCRIPTION: A human genomic Alu I fragment
was cloned into mp10 and selected by hybridization to
poly(dC-dA) · poly(dG-dT). The cloned fragment was
designated Mfd36. Sequencing of Mfd36 provided the
information necessary for polymerase chain reaction
primer synthesis. The clone length was 238 bp, and the
predicted length of the amplified fragment was 165 bp.
PRIMER SEQUENCES: AGCTATAATTGCATCATTGCA
(CA strand) (SEQ ID NO:158);
TGGTCTATAACTGGTCTATG (GT strand)
(SEQ ID NO:159)
FREQUENCY: Estimated from 120 chromosomes of unrelated
CEPH family grandparents (Caucasians). PIC = 0.71.

| Allele (bp) | Frequency | Allele (bp) | Frequency |
|---|---|---|---|
| 173 | 0.02 | 165 | 0.20 |
| 171 | 0.14 | 163 | 0.30 |
| 169 | 0.02 | 161 | 0.01 |
| 167 | 0.31 | 159 | 0.01 |

CHROMOSOMAL LOCALIZATION: Assigned to chromosome
2 using DNA templates isolated from panels of somatic cell
hybrids.
MENDELIAN INHERITANCE: Co-dominant segregation was
observed in 15 two generation families.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders and were the averages of the sizes of
the GT-strand and CA-strand bands. The dinucleotide
repeat sequence in Mfd36 was of the form $(AC)_{15}AT(AC)_6A$
(SEQ ID NO:157). The sequence of Mfd36 has been
submitted to GenBank.
REFERENCES: Weber, J. L. and May, P. E. (1989) Am. J. Hum.
Genet. 44:388–396.

TABLE 24

Dinucleotide Repeat Polymorphism Mfd37
at the D19S76 Locus

SOURCE/DESCRIPTION: A human genomic Alu I fragment
was cloned into mp10 and selected by hybridization to

TABLE 24-continued poly(dC-dA) · poly(dG-dT). The cloned fragment was designated Mfd37. Sequencing of Mfd37 provided the information necessary for polymerase chain reaction primer synthesis. The clone length was 211 bp, and the predicted length of the amplified fragment was 65 bp.
PRIMER SEQUENCES: AAAAGTGTGTTACTTTCAGAAC (CA strand) (SEQ ID NO:161);
ACAAGGTGACAAGGTGCCTA (GT strand) (SEQ ID NO:162)
FREQUENCY: Estimated from 122 chromosomes of unrelated CEPH family grandparents (Caucasians). PIC = 0.40.

| Allele (bp) | Frequency |
|---|---|
| 70 | 0.03 |
| 68 | 0.62 |
| 66 | 0.35 |

CHROMOSOMAL LOCALIZATION: Assigned to chromosome 19 using DNA templates isolated from panels of somatic cell hybrids.
MENDELIAN INHERITANCE: Co-dominant segregation was observed in 40 two or three generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders and were the averages of the sizes of the GT-strand and CA-strand bands. The dinucleotide repeat sequence in Mfd37 was of the form $(AC)_{10}A$ (SEQ ID NO:160). The sequence of Mfd37 has been submitted to GenBank.
REFERENCES: Weber, J. L. and May, P. E. (1989) Am. J. Hum. Genet. 44:388–396.

TABLE 25

Dinucleotide Repeat Polymorphisms Mfd15 and Mfd41 at the D17S250 and D17S261 Loci
SOURCE/DESCRIPTION: Human genomic DNA fragments were cloned into m13 and selected by hybridization to poly(dC-dA) · poly(dG-dT). Sequencing of the clones provided the information necessary for polymerase chain reaction primer synthesis.
Locus: D17S250
Clone Designation: Mfd15
Clone Length: 261 bp
Predicted Length of Amplified Fragment: 162 bp
Primer Sequences: GGAAGAATCAAATAGACAAT (CA strand) (SEQ ID NO:96)
GCTGGCCATATATATATTTAAACC (GT strand) (SEQ ID NO:97)
Locus: D17S261
Clone Designation: Mfd41
Clone Length: >293 bp
Predicted Length of Amplified Fragment: 159 bp
Primer Sequences: CAGGTTCTGTCATAGGACTA (CA strand) (SEQ ID NO:173)
TTCTGGAAACCTACTCCTGA (GT strand) (SEQ ID NO:174)
FREQUENCY: Mfd15: Estimated from 112 chromosomes of unrelated CEPH family grandparents (Caucasians). PIC = 0.81.

| Allele (bp) | Frequency | Allele (bp) | Frequency |
|---|---|---|---|
| 169 | 0.01 | 159 | 0.08 |
| 167 | 0.05 | 157 | 0.16 |
| 165 | 0.05 | 155 | 0.12 |
| 163 | 0.05 | 153 | 0.32 |

4. Weber, J. L. and May, P. E. (1989) Am. J. Hum. Genet. 44:388–396.

TABLE 26

Dinucleotide Repeat Polymorphism Mfd42 at the D14S34 Locus
SOURCE/DESCRIPTION: A human genomic Sau3A I fragment was cloned into mp19 and selected by hybridization to poly(dC-dA) · poly(dG-dT). The cloned fragment was designated Mfd42. Sequencing of Mfd42 provided the information necessary for polymerase chain reaction primer synthesis. The clone length was 179 bp, and the predicted length of the amplified fragment was 114 bp.
PRIMER SEQUENCES: GGCCTCAAAGAATCCTACAG (CA strand) (SEQ ID NO:176);
GACACGTAGTTGCTTATTAC (GT strand) (SEQ ID NO:177)
FREQUENCY: Estimated from 112 chromosomes of unrelated CEPH family grandparents (Caucasians). PIC = 0.59.

| Allele (bp) | Frequency | Allele (bp) | Frequency |
|---|---|---|---|
| 117 | 0.38 | 111 | 0.01 |
| 115 | 0.14 | 107 | 0.05 |
| 113 | 0.42 | | |

CHROMOSOMAL LOCALIZATION: Assigned to chromosome 14 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to obtain allele size. The dinucleotide repeat sequence in Mfd42 was of the form $(CA)_{16}T(AC)_3A$ (SEQ ID NO:175). The sequence of Mfd42 has been submitted to GenBank.
REFERENCES: Weber, J. L. and May, P. E. (1989) Am. J. Hum. Genet. 44:388–396.

TABLE 27

Dinucleotide Repeat Polymorphism Mfd44 at the D13S71 Locus
SOURCE/DESCRIPTION: A human genomic Sau3A I fragment was cloned into mp19 and selected by hybridization to poly(dC-dA) · poly(dG-dT). The cloned fragment was designated Mfd44. Sequencing of Mfd44 provided the information necessary for polymerase chain reaction primer synthesis. The clone length was >250 bp, and the predicted length of the amplified fragment was 75 bp.
PRIMER SEQUENCES: GTATTTTTGGTATGCTTGTGC (CA strand) (SEQ ID NO:181);
CTATTTTGGAATATATGTGCCT (GT strand) (SEQ ID NO:182)
FREQUENCY: Estimated from 126 chromosomes of unrelated CEPH family grandparents (Caucasians). PIC = 0.67.

| Allele (bp) | Frequency | Allele (bp) | Frequency |
|---|---|---|---|
| 79 | 0.05 | 73 | 0.26 |
| 77 | 0.25 | 67 | 0.06 |
| 75 | 0.38 | | |

CHROMOSOMAL LOCALIZATION: Assigned to chromosome 13 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to obtain allele size. The dinucleotide repeat sequence in Mfd44 was of the form $(CA)_{17}$ (SEQ ID NO:180). The sequence of Mfd44 has been submitted to GenBank.
REFERENCES: Weber, J. L. and May, P. E. (1989) Am. J. Hum. Genet. 44:388–396.

TABLE 28

Dinucleotide Repeat Polymorphism Mfd47 at the D6S87 Locus
SOURCE/DESCRIPTION: A human genomic Sau3A I fragment was cloned into mp19 and selected by hybridization to poly(dC-dA) · poly(dG-dT). The cloned fragment was designated Mfd47. Sequencing of Mfd47 provided the information necessary for polymerase chain reaction primer synthesis. The clone length was >280 bp, and the predicted length of the amplified fragment was 148 bp.
PRIMER SEQUENCES: ACAGAGTGAGACCGTGTAAC (CA strand) (SEQ ID NO:190);
AGAGAAGCATCTCACTTAGT (GT strand) (SEQ ID NO:191)
FREQUENCY: Estimated from 106 chromosomes of unrelated CEPH family grandparents (Caucasians). PIC = 0.53.

| Allele (bp) | Frequency | Allele (bp) | Frequency |
|---|---|---|---|
| 155 | 0.01 | 143 | 0.01 |
| 153 | 0.02 | 141 | 0.33 |
| 149 | 0.04 | 139 | 0.02 |
| 147 | 0.53 | 137 | 0.01 |
| 145 | 0.03 | | |

CHROMOSOMAL LOCALIZATION: Assigned to chromosome 6 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to obtain allele size. The dinucleotide repeat sequence in Mfd47 was of the form $(AC)_{17}A$ (SEQ ID NO:189). The sequence of Mfd47 has been submitted to GenBank.
REFERENCES: Weber, J. L. and May, P. E. (1989) Am. J. Hum. Genet. 44:388–396.

TABLE 29

Dinucleotide Repeat Polymorphism Mfd49 at the D15S87 Locus
SOURCE/DESCRIPTION: A human genomic Sau3A I fragment was cloned into mp19 and selected by hybridization to poly(dC-dA) · poly(dG-dT). The cloned fragment was designated Mfd49. Sequencing of Mfd49 provided the information necessary for polymerase chain reaction primer synthesis. The clone length was >240 bp, and the predicted length of the amplified fragment was 87 bp.
PRIMER SEQUENCES: GATAAATGCCAAACATGTTGT (CA strand) (SEQ ID NO:196);
TGCTCTCAGGATTTCCTCCA (GT strand) (SEQ ID NO:197)
FREQUENCY: Estimated from 120 chromosomes of unrelated CEPH family grandparents (Caucasians). PIC = 0.85.

| Allele (bp) | Frequency | Allele (bp) | Frequency |
|---|---|---|---|
| 98 | 0.01 | 86 | 0.15 |
| 96 | 0.02 | 84 | 0.14 |
| 94 | 0.03 | 82 | 0.07 |
| 92 | 0.05 | 80 | 0.23 |
| 90 | 0.09 | 78 | 0.08 |
| 88 | 0.13 | | |

CHROMOSOMAL LOCALIZATION: Assigned to chromosome 15 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to obtain allele size. The dinucleotide repeat sequence in

TABLE 29-continued

Mfd49 was of the form $(CA)_{22}$ (SEQ ID NO:195). The sequence of Mfd49 has been submitted to GenBank.
REFERENCES: Weber, J. L. and May, P. E. (1989) Am. J. Hum. Genet. 44:388–396.

TABLE 30

Dinucleotide Repeat Polymorphism Mfd52 at the D1S102 Locus
SOURCE/DESCRIPTION: A human genomic Sau3A I fragment was cloned into mp19 and selected by hybridization to poly(dC-dA) · poly(dG-dT). The cloned fragment was designated Mfd52. Sequencing of Mfd52 provided the information necessary for polymerase chain reaction primer synthesis. The clone length was 365 bp, and the predicted length of the amplified fragment was 200 bp.
PRIMER SEQUENCES: AAATCAGACAAGTACAGGTG (CA strand) (SEQ ID NO:204);
ATGAACTTGTTCTGGGAGGA (GT strand) (SEQ ID NO:205)
FREQUENCY: Estimated from 120 chromosomes of unrelated CEPH family grandparents (Caucasians). PIC = 0.50.

| Allele (bp) | Frequency | Allele (bp) | Frequency |
|---|---|---|---|
| 204 | 0.01 | 190 | 0.60 |
| 202 | 0.03 | 186 | 0.26 |
| 200 | 0.10 | | |

CHROMOSOMAL LOCALIZATION: Assigned to chromosome 1 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to determine allele size. The dinucleotide repeat sequence in Mfd52 was of the form $(AC)_{18}TTG(CA)_3$ (SEQ ID NO:203). The sequence of Mfd52 has been submitted to GenBank.
REFERENCES: Weber, J. L. and May, P. E. (1989) Am. J. Hum. Genet. 44:388–396.

TABLE 31

$(dC-dA)_n \cdot (dG-dT)_n$ Polymorphism Mfd55 on Chromosome 21
SOURCE/DESCRIPTION: This polymorphism is based on a human genomic sequence reported by Hamada et al. The phage clone containing the sequence was identified by hybridization to a Dictyostelium actin cDNA clone. There is no confirmation that the clone actually contains a human actin gene. Amplification was expected to produce a fragment of 77 bp.
PRIMER SEQUENCES: GTCAACATAGTGAGACCCCA (CA-strand) (SEQ ID NO:211);
ATCCAGCCTGTAACACATTC (GT-strand) (SEQ ID NO:212)
FREQUENCY: Estimated from XX CEPH family grandparents (Caucasians). PIC = 0.82.

| Allele (bp) | Frequency | Allele (bp) | Frequency |
|---|---|---|---|
| 76 | 0.31 | 94 | 0.03 |
| 78 | 0.01 | 96 | 0.09 |
| 86 | 0.03 | 98 | 0.11 |
| 88 | 0.14 | 100 | 0.10 |
| 90 | 0.10 | 104 | 0.06 |
| 92 | 0.02 | | |

CHROMOSOMAL LOCALIZATION: Assigned to chromosome 21 by using DNA templates isolated from panels of somatic cell hybrids.
MENDELIAN INHERITANCE: Co-dominant segregation of Mfd55 was observed in XX two or three generation families.
OTHER COMMENTS: Sizes of the alleles were determined by comparison to mp8 DNA sequencing ladders. The sequence

TABLE 31-continued of Mfd55 is (AC)$_{16}$ (SEQ ID NO:210) and is present in
GenBank with Accession Number J00075 and Locus
HUMACTFIB. Mfd55 is one of the most informative
(dC-dA)$_n$ · (dG-dT)$_n$ polymorphisms found to date.
REFERENCES: Weber, J. L. and May, P. E. (1989) Am. J. Hum.
Genet. 43:388–396.
Hamada, H., Petrino, M. G. and Kakunaga, T. (1982) Proc.
Nat. Acad. Sci. U.S.A. 79:6465–6469.

TABLE 32

Dinucleotide Repeat Polymorphism Mfd57 at the CRP Locus
SOURCE/DESCRIPTION: A (dC-dA)$_n$ · (dG-dT)$_n$ sequence was
found within an intron of the human C-reactive protein
gene by computer search of GenBank (Accession number
M11880). Polymerase chain reaction primers were selected
from the sequence to give an amplified fragment with
predicted length of 131 bp. The pair of primers was
designated Mfd57.
PRIMER SEQUENCES: GATCTATCCCCTCACTTACG
(CA strand) (SEQ ID NO:216);
TATGAACAGAACAGTGGAGC (GT strand)
(SEQ ID NO:217)
FREQUENCY: Estimated from 114 chromosomes of unrelated
CEPH family grandparents (Caucasians). PIC = 0.53.

| Allele (bp) | Frequency | Allele (bp) | Frequency |
|---|---|---|---|
| 145 | 0.01 | 133 | 0.02 |
| 141 | 0.32 | 131 | 0.55 |
| 139 | 0.04 | 129 | 0.01 |
| 137 | 0.01 | 127 | 0.03 |
| 135 | 0.01 | | |

CHROMOSOMAL LOCALIZATION: Floyd-Smith et. al. (1)
mapped CRP to 1q21–q23. Assignment to chromosome 1 was
confirmed by using DNA templates isolated from panels of
somatic cell hybrids.
MENDELIAN INHERITANCE: Co-dominant segregation was
observed in 15 two generation families.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders. The most intense band for each
allele on the denaturing polyacrylamide gels was used to
obtain allele size. The dinucleotide repeat sequence at
CRP was of the form (CA)$_{15}$C (SEQ ID NO:215).
REFERENCES: 1. Floyd-Smith, G., Whitehead, A. S., Colten,
H. R., and Francke, U. (1986) Immunogenetics 24:171–176.
2. Weber, J. L. and May, P. E. (1989) Am. J. Hum. Genet.
44:388–396.

TABLE 33

Dinucleotide Repeat Polymorphism Mfd59
at the D4S174 Locus
SOURCE/DESCRIPTION: A human genomic Sau3A I fragment
was cloned into mp19 and selected by hybridization to
poly(dC-dA) · poly(dG-dT). The cloned fragment was
designated Mfd59. Sequencing of Mfd59 provided the
information necessary for polymerase chain reaction
primer synthesis. The clone length was 318 bp, and the
predicted length of the amplified fragment was 183 bp.
PRIMER SEQUENCES: AAGAACCATGCGATACGACT
(CA strand) (SEQ ID NO:222);
CATTCCTAGATGGGTAAAGC (GT strand)
(SEQ ID NO:223)
FREQUENCY: Estimated from 120 chromosomes of unrelated
CEPH family grandparents (Caucasians). PIC = 0.86.

| Allele (bp) | Frequency | Allele (bp) | Frequency |
|---|---|---|---|
| 195 | 0.01 | 183 | 0.11 |
| 193 | 0.04 | 181 | 0.08 |
| 191 | 0.14 | 179 | 0.14 |
| 189 | 0.06 | 177 | 0.12 |
| 187 | 0.11 | 175 | 0.01 |

TABLE 33-continued

| | |
|---|---|
| 185 | 0.18 |

CHROMOSOMAL LOCALIZATION: Assigned to chromosome
4 using DNA templates isolated from panels of somatic cell
hybrids. Sue Naylor provided DNA from a chromosome 4-
specific hybrid.
MENDELIAN INHERITANCE: Co-dominant segregation was
observed in 15 two generation families.
OTHER COMMENTS: Conditions for the amplification
reactions were as described herein the reference except
that samples were processed through 27 temperature cycles
consisting of 1 min at 94° C., 2 min at 55° C. and 2 min at
72° C. Sizes of the alleles were determined by comparison
to mp8 DNA sequencing ladders. The most intense band for
each allele on the denaturing polyacrylamide gels was
used to obtain allele size. The dinucleotide repeat
sequence in Mfd59 was of the form (AC)$_{23}$A (SEQ ID
NO:221). The sequence of Mfd59 has been submitted to GenBank.
REFERENCES: Weber, J. L. and May, P. E. (1989) Am. J. Hum.
Genet. 44:388–396.

TABLE 34

Dinucleotide Repeat Polymorphism Mfd61
at the D6S105 Locus
SOURCE/DESCRIPTION: A human genomic Sau3A I fragment
was cloned into mp19 and selected by hybridization to
poly(dC-dA) · poly(dG-dT). The cloned fragment was
designated Mfd61. Sequencing of Mfd61 provided the
information necessary for polymerase chain reaction
primer synthesis. The clone length was 214 bp, and the
predicted length of the amplified fragment was 131 bp.
PRIMER SEQUENCES: GCCCTATAAAATCCTAATTAAC
(CA strand) (SEQ ID NO:227);
GAAGGAGAATTGTAATTCCG (GT strand)
(SEQ ID NO:228)
FREQUENCY: Estimated from 62 chromosomes of unrelated
CEPH family members (Caucasians). PIC = 0.77.

| Allele (bp) | Frequency | Allele (bp) | Frequency |
|---|---|---|---|
| 138 | 0.03 | 128 | 0.39 |
| 136 | 0.03 | 126 | 0.08 |
| 134 | 0.05 | 124 | 0.13 |
| 132 | 0.11 | 122 | 0.02 |
| 130 | 0.14 | 116 | 0.02 |

CHROMOSOMAL LOCALIZATION: Assigned to chromosome
6p using DNA templates isolated from panels of somatic cell
hybrids. Typing of CEPH families 1332 and 884 led to
maximum LOD scores of 6.9 at θ = 0 with HLA-B and 4.4 at
θ = 0.07 with HLA-DR. The use of a panel of 6p radiation
hybrids gave the following order of markers: pter-D6S88-
D6S108-D6S105-HLA-cen (1).
MENDELIAN INHERITANCE: Co-dominant segregation was
observed in 6 multi-generation families.
OTHER COMMENTS: Conditions for the amplification
reactions were as described herein except that samples
were processed through 27 temperature cycles consisting
of 1 min at 94° C., 2 min at 55° C. and 1 min at 72° C. Sizes
of the alleles were determined by comparison to mp8 DNA
sequencing ladders. The most intense band for each
allele on the denaturing polyacrylamide gels was used to
obtain allele size. The dinucleotide repeat sequence in
Mfd61 was of the form (CA)$_{23}$ (SEQ ID NO:226). The
sequence of Mfd61 has been submitted to GenBank.
REFERENCES: 1. Zoghbi, H. Y., McCall, A. E., LeBorgne-
Demarquoy, F. (1990) Am. J. Hum. Genet. 47:A206.
2. Weber, J. L. and May, P. E. (1989) Am. J. Hum. Genet.
44:388–396.

TABLE 35

Dinucleotide Repeat Polymorphism Mfd64
at the D1S103 Locus
SOURCE/DESCRIPTION: A human genomic Sau3A I fragment
was cloned into mp19 and selected by hybridization to
poly(dC-dA) · poly(dG-dT). The cloned fragment was
designated Mfd64. Sequencing of Mfd64 provided the

TABLE 35-continued information necessary for polymerase chain reaction
primer synthesis. The clone length was >243 bp, and the
predicted length of the amplified fragment was 85 bp.
PRIMER SEQUENCES: ACGAACATTCTACAAGTTAC
(CA strand) (SEQ ID NO:236);
TTTCAGAGAAACTGACCTGT (GT strand)
(SEQ ID NO:237)
FREQUENCY: Estimated from 118 chromosomes of unrelated
CEPH family grandparents (Caucasians). PIC = 0.78.

| Allele (bp) | Frequency | Allele (bp) | Frequency |
|---|---|---|---|
| 102 | 0.01 | 90 | 0.38 |
| 100 | 0.03 | 88 | 0.08 |
| 98 | 0.05 | 86 | 0.17 |
| 96 | 0.03 | 84 | 0.04 |
| 94 | 0.11 | 82 | 0.03 |
| 92 | 0.06 | | |

CHROMOSOMAL LOCALIZATION: Assigned to chromosome
1 using DNA templates isolated from panels of somatic cell
hybrids.
MENDELIAN INHERITANCE: Co-dominant segregation was
observed in 15 two generation families.
OTHER COMMENTS: Conditions for the amplification
reactions were as described herein the reference except
that samples were processed through 27 temperature cycles
consisting of 1 min at 94° C., 2 min at 55° C. and 2 min at
72° C. Sizes of the alleles were determined by comparison
to mp8 DNA sequencing ladders. The most intense band for
each allele on the denaturing polyacrylamide gels was
used to determine allele size. The dinucleotide repeat
sequence in Mfd64 was of the form $(AC)_{15}A$ (SEQ ID
NO:235). The sequence of Mfd64 has been submitted to GenBank.
REFERENCES: Weber, J. L. and May, P. E. (1989) Am. J. Hum.
Genet. 44:388–396.

TABLE 36

Dinucleotide Repeat Polymorphisms Mfd66, Mfd72 and Mfd79
at the DXS453, DXS454 and DXS458 Loci
SOURCE/DESCRIPTION: Human genomic DNA fragments
were cloned into m13 and selected by hybridization to poly(dC-
dA) · poly(dG-dT). Sequencing of the clones provided the
information necessary for polymerase chain reaction
primer synthesis.
Locus: DXS453
Clone Designation: Mfd66
Clone Length: >235 bp
Predicted Length of Amplified Fragment: 170 bp
Primer Sequences: GCCCCTACCTTGGCTAGTTA
(CA strand) (SEQ ID NO:242)
AACCTCAGCTTATACCCAAG (GT strand)
(SEQ ID NO:243)
Locus: DXS454
Clone Designation: Mfd72
Clone Length: 387 bp
Predicted Length of Amplified Fragment: 145 bp
Primer Sequences: AGAAGACATAAGGATACTGC
(CA strand) (SEQ ID NO:257)
GATCCCAACTATTTCTTTCT (GT strand)
(SEQ ID NO:258)
Locus: DXS458
Clone Designation: Mfd79
Clone Length: 300 bp
Predicted Length of Amplified Fragment: 186 bp
Primer Sequences: GATAAAACTGCATAGAAATGCG
(CA strand) (SEQ ID NO:272)
CAACTGGGATATTGACATTG (GT strand)
(SEQ ID NO:273)
FREQUENCY: Mfd66: Estimated from 87 chromosomes of
unrelated CEPH family grandparents (Caucasians). PIC = 0.63.

| Allele (bp) | Frequency | Allele (bp) | Frequency |
|---|---|---|---|
| 170 | 0.21 | 164 | 0.01 |
| 168 | 0.48 | 160 | 0.12 |
| 166 | 0.18 | | |

Mfd72: Estimated from 73 chromosomes of unrelated CEPH
family grandparents (Caucasians). PIC = 0.59.

TABLE 36-continued

| Allele (bp) | Frequency | Allele (bp) | Frequency |
|---|---|---|---|
| 152 | 0.07 | 146 | 0.49 |
| 148 | 0.16 | 144 | 0.27 |

Mfd79: Estimated from 103 chromosomes of unrelated CEPH
family parents (Caucasians). PIC = 0.62.

| Allele (bp) | Frequency | Allele (bp) | Frequency |
|---|---|---|---|
| 190 | 0.05 | 182 | 0.08 |
| 188 | 0.52 | 180 | 0.13 |
| 186 | 0.20 | 178 | 0.01 |
| 184 | 0.01 | | |

CHROMOSOMAL LOCALIZATION: Mfd66 was provisionally
assigned to Xp11.23–q21.1, and Mfd72 and Mfd79 were both
provisionally assigned to Xq21.1–q23 using DNA templates
isolated from panels of chromosomal and subchromosomal
somatic cell hybrids (1,2).
MENDELIAN INHERITANCE: Co-dominant segregation of
Mfd66, Mfd72, and Mfd79 were observed in 15, 14 and 1 two
generation families respectively.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders. The most intense band on the
autoradiographs for each allele was used to obtain allele
sizes. The dinucleotide repeat sequence in Mfd66 was of
the form $(AC)_{22}$ (SEQ ID NO:241), in Mfd72 $(AC)_{17}G(GA)_8$
(SEQ ID NO:256) and in Mfd79 $(AC)_{15}A$ (SEQ ID NO:271).
All three sequences have been submitted to GenBank.
REFERENCES: 1. Luty, J. A., Guo, Z., Willard, H. F.,
Ledbetter, D. H., Ledbetter, S. and Litt, M. (1990) Am. J. Hum.
Genet. 46:776–783.
2. Ledbetter, S. A., Schwartz, C. E., Davies, K. E. and
Ledbetter, D. H. (1990) Am. J. Med. Genet. in press.
3. Weber, J. L. and May, P. E. (1989) Am. J. Hum. Genet.
44:388–396.

TABLE 37

Dinucleotide Repeat Polymorphism Mfd67
at the D1S104 Locus
SOURCE/DESCRIPTION: A human genomic Sau3A I fragment
was cloned into mp19 and selected by hybridization to
poly(dC-dA) · poly(dG-dT). The cloned fragment was
designated Mfd67. Sequencing of Mfd67 provided the
information necessary for polymerase chain reaction
primer synthesis. The clone length was >242 bp, and the
predicted length of the amplified fragment was 156 bp.
PRIMER SEQUENCES: ATCCTGCCCTTATGGAGTGC
(CA strand) (SEQ ID NO:245);
CCCACTCCTCTGTCATTGTA (GT strand)
(SEQ ID NO:246)
FREQUENCY: Estimated from 116 chromosomes of unrelated
CEPH family grandparents (Caucasians). PIC = 0.66.

| Allele (bp) | Frequency | Allele (bp) | Frequency |
|---|---|---|---|
| 168 | 0.01 | 158 | 0.15 |
| 164 | 0.15 | 156 | 0.22 |
| 162 | 0.45 | 154 | 0.01 |
| 160 | 0.01 | 152 | 0.01 |

CHROMOSOMAL LOCALIZATION: Assigned to chromosome
1 using DNA templates isolated from panels of somatic cell
hybrids.
MENDELIAN INHERITANCE: Co-dominant segregation was
observed in 15 two generation families.
OTHER COMMENTS: Conditions for the amplification
reactions were as described herein except that samples
were processed through 27 temperature cycles consisting
of 1 min at 94° C., 2 min at 55° C. and 2 min at 72° C. Sizes
of the alleles were determined by comparison to mp8 DNA
sequencing ladders. The most intense band for each
allele on the denaturing polyacrylamide gels was used to
determine allele size. The dinucleotide repeat sequence
in Mfd67 was of the form $(TC)_{12}(AC)_{18}$ (SEQ ID NO:244).
The sequence of Mfd67 has been submitted to GenBank.

TABLE 37-continued

REFERENCES: Weber, J. L. and May, P. E. (1989) Am. J. Hum. Genet. 44:388–396.

TABLE 38

Dinucleotide Repeat Polymorphism Mfd69 at the CD3D Locus
SOURCE/DESCRIPTION: A human genomic Alu I fragment was cloned into mp10 and selected by hybridization to poly(dC-dA) · poly(dG-dT). The cloned fragment was designated Mfd69. Sequencing of Mfd69 provided the information necessary for polymerase chain reaction primer synthesis. The predicted length of the amplified fragment was 93 bp.
PRIMER SEQUENCES: TAGCTGGTGCATAAGCTCAC (CA strand) (SEQ ID NO:250);
GTTAGTGGAAGAGCAGAGC (GT strand) (SEQ ID NO:251)
FREQUENCY: Estimated from 114 chromosomes of unrelated CEPH family grandparents (Caucasians). PIC = 0.69.

| Allele (bp) | Frequency | Allele (bp) | Frequency |
| --- | --- | --- | --- |
| 99 | 0.01 | 89 | 0.35 |
| 95 | 0.10 | 87 | 0.20 |
| 93 | 0.30 | 85 | 0.01 |
| 91 | 0.01 | | |

CHROMOSOMAL LOCALIZATION: Woo et al. mapped CRP to 1q21-q23. Assigned to chromosome 18 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to determine allele size. The dinucleotide repeat sequence in Mfd69 was of the form $(AC)_{18.5}A(AC)_3$ (SEQ ID NO:249). The sequence of Mfd69 has been submitted to GenBank.
REFERENCES: Weber, J. L. and May, P. E. (1989) Am. J. Hum. Genet. 44:388–396.

TABLE 39

Dinucleotide Repeat Polymorphism Mfd84 at the D12S43 Locus
SOURCE/DESCRIPTION: A human genomic Sau3A I fragment was cloned into mp19 and selected by hybridization to poly(dC-dA) · poly(dG-dT). The cloned fragment was designated Mfd84. Sequencing of Mfd84 provided the information necessary for polymerase chain reaction primer synthesis. The clone length was >323 bp, and the predicted length of the amplified fragment was 111 bp.
PRIMER SEQUENCES: AATGTCCTTGTACTTAGGAT (CA strand) (SEQ ID NO:283);
CACTTAATATCTCAATGTATAC (GT strand) (SEQ ID NO:284)
FREQUENCY: Estimated from 116 chromosomes of unrelated CEPH family grandparents (Caucasians). PIC = 0.71.

| Allele (bp) | Frequency | Allele (bp) | Frequency |
| --- | --- | --- | --- |
| 113 | 0.04 | 105 | 0.33 |
| 109 | 0.26 | 103 | 0.03 |
| 107 | 0.09 | 99 | 0.25 |

CHROMOSOMAL LOCALIZATION: Assigned to chromosome 12 using DNA templates isolated from panels of somatic cell hybrids.
MENDELIAN INHERITANCE: Co-dominant segregation was observed in 15 two generation families.
OTHER COMMENTS: Conditions for the amplification reactions were as described herein the reference except that samples were processed through 27 temperature cycles consisting of 1 min at 94° C., 2 min at 55° C. and 2 min at 72° C. Sizes of the alleles were determined by comparison to mp8 DNA sequencing ladders. The most intense band for each allele on the denaturing polyacrylamide gels was used to obtain allele size. The dinucleotide repeat sequence in Mfd84 was of the form $(AC)_5AT(AC)_2AGAT(AC)_2GG(AC)_{17}$ (SEQ ID NO:282). The sequence of Mfd84 has been submitted to GenBank.
REFERENCES: Weber, J. L. and May, P. E. (1989) Am. J. Hum. Genet. 44:388–396.

TABLE 40

CLONE: Mfd11 (SEQ ID NO:1)

| | | | | | |
| --- | --- | --- | --- | --- | --- |
| GATCCACTCT | TCCTGGCCAG | CTGTCAAAAC | ACTCTGCACC | TGCTCTCGGA | CCATAACAAG |
| TATTACTCAT | GAAGGTGACA | GTTCCTCAGG | CCCACAGTAA | TAAAGACACA | CACACACACA |
| CACACACACA | CACACACACA | CACACACACA | CAGGCATTTA | AAAAAATGCA | ATAGGTCAAC |
| AACACTCAAT | CTAAAACCCT | AGGGGCTGGG | CACGGTAGCT | CACGCCTCTA | ATCCCTGCAC |
| TTTGGGAGGC | TGAGGTGAGT | GGATC | | | |

CLONE: Mfd12 (SEQ ID NO:2)

| | | | | | |
| --- | --- | --- | --- | --- | --- |
| GATCAAAATG | CTTTGAAAAA | GGCTGAGCAA | AACTTTCTTT | GTGGCCGTGG | GACTTGAGAG |
| AGGTTGAGAT | GCTGACATGC | ATTAAAAATC | TACAGAGGAG | AAACGAGTAT | GAAGTGCTAC |
| CCAGGCTCAT | GTCACCATAC | CTAACACTTG | CCTTCCCAAC | ACACACACAC | ACACACACAC |
| ATACACACAC | ACACACACAG | TGTTTTTCAC | CTAGGAGGCC | CTCTGAACAG | CTGCTACTGG |
| CAATCCATGG | AGCAATTTAG | GATGGGATGG | AGATTGCATT | ATAACAGCCA | CCCTGAGTAG |
| GTATGCACAA | CCGTGATC | | | | |

CLONE: Mfd13 (SEQ ID NO:3)

| | | | | | |
| --- | --- | --- | --- | --- | --- |
| GATCAGCTTC | CCTTTGCTCC | CCAAACGAGA | GCCTCTGCTC | TTGGGCACCT | CAGAGATGCG |
| TGTGTGTGTG | TGTGTGTGTG | TGTGTGTGTG | TGTGTGTGCG | CGTGTGTGTG | CATGCAGACT |
| ATTTGGAAAT | TCGCTTTTAG | ATGGATTAAT | GCTCGGTAAA | GCTCTCATGT | TTCTCCAAAG |
| TATATCCAGT | GAGTAACAGT | AGTATTTTCA | ATCAATAGTA | TTGCTTGCTA | AAATAACAGA |
| TC | | | | | |

CLONE: Mfd14 (SEQ ID NO:4)

| | | | | | |
| --- | --- | --- | --- | --- | --- |
| AGCTGCTGAA | TTTGGTTTGC | TGGTGTTTTG | TTCAGGATTT | TTGTGTATAT | GTTCATCAAG |
| GATATTGTCC | TGAGGATTTT | CTGTGTGTGT | GTGTGTGTGT | GTGTGTGTGT | GTGTGTGTGT |
| GTGTGTGTCT | GCCAGGTTTT | GATATCAGAA | TAATGCTGGC | CTCATAGAAT | GAGCT |

TABLE 40-continued

CLONE: Mfd15 (SEQ ID NO:5)

| | | | | | |
|---|---|---|---|---|---|
| AGCTTCCAAA | CTAGTAGAGG | GGGAAAAATA | AGAAAAAAAT | GAAGTGATGA | AAAGTAATTG |
| ATCAAAAAGA | AGAGAGAAGA | AAAAAGTAAG | CATAAAAAGG | AAGAATCAAA | TAGACAATAA |
| AAATATGTGT | GTGTTTATAT | ATATATATAC | ACATACATAA | ACTTTCAAAT | GGTTTCAAAC |
| ACACACACAC | ACACACACAC | ACACACACAC | ACACACACAC | ACACACACTT | TCAAATGGTT |
| TAAATATATA | TATGGCCAGC | T | | | |

CLONE: Mfd17 (SEQ ID NO:6)

| | | | | | |
|---|---|---|---|---|---|
| AGCTCAGTCT | TTCCACTGGG | GAACATGGTG | GGGTGTGTGT | GTGTGTGTGT | GTGTGTGTGT |
| GTGTGTGTGT | GTGTGTGTTC | ATTATGGGAA | TTCAACAAAG | AGTTGATGTG | AATATTTGTG |
| AAGACAGAAA | AAATTGCCAT | GAGATTTGGA | ATTCCCTTTG | GCAATCATCA | TATTGTAGCT |

CLONE: Mfd18 (SEQ ID NO:7)

| | | | | | |
|---|---|---|---|---|---|
| AGCTATCATC | ACCCTATAAA | ATACACACAC | ACACACACAC | ACACACACAC | ACACACACTC |
| GGGAGAGACA | TGGTTAAACT | GTAGAAACAA | ACAATCTCAA | GTTAAGTCA | CTTTATTCAA |
| CAAGAATTTC | TTGCTCATGC | TCTATGTCTA | AGATAAGTAA | GTGTAAGTGA | TGGGCAAGGA |
| AAGATGGAGG | TAGTGATTCA | GCT | | | |

CLONE: Mfd19 (SEQ ID NO:8)

| | | | | | |
|---|---|---|---|---|---|
| AGCTGAAGTA | TTGTCAACTC | CAAATAATGC | TTTGAGGACC | TCCAAAGGGA | GTTCTAACCC |
| TTTGGCCATT | TGCTTCCTAA | GTCAGACAGA | GAGAGAGAGA | GTGAGTGTGT | GTGTGTGTGT |
| GTGTGTGTGT | GTGTGTGTGT | GTGTGTGTGT | GTCTGTGTGT | CTGTGTGTGT | GTGTGTGTTG |
| AAGCAACAAT | GTAACAAGCT | | | | |

CLONE: Mfd20 (SEQ ID NO:9)

| | | | | | |
|---|---|---|---|---|---|
| AGCTTTGAGT | AGGTGGCATC | TCAGGGATTT | GCATTTGTGT | GCAGTCTGTC | GTGTGTGTGT |
| GTGTGTGTGT | GTGTGTGTGT | GTGTCTCTAT | TTATCTTTGA | AAAAAAATATT | TTTGAAGATG |
| CCTTCAACAT | TTTAACATAG | AGGGCCGGGG | CACGGTGGCT | CATGCCTGTA | ATCCCAGCAC |
| TTTGAGAGGC | TGAGGCGGGT | GGATCACTTG | AGGTCAGGAA | TTCAAGACCA | GCCTGGCCAA |

CLONE: Mfd22 (SEQ ID NO:10)

| | | | | | |
|---|---|---|---|---|---|
| AGCTACTCAG | GGGGCTAAGG | CACAAGAATT | CTTGAACCAG | AGAAGCGGAG | GTTGCAGTGA |
| GCCAAGATCG | CACCACTGCA | CTCCAGCCTG | GGTAAAGAGT | GAGGCTGTCT | GAAAAAATAA |
| AAATGAAAAT | AAAAAATTAT | ATATACATAC | ATACACACAC | ACACACACAC | ACACACACAC |
| ACACACACAC | ACAGAGACAG | ACAGACAGAC | AGACAGAATA | CTGTCCTCTT | ACTGGACCAT |
| CATTTACATA | CTTTCAAATG | AGCT | | | |

CLONE: Mfd23 (SEQ ID NO:11)

| | | | | | |
|---|---|---|---|---|---|
| AGCTCTCTGA | GTCCTCTGTG | CACTTTGTGG | TGTGTGTGTG | TGTGTGTGTG | TGTGTGTGTG |
| TGTGTGTGTT | GATGCCTGTC | ACACTCTTCC | TAGAGACTGC | CATGTCTGGC | CATCAGACTG |
| AATTGGTGAC | AATTCAGTCG | AGAGACACCA | TGCTTCCCAA | ATTCCCTGAC | CTTGAGCT |

CLONE: Mfd24 (SEQ ID NO:12)

| | | | | | |
|---|---|---|---|---|---|
| AGCTCTCTGC | AAGGACAGAC | AAGGGGCCTT | TGACCTTGAG | AAGCTTGTAT | CTTTCTCAGG |
| ACACACACAC | ACACAGAGAC | ACACACACAC | ACACACACAC | ACACACAGGC | AATGACAGCC |
| AAGGTAGATG | GGAGCTGCCC | TCTCCAGCCA | GAGCATGGGG | CAGGGCAAGC | AAGTCAGTGT |
| GGCCTC | | | | | |

CLONE: Mfd25 (SEQ ID NO:13)

| | | | | | |
|---|---|---|---|---|---|
| AGCTTCGCTT | GTACCAGTAG | AGTTAAAACT | GGGTCACCAT | TTTTATGCGA | GCGTATGGAT |
| ACACATACAT | CCACACTCGA | ACCCCAAACA | CACACACACA | CACACACACT | TCATTTCAGA |
| GTCTAATTAA | AACTCTATTA | TACATAATTT | TCTTCCAGAT | CAATGGTGGT | GTTGGATCAA |
| AATTGTAGCT | | | | | |

CLONE: Mfd26 (SEQ ID NO:14)

| | | | | | |
|---|---|---|---|---|---|
| AGCTCAGTAT | GAAAGAGAAG | CAGCAAAATT | ACCATTTCAT | CAAATGCAAA | AAAATCAGTG |
| CAATTCTTTT | AATGAAACTC | CCAAGACTTC | AGAAAATTCT | CTCTGGCTAT | TTTTCATTAT |
| TTCTTTAGAC | ACACACACAC | ACACACACAC | ACACACACAC | ACACACACAC | ACACACACAC |
| ACACATTCTT | GCCAGGAACA | TGAGTGAGGG | TTGAAGAAGA | GCT | |

CLONE: Mfd27 (SEQ ID NO:15)

| | | | | | |
|---|---|---|---|---|---|
| AGCTGTAAAA | CGGTATATAT | AGCATGATCC | ACTTTAACCC | AAATACTTAT | TCATAGACAC |
| ATGTGTGGGC | ATGCATGCAC | ACACACACAC | ACACAAACAC | ACACACACAC | ACACACACAC |
| ACACACACAC | ACACAGAGAG | AGAGAGAGAC | ATGCTGTTCA | AGTTGATGCC | TCCGGGAAGT |
| GGAATTAAAG | AGCT | | | | |

CLONE: Mfd28 (SEQ ID NO:16)

| | | | | | |
|---|---|---|---|---|---|
| AGCTAGGCCT | GAAGGCTTCT | GGAGCATGTG | TGTGTGTGTG | TGTGTGTGTG | TGTGTGTGTG |
| TGTGTGTGTC | TGTGTGTGTG | TGTGTGTGTG | TAATAATGTC | TTTTATAAAT | GAAAACTCTA |
| TACATATATG | AAAATAATGT | CACTAGTGTT | CTTAACTTAT | GCCAAGAAAC | ATAGAAGAGA |
| GATGATTAAA | GAACACTTTG | TTTTATTTCC | TTTAATTTTC | TATTTTAGCT | |

CLONE: Mfd30 (SEQ ID NO:17)

| | | | | | |
|---|---|---|---|---|---|
| AGCTAAAAGA | TGGTAGGTCA | GGTGTGGCAA | TGTTCTGAAA | ATGGAGGCAA | GTTCATGGAA |
| ATGTTGGTGT | TTGAAATCAC | TGATGACAAT | GACATATATA | ACTGTGTGTG | TGTGTGTGTG |
| TGTGTGTGTG | TGTGTGTGTA | AAATGTAGAG | ATATGGGACA | TGGGTGCTGG | TCCCTATATG |
| AATATTTAAG | GATCACTAAC | AGTTTCACCT | TGCATGAAGC | T | |

TABLE 40-continued

CLONE: Mfd32 (SEQ ID NO:18)

| | | | | | |
|---|---|---|---|---|---|
| AGCTAGATTT | TTACTTCTCT | GACCAAAACA | CAGCAATGTG | ATTGAAATAT | TATGGACACA |
| CACACACACA | CACACACACA | GATTAGTCAG | GCATGTACAA | CCAGGAAGAA | AAAGAAGTGA |
| AGCAATTTTA | GTCAATACAA | GCT | | | |

CLONE: Mfd33 (SEQ ID NO:19)

| | | | | | |
|---|---|---|---|---|---|
| AGCTTGGAGG | TCGAGGCTGC | AGTGAGCCAA | AATCTCTCCT | CTGCACTCCA | GCCTGGGAGT |
| CAGAGTGAGG | CCCTGTCTCA | AACACACACA | CACACACACA | CACACACACA | TACACACACA |
| CACACACACA | CACACACGTC | TTTGGATTTG | GAGCT | | |

CLONE: Mfd34 (SEQ ID NO:20)

| | | | | | |
|---|---|---|---|---|---|
| AGCTTCTAAC | TTTACTAAGC | TTTTTTCAAC | ACTTACCTGT | GACTATGATA | CATATCAATT |
| CATTAGAGTG | AAGACCTCAT | ATAGCCTTTT | GTTTGCATTC | GTGTGTGTGT | GTGTGTGTGT |
| GTGTGTGTGT | ATGTGTGTGT | ATGAAGAACT | AGAAAAAAGA | AACCCTGAAA | GCAGGAAATA |
| GCT | | | | | |

CLONE: Mfd36 (SEQ ID NO:21)

| | | | | | |
|---|---|---|---|---|---|
| AGCTATAATT | GCATCATTGC | ACTCTTGTCT | GGGTGACAGA | GTGAGACCCT | GTCTGAAAAC |
| ACACACACAC | ACACACACAC | ACACACACAT | ACACACACAC | ACATCCCCAC | AACAACAACA |
| CAAAAAACTG | CTGCTTGGGT | CCCAACATAG | ACCAGTTATA | GACCAATTGA | ATTAGAACCA |
| CCAGTGCTGG | G | | | | |

CLONE: Mfd37 (SEQ ID NO:22)

| | | | | | |
|---|---|---|---|---|---|
| AGCTGACATT | TACATTTGTG | TGAATTTGTG | AATATTTGTG | TGAGTCTGTG | AGCACTTATT |
| CCTGTTCACA | AGGTGACAAG | GTGCCTATGT | ATGTGTGTGT | GTGTGTGTGT | GTTCTGAAAG |
| TAACACACTT | TTTTCTTTTC | TTTTTTTTTT | TTTTTTGAGA | CAGAGTCTGG | CTCTGTCACC |
| CAGGCTGGAG | TGCAGTGGCA | AGATCTCAGC | T | | |

CLONE: Mfd39 (SEQ ID NO:23)

| | | | | | |
|---|---|---|---|---|---|
| AGCTATTATA | ATGCTTAGAT | TATATGAGAG | CAAACCCAAT | TCAGACAAGT | AATTACCTTG |
| GGTTGGTTGT | AAATTAAAAC | TCTATTTCTT | ACACCATCTC | TCTCTCTCTC | TCTCTCTCTC |
| TGTTTCTCTC | TCTCTCTCTC | TCTCTCTCAC | ACACACACAC | ACACACACAC | ACACAACACA |
| CACACACCAC | TGTGCTTAAG | TATTTGACAG | | | |

CLONE: Mfd40 (SEQ ID NO:24)

| | | | | | |
|---|---|---|---|---|---|
| AGCTGTTAAA | ATCTCAAGGT | CCTATTATAG | GTACTACCAG | CCTTTGGTTA | TCTTTTATAT |
| GAATGGCATC | ATTTTAGAAG | GAAATAGGTA | GCCGTGGAAG | TGCTGGGATT | TTATAAAACT |
| AAAAATTATA | CATTAACACT | AATTTTCCAC | TCAAAGTTCC | AAAGCACACA | CACACACACA |
| CACACACACA | CCACACACAC | ACATACACAC | ACACTTTGGT | CCTGAACAAA | TGTGTTGCCA |
| TCTGCAGGAC | TCAAAAGCT | | | | |

CLONE: Mfd41 (SEQ ID NO:25)

| | | | | | |
|---|---|---|---|---|---|
| GATCAAAGTG | TCAGGTTCTG | TCATAGGACT | ATTTTATTCA | ACCCTACTAC | ATAAACACTG |
| TTTGGACTCC | ACCTAGGCAC | TGAAGCCAGG | AAGATTGCCG | CTAATCTTCC | TTTACACACA |
| CACACACACA | CACACACACA | CACACACGGC | TCAGGAGTAG | GTTCCAGAA | TCCAACAGCA |
| CGGGGTCTAG | AATGGAGTAA | GTTTTAAGGC | CATCACCTGT | CACATGCCTG | ACTTGGATTT |

CLONE: Mfd42 (SEQ ID NO:26)

| | | | | | |
|---|---|---|---|---|---|
| GATCCCCCCT | TGAACAAGTC | CTCTTTAACT | CAGGCCTCAA | AGAATCCTAC | AGATAGAGTT |
| CTAACAAATA | TGACCTTATT | CACACACACA | CACACACACA | CACACACACA | CATACACACA |
| GAGAGAGTAA | TAAGCAACTA | CGTGTCAGAT | TGAGCAGAAA | CAACAAAGTA | AACCAGATC |

CLONE: Mfd43 (SEQ ID NO:27)

| | | | | | |
|---|---|---|---|---|---|
| GATCAGGTAA | AAGTATTTCA | AAAAATTATC | ACCTCACTTA | GATTGGAAGC | CTTAGGAAGT |
| GCTGTGTTAA | CATATTCTCT | CAACCTTTAG | AATCCACTCT | CCTGGACTAC | ACACATACGC |
| GCGCACGCAC | ACACACACAC | ACACACACAC | ACACACACAC | GGTATTGAAA | CTAGAATTCT |
| TTCAATGTTG | TATTCCCATA | CTTATTTATG | TCTCAAAGAC | TGATC | |

CLONE: Mfd44 (SEQ ID NO:28)

| | | | | | |
|---|---|---|---|---|---|
| GATCAGGTAT | TTTTGGTATG | CTTGTGCACA | CACACACACA | CACACACACA | CACACACACA |
| GGCACATATA | TTCCAAAATA | GAGAATTATC | TTACCTTATT | TATCTTCCCT | CATCTTGACT |
| CCTCTCCTTT | TAAAATAATA | GGAGAAACAG | AGGCACAAAG | TTAAGATTTA | TGGCACAAGG |
| ACAGCATATC | AGAAGTGCAG | AGATAAGGAG | CCAGAACAAG | ACCTAGGTTT | TTTATTTCTG |
| GAACAGAAA | | | | | |

CLONE: Mfd45 (SEQ ID NO:29)

| | | | | | |
|---|---|---|---|---|---|
| GATCATAAGC | GAGTGCTTTT | AATATTAAGT | ATGCACCTCC | CCCCCACCCA | AATTATACTG |
| GTTGAATTTT | CATGTTAAAA | TAAAGCAAAA | ATAAATATTA | ATATAAAATA | TTTAATCAAA |
| TATTTTAAAA | ATTTCAGTAG | TAAAGTAAAC | CAACTCCAGC | AGAGAAAGGG | TTATCACACA |
| CACACACACA | CACACACACA | CACACACACA | CACACCCCCT | ATCTGATGAG | TTCTCTTTGC |
| CAAT | | | | | |

CLONE: Mfd47 (SEQ ID NO:30)

| | | | | | |
|---|---|---|---|---|---|
| GATCACTTAA | GCCTAGGGAG | GCCAAGGCTG | CAGTGAGCCG | AGATTGCACC | ATTGCTCTGC |
| AGCCAGCCTG | GGTGACAGAG | TGAGACCGTG | TAACAAAAAA | CAACAAAAAA | AAAACAAGAA |
| TATATATATA | TACACATATA | TGTGTGTATA | CACACACACA | CACACACACA | CACACACACA |
| CACAGAGTAA | GACATTTGTT | TTACTAAGTG | AGATGCTTCT | CTGAGCCTTC | CTTTGTGTAA |

TABLE 40-continued

CLONE: Mfd48 (SEQ ID NO:31)

| | | | | | |
|---|---|---|---|---|---|
| GATCCTTTAG | ATACTGAGAT | AATATGATAC | AAATTATTAC | TAGTGAGAGG | TTATTTTAAA |
| ATATAGGCAT | TGTTCAGCAA | GCGAAACTTT | CTTCAGCCCC | TTGGCCCCTG | TCATATTTTT |
| ACAAGAAGTC | TCCAAAGCAG | GCCTTGCCTT | GCTGTCTCCT | GCTGAGAATA | GAAGGCTTCC |
| TCCTACCAGG | TTGCTTCCCC | TAGTGCCCCT | GTGTATTGCG | CCCTGTGACG | ATTCCCTTGT |
| GTACACACAC | ACACACACAC | ACACACACAC | ACACACTACT | CTACCTTTGT | GGTTTGGATA |
| TTACTCTACA | GGCATAGCTG | ATC | | | |

CLONE: Mfd49 (SEQ ID NO:32)

| | | | | | |
|---|---|---|---|---|---|
| GATCTTTCAC | ATGGAAATCC | AAATGTCTGG | GGAAATCTAT | CTTGTCTGCA | AGAATTTTCT |
| GATAAATGCC | AAACATGTTG | TCACACACAC | ACACACACAC | ACACACACAC | ACACACACAC |
| ACACAAATGG | AGGAAATCCT | GAGAGCATCT | CGAATATCAG | GATGCTGAGG | GCCCACCAGT |
| CCACAGCCCT | TCCGTGACCC | TCGCTCTGAA | TGACTTCGGG | GGCCAGGTAC | TCGGGTATTC |

CLONE: Mfd50 (SEQ ID NO:33)

| | | | | | |
|---|---|---|---|---|---|
| GATCAGAAGA | CAATGGTGTG | CAAAATAGGA | AAAATCCAAT | ATGAATGGGG | AGCGCCTTTC |
| CTTTCAATTT | TTTAAAAGGG | ACATGTCAGA | GATTTTATGA | AAGAACATTC | TAAGACTTTC |
| CCAATCCTCC | TATAATTCTT | TGGGACAAAA | CCTGCAATGA | ATTTCAGATA | AAAATGAAGT |
| ACAAACAATA | TCAATGAGTT | CACCAGACAA | CCCCCCCCAC | CTCCACACAC | ACACACACAC |
| ACACACACAC | ACACACACAC | AATTCAGGGT | GCATGCTCTA | TGTTGCAAAT | ATGTACC |

CLONE: Mfd52 (SEQ ID NO:34)

| | | | | | |
|---|---|---|---|---|---|
| GATCCAGGCT | TCTGTGGTTC | TAAAGCAGCT | TCTAGATGAG | GTAGAGATTA | AATCACTTTG |
| GCTCAAAACA | TTATCCTTTC | AAATCAGACA | AGTACAGGTG | CCCCATAGTT | TCTCTCTCTG |
| TGTCTCTCTC | TCCTCTCTCA | GCCACACACA | CAGACACACA | TGCACACAGG | CACACACACA |
| TATGCATGCA | TGAATGTGTG | CACAAGCAAA | ACACACACAC | ACACACACAC | ACACACACAC |
| ACACACTTGC | ACACATACAC | TCCTCCCAGA | ACAAGTTCAT | CAGCTATTAT | AAAACTCATG |
| TCCACACCAT | CGCCTCTCTA | GAGATTTGGG | TGAGAAAAAG | AGGCATAGAA | GGCTCTGAAA |
| TGATC | | | | | |

CLONE: Mfd58 (SEQ ID NO:35)

| | | | | | |
|---|---|---|---|---|---|
| GATCCTCCCA | CTGTTCCTGA | AAGGGCCCCA | GCCAGCTACT | GTAAAGTCCT | CATTTGAAGA |
| CTGCAGCAGA | ATTACAGCTC | TCCTCCCCTC | TCTACACCAC | ACACACACAC | ACACACACAC |
| ACACACACAC | TTCACATATT | AATAGATGGA | CAGGAAGCCC | TGCCATGGGG | GGAAGAGGGT |
| TGGATTAGGA | ATCACACACC | CGAGTTCTGG | TCTGGGCTCT | GTCACTTTCA | GAGCTTCATC |
| TGTAACGCAC | ACTGTGAGGC | TTCTGTGAGC | AGCTAGATGT | GGGGGGATGT | TCTGGCGAAA |
| GGTAAGAAGA | TGCTTACTGG | CAGCATCGTT | ATCCTCATTC | AGGAC | |

CLONE: Mfd59 (SEQ ID NO:36)

| | | | | | |
|---|---|---|---|---|---|
| GATCTCAGAG | CGACGGCAGC | GGCGGCACAT | CATTTATTGC | TTGCTGAGAC | ACCTTGGTGA |
| GCATGCAGCC | GATGTTGGGT | GTTCGCATTT | TTTCTACTGA | TAAAAAGGAT | ACTGACTGTG |
| ACATTACTTG | GCTTCAAAAG | AACCATGCGA | TACGACTGTA | TTTCTCAATG | TTAACATTGG |
| AAGACAGCAG | TTCAAAGATG | AAAGTGTTTT | TACACACACA | CATATTTATA | TATTTATTTA |
| TATACACACA | CACACACACA | CACACACACA | CACACACACA | CACACACACA | TATACACCAA |
| GCTTTACCCA | TCTAGGAATG | GATC | | | |

CLONE: Mfd61 (SEQ ID NO:37)

| | | | | | |
|---|---|---|---|---|---|
| GATCTGCCCA | CCTCGGCCTC | CCAAAGTGCT | GGGATTACAG | GCAGGAGCCA | CCGCGCTTGG |
| CCCTATAAAA | TCCTAATTAA | CAAAATCATT | CACACACACA | CACACACACA | CACACACACA |
| CACACACACA | CACACAGATG | TAAGGGCATG | GTCTCTCTTC | CTTGAAGCTA | CGGAATTACA |
| ATTCTCCTTC | ACAAAGACAG | TAAAGGATGT | GATC | | |

CLONE: Mfd62 (SEQ ID NO:38)

| | | | | | |
|---|---|---|---|---|---|
| GATCTGTCAA | ATATTATCTA | TTTCAAAAGT | GTCATTGGGT | CAAGCTTTAC | AGATGAGACC |
| AGATTTTCTG | TTTAATGTAC | ATACACACAC | ACACACACAC | ACACACACAC | ACACACACAC |
| ACACGGACTC | AAGAAATTGG | CTGGTGGAAA | TACGAAGTAA | AGTTTTAAGA | TAATTGGCAT |
| AAAAGTAAAA | CATTCTCGGA | TC | | | |

CLONE: Mfd63 (SEQ ID NO:39)

| | | | | | |
|---|---|---|---|---|---|
| GATCAGGCCA | TATCACCACT | AGGTTTTCTT | CCCAGCATCT | GAAAATCCTA | TCTTAATCAC |
| GAGAAAATAT | GAAACAAACA | CAAATTGAGG | AACATTCTAC | AAAATCACTG | AAGAGTAGTC |
| TTTAAACTGA | AAGGTCACCA | AAATAAAAAA | ACAAAAAAAA | ACCAAAACCA | AAAAACCAAA |
| GGCACACACA | CACACACACA | CACACACACA | CACACACACA | CACGAAAAGA | ATGAGAAACT |
| GTCACAGATT | GGAGAAGACT | AAGG | | | |

CLONE: Mfd64 (SEQ ID NO:40)

| | | | | | |
|---|---|---|---|---|---|
| GATCTCTCAG | CTATTACAAG | GATACAAAAT | ACGAACATTC | TACAAGTTAC | TTAACACACA |
| CACACACACA | CACACACACA | CACAAAATTA | ATTCCACAGG | TCAGTTTCTC | TGAAACATTT |
| TTTCACTAAA | TTCTAAGTCT | TCCTGGAGTT | GCAAGTGCCT | ATCTCCTAGA | CAAGGCAATT |
| ACTCACCAAC | TAAAATCACT | GTCAATCTGA | GATTTCGGCT | GGGCATGAGA | CCATGGTCAG |
| GGG | | | | | |

CLONE: Mfd65 (SEQ ID NO:41)

| | | | | | |
|---|---|---|---|---|---|
| GATCCTATGC | AAACCACAAT | GGAATGCATT | AAATATAAAA | CCCATCTTCC | TTGTTCTGTT |
| CACACACACA | CACACACACA | CACACACACT | CTCTCTGAAG | TATGTAAACA | AGATGTCATT |
| TTCATTTTAT | TAATACACAT | ACTGAGGCAA | AGGAAGTAAA | GTGATAATCA | TGATGATGAT |
| AACACTAATG | AAAATCTACA | GCCATAAA | | | |

TABLE 40-continued

CLONE: Mfd66 (SEQ ID NO:42)

| GATCTTTGCT | GCCCCTACCT | TGGCTAGTTA | TATACACACA | CACACACACA | CACACACACA |
| CACACACACA | CACACACCCT | ACAGCATGAA | TTCATCCAAT | TGTTTTGCAC | AAAAACATGT |
| TTAAAATGAA | AAGGCAGAAA | GCCAGAGCGA | GGTAGGGTAA | CTTGGGTATA | AGCTGAGGTT |
| AGCCAGTGCA | CATGCATG | | | | |

CLONE: Mfd67 (SEQ ID NO:43)

| GATCCTGCCC | TTATGGAGTG | CTTTCTTCTC | TCTCTCTCTC | TCTCTCTCTC | ACACACACAC |
| ACACACACAC | ACACACACAC | ACACACGGTT | TTTTGGGAGA | TACTAAGTAC | TAGGAAGTAA |
| AATAAAGCAG | GATGATATAC | AATGACAGAG | GAGTGGGGGA | CAGCCTGTAC | TACATTTGAT |
| GGAAGGATGA | GGGAAGCTCT | CTCGATGAAA | TGGAATTTGA | GTAAAGAA | |

CLONE: Mfd72 (SEQ ID NO:44)

| GATCCAAAAG | ACTGAATATA | TCATTCAAAG | TTGAGCACAC | TTAGAGAATA | AGCATAGTCA |
| TATGGTGAGG | TCTTTTTTGT | TGCCACCTAA | TATATATTGC | TACAATAAAA | GGAAAACATT |
| TTGTTTAAAA | CTTTGTAATT | GCATTTGGCA | AGATTCCCTA | TCCTCTTGTC | TGTAAGAACT |
| AATCAGAATT | CACAGTGACT | GTTAAACAGA | AACAAATTGA | AAGTGTAAGC | TTACCATTGA |
| AAAGAAGACA | TAAGGATACT | GCATTATTGC | CAGTGGTGAG | AAGCAAAATA | GGTATAAACA |
| CACACACACT | CAAACACACA | CACACACACA | CACACACACA | CACACACGGA | GAGAGAGAGA |
| GAGAAAGAGA | AAGAAATAGT | TGGGATC | | | |

CLONE: Mfd79 (SEQ ID NO:45)

| GATCCTTGTG | GTGATGGAAC | TGTTCCATAT | CTTGATTGTG | GTGTTGGTAT | ACCTGAATTT |
| ACACATGATA | AAACTGCATA | GAAATGCGTA | TATATATACA | CACACACACA | CACACACACA |
| CACACACATA | TAAAAATATA | TATACACATG | TATATATACA | CACACACATA | TATAACACAC |
| AAATAAGTAC | AAATAAAACT | AGGGAAATTT | GAATAAGATA | GATGGGTTTT | ATCAATGTCA |
| ATATCCCAGT | TGTGATATCA | TAATATAGAT | TACCAGGATG | TTACCATTGG | GGAAAGGATC |

CLONE: Mfd84 (SEQ ID NO:46)

| GATCCTGTAC | ATATAAAGGA | TATTATTGGA | ACAATTAGTG | AAATTTGAAT | GGGGCCTGTT |
| GATTAGATGG | TAATTTTAAT | CAATGTTAAC | TTCCAGATTT | TGATGATGAT | TTTGTGGTTA |
| GATAGAATGT | CCTTGTACTT | AGGATACACA | CACACATACA | CAGATACACG | GACACACACA |
| CACACACACA | CACACACACA | CACACTGTGT | ATATGTATAC | ATTGAGATAT | TAAGTGGGCA |
| TCATGTCTGA | AACATTCTTA | AA | | | |

CLONE: Mfd88 (SEQ ID NO:47)

| GATCAGTTTG | TAGAAGAGAC | ATCTGAACTT | TCATGTTCTT | AGTGCCACTC | TTTACATTAG |
| CCGAGATGTG | GAATCAACCT | GAGTGTTCAT | CAATACATGA | ATAGGTAGTA | AAAATACACA |
| CACACACACA | CACACACACA | CACACACACA | CACACACACA | CAATGGAATA | CTATTCAGCC |
| ATAAAAAGAA | TGAAACCCTG | TCATTTTGAC | AACATGGATG | ATTCTGGAGG | ACATTATGAT |
| AACTGAAATA | AGATAAGCC | | | | |

CLONE: Mfd116 (SEQ ID NO:48)

| GATCTGAAGT | GATAAATCTC | CTGTGACATT | TTGGTCTCTG | CACTAGAAAG | GCAGAGTAAC |
| TTCATGTATA | GTCACCAAGA | CATCACACGA | CAGGCAAAAA | ATAACTTCTT | ATACCCACCA |
| CGCCCCCACC | CAACACACAC | ACACACACAC | ACACACACAC | ACACACACAC | ACCCTGCAAT |
| TAGAAATTAG | AAAGAGGGAT | GCAATTAGAA | AGAGGGACTT | GGTGTTTGGT | GCTGCATAGC |
| TCCC | | | | | |

CLONE: Mfd122 (SEQ ID NO:49)

| GATCTTTAAC | ATCCTTTAAC | AGCTAGCCGT | ATTCCTAGGG | GTGTGTGTGT | GTGTGTGTGT |
| GTGTGTGTGT | GTGTCTACTG | TAAATGAGAT | TACATTCTTA | ACTTGGCACT | CAGCTTCAAT |
| ATTTTTGATG | TATAAATATG | CTACTGTTCA | TATTCTTTGC | CCACTTTTTG | ATGGGGTTGT |
| TTTTTTCTTG | TAAATTTGTT | TAAGGTCCTT | GTAGATTCTG | CATATTAGCC | CTTTTTTAGA |
| TGGATAGATT | ACAACAGACC | CTTCTCAAAA | GAAGACATTT | ATGTGGCCAA | AAA |

CLONE: Mfd134 (SEQ ID NO:50)

| GATCAGTGCC | TGACCAGATG | CCTTTGCCTT | TTACTGGCTG | GTGCTGCCAC | ACACACACAC |
| ACACACACAC | ACACACACAC | ACACACACAC | CCCTGCTGCT | GTGAGACTTG | GCAGCTACAG |
| GCTCACTGGG | CATCCTTCCC | TGGAGAACTG | CCCGAGGCTG | GCAGAACCAC | CTGGCTCCAA |
| AATGCCTGGA | GGCCCAGCTT | CCTCCACTCA | CCCTCAGCTG | ACCCGATGGG | TCCTGC |

CLONE: Mfd136 (SEQ ID NO:51)

| GATCTGGTTG | GTGGGTGGGT | GGGTCCTGAG | AATGTACTTG | TTAAGTTTCA | AGCAGTGTTG |
| ATATGGGTGG | CCTGAGGAAT | GGATTCTGTG | AACTAAACAT | TACTTCAAGA | AAAAATCTGT |
| GTGTGTGTGT | GTGTGTGTGT | GTGTGTGTGT | GTGTTGTGTG | TGTGTGTGTT | ATTCATCTTT |
| AAATTCTGCA | AGGTCCAATA | TAATGCTTTG | AATATATTAT | CGACTCAATA | CATAAGAGTT |
| TGTTTTGAAT | CATGTTAGTG | GTGTGATTTT | | | |

CLONE: Mfd154 (SEQ ID NO:52)

| GATCCATTTC | TGGGCGCACA | TGTATCTAGC | CATGGTAGCA | CAGGCCGGGA | AGCTCTGTGC |
| TGGAAATTCT | GAGTTTGTGT | GTGTGTGTGT | GTGTGTGTGT | GTGTGTGTGT | GTGTGTGTTA |
| CCTTTCTTCC | TTCTCTTTAC | TCTCCTTTTC | TGCCTTCTGT | CGAGCACAGC | CTGCCTGTGA |
| CCTCACAGCA | ATAAGTTAGG | CCAGTGGTTT | TCAAAGTGCA | GTTCCCAGAA | TAGTAACAGC |
| AGCATCACCT | GGTTCCTGTT | AGAAATGCAA | ATTCTCAG | | |

The following examples are intended to illustrate, but not limit, the scope of the invention.

EXAMPLES

Example I

This example describes the method used to identify and isolate specific $(dC-dA)_n.(dG-dT)_n$ fragments.

General Procedure

Total human genomic DNA or total DNA from a chromosome 10-specific large insert page library (LL19NL01) was digested to completion with Sau3A I, Alu I, Taq I, or a combination of Sau3A I and Taq I. DNA fragments ranging in size from about 150 to 400 base pairs were purified by preparative agarose gel electrophoresis (Weber at al. (1988), *J. Biol. Chem.* 3:11321–11425), and ligated into mp18 or mp19 m13 vectors. Nitrocellulose plaque lifts (Benton and Davis (1977), *Science* 196:180–182) prepared from the resulting clones were screened by hybridization to synthetic poly(dC-dA).poly(dG-dT) which had been nick-translated using both $\propto^{32}P$-dATP and $\propto^{32}P$-dTTP to a specific activity of about $5\times10^7$ cpm/ug. Hybridizations were carried out in 6×SSC, pH 7.0, 2.5 mM EDTA, 5.0% (v/v) O'Darby Irish Cream Liqueur (Elbrecht, A., March 1987, *B. M. Biochemica*, 12–13, at 60° C. After hybridization, filters were washed in 2×SSC, 25 mM NaPO$_4$, 0.10% SDS, 5.0 mM EDTA, 1.5 mM Na$_4$P$_2$O$_7$, pH 7.0, and then in 1SSC, 0.10% SDS, 5.0 mM EDTA, pH 7.0. Phage from the first screen were usually diluted and then screened a second time to insure plaque purity, Single stranded DNA was isolated from the positive clones and sequenced as described (Biggin et al. (1983), *Proc. Natl. Acad, Sci. USA* 80:3063–3965).

GenBank DNA databases were screened for the presence of sequences with $(dC-dA)_6$ or $(dG-dT)_6$ (see, for instance, nucleotides 1–12 of SEQ. ID. NO.:59 using the QUEST program made available by Intelligenetics Inc. through the national BIONET computing network. Since the sequences of only one of the two strands of each DNA fragment are compiled in GenBank, separate screens for both CA and GT repeats were necessary.

Results.

The hybridization procedure was used to isolate and sequence over one hundred $(dC-dA)_n.(dG-dT)_n$ blocks and the DNA immediately flanking the repeats. Examples are listed in Table 1 (Mfd6–125). Numbers of $(dC-dA)_n.(dG-dT)_n$ dinucleotide repeats within the blocks ranged from 10 to over 30. Many of the blocks had imperfect repeats or were adjacent to tandem repeats with different sequences.

$(dC-dA)_n.(dG-dT)_n$ sequences obtained from the GenBank screens (Mfd1–5) were similar to those obtained through the hybridization procedure, except that sequences containing as few as six repeats could be selected.

Example II

In this example a subset of the sequences isolated and identified as in Example I were amplified and labeled using the polymerase chain reaction, and were then resolved on polyacrylamide gels to demonstrate length polymorphisms in these sequences.

General Procedures.

Oligodeoxynucleotide primers were synthesized on a Cyclone DNA synthesizer (Biosearch, Inc., San Rafael, Calif.). Primers were 19–22 total bases in length, and contained 7–11 G+C bases. Self-complementary regions in the primers were avoided.

Genomic DNA was isolated from nucleated blood cells as described (Aidridge et al., 1984, *Am. J. Hum. Genet.* 36:546–564). Standard polymerase chain reactions (Saiki et al., 1985, *Science* 230:1350–1354; Mullis and Faloona, 1987, *Method Enzymol.* 155:335–350; Saiki et al., 1988, *Science* 239:487–491) were carried out in a 25 ul volume containing 10–20 ng of genomic DNA template, 100 ng each oligodeoxynucleotide primer, 200 uM each dGTP, dCTP and dTTP, 2.5 uM dATP, 1–2 uCi of $\propto^{32}P$-dATP at 800 Ci/mmole or $\propto^{35}S$-dATP at 500 Ci/mmole, 50 mM KCl, 10 mM Tris, pH 8.3, 1.5 mM MgCl$_2$, 0.01% gelatin and about 0.75 unit of Taq polymerase (Perkin Elmer Cetus, Norwalk, Conn.). Samples were overlaid with mineral oil and processed through 25 temperature cycles consisting of 1 min at 94° C. (denaturation), 2 min at 55° C. (annealing), and 2.5 min at 72° C. (elongation). The last elongation step was lengthened to 10 min.

Results shown in FIG. 1 were obtained using conditions slightly different that the standard conditions. Templates were 100–200 ng of genomic DNA, annealing steps were 2.5 min at 37° C., elongation steps were 3.5 min at 72° C., and $\propto^{35}S$-dATP was added after the 18th cycle rather than at the beginning of the reactions. The plasmid DNA sample was amplified starting with 50 pg of total plasmid DNA as template.

Figure 2:
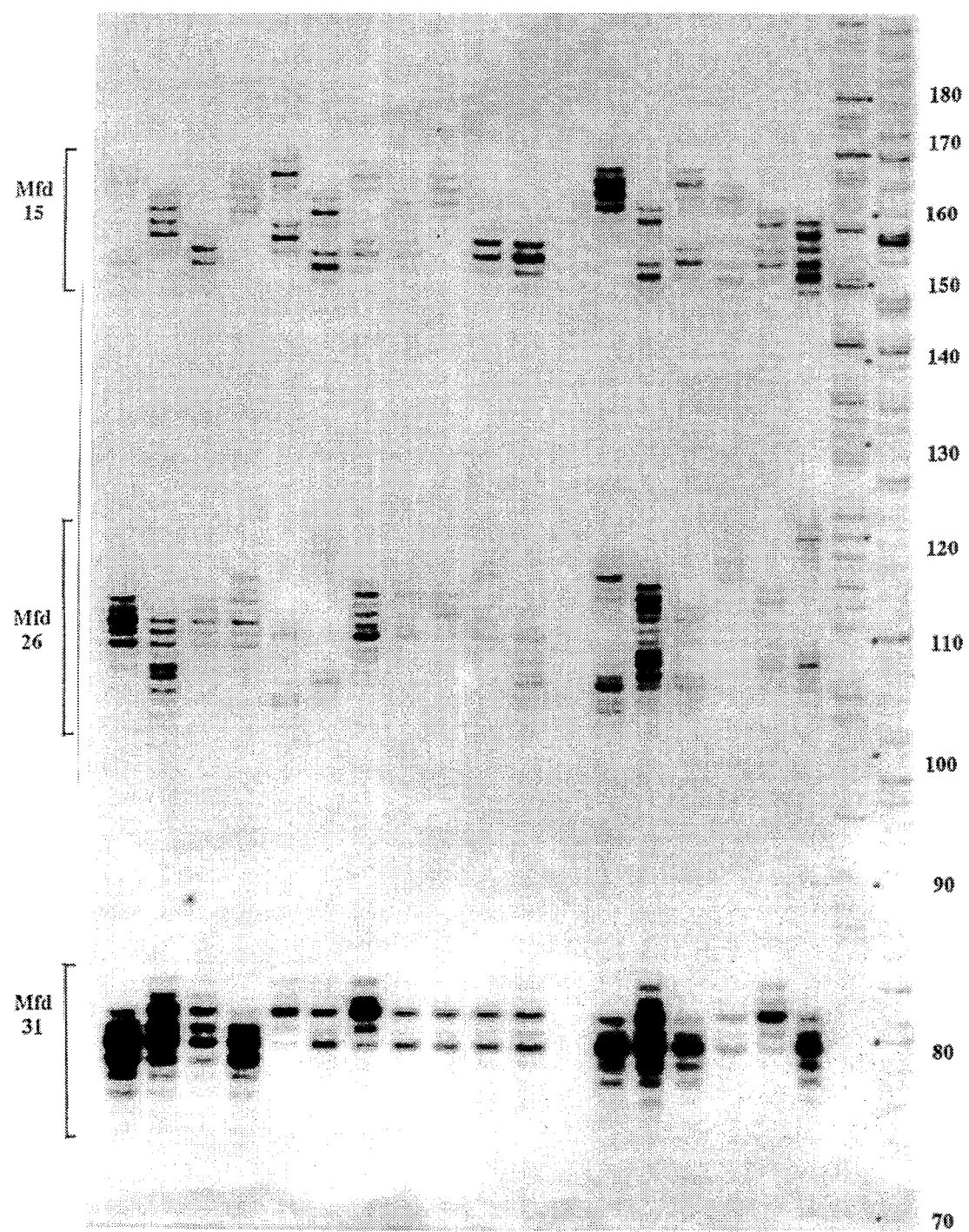
FIG. 2 is an additional example of length polymorphisms in amplified fragments containing $(dC-dA)_n.(dG-DT)_n$ sequences. Shown is an autoradiograph of a polyacrylamide gel.

Primers for the Mfd15 marker shown in Figure 2 are listed in Table 1. Primers for the Mfd26 marker also shown in FIG. 2 are CAGAAAATTCTCTCTGGCTA (SEQ ID NO:129) and CTCATGTTCCTGGCAAGAAT (SEQ ID NO:130), and primers for the Mfd31 marker are TAATAAAGGAGC-CAGCTATG (SEQ ID N0:144) and ACATCTGATG-TAAATGCAAGT (SEQ ID NO:145).

Aliquots of the amplified DNA were mixed with two volumes of formamide sample buffer and electrophoresed on standard denaturing polyacrylamide DNA sequencing gels. Exposure times were about 2 days. Gel size standards were dideoxy sequencing ladders produced using m13, mp10 or mp8 DNA as template.

Results

FIG. 1 shows the amplified DNA fragments for the IGF1 $(dC-dA)_n.(dG-dT)_n$ marker in seven unrelated individuals (1–7). Z represents the most frequent allele; Z-2, the allele that is two bp larger than the most frequent; Z-2, the allele that is 2 bp small, etc. K indicates Kpn I digestion of amplified samples 1 and 7. Kpn digestions reduce the number of bands to half the original number because the CA strand, which normally migrates with an apparent size of about four bases less than the GT strand, is after Kpn I digestion, four bases longer than the GT strand resulting in co-migration of the two strands. P refers to DNA amplified from a plasmid DNA sample containing the IGF1 $(dC-dA)_n.(dG-dT)_n$ block. Sizes of the DNA fragments in bases are indicated on the left. At the top of the figure are shown the sequence of amplified DNA along with the primer sequences and the site of Kpn I cleavage.

Because the CA and GT strands of the amplified DNA fragments migrate with different mobilities under the denaturing electrophoresis conditions (see Example III below), homozygotes yield two bands and heterozygotes four bands. The band corresponding to the faster moving CA strand is more intense on the autoradiographs than the band for the slower GT strand because the adenine content of the CA strand is higher and labeling is with $\alpha^{35}$S-dATP. Two of the seven individuals shown in FIG. 1 (1 and 3) were homozygous for the predominant allele (Z) of the IGF1 (dC-dA)$_n$·(dGdT)$_n$ block; the remainder were heterozygotes of various types.

Proof that the amplified DNA was really from the IGF1 gene and not from some other portion of the genome includes; that the amplified DNA was of the general expected size range for the primers used, that the amplified DNA hybridized to nick-translated poly(dC-dA).poly(dG-dT) (not shown), that this DNA was cleaved by a restriction enzyme, Kpn I, at the expected position (FIG. 1, lanes 1K and 7K), and that plasmid DNA containing the IGF1 sequence could be used as a polymerase chain reaction template to yield DNA of the same size as was amplified from the genomic DNA templates (FIG. 1, lane P).

FIG. 2 shows additional examples of polymorphic amplified DNA fragments containing (dC-dA)$_n$·(dG-dT)$_n$ sequences. In this case three different markers fragments, Mfd15, Mfd26 and Mfd31 were amplified simultaneously from genomic DNA templates from several different individuals.

Example III

Comparison of different labeling approaches.

General Procedures.

The ApoAII (Mfd3) CA or GT strand oligodeoxynucleotide primers were end-labeled for 1 h at 37° C. in a 50 ul reaction containing 90 pmoles (600 ng) of primers, 33 pmoles of $\gamma^{32}$P-ATP at 3000 Ci/mmole, 10 mM MgCl$_2$, 5 mM DTT 50 mM Tris, pH 7 6, and 50 unites of T4 polynucleotide kinase. Polymerase chain reactions were carried out in 25 ul volumes with 50 ng of end-labeling primer and 86 ng of each unlabeled primer. Interior labeling was performed as in Example II.

Results

Figure 3:
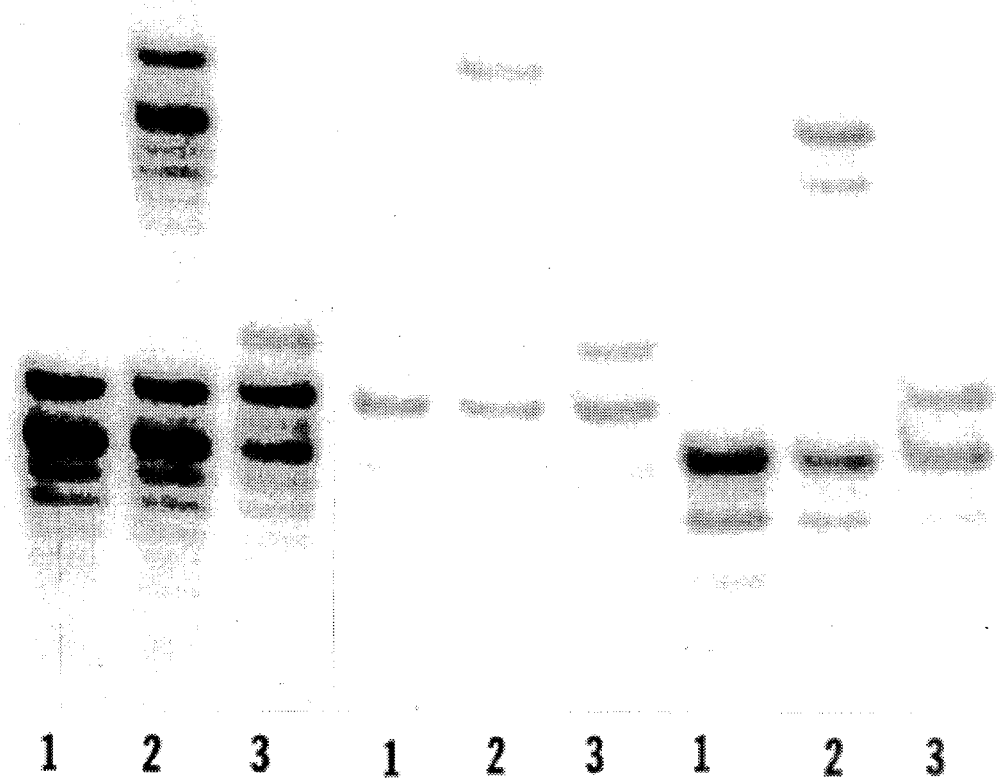
FIG. 3 is an autoradiograph of a polyacrylamide gel loaded with DNA amplified from the human Mfd3, ApoAII locus using DNA from three unrelated individuals as template and labeled through three different approaches: labeling the interiors of both strands with $\propto^{32}$P-dATP, end-labeling the GT-strand primer with $^{32}$P phosphate, or end-labeling the CA-strand primer with $^{32}$P phosphate.

Rather than labeling the amplified DNA throughout the interiors of both strands, one or both of the polymerase chain reaction primers can be end-labeled using polynucleotide kinase. FIG. 3 shows the results of such an experiment using as template, DNA from three different individuals (1–3) and labeling throughout the interiors of both strands versus labeling of the GT strand primer only versus labeling of the CA strand primer only. Individual 1 is a homozygote and individuals 2 and 3 are heterozygotes. Because of strand separation during the denaturing gel electrophoresis, labeling of both strands produces two major bands per allele on the autoradiograph, whereas labeling of the GT strand primer gives predominantly only the upper band for each allele and labeling the CA strand primer gives predominantly only the lower band for each allele. Additional fainter bands on the autoradiograph are artifacts of the polymerase chain reaction and will be discussed in Example IV.

Example IV

Estimates of informativeness and allele frequencies for the (dC-dA)$_n$·(dG-dT)$_n$ markers.

General Procedure

Estimates of PIC (polymorphism information content) (Bostein et al., 1980, *Amer. J. Hum. Genet.* 32:314–331 and heterozygosity were obtained by typing DNA from 41–45 unrelated Caucasians for markers Mfd1–Mfd4, or by typing DNA from 75–78 parents of the 40 CEPH (Centre d'Etude du Polymorphisme Humain, Paris, France) reference families for markers Mfd514 Mfd10. The CEPH families are from the U.S.A., France and Venezuela. Estimates of allele frequencies were calculated from the same data.

Results.

PIC and heterozygosity values for the first 10 (dC-dA)$_n$·(dG-dT)$_n$ markers are shown in Table 41. Values ranged from 0.31 to 0.80 with an average PIC of 0.54±0.14 and average heterozygosity of 0.56±0.15. The informativeness of the (dC-dA)$_n$·(dG-dT)$_n$ block markers is generally superior to standard unique sequence probe polymorphisms (Gilliam et al., 1987, *Nucleic Acids Res.* 15:4617–4627; Schumm et al., 1988, *Am. J. Hum. Genet.* 42:143–159) and as good as many minisatellite polymorphisms (Nakamura et al., 1987, *Science* 235:1612–1622). Considering the vast number of (dC-dA)$_n$·(dG-dT)$_n$ blocks in the human genome, it is likely that a subset of up to several thousand can be identified with average heterozygosities of 70% or better.

The number of different alleles detected for the first ten markers (Table 41) ranged from 4 to 11. Alleles always differed in size by multiples of two bases (from CA strand to CA strand bands), consistent with the concept that the number of tandem dinucleotide repeats is the variable factor. Allele frequencies for the first ten markers are shown in Table 42. For most of the test markers, major alleles were clustered in size within about 6 bp on either side of the predominant allele. Amplified fragments must be small enough so that alleles differing in size by as little as two bases can easily be resolved on the polyacrylamide gels. The size differences between the largest and smallest alleles were ≦20 bp for most of the markers, and therefore several markers can be analyzed simultaneously on the same gel lane (see FIGS. 2 and 4).

TABLE 41

| | | | Informativeness of (dC-dA)$_n$ · (dG-dT)$_n$ Markers | | | |
|---|---|---|---|---|---|---|
| Marker[a] | Chromosome Location | Length Amplified DNA[b] | Repeat Sequence[c] | # of Alleles | Heterozygosity | PIC[d] |
| Mfd1 | 12p22–q24.1 | 192 bp | CATA(CA)$_{19}$ (SEQ. ID. NO: 53) | 5 | 54% | 0.53 |
| Mfd2 | 3q21–qter | 120 bp | (AC)$_{13}$A(AC)$_{17}$A (SEQ. ID. NO: 56) | 4 | 34% | 0.31 |
| Mfd3 | 1q21–q23 | 137 bp | (CA)$_{16}$C (SEQ. ID. NO: 59) | 6 | 74% | 0.65 |
| Mfd4 | 3q28 | 160 bp | (AC)$_{12}$GCACAA(AC)$_{13}$A (SEQ. ID. NO: 62) | 6 | 51% | 0.46 |
| Mfd5 | 19q12–q13.2 | 151 bp | (CT)$_7$(CA)$_{23}$ (SEQ. ID. NO: 65) | 11 | 80% | 0.79 |

TABLE 41-continued

Informativeness of $(dC-dA)_n \cdot (dG-dT)_n$ Markers

| Marker[a] | Chromosome Location | Length Amplified DNA[b] | Repeat Sequence[c] | # of Alleles | Heterozygosity | PIC[d] |
|---|---|---|---|---|---|---|
| Mfd6 | — | 192 bp | $(CA)_5AA(CA)_{13}$ (SEQ. ID. NO: 68) | 7 | 49% | 0.50 |
| Mfd7 | — | 213 bp | $(CA)_{20}TA(CA)_2$ (SEQ. ID. NO: 71) | 6 | 54% | 0.51 |
| Mfd8 | — | 185 bp | $(AC)_{20}A$ (SEQ. ID. NO: 74) | 8 | 58% | 0.58 |
| Mfd9 | 19[e] | 100 bp | $(CA)_{17}G$ (SEQ. ID. NO: 77) | 9 | 72% | 0.69 |
| Mfd10 | 19 | 138 bp | $(AC)_{14}A$ (SEQ. ID. NO: 80) | 6 | 39% | 0.42 |

[a]Mfd stands for Marshfield. The marker name substitutes for the probe name in RFLP markers and denotes a specific pair of amplification primers for each locus.
[b]Sizes of amplified DNA fragments corresponded to the predominant allele for each marker. Estimated error is 2 bp.
[c]Sequences for Mfd1–Mfd5 were taken from GenBank. Sequences for Mfd6–Mfd10 were determined in the laboratory. Sequence identification numbers (SEQ ID NO:) are listed on Table 1.
[d]PIC is Polymorphic Information Content (Botstein et al. (1980), Am. J. Hum. Genet. 32:314–331).
[e]Markers 9 and 10 were developed using clones selected from a chromosome 19-specific phage library.

TABLE 42

Allele Frequencies for $(dC-dA)_n \cdot (dG-dT)_n$ Markers

| Allele[a] | Marker | | | | | | | | | |
|---|---|---|---|---|---|---|---|---|---|---|
|  | 1 | 2 | 3 | 4 | 5 | 6 | 7 | 8 | 9 | 10 |
| Z + 14 | —[b] | — | — | — | 1% | — | — | — | — | — |
| Z + 10 | — | — | — | — | — | 3% | — | 1% | — | — |
| Z + 8 | — | — | 3% | — | 3% | 11% | — | 3% | — | — |
| Z + 6 | — | — | 35% | 2% | 4% | 1% | — | 7% | 3% | 1% |
| Z + 4 | 18% | 6% | — | 6% | 15% | 1% | 6% | 2% | 1% | — |
| Z + 2 | 16% | 11% | 1% | 13% | 15% | 3% | 4% | 27% | 12% | 5% |
| Z | 60% | 81% | 39% | 70% | 34% | 64% | 66% | 54% | 38% | 73% |
| Z – 2 | 5% | 2% | — | 1% | 3% | 18% | 15% | 4% | 6% | — |
| Z – 4 | — | — | 8% | — | 2% | — | 7% | 1% | 4% | 10% |
| Z – 6 | — | — | 14% | 8% | 1% | — | — | — | 4% | 9% |
| Z – 8 | — | — | — | — | — | — | 2% | — | 31% | 1% |
| Z – 12 | — | — | — | — | — | — | — | — | 1% | — |
| Z – 14 | — | — | — | — | 11% | — | — | — | — | — |
| Z – 16 | 1% | — | — | — | — | — | — | — | — | — |
| Z – 22 | — | — | — | — | 12% | — | — | — | — | — |
| Spread[c] (bp) | 20 | 6 | 14 | 12 | 36 | 12 | 12 | 14 | 18 | 14 |

[a]Z indicates the predominant allele for each marker.
[b]A dash means this allele was not found.
[c]Spread is the size difference between amplified DNA fragments corresponding to the largest and smallest alleles.

Example V

Demonstration of Mendelian codominant Inheritance of $(dC-dA)_n \cdot (dG-dT)_n$ Markers.

General Procedure

DNA from individuals of the CEPH families and from other three generation families was used as template for the amplification of various $(dC-dA)_n \cdot (dG-dT)_n$ markers using the procedure described in Example II.

Results

Figure 4:
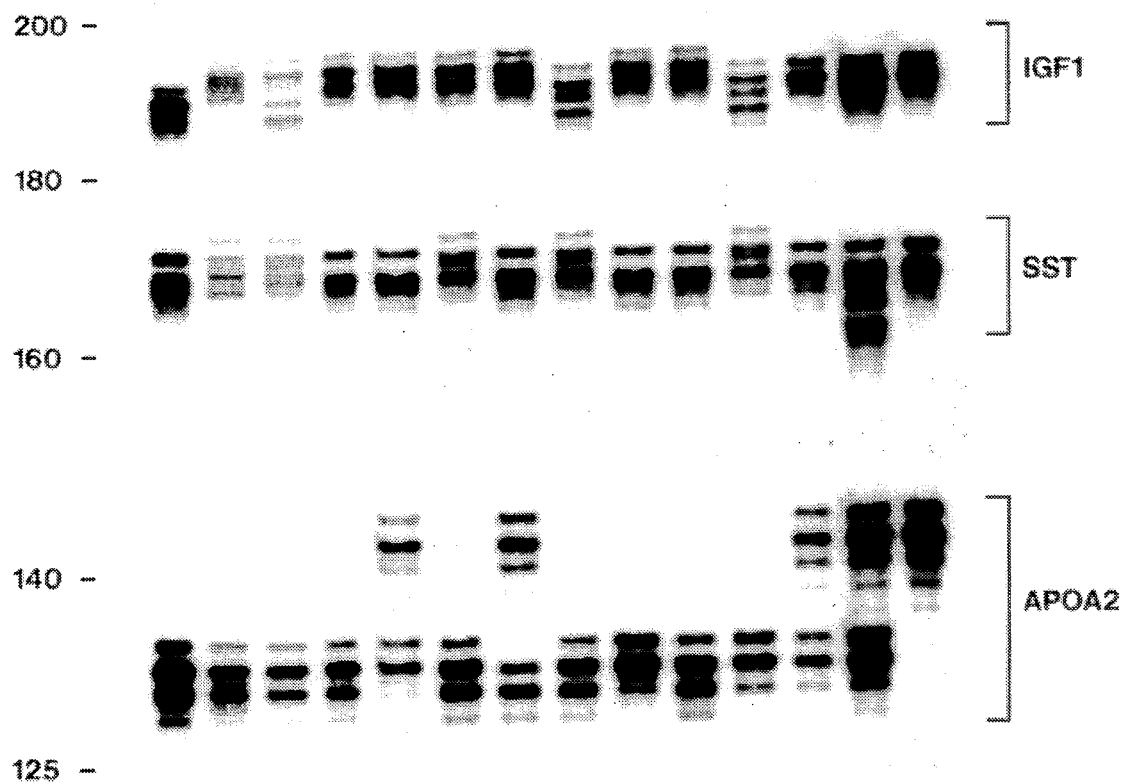
FIG. 4 is an example of the Mendelian inheritance of three different human $(dC-dA)_n.(dG-dT)_n$ markers through three generations. Shown are the pedigree of this family, an autoradiograph of a gel loaded with the amplified DNA and a list of the genotypes of the individual family members.

FIG. 4 shows the amplified DNA from markers Mfd1, Mfd3 and Mfd4 from CEPH family 1423. DNA fragment sized in bases are marked to the left of the gel. individual genotypes are listed below the gel. All three markers showed Mendelian behavior for this family.

A total of approximately 500 family/marker combinations have been tested to date. Mendelian codominant inheritance has been observed in all cases; no new mutations have been found. Therefore new mutations are unlikely to be a general problem with the $(dC-dA)_n \cdot (dG-dT)_n$ markers.

Example VI

Artifacts of the amplification reactions.

General Procedures

Aliquots of two different $(dC-dA)_n \cdot (dG-dT)_n$ amplified fragments (two different markers from two individuals), untreated from the polymerase chain reaction (C), were brought up to uM dATP and then incubated at 37° for 30 min with 6 units of Klenow enzyme (K), 1 unit of T4 DNA polymerase (P), or with no additional enzyme (T). Samples were then mixed with formamide sample buffer and loaded on polyacrylamide gels.

Figure 6:
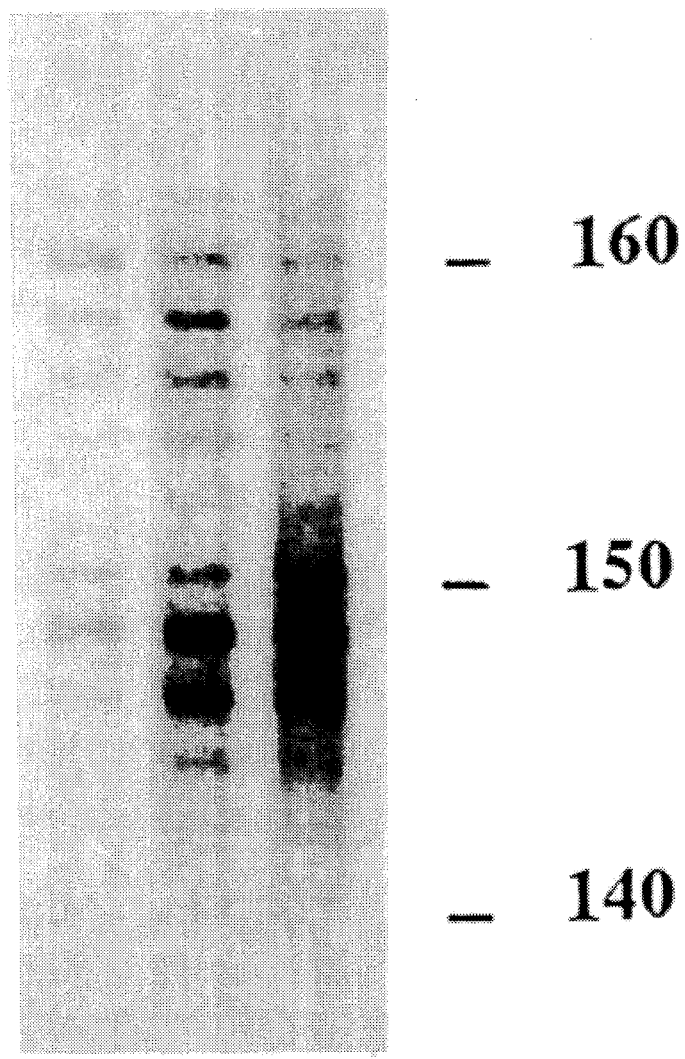
FIG. 6 is an autoradiograph showing the effect of additional polymerase chain reaction cycles on amplified DNA for the Mfd3 marker from a single individual.

For the results shown in FIG. 6, DNA from an individual with the Mfd3 genotype Z+6, Z–6 was amplified with modified Mfd3 primers (AGGCTGCAGGATTCACTGCT-GTGGACCCA (SEQ. ID. NO:459) and GTCGGTACCG-GTCTGGAAGTACTGAGAAA) (SEQ. ID. No:460) so that sites for the restriction enzymes Pst I and Kpn I were located at opposite ends of the amplified DNA. An aliquot of the amplified DNA from a 27 cycle reaction was diluted 60,000 fold with 0.2× TE, and 10 μl of the dilution (approximately $10^5$ molecules) were amplified with the same primers for another 27 cycles. An aliquot of the second amplification reaction was diluted as above and subjected to a third 27 cycle reaction. Amplified DNA samples were treated with T4 DNA polymerase prior to electrophoresis.

Amplified DNA from the first reaction described in the above paragraph was digested with Kpn I and Pst I, extracted with phenol, and simultaneously concentrated and dialyzed into 0.2× TE using a Centricon 30 cartridge. This DNA was then ligated into mp19 and transformed in *E. coli*. Clear plaques on X-gal/IPTG plates from the transformed cells were picked, amplified and used to isolate single-stranded DNA. DNA from 102 such clones was sequenced. The distribution of the numbers of dinucleotide repeats in these clones is shown in Table 43.

Results.

Additional bands, less intense than the major pair of bands for each allele and smaller in size than the major bands, were usually seen for the amplified DNA fragments. These bands are particularly apparent in FIGS. 2–4. The additional bands were present when cloned DNA versus genomic DNA was used as template (FIG. 1, lane P), and even when such small amounts of heterozygote genomic DNA were used as template that only one of the two alleles was amplified. Also, DNA amplified from 63 lymphocyte clones (gift of J. Nicklas) (Nicklas et al (1987), *Mutagenesis* 2:341–347) produced from two individuals showed no variation in genotype for all clones from a single donor. These results indicate that the additional bands are generated as artifacts during the amplification reactions, and are not reflections of somatic mosaicism.

Figure 5:
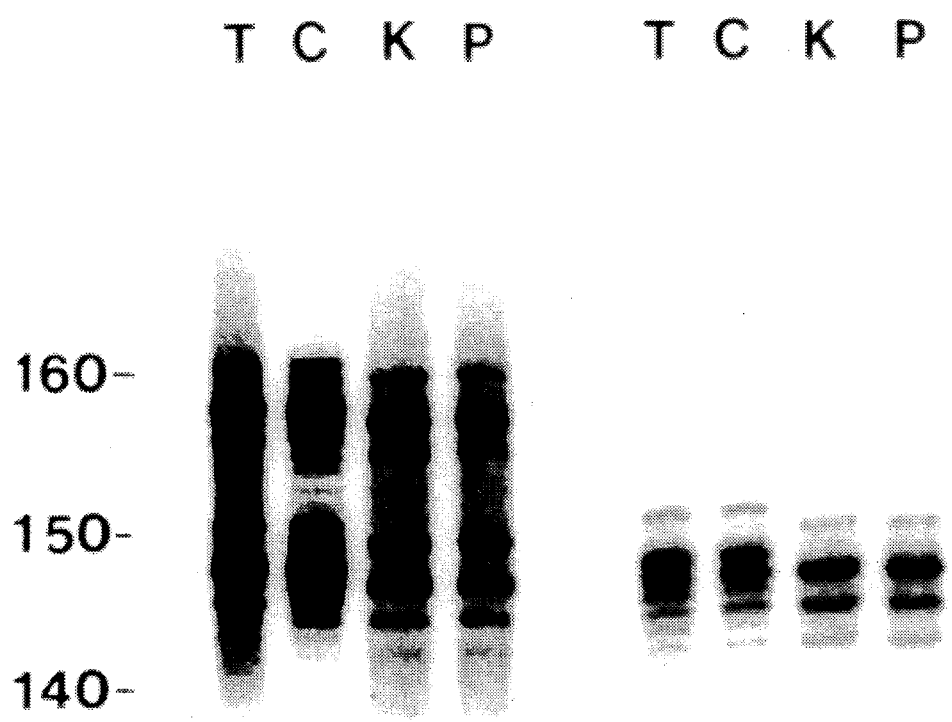
FIG. 5 is an autoradiograph showing treatment of amplified DNA containing $(dC-dA)_n.(dG-dT)_n$ sequences with either the Klenow fragment of DNA polymerase I or with T4 DNA polymerase.

Griffin et al. (1988), (*Am. J. Hum. Genet.* 43(Suppl.):A185) demonstrated that DNA fragments amplified by the PCR could not be efficiently ligated to blunt ended vectors without first repairing the ends of the fragments with T4 DNA polymerase. To test whether "ragged" ends were responsible for the extra bands associated with (dC-dA)$_n$.(dG-dT)$_n$ amplified fragments, amplified DNA (C) was treated with the Klenow fragment of DNA polymerase I (K), with T4 DNA polymerase (P) or with no enzyme (T) as shown in FIG. 5. Both Klenow enzyme and T4 DNA polymerase simplified the banding pattern somewhat by eliminating extra bands which differed in size from the most intense bands by 1 base. These enzymes also reduced the size of the most intense bands by 1 base. The most likely explanation for these results is the Taq polymerase produces a mixture of fragments during the PCR with different types of ends. The most intense bands in the untreated samples are likely derived from double stranded molecules with single base noncomplementary 3' overhangs. The fainter bands which are 1 base smaller than the major bands are likely to be blunt ended. The 3'-5' exonuclease activity of Klenow or T4 DNA polymerase converts the molecules with overhangs into blunt ended molecules. Clark (1988), (*Nucleic Acids Res.* 16:9677) showed that a variety of DNA polymerases including Taq polymerase can add a noncomplementary extra base to the 3' ends of blunt ended molecules.

Remaining after Klenow or T4 DNA polymerase treatment are extra bands which differ in size from the major bands by multiples of two bases. The data in Table 4 and FIG. 6 strongly indicate that these particular extra bands are the result of the skipping of repeats by the Taq polymerase during the amplification cycles. Sequencing of individual clones of DNA amplified for 27 cycles (first lane, FIG. 6) verifies that repeats have been deleted in the amplified DNA (Table 4). The largest of the predominant-sized fragments in the amplified DNA (with the exception of the one 20-mer) are 19 and 13 repeats in length, consistent with the Z+6, Z–6 genotype of the donor of the template DNA. Substantial numbers of clones containing fewer repeats are also seen, and this distribution matches the pattern of fragments shown in the first lane of FIG. 6. If the Taq polymerase is skipping repeats during the amplification cycles, as seems likely from the sequencing data, then further cycles of amplification in addition to the first 27 should reduce the intensities of the bands corresponding to the original DNA in the template and increase the intensities of the bands corresponding to fragments with skipped repeats. This is exactly what is observed in FIG. 6 for the amplified DNA from the reactions with 54 and 81 total amplification cycles.

TABLE 43

Distribution of Number of Repeats in Clones of Amplified DNA

| Number of Repeats | Number of Clones |
|---|---|
| 20 | 1 |
| 19 | 20 |
| 18 | 22 |
| 17 | 4 |
| 16 | 5 |
| 15 | 1 |
| 14 | 0 |
| 13 | 22 |
| 12 | 18 |
| 11 | 3 |
| 10 | 3 |
| 9 | 3 |

Example VII

Use of (dC-dA)$_n$.(dG-dT)$_n$ polymorphisms to identify individuals.

General Procedure

Genomic DNA from a collection of 18 unrelated individuals and from an unknown individual was isolated from blood and amplified with various (dC-dA)$_n$.(dG-dT)$_n$ markers as described under Example II. Genotype frequencies were calculated from the allele frequencies shown in Table 43 assuming Hardy-Weinberg equilibria.

Results

One individual out of a group of 18 unrelated volunteers was selected so that the identity of this individual was unknown. The unknown DNA sample and the control samples were then typed for the Mfd3 and Mfd4 markers. As shown in Table 44, only three of the 18 controls had Mfd3 and Mfd4 genotypes consistent with the unknown sample, namely, individuals 22, 35 and 42. Further typing of these three samples and the unknown with four additional markers as shown in Table 44, conclusively demonstrated that the unknown DNA sample came from individual 22.

Table 45 shows the expected genotype frequencies for the six typed markers for individual 22 using the allele frequency data from Table 46. Single genotypes range in frequency from 0.04 to 0.49. The frequency for the entire collection of six markers is the product of the individual probabilities or $1.5 \times 10^{-5}$ or about 1 in 65,000 people. Choosing a better, more informative collection of (dC-dA)$_n$.(dG-dT)$_n$ markers would result in considerably greater discriminant ion.

TABLE 44

Genotypes for Identification Test

| | Markers | | | | | |
|---|---|---|---|---|---|---|
| Indiv. | Mfd3 | Mfd4 | Mfd9 | Mfd1 | Mfd8 | Mfd11 |
| 7 | 137,137 | 169,171 | | | | |
| 8 | 131,137 | 169,169 | | | | |
| 10 | 131,143 | 169,169 | | | | |
| 11 | 131,143 | 169,163 | | | | |
| 12 | 143,133 | 169,173 | | | | |
| 14 | 137,143 | 169,169 | | | | |
| 22 | 137,137 | 169,169 | 98,92 | 194,192 | 187,185 | 108,116 |
| ukn | 137,137 | 169,169 | 98,92 | 194,192 | 187,185 | 108,116 |
| 23 | 139,143 | 169,167 | | | | |
| 25 | 137,143 | 169,163 | | | | |
| 26 | 133,143 | 169,171 | | | | |
| 27 | 143,143 | 169,169 | | | | |
| 30 | 137,143 | 169,171 | | | | |
| 31 | 137,143 | 169,169 | | | | |
| 33 | 137,143 | 169,171 | | | | |
| 34 | 143,143 | 169,169 | | | | |
| 35 | 137,137 | 169,169 | 100,92 | 192,192 | 185,183 | 108,108 |
| 41 | 137,131 | 169,171 | | | | |
| 42 | 137,137 | 169,169 | 104,100 | 192,192 | 185,185 | 120,108 |

TABLE 46

Examples of Different Categories of $(dC-dA)_n \cdot (dG-dT)_n$ Repeat Sequences

| Category | 5' Flanking Sequence | Repeat Sequence | 3' Flanking Sequence |
|---|---|---|---|
| Perfect | TTTAGAAAAA (SEQ. ID. NO: 398) | $(AC)_{19}$ (SEQ. ID. NO: 397) | CCCCAAAGCT (SEQ. ID. NO: 399) |
| | ACAGGCATCA (SEQ. ID. NO: 401) | $(AC)_{20}$ (SEQ. ID. NO: 400) | CACAAAGTGC (SEQ. ID. NO: 402) |
| | CATGCACGTG (SEQ. ID. NO: 404) | $(CA)_{20}$ (SEQ. ID. NO: 403) | TACACCAGCT (SEQ. ID. NO: 405) |
| Imperfect | TTGTTGATTT (SEQ. ID. NO: 407) | $(CA)_{11}CT(CA)_4$ (SEQ. ID. NO: 406) | TACTGATGTG (SEQ. ID. NO: 408) |
| | CTTTCTCAGG (SEQ. ID. NO: 410) | $A(CA)_7GAG(AC)_{14}A$ (SEQ. ID. NO: 409) | GGCAATGACA (SEQ. ID. NO: 411) |
| | CAGTCCAAGC (SEQ. ID. NO: 413) | $(CA)_8G(AC)_4AG(AC)_3AT(AC)_{10}A$ (SEQ. ID. NO. 412) | ATTTTCATTC (SEQ. ID. NO: 414) |
| | ATATAAACAT (SEQ. ID. NO: 416) | $(CA)_5G(ACA)G(AC)_7A$ (SEQ. ID. NO: 415) | ACAATTAACA (SEQ. ID. NO: 417) |
| Compound (Perfect) | CCTTGTCTC (SEQ. ID. NO: 419) | $(AC)_{16}(TC)_{10}$ (SEQ. ID. NO: 418) | AGCCAGGCAC (SEQ. ID. NO: 420) |
| | ATACATACAT (SEQ. ID. NO: 422) | $(AC)_{20}AG(AGAC)_5AGA$ (SEQ. ID. NO: 421) | ATACTGTCCT (SEQ. ID. NO: 423) |
| | ACTCCATCTC (SEQ. ID. NO: 425) | $(A)_{17}G(CA)_{16}C$ (SEQ. ID. NO: 424) | TCACTACATT (SEQ. ID. NO: 426) |
| Compound (Imperfect) | GGCATGCATG (SEQ. ID. NO: 428) | $(CA)_9A(AC)_{19}A(GA)_7$ (SEQ. ID. NO: 427) | CATGCTGTTC (SEQ. ID. NO: 429) |
| | TCTTACACCA (SEQ. ID. NO: 431) | $T(CT)_{12}GTT(TC)_{11}T(CA)_{14}A(AC)_6$ (SEQ. ID. NO: 430) | CCACTGTGCT (SEQ. ID. NO: 432) |

TABLE 45

Genotype Frequencies

| Marker | Genotype for #22 | Allele Frequency for #22 | Genotype* Frequency for #22 |
|---|---|---|---|
| Mfd3 | 137,137 | 39% 137 | 15% |
| Mfd4 | 169,169 | 70% 169 | 49% |
| Mfd9 | 98,92 | 6% 98, 31% 92 | 4% |
| Mfd1 | 192,194 | 60% 192, 16% 194 | 20% |
| Mfd8 | 185,187 | 54% 185, 27% 187 | 29% |
| Mfd11 | 108,116 | 43% 108, 10% 116 | 9% |
| | | | Total = 0.0015% |

*Homozygote genotype frequency = (allele frequency)$^2$
Heterozygote genotype frequency = 2(allele$_1$)(allele$_2$)

EXAMPLE VIII

Analyzing the dependence of $(dC-dA)_n \cdot (dG-dT)_n$ marker informativeness of repeat sequence length and sequence type.

Repeat Sequences $(dC-dA)_n \cdot (dG-dT)_n$ sequences were obtained either by computer search of GenBank, Version 54, for all sequences with six or more consecutive CA or GT repeats, or by sequencing m13 clones selected by stringent hybridization to poly (dC-dA).poly(dG-dT) (Weber and May, 1989, supra.). m13 libraries were produced by ligating size-selected human genomic Sau3A I, Alu I, or Sau3A I/Taq I fragments in the range of 150–400 bp into mp10, mp18 or mp19 vectors. Size-selected fragments were obtained by electrophoresis on preparative agarose gels and elution using GENECLEAN (Bio 101 Inc., LaJolla, Calif.).

Rules for categorizing $(dC-dA)_n \cdot (dG-dT)_n$ sequences, i.e. perfect sequence, imperfect sequence, compound repeat sequence; are described elsewhere in this application. Examples are listed in Table 46 as follows:

A total of 55 human $(dC-dA)_n \cdot (dG-dT)_n$ sequences were obtained by searching GenBank Version 54 for all sequences with six or more CA or GT repeats. 57 $(dC-dA)_n \cdot (dG-dT)_n$ sequences were determined in the lab after selecting random human genomic DNA clones by hybridization to poly(dC-dA).poly(dG-dT). These repeat sequences were classified as either perfect (no interruptions in the run of dinucleotide repeats), imperfect (one or more interruptions in the run of repeats), or compound (a run of perfect or imperfect CA or GT repeats adjacent to a run of another simple sequence repeat). Examples of repeat sequences in each of the categories are shown in Table 46 above; numbers of sequences in each category are listed in Table 47 as follows:

TABLE 47

Numbers of $(dC-dA)_n \cdot (dG-dT)_n$ Sequences
in Different Sequence Categories

| Category | GenBank | Clones | Totals |
|---|---|---|---|
| Perfect | 37 | 35 | 72 (64%) |
| Imperfect | 13 | 15 | 28 (25%) |
| Compound (Perfect) | 0 | 4 | 4 (4%) |
| Compound (Imperfect) | 5 | 3 | 8 (7%) |

Perfect repeat sequences predominated and compound repeat sequences were relatively infrequent. The proportions of sequences of the various types were similar for the GenBank and clone sequences.

Length distributions of the GenBank and clone $(dC-dA)_n \cdot (dG-dT)_n$ sequences are shown in FIG. 7. The two distributions were similar except that a much greater proportion of the GenBank $(dC-dA)_n \cdot (dG-dT)_n$ sequences contained 6–9 repeats. Few sequences were found with more than 24 repeats.

Example IX

PIC Determination.

Conditions for the amplification reactions were essentially as described in Weber and May, 1989, supra. except that a recombinant Taq polymerase (AmpliTaq, Perkin Elmer Cetus, Norwalk, Conn.) was used and samples were processed through 27 temperature cycles consisting of 1 min at 94°, 2 min at 55° and 2 min at 72°. Denaturing polyacrylamide DNA sequencing gels contained 6.5% acrylamide and were 0.4 mm thick. Size standards were mp8 dideoxynucleotide sequencing ladders obtained using a −20 primer (Catalog #1211, New England Biolabs, Beverly, Mass.).

Allele sizes were measured as the midpoint between the CA-strand and GT-strand bands (Weber and May 1989). The error in this procedure is estimated at 1–2 bases. Relative sizes of the different alleles for a single marker, however, were determined without appreciable error by loading a common set of amplified DNA fragments on all gels used to determine PIC values for that marker.

For all polymorphisms, the size of one of the allelic fragments either matched exactly or differed by only one base from the size determined by knowledge of the original genomic sequences used to synthesize the PCR primers. In cases where the allele sizes differed from the expected fragment size by a single base, the most frequent of the two alleles nearest in size to the expected allele was taken to represent the sequenced allele. The size-matched allele was used to set the number of repeats for each of the other alleles simply by assuming that every 2 bp difference in allele size corresponded to a difference of one repeat unit. For amplified fragments which did not show any size polymorphism, the identity of the fragment of the expected size was verified by digesting the amplified DNA with a restriction enzyme which was predicted to cut within the interior of the fragment.

Allele sizes from 82–146 chromosomes were measured for estimations of allele frequencies and PIC values. For four of the markers, DNA samples were obtained from unrelated Caucasian volunteers from the Marshfield, Wis. area; for another six markers, DNA samples were from CEPH family parents (Caucasians from France, Venezuela, and the US); and for the remaining markers, DNA samples were from selected CEPH family grandparents.

Statistical Analysis

The weighted average number of repeats for a marker was defined as $$\sum_{i=1}^{p} f_i n_i$$

where p is the total number of alleles for that marker, $f_i$ was the estimate of allele frequency for the ith allele and $n_i$ was the number of repeats for the ith allele. The relationship between PIC and the weighted average number of repeats (for the perfect repeat sequence markers) was approximated by applying SPSS/PC+ software (SPSS Inc., Chicago, Ill.) to fit a logistic type curve to the data using an iterative least squares method. Other types of curves were not judged to fit the data as well as the logistic curve. The equation of the least squares curve shown in FIGS. 2 and 3 is $$PIC = \frac{c}{1 + e^{a-bw}}$$

where w is the weighted average number of repeats, a=4.388, b=0.297 and c=0.85. To compare the fit of the logistic curve to the two sets of data shown in FIG. 2, residuals were calculated for each data set, and differences between residuals for the two sets were analyzed using a paired t-test.

A plot of PIC values versus numbers of repeats for markers with perfect repeat sequences is shown in the FIG. 8A. Information describing the least informative markers, including PCR primer sequences, is listed in Table 48 as follows:

TABLE 48

$(dC-dA)_n \cdot (dG-dT)_n$ Markers with Low Informativeness

| Gene or Clone Name[a] | Chromosome Location[b] | Expected size of amplified DNA (bp)[c] | Repeat Sequence | Primer Sequence[d] | No. of Alleles |
|---|---|---|---|---|---|
| Plasminogen activator-urokinase | 10q24–qter | 111 | $(AC)_6$ (SEQ. ID. NO: 433) | AGGAGTTAGGAGCTGGAGGT (SEQ. ID. NO: 434) CAACCCCACCTCACATTTGT (SEQ. ID. NO: 435) | 0.00 1 |
| Hemoglobin, epsilon | 11p15.5 | 76 | $(AC)_7$ (SEQ. ID. NO: 436) | CTCACAGCCAGAAATTAGCA (SEQ. ID. NO: 437) ACAGAGAATATGGAATTGGT (SEQ. ID. NO: 438) | 0.00 1 |
| ADP/ATP translocase | | 87 | $(CA)_8$ (SEQ. ID. NO: 439) | CGAGCTCAAGAAGGTGATCT (SEQ. ID. NO: 440) GAGGATTCTACGTGGTTCTC (SEQ. ID. NO: 441) | 0.00 1 |
| Hemoglobin, gamma G | 11p15.5 | 96 | $(AC)_9A$ (SEQ. ID. NO: 442) | AGATTTAGATATTGCCAATTC (SEQ. ID. NO: 443) TTAAAAATCTTGTCATGCAGA (SEQ. ID. NO: 444) | 0.00 1 |

TABLE 48-continued (dC-dA)$_n$ · (dG-dT)$_n$ Markers with Low Informativeness

| Gene or Clone Name[a] | Chromosome Location[b] | Expected size of amplified DNA (bp)[c] | Repeat Sequence | Primer Sequence[d] | | No. of Alleles |
|---|---|---|---|---|---|---|
| JW42 | | 120 | (CA)$_{12}$ (SEQ. ID. NO: 445) | CAAAATCTAAGAAAATAAACTG (SEQ. ID. NO: 446) CTACTTTTATTGATGCAATACT (SEQ. ID. NOL 447) | | 0.00 1 |
| Angiogenin | 14q11–q13 | 119 | (AC)$_8$A (SEQ. ID. NO: 448) | CCAAGTACCAACATACCAAC (SEQ. ID. NO: 449) AAAGGTGGCTACCCTGAATG (SEQ. ID. NO: 450) | | 0.06 2 |
| SW10 | | 157 | (AC)$_{14}$ (SEQ. ID. NO: 451) | GTGCTCAGTGACTTTCCCT (SEQ. ID. NO: 452) CGAGGACCATTTTTTATTCA (SEQ. ID. NO: 453) | | 0.18 3 |
| SW13 | | 137 | (AC)$_{11}$A (SEQ. ID. NO: 454) | TCGACCAGCCCCTATAATCA (SEQ. ID. NO: 455) ATGCCCTAAGCCCTGTGTC (SEQ. ID. NO: 456) | | 0.21 3 |

[a]Sequences of the genes were taken from GenBank. Sequences for JW42, SW10 and SW13 were determined in the laboratory. GenBank accession numbers: Plasminogen activator-urokinase, X02419; Hemoglobin, J00179; ADP/ATP translocase, J03592; Angiogenin, M11567.
[b]Chromosome locations for ADP/ATP translocase, JW42, SW10 and SW13 are unknown.
[c]Based on the original DNA sequence used to determine primer sequences.
[d]CA-strand primers are listed first for each pair.
[e][433] = Sequence Identification Number (SEQ ID NO:)

The weighted average number of repeats for each marker was chosen as the most appropriate measure of repeat length. Only sequences with 12 or fewer repeats were found to be nonpolymorphic (PIC=0). Informativeness of the markers generally increased as the average number of repeats increased, especially in the range of about 11–17 repeats. Maximum informativeness of the markers tested was 0.81 PIC.

Usually, at the time of PCR primer synthesis, the repeat sequence of only one allele is available. To determine if the numbers of repeats in the original sequences were good predictors of marker informativeness, these repeat lengths were plotted versus PIC values as shown in FIG. 8B. The fit of this data to the curve (the identical curve was shown in both plots) was not significantly different from the weighted average points shown at the top (p=0.57).

Informativeness for markers with imperfect repeat sequences was plotted versus repeat length in FIG. 9. The open squares were obtained by counting all the repeats, including imperfect repeats, within the repeat sequence. These points were all below the least squares curve (from FIGS. 8A and 8B) with especially disappointing PIC values for some sequences with the greatest numbers of repeats. The probability that all nine data points lie below the curve on the basis of chance alone is very small (0.002). The filled squares were obtained using the longest run of perfect repeats as a measure of repeat length. When plotted in this fashion, the data for the imperfect repeat sequence markers exhibited a much better fit to the least squares curve.

Various modes of carrying out the invention are contemplated as being within the scope of the following claims particularly pointing out and distinctly claiming the subject matter which is regarded as the invention.

I claim:

1. An isolated nucleic acid molecule consisting of a sequence selected from the group consisting of SEQ. ID. NOS: 1 to 26, 28 to 53, 56, 59, 62, 65, 68, 71, 74, 77, 80, 98, 113, 137, 143, 163, 186, 215, 249, 301, 304, 307, 312, 317, 322, 325, 328, 331, 334, 337, 340, 343, 346, 352, 355, 358, 361, 364, 370, 373, 376, 379, 382, 388, 391, and 394.

2. A method for detecting a polymorphic genetic marker of the form $(dC\ dA)_n \cdot (dG\ dT)_n$, wherein $n \geq 6$, comprising:
   a. isolating genomic DNA from a subject;
   b. analyzing the isolated genomic DNA for the presence of said polymorphic genetic marker using a nucleic acid molecule consisting of a sequence selected from the group consisting of SEQ. ID. NOS: 1 to 26, 28 to 53, 56, 59, 62, 65, 68, 71, 74, 77, 80, 98, 113, 137, 143, 163, 186, 215, 249, 301, 304, 307, 312, 317, 322, 325, 328, 331, 334, 337, 340, 343, 346, 352, 355, 358, 361, 364, 370, 373, 376, 379, 382, 388, 391, and 394 to detect said polymorphic genetic marker.

3. The method of claim 2 wherein step (b) further comprises:
   a. amplifying DNA molecules from the genomic DNA by the polymerase chain reaction;
   b. resolving the amplified DNA molecules by electrophoresis;
   c. detecting the amplified DNA molecules; and
   d. determining the allele of the polymorphic marker present in the genomic DNA.

4. The method of claim 2 wherein the sequence of the nucleic acid molecule used in step (b) is a perfect repeat sequence.

5. The method of claim 2 wherein the sequence of the nucleic acid molecule used in step (b) is an imperfect repeat sequence.

6. The method of claim 2 wherein the sequence of the nucleic acid molecule used in step (b) is a compound repeat sequence.

7. A kit for performing the method of claim 2 comprising:

a. oligonucleotide primer pairs consisting of sequence pairs selected from the group consisting of: SEQ. ID. NOS: 54 and 55, SEQ. ID. NOS: 57 and 58, SEQ. ID. NOS: 60 and 61, SEQ. ID. NOS: 63 and 64, SEQ. ID. NOS: 66 and 67, SEQ. ID. NOS: 69 and 70, SEQ. ID. NOS: 72 and 73, SEQ. ID. NOS: 75 and 76, SEQ. ID. NOS: 78 and 79, SEQ. ID. NOS: 81 and 82, SEQ. ID. NOS: 99 and 100, SEQ. ID. NOS: 114 and 115, SEQ. ID. NOS: 138 and 139, SEQ. ID. NOS: 144 and 145, SEQ. ID. NOS: 164 and 165, SEQ. ID. NOS: 187 and 188, SEQ. ID. NOS: 211 and 212, SEQ. ID. NOS: 216 and 217, SEQ. ID. NOS: 250 and 251, SEQ. ID. NOS: 302 and 303, SEQ. ID. NOS: 305 and 306, SEQ. ID. NOS: 308 and 309, SEQ. ID. NOS: 313 and 314, SEQ. ID. NOS: 318 and 319, SEQ. ID. NOS: 323 and 324, SEQ. ID. NOS: 326 and 327, SEQ. ID. NOS: 329 and 330, SEQ. ID. NOS: 332 and 333, SEQ. ID. NOS: 335 and 336, SEQ. ID. NOS: 338 and 339, SEQ. ID. NOS: 341 and 342, SEQ. ID. NOS: 344 and 345, SEQ. ID. NOS: 347 and 348, SEQ. ID. NOS: 350 and 351, SEQ. ID. NOS: 353 and 354, SEQ. ID. NOS: 356 and 357, SEQ. ID. NOS: 359 and 360, SEQ. ID. NOS: 362 and 363, SEQ. ID. NOS: 365 and 366, SEQ. ID. NOS: 371 and 372, SEQ. ID. NOS: 374 and 375, SEQ. ID. NOS: 377 and 378, SEQ. ID. NOS: 380 and 381, SEQ. ID. NOS: 383 and 384, SEQ. ID. NOS: 389 and 390, SEQ. ID. NOS: 392 and 393, and SEQ. ID. NOS: 395 and 396; and b. reagents necessary for the amplification of DNA sequences using the polymerase chain reaction.

8. The kit of claim 7 wherein the sequence of the amplified DNA is a perfect repeat sequence.

9. The kit of claim 7 wherein the sequence of the amplified DNA is an imperfect repeat sequence.

10. The kit of claim 7 wherein the sequence of the amplified DNA is a compound repeat sequence.

* * * * *

SEQUENCE LISTING ( 1 ) GENERAL INFORMATION:

( i i i ) NUMBER OF SEQUENCES: 460

( 2 ) INFORMATION FOR SEQ ID NO:1:

( i ) SEQUENCE CHARACTERISTICS:
      ( A ) LENGTH: 265 base pairs
      ( B ) TYPE: nucleic acid
      ( C ) STRANDEDNESS: double
      ( D ) TOPOLOGY: linear ( i i ) MOLECULE TYPE: DNA (genomic)

( v i i ) IMMEDIATE SOURCE:
      ( B ) CLONE: Mfd11

( x i ) SEQUENCE DESCRIPTION: SEQ ID NO:1:

```
GATCCACTCT  TCCTGGCCAG  CTGTCAAAAC  ACTCTGCACC  TGCTCTCGGA  CCATAACAAG    60
TATTACTCAT  GAAGGTGACA  GTTCCTCAGG  CCCACAGTAA  TAAAGACACA  CACACACACA   120
CACACACACA  CACACACACA  CACACACACA  CAGGCATTTA  AAAAAATGCA  ATAGGTCAAC   180
AACACTCAAT  CTAAAACCCT  AGGGGCTGGG  CACGGTAGCT  CACGCCTCTA  ATCCCTGCAC   240
TTTGGGAGGC  TGAGGTGAGT  GGATC                                            265
```

( 2 ) INFORMATION FOR SEQ ID NO:2:

( i ) SEQUENCE CHARACTERISTICS:
      ( A ) LENGTH: 318 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Homo sapiens
      ( C ) INDIVIDUAL ISOLATE: Caucasian
      ( F ) TISSUE TYPE: Blood ( v i i ) IMMEDIATE SOURCE:
      ( B ) CLONE: Mfd12

( v i i i ) POSITION IN GENOME:
      ( A ) CHROMOSOME/SEGMENT: 16

( i x ) FEATURE:
      ( A ) NAME/KEY: repeat_region
      ( B ) LOCATION: 159..199
      ( D ) OTHER INFORMATION: /rpt_type="tandem"
          / rpt_family="(dC-dA)n.(dG-dT)n"
          / citation=([2])

( i x ) FEATURE:
      ( A ) NAME/KEY: misc_feature
      ( B ) LOCATION: 62..80
      ( C ) IDENTIFICATION METHOD: experimental
      ( D ) OTHER INFORMATION: /evidence=EXPERIMENTAL
          / standard_name="PCR primer"
          / citation=([1])

( i x ) FEATURE:
      ( A ) NAME/KEY: misc_feature
      ( B ) LOCATION: complement (277..295)
      ( C ) IDENTIFICATION METHOD: experimental
      ( D ) OTHER INFORMATION: /evidence=EXPERIMENTAL
          / standard_name="PCR primer"
          / citation=([1])

( i x ) FEATURE:
      ( A ) NAME/KEY: -

(B) LOCATION: 1..2

(x) PUBLICATION INFORMATION:
(A) AUTHORS: Weber, J. L.
Kwitek, A. E.
May, A. E.
(B) TITLE: Dinucleotide repeat polymorphisms at the
D16S260, D16S261, D16S265, D16S266 and D16S267
loci
(C) JOURNAL: Nucleic Acids Res.
(D) VOLUME: 18
(F) PAGES: 4034-
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:2:

| | | | | | |
|---|---|---|---|---|---|
| GATCAAAATG | CTTTGAAAAA | GGCTGAGCAA | AACTTTCTTT | GTGGCCGTGG | GACTTGAGAG | 60
| AGGTTGAGAT | GCTGACATGC | ATTAAAAATC | TACAGAGGAG | AAACGAGTAT | GAAGTGCTAC | 120
| CCAGGCTCAT | GTCACCATAC | CTAACACTTG | CCTTCCCAAC | ACACACAC | ACACACAC | 180
| ATACACACAC | ACACACACAG | TGTTTTTCAC | CTAGGAGGCC | CTCTGAACAG | CTGCTACTGG | 240
| CAATCCATGG | AGCAATTTAG | GATGGGATGG | AGATTGCATT | ATAACAGCCA | CCCTGAGTAG | 300
| GTATGCACAA | CCGTGATC | | | | | 318

(2) INFORMATION FOR SEQ ID NO:3:

(i) SEQUENCE CHARACTERISTICS:
(A) LENGTH: 242 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd13

(viii) POSITION IN GENOME:
(A) CHROMOSOME/SEGMENT: 19

(ix) FEATURE:
(A) NAME/KEY: repeat_region
(B) LOCATION: 60..110
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 8..27
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (130..150)
(C) IDENTIFICATION METHOD: experimental ( D ) OTHER INFORMATION: /evidence=EXPERIMENTAL
/ standard_name="PCR primer"
/ citation=([1])

( i x ) FEATURE:
( A ) NAME/KEY: misc_feature
( B ) LOCATION: 1..242
( C ) IDENTIFICATION METHOD: experimental
( D ) OTHER INFORMATION: /evidence=EXPERIMENTAL
/ standard_name="Only one strand sequenced"

( x ) PUBLICATION INFORMATION:
( A ) AUTHORS: Weber, J. L.
Kappel, C.
May, P. E.
Kwitek, A. E.
( B ) TITLE: Dinucleotide repeat polymorphism at the
D19S75 locus
( C ) JOURNAL: Nucleic Acids Res.
( D ) VOLUME: 18
( F ) PAGES: 4639-
( G ) DATE: 1990

( x ) PUBLICATION INFORMATION:
( A ) AUTHORS: Weber, James L.
May, Paula E.
( B ) TITLE: Abundant Class of Human DNA Polymorphisms
Which Can Be Typed Using the Polymerase Chain
Reaction
( C ) JOURNAL: Am. J. Hum. Genet.
( D ) VOLUME: 44
( F ) PAGES: 388-396
( G ) DATE: 1989

( x i ) SEQUENCE DESCRIPTION: SEQ ID NO:3:

| | | | | | |
|---|---|---|---|---|---|
| GATCAGCTTC | CCTTTGCTCC | CCAAACGAGA | GCCTCTGCTC | TTGGGCACCT | CAGAGATGCG | 60 |
| TGTGTGTGTG | TGTGTGTGTG | TGTGTGTGTG | TGTGTGTGCG | CGTGTGTGTG | CATGCAGACT | 120 |
| ATTTGGAAAT | TCGCTTTTAG | ATGGATTAAT | GCTCGGTAAA | GCTCTCATGT | TTCTCCAAAG | 180 |
| TATATCCAGT | GAGTAACAGT | AGTATTTTCA | ATCAATAGTA | TTGCTTGCTA | AAATAACAGA | 240 |
| TC | | | | | | 242 |

( 2 ) INFORMATION FOR SEQ ID NO:4:

( i ) SEQUENCE CHARACTERISTICS:
( A ) LENGTH: 175 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Homo sapiens
( C ) INDIVIDUAL ISOLATE: Caucasian
( F ) TISSUE TYPE: Blood ( v i i ) IMMEDIATE SOURCE:
( B ) CLONE: Mfd14

( v i i i ) POSITION IN GENOME:
( A ) CHROMOSOME/SEGMENT: 9

( i x ) FEATURE:
( A ) NAME/KEY: repeat_region
( B ) LOCATION: 82..128
( D ) OTHER INFORMATION: /rpt_type="tandem"
/ rpt_family="(dC-dA)n.(dG-dT)n"
/ citation=([2])

( i x ) FEATURE:
( A ) NAME/KEY: misc_feature
( B ) LOCATION: 58..76
( C ) IDENTIFICATION METHOD: experimental
( D ) OTHER INFORMATION: /evidence=EXPERIMENTAL / standard_name="PCR primer"
/ citation=([1])

( i x ) FEATURE:
    ( A ) NAME/KEY: misc_feature
    ( B ) LOCATION: complement (131..150)
    ( C ) IDENTIFICATION METHOD: experimental
    ( D ) OTHER INFORMATION: /evidence=EXPERIMENTAL
        / standard_name="PCR primer"
        / citation=([1])

( i x ) FEATURE:
    ( A ) NAME/KEY: misc_feature
    ( B ) LOCATION: 1..175
    ( C ) IDENTIFICATION METHOD: experimental
    ( D ) OTHER INFORMATION: /evidence=EXPERIMENTAL
        / standard_name="Only one strand sequenced"

( x ) PUBLICATION INFORMATION:
    ( A ) AUTHORS: Weber, J. L.
        May, P. E.
    ( B ) TITLE: Dinucleotide repeat polymorphism at the D9S43
        locus
    ( C ) JOURNAL: Nucleic Acids Res.
    ( D ) VOLUME: 18
    ( F ) PAGES: 2203-
    ( G ) DATE: 1990

( x ) PUBLICATION INFORMATION:
    ( A ) AUTHORS: Weber, James L.
        May, Paula E.
    ( B ) TITLE: Abundant Class of Human DNA Polymorphisms
        Which Can Be Typed Using the Polymerase Chain
        Reaction
    ( C ) JOURNAL: Am. J. Hum. Genet.
    ( D ) VOLUME: 44
    ( F ) PAGES: 388-396
    ( G ) DATE: 1989

( x i ) SEQUENCE DESCRIPTION: SEQ ID NO:4:

```
AGCTGCTGAA    TTTGGTTTGC    TGGTGTTTTG    TTCAGGATTT    TTGTGTATAT    GTTCATCAAG         60

GATATTGTCC    TGAGGATTTT    CTGTGTGTGT    GTGTGTGTGT    GTGTGTGTGT    GTGTGTGTGT        120

GTGTGTGTCT    GCCAGGTTTT    GATATCAGAA    TAATGCTGGC    CTCATAGAAT    GAGCT             175
```

( 2 ) INFORMATION FOR SEQ ID NO:5:

( i ) SEQUENCE CHARACTERISTICS:
        ( A ) LENGTH: 261 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd15

( v i i i ) POSITION IN GENOME:
        ( A ) CHROMOSOME/SEGMENT: 17q11.2- q12

( i x ) FEATURE:
        ( A ) NAME/KEY: repeat_region
        ( B ) LOCATION: 179..228
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 1..261
        ( C ) IDENTIFICATION METHOD: experimental ( D ) OTHER INFORMATION: /evidence=EXPERIMENTAL
                            / standard_name="Only one strand sequenced"

( i x ) FEATURE:
                    ( A ) NAME/KEY: misc_feature
                    ( B ) LOCATION: 99..118
                    ( C ) IDENTIFICATION METHOD: experimental
                    ( D ) OTHER INFORMATION: /evidence=EXPERIMENTAL
                            / standard_name="PCR primer"
                            / citation=([1])

( i x ) FEATURE:
                    ( A ) NAME/KEY: misc_feature
                    ( B ) LOCATION: complement (237..260)
                    ( C ) IDENTIFICATION METHOD: experimental
                    ( D ) OTHER INFORMATION: /evidence=EXPERIMENTAL
                            / standard_name="PCR primer"
                            / citation=([1])

( x ) PUBLICATION INFORMATION:
                    ( A ) AUTHORS: Weber, J. L.
                            Kwitek, A. E.
                            May, P. E.
                            Wallace, M. R.
                            Collins, F. S.
                            Ledbetter, D. H.
                    ( B ) TITLE: Dinucleotide repeat polymorphisms at the
                            D17S250 and D17S261 loci
                    ( C ) JOURNAL: Nucleic Acids Res.
                    ( D ) VOLUME: 18
                    ( F ) PAGES: 4635-4635
                    ( G ) DATE: 1990

( x ) PUBLICATION INFORMATION:
                    ( A ) AUTHORS: Weber, James L.
                            May, Paula E.
                    ( B ) TITLE: Abundant Class of Human DNA Polymorphisms
                            Which Can Be Typed Using the Polymerase Chain
                            Reaction
                    ( C ) JOURNAL: Am. J. Hum. Genet.
                    ( D ) VOLUME: 44
                    ( F ) PAGES: 388-396
                    ( G ) DATE: 1989

( x i ) SEQUENCE DESCRIPTION: SEQ ID NO:5:

AGCTTCCAAA    CTAGTAGAGG    GGGAAAAATA    AGAAAAAAAT    GAAGTGATGA    AAAGTAATTG        60

ATCAAAAAGA    AGAGAGAAGA    AAAAGTAAG     CATAAAAAGG    AAGAATCAAA    TAGACAATAA       120

AAATATGTGT    GTGTTTATAT    ATATATATAC    ACATACATAA    ACTTTCAAAT    GGTTTCAAAC       180

ACACACACAC    ACACACACAC    ACACACACAC    ACACACACAC    ACACACACTT    TCAAATGGTT       240

TAAATATATA    TATGGCCAGC    T                                                         261

( 2 ) INFORMATION FOR SEQ ID NO:6:

( i ) SEQUENCE CHARACTERISTICS:
                    ( A ) LENGTH: 180 base pairs
                    ( B ) TYPE: nucleic acid
                    ( C ) STRANDEDNESS: double
                    ( D ) TOPOLOGY: linear ( i i ) MOLECULE TYPE: DNA (genomic)

( v i ) ORIGINAL SOURCE:
                    ( A ) ORGANISM: Homo sapiens
                    ( C ) INDIVIDUAL ISOLATE: Caucasian
                    ( F ) TISSUE TYPE: Blood ( v i i ) IMMEDIATE SOURCE:
                    ( B ) CLONE: Mfd17

( v i i i ) POSITION IN GENOME:
                    ( A ) CHROMOSOME/SEGMENT: 3q ( i x ) FEATURE:
                    ( A ) NAME/KEY: repeat_region (B) LOCATION: 33..78
(D) OTHER INFORMATION: /rpt_type="tandem"
    / rpt_family="(dC-dA)n.(dG-dT)n"
    / citation=([2])

(ix) FEATURE:
    (A) NAME/KEY: misc_feature
    (B) LOCATION: 10..29
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: complement (84..103)
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: 1..180
    (C) IDENTIFICATION METHOD: experimental
    (D) OTHER INFORMATION: /evidence=EXPERIMENTAL
        / standard_name="Only one strand sequenced"

(x) PUBLICATION INFORMATION:
    (A) AUTHORS: Weber, J. L.
        May, P. E.
        Patterson, D.
        Drabkin, H.
        Killary, A.
    (B) TITLE: Dinucleotide repeat polymorphism at the
        D3S196 locus
    (C) JOURNAL: Nucleic Acids Res.
    (D) VOLUME: 18
    (F) PAGES: 4635-
    (G) DATE: 1990

(x) PUBLICATION INFORMATION:
    (A) AUTHORS: Weber, James L.
        May, Paula E.
    (B) TITLE: Abundant Class of Human DNA Polymorphisms
        Which Can Be Typed Using the Polymerase Chain
        Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:6:

```
AGCTCAGTCT TTCCACTGGG GAACATGGTG GGGTGTGTGT GTGTGTGTGT GTGTGTGTGT        60
GTGTGTGTGT GTGTGTGTTC ATTATGGGAA TTCAACAAAG AGTTGATGTG AATATTTGTG       120
AAGACAGAAA AAATTGCCAT GAGATTTGGA ATTCCCTTTG GCAATCATCA TATTGTAGCT       180
```

(2) INFORMATION FOR SEQ ID NO:7:

(i) SEQUENCE CHARACTERISTICS:
    (A) LENGTH: 203 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian
    (F) TISSUE TYPE: Blood (vii) IMMEDIATE SOURCE:
    (B) CLONE: Mfd18

(viii) POSITION IN GENOME:

(A) CHROMOSOME/SEGMENT: 8

(ix) FEATURE:
    (A) NAME/KEY: repeat_region
    (B) LOCATION: 23..58
    (D) OTHER INFORMATION: /rpt_type="tandem"
        / rpt_family="(dC-dA)n.(dG-dT)n"
        / citation=([2])

(ix) FEATURE:
    (A) NAME/KEY: misc_feature
    (B) LOCATION: 1..22
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: complement (60..80)
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: 1..203
    (C) IDENTIFICATION METHOD: experimental
    (D) OTHER INFORMATION: /evidence=EXPERIMENTAL
        / standard_name="Only one strand sequenced"

(x) PUBLICATION INFORMATION:
    (A) AUTHORS: Weber, J. L.
        Kwitek, A. E.
        May, P. E.
        Patterson, D.
        Drabkin, H.
    (B) TITLE: Dinucleotide repeat polymorphisms at the
        D8S85, D8S87 and D8S88 loci
    (C) JOURNAL: Nucleic Acids Res.
    (D) VOLUME: 18
    (F) PAGES: 4038-
    (G) DATE: 1990

(x) PUBLICATION INFORMATION:
    (A) AUTHORS: Weber, James L.
        May, Paula E.
    (B) TITLE: Abundant Class of Human DNA Polymorphisms
        Which Can Be Typed Using the Polymerase Chain
        Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:7:

```
AGCTATCATC  ACCCTATAAA  ATACACACAC  ACACACACAC  ACACACACAC  ACACACACTC      60

GGGAGAGACA  TGGTTAAACT  GTAGAAACAA  ACAATCTCAA  GTTTAAGTCA  CTTTATTCAA     120

CAAGAATTTC  TTGCTCATGC  TCTATGTCTA  AGATAAGTAA  GTGTAAGTGA  TGGGCAAGGA     180

AAGATGGAGG  TAGTGATTCA  GCT                                                203
```

(2) INFORMATION FOR SEQ ID NO:8:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens
        (C) INDIVIDUAL ISOLATE: Caucasian (F) TISSUE TYPE: Blood (vii) IMMEDIATE SOURCE:
　　　　(B) CLONE: Mfd19

(viii) POSITION IN GENOME:
　　　　(A) CHROMOSOME/SEGMENT: 2

(ix) FEATURE:
　　　　(A) NAME/KEY: repeat_region
　　　　(B) LOCATION: 105..178
　　　　(D) OTHER INFORMATION: /rpt_type="tandem"
　　　　　　/ rpt_family="(dC-dA)n.(dG-dT)n"
　　　　　　/ citation=([2])

(ix) FEATURE:
　　　　(A) NAME/KEY: misc_feature
　　　　(B) LOCATION: 53..72
　　　　(C) IDENTIFICATION METHOD: experimental
　　　　(D) OTHER INFORMATION: /evidence=EXPERIMENTAL
　　　　　　/ standard_name="PCR primer"
　　　　　　/ citation=([1])

(ix) FEATURE:
　　　　(A) NAME/KEY: misc_feature
　　　　(B) LOCATION: complement (180..199)
　　　　(C) IDENTIFICATION METHOD: experimental
　　　　(D) OTHER INFORMATION: /evidence=EXPERIMENTAL
　　　　　　/ standard_name="PCR primer"
　　　　　　/ citation=([1])

(ix) FEATURE:
　　　　(A) NAME/KEY: misc_feature
　　　　(B) LOCATION: 1..200
　　　　(C) IDENTIFICATION METHOD: experimental
　　　　(D) OTHER INFORMATION: /evidence=EXPERIMENTAL
　　　　　　/ standard_name="Only one strand sequenced"

(x) PUBLICATION INFORMATION:
　　　　(A) AUTHORS: Weber, J. L.
　　　　　　　　May, P. E.
　　　　(B) TITLE: Dinucleotide repeat polymorphism at the D2S71
　　　　　　　locus
　　　　(C) JOURNAL: Nucleic Acids Res.
　　　　(D) VOLUME: 18
　　　　(F) PAGES: 2203-
　　　　(G) DATE: 1990

(x) PUBLICATION INFORMATION:
　　　　(A) AUTHORS: Weber, James L.
　　　　　　　　May, Paula E.
　　　　(B) TITLE: Abundant Class of Human DNA Polymorphisms
　　　　　　　Which Can Be Typed Using the Polymerase Chain
　　　　　　　Reaction
　　　　(C) JOURNAL: Am. J. Hum. Genet.
　　　　(D) VOLUME: 44
　　　　(F) PAGES: 388-396
　　　　(G) DATE: 1989

(xi) SEQUENCE DESCRIPTION: SEQ ID NO:8:

```
AGCTGAAGTA TTGTCAACTC CAAATAATGC TTTGAGGACC TCCAAAGGGA GTTCTAACCC    60

TTTGGCCATT TGCTTCCTAA GTCAGACAGA GAGAGAGAGA GTGAGTGTGT GTGTGTGTGT   120

GTGTGTGTGT GTGTGTGTGT GTGTGTGTGT GTCTGTGTGT CTGTGTGTGT GTGTGTGTTG   180

AAGCAACAAT GTAACAAGCT                                               200
```

(2) INFORMATION FOR SEQ ID NO:9:

(i) SEQUENCE CHARACTERISTICS:
　　　　(A) LENGTH: 240 base pairs
　　　　(B) TYPE: nucleic acid
　　　　(C) STRANDEDNESS: double
　　　　(D) TOPOLOGY: linear (ii) MOLECULE TYPE: DNA (genomic)

( v i ) ORIGINAL SOURCE:
    ( A ) ORGANISM: Homo sapiens
    ( C ) INDIVIDUAL ISOLATE: Caucasian
    ( F ) TISSUE TYPE: Blood ( v i i ) IMMEDIATE SOURCE:
    ( B ) CLONE: Mfd20

( v i i i ) POSITION IN GENOME:
    ( A ) CHROMOSOME/SEGMENT: 7

( i x ) FEATURE:
    ( A ) NAME/KEY: repeat_region
    ( B ) LOCATION: 51..84
    ( D ) OTHER INFORMATION: /rpt_type="tandem"
            / rpt_family="(dC-dA)n.(dG-dT)n"
            / citation=([2])

( i x ) FEATURE:
    ( A ) NAME/KEY: misc_feature
    ( B ) LOCATION: 4..23
    ( C ) IDENTIFICATION METHOD: experimental
    ( D ) OTHER INFORMATION: /evidence=EXPERIMENTAL
            / standard_name="PCR primer"
            / citation=([1])

( i x ) FEATURE:
    ( A ) NAME/KEY: misc_feature
    ( B ) LOCATION: complement (114..135)
    ( C ) IDENTIFICATION METHOD: experimental
    ( D ) OTHER INFORMATION: /evidence=EXPERIMENTAL
            / standard_name="PCR primer"
            / citation=([1])

( i x ) FEATURE:
    ( A ) NAME/KEY: misc_feature
    ( B ) LOCATION: 1..240
    ( C ) IDENTIFICATION METHOD: experimental
    ( D ) OTHER INFORMATION: /evidence=EXPERIMENTAL
            / standard_name="Only one strand sequenced"

( x ) PUBLICATION INFORMATION:
    ( A ) AUTHORS: Weber, J. L.
            Kwitek, A. E.
            May, A. E.
    ( B ) TITLE: Dinucleotide repeat polymorphisms at the
            D7S435 and D7S440 loci
    ( C ) JOURNAL: Nucleic Acids Res.
    ( D ) VOLUME: 18
    ( F ) PAGES: 4039-
    ( G ) DATE: 1990

( x ) PUBLICATION INFORMATION:
    ( A ) AUTHORS: Weber, James L.
            May, Paula E.
    ( B ) TITLE: Abundant Class of Human DNA Polymorphisms
            Which Can Be Typed Using the Polymerase Chain
            Reaction
    ( C ) JOURNAL: Am. J. Hum. Genet.
    ( D ) VOLUME: 44
    ( F ) PAGES: 388-396
    ( G ) DATE: 1989

( x i ) SEQUENCE DESCRIPTION: SEQ ID NO:9:

```
AGCTTTGAGT AGGTGGCATC TCAGGGATTT GCATTTGTGT GCAGTCTGTC GTGTGTGTGT      60
GTGTGTGTGT GTGTGTGTGT GTGTCTCTAT TTATCTTTGA AAAAAATATT TTTGAAGATG     120
CCTTCAACAT TTTAACATAG AGGGCCGGGG CACGGTGGCT CATGCCTGTA ATCCCAGCAC     180
TTTGAGAGGC TGAGGCGGGT GGATCACTTG AGGTCAGGAA TTCAAGACCA GCCTGGCCAA     240
```

( 2 ) INFORMATION FOR SEQ ID NO:10:

( i ) SEQUENCE CHARACTERISTICS:
        ( A ) LENGTH: 264 base pairs
        ( B ) TYPE: nucleic acid
        ( C ) STRANDEDNESS: double ( D ) TOPOLOGY: linear ( i i ) MOLECULE TYPE: DNA (genomic)

( v i ) ORIGINAL SOURCE:
    ( A ) ORGANISM: Homo sapiens
    ( C ) INDIVIDUAL ISOLATE: Caucasian
    ( F ) TISSUE TYPE: Blood ( v i i ) IMMEDIATE SOURCE:
    ( B ) CLONE: Mfd22

( v i i i ) POSITION IN GENOME:
    ( A ) CHROMOSOME/SEGMENT: 4

( i x ) FEATURE:
    ( A ) NAME/KEY: repeat_region
    ( B ) LOCATION: 153..193
    ( D ) OTHER INFORMATION: /rpt_type="tandem"
        / rpt_family="(dC-dA)n.(dG-dT)n"
        / citation=([2])

( i x ) FEATURE:
    ( A ) NAME/KEY: misc_feature
    ( B ) LOCATION: 89..107
    ( C ) IDENTIFICATION METHOD: experimental
    ( D ) OTHER INFORMATION: /evidence=EXPERIMENTAL
        / standard_name="PCR primer"
        / citation=([1])

( i x ) FEATURE:
    ( A ) NAME/KEY: misc_feature
    ( B ) LOCATION: complement (220..238)
    ( C ) IDENTIFICATION METHOD: experimental
    ( D ) OTHER INFORMATION: /evidence=EXPERIMENTAL
        / standard_name="PCR primer"
        / citation=([1])

( i x ) FEATURE:
    ( A ) NAME/KEY: misc_feature
    ( B ) LOCATION: 1..264
    ( C ) IDENTIFICATION METHOD: experimental
    ( D ) OTHER INFORMATION: /evidence=EXPERIMENTAL
        / standard_name="Only one strand sequenced"

( x ) PUBLICATION INFORMATION:
    ( A ) AUTHORS: Weber, J. L.
        May, P. E.
    ( B ) TITLE: Dinucleotide repeat polymorphism at the
        D4S171 locus
    ( C ) JOURNAL: Nucleic Acids Res.
    ( D ) VOLUME: 18
    ( F ) PAGES: 2202-
    ( G ) DATE: 1990

( x ) PUBLICATION INFORMATION:
    ( A ) AUTHORS: Weber, James L.
        May, Paula E.
    ( B ) TITLE: Abundant Class of Human DNA Polymorphisms
        Which Can Be Typed Using the Polymerase Chain
        Reaction
    ( C ) JOURNAL: Am. J. Hum. Genet.
    ( D ) VOLUME: 44
    ( F ) PAGES: 388-396
    ( G ) DATE: 1989

( x i ) SEQUENCE DESCRIPTION: SEQ ID NO:10:

```
AGCTACTCAG GGGGCTAAGG CACAAGAATT CTTGAACCAG AGAAGCGGAG GTTGCAGTGA        60

GCCAAGATCG CACCACTGCA CTCCAGCCTG GGTAAAGAGT GAGGCTGTCT GAAAAAATAA      120

AAATGAAAAT AAAAAATTAT ATATACATAC ATACACACAC ACACACACAC ACACACACAC      180

ACACACACAC ACAGAGACAG ACAGACAGAC AGACAGAATA CTGTCCTCTT ACTGGACCAT      240

CATTTACATA CTTTCAAATG AGCT                                              264
```

( 2 ) INFORMATION FOR SEQ ID NO:11:

(i) SEQUENCE CHARACTERISTICS:
        (A) LENGTH: 178 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens
        (C) INDIVIDUAL ISOLATE: Caucasian
        (F) TISSUE TYPE: Blood (vii) IMMEDIATE SOURCE:
        (B) CLONE: Mfd23

(viii) POSITION IN GENOME:
        (A) CHROMOSOME/SEGMENT: 16

(ix) FEATURE:
        (A) NAME/KEY: repeat_region
        (B) LOCATION: 30..69
        (D) OTHER INFORMATION: /rpt_type="tandem"
            / rpt_family="(dC-dA)n.(dG-dT)n"
            / citation=([2])

(ix) FEATURE:
        (A) NAME/KEY: misc_feature
        (B) LOCATION: 10..28
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: complement (91..109)
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: 1..178
        (C) IDENTIFICATION METHOD: experimental
        (D) OTHER INFORMATION: /evidence=EXPERIMENTAL
            / standard_name="Only one strand sequenced"

(x) PUBLICATION INFORMATION:
        (A) AUTHORS: Weber, J. L.
            Kwitek, A. E.
            May, A. E.
        (B) TITLE: Dinucleotide repeat polymorphisms at the
            D16S260, D16S261, D16S265, D16S266 and D16S267
            loci
        (C) JOURNAL: Nucleic Acids Res.
        (D) VOLUME: 18
        (F) PAGES: 4034-
        (G) DATE: 1990

(x) PUBLICATION INFORMATION:
        (A) AUTHORS: Weber, James L.
            May, Paula E.
        (B) TITLE: Abundant Class of Human DNA Polymorphisms
            Which Can Be Typed Using the Polymerase Chain
            Reaction
        (C) JOURNAL: Am. J. Hum. Genet.
        (D) VOLUME: 44
        (F) PAGES: 388-396
        (G) DATE: 1989

(xi) SEQUENCE DESCRIPTION: SEQ ID NO:11:

```
AGCTCTCTGA GTCCTCTGTG CACTTTGTGG TGTGTGTGTG TGTGTGTGTG TGTGTGTGTG        60

TGTGTGTGTT GATGCCTGTC ACACTCTTCC TAGAGACTGC CATGTCTGGC CATCAGACTG       120

AATTGGTGAC AATTCAGTCG AGAGACACCA TGCTTCCCAA ATTCCCTGAC CTTGAGCT         178
```

( 2 ) INFORMATION FOR SEQ ID NO:12:

( i ) SEQUENCE CHARACTERISTICS:
        ( A ) LENGTH: 186 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd24

( v i i i ) POSITION IN GENOME:
        ( A ) CHROMOSOME/SEGMENT: 16

( i x ) FEATURE:
        ( A ) NAME/KEY: repeat_region
        ( B ) LOCATION: 61..107
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 41..60
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (110..129)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..186
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
                Kwitek, A. E.
                May, A. E.
        ( B ) TITLE: Dinucleotide repeat polymorphisms at the
            D16S260, D16S261, D16S265, D16S266 and D16S267
            loci
        ( C ) JOURNAL: Nucleic Acids Res.
        ( D ) VOLUME: 18
        ( F ) PAGES: 4034-
        ( G ) DATE: 1990

( x ) PUBLICATION INFORMATION:
        ( A ) AUTHORS: Weber, James L.
                May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:12:

```
AGCTCTCTGC  AAGGACAGAC  AAGGGGCCTT  TGACCTTGAG  AAGCTTGTAT  CTTTCTCAGG      60
```

ACACACACAC ACACAGAGAC ACACACACAC ACACACACAC ACACACAGGC AATGACAGCC        120

AAGGTAGATG GGAGCTGCCC TCTCCAGCCA GAGCATGGGG CAGGGCAAGC AAGTCAGTGT        180

GGCCTC        186

( 2 ) INFORMATION FOR SEQ ID NO:13:

( i ) SEQUENCE CHARACTERISTICS:
        ( A ) LENGTH: 190 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd25

( v i i i ) POSITION IN GENOME:
        ( A ) CHROMOSOME/SEGMENT: 20

( i x ) FEATURE:
        ( A ) NAME/KEY: repeat_region
        ( B ) LOCATION: 88..109
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 42..61
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (152..171)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..190
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            May, P. E.
        ( B ) TITLE: Dinucleotide repeat polymorphism at the
            D20S27 locus
        ( C ) JOURNAL: Nucleic Acids Res.
        ( D ) VOLUME: 18
        ( F ) PAGES: 2202-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:13:

| AGCTTCGCTT | GTACCAGTAG | AGTTAAAACT | GGGTCACCAT | TTTTATGCGA | GCGTATGGAT | 60 |
| ACACATACAT | CCACACTCGA | ACCCCAAACA | CACACACACA | CACACACACT | TCATTTCAGA | 120 |
| GTCTAATTAA | AACTCTATTA | TACATAATTT | TCTTCCAGAT | CAATGGTGGT | GTTGGATCAA | 180 |
| AATTGTAGCT | | | | | | 190 |

( 2 ) INFORMATION FOR SEQ ID NO:14:

( i ) SEQUENCE CHARACTERISTICS:
        ( A ) LENGTH: 223 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd26

( v i i i ) POSITION IN GENOME:
        ( A ) CHROMOSOME/SEGMENT: 18

( i x ) FEATURE:
        ( A ) NAME/KEY: repeat_region
        ( B ) LOCATION: 129..185
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 90..109
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (185..204)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..223
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            May, P. E.
        ( B ) TITLE: Dinucleotide repeat polymorphism at the
            D18S34 locus
        ( C ) JOURNAL: Nucleic Acids Res.
        ( D ) VOLUME: 18
        ( F ) PAGES: 2201-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396

(G) DATE: 1989

(xi) SEQUENCE DESCRIPTION: SEQ ID NO:14:

| | | | | | | |
|---|---|---|---|---|---|---|
| AGCTCAGTAT | GAAAGAGAAG | CAGCAAAATT | ACCATTTCAT | CAAATGCAAA | AAAATCAGTG | 60 |
| CAATTCTTTT | AATGAAACTC | CCAAGACTTC | AGAAAATTCT | CTCTGGCTAT | TTTTCATTAT | 120 |
| TTCTTTAGAC | ACACACACAC | ACACACACAC | ACACACACAC | ACACACACAC | ACACACACAC | 180 |
| ACACATTCTT | GCCAGGAACA | TGAGTGAGGG | TTGAAGAAGA | GCT | | 223 |

(2) INFORMATION FOR SEQ ID NO:15:

(i) SEQUENCE CHARACTERISTICS:
        (A) LENGTH: 194 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens
        (C) INDIVIDUAL ISOLATE: Caucasian
        (F) TISSUE TYPE: Blood (vii) IMMEDIATE SOURCE:
        (B) CLONE: Mfd27

(viii) POSITION IN GENOME:
        (A) CHROMOSOME/SEGMENT: 5

(ix) FEATURE:
        (A) NAME/KEY: repeat_region
        (B) LOCATION: 78..135
        (D) OTHER INFORMATION: /rpt_type="tandem"
            / rpt_family="(dC-dA)n.(dG-dT)n"
            / citation=([2])

(ix) FEATURE:
        (A) NAME/KEY: misc_feature
        (B) LOCATION: 26..46
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: complement (151..170)
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: 1..194
        (C) IDENTIFICATION METHOD: experimental
        (D) OTHER INFORMATION: /evidence=EXPERIMENTAL
            / standard_name="Only one strand sequenced"

(x) PUBLICATION INFORMATION:
        (A) AUTHORS: Weber, J. L.
            Kwitek, A. E.
            May, A. E.
        (B) TITLE: Dinucleotide repeat polymorphisms at the
            D5S107, D5S108, D5S111, D5S117, and D5S118 loci
        (C) JOURNAL: Nucleic Acids Res.
        (D) VOLUME: 18
        (F) PAGES: 4035-
        (G) DATE: 1990

(x) PUBLICATION INFORMATION:
        (A) AUTHORS: Weber, James L.
            May, Paula E.
        (B) TITLE: Abundant Class of Human DNA Polymorphisms
            Which Can Be Typed Using the Polymerase Chain Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:15:

```
AGCTGTAAAA CGGTATATAT AGCATGATCC ACTTTAACCC AAATACTTAT TCATAGACAC      60

ATGTGTGGGC ATGCATGCAC ACACACACAC ACACAAACAC ACACACACAC ACACACACAC     120

ACACACACAC ACACAGAGAG AGAGAGAGAC ATGCTGTTCA AGTTGATGCC TCCGGGAAGT     180

GGAATTAAAG AGCT                                                       194
```

(2) INFORMATION FOR SEQ ID NO:16:

(i) SEQUENCE CHARACTERISTICS:
        (A) LENGTH: 230 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens
        (C) INDIVIDUAL ISOLATE: Caucasian
        (F) TISSUE TYPE: Blood (vii) IMMEDIATE SOURCE:
        (B) CLONE: Mfd28

(viii) POSITION IN GENOME:
        (A) CHROMOSOME/SEGMENT: 10

(ix) FEATURE:
        (A) NAME/KEY: repeat_region
        (B) LOCATION: 27..91
        (D) OTHER INFORMATION: /rpt_type="tandem"
            / rpt_family="(dC-dA)n.(dG-dT)n"
            / citation=([2])

(ix) FEATURE:
        (A) NAME/KEY: misc_feature
        (B) LOCATION: 1..20
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: complement (129..150)
        (C) IDENTIFICATION METHOD: experimental
        (D) OTHER INFORMATION: /evidence=EXPERIMENTAL
            / standard_name="PCR primer"
            / citation=([1])

(ix) FEATURE:
        (A) NAME/KEY: misc_feature
        (B) LOCATION: 1..230
        (C) IDENTIFICATION METHOD: experimental
        (D) OTHER INFORMATION: /evidence=EXPERIMENTAL
            / standard_name="Only one strand sequenced"

(x) PUBLICATION INFORMATION:
        (A) AUTHORS: Weber, James L.
            May, Paula E.
        (B) TITLE: Dinucleotide repeat polymorphism at the
            D10S89 locus
        (C) JOURNAL: Nucleic Acids Res.
        (D) VOLUME: 18
        (F) PAGES: 4637-
        (G) DATE: 1990

(x) PUBLICATION INFORMATION:
        (A) AUTHORS: Weber, James L.

May, Paula E.
            ( B ) TITLE: Abundant Class of Human DNA Polymorphisms
                        Which Can Be Typed Using the Polymerase Chain
                        Reaction
            ( C ) JOURNAL: Am. J. Hum. Genet.
            ( D ) VOLUME: 44
            ( F ) PAGES: 388-396
            ( G ) DATE: 1989

( x i ) SEQUENCE DESCRIPTION: SEQ ID NO:16:

| | | | | | | |
|---|---|---|---|---|---|---|
| AGCTAGGCCT | GAAGGCTTCT | GGAGCATGTG | TGTGTGTGTG | TGTGTGTGTG | TGTGTGTGTG | 60 |
| TGTGTGTGTC | TGTGTGTGTG | TGTGTGTGTG | TAATAATGTC | TTTTATAAAT | GAAAACTCTA | 120 |
| TACATATATG | AAAATAATGT | CACTAGTGTT | CTTAACTTAT | GCCAAGAAAC | ATAGAAGAGA | 180 |
| GATGATTAAA | GAACACTTTG | TTTTATTTCC | TTTAATTTTC | TATTTTAGCT | | 230 |

( 2 ) INFORMATION FOR SEQ ID NO:17:

( i ) SEQUENCE CHARACTERISTICS:
            ( A ) LENGTH: 221 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd30

( v i i i ) POSITION IN GENOME:
            ( A ) CHROMOSOME/SEGMENT: 3

( i x ) FEATURE:
            ( A ) NAME/KEY: repeat_region
            ( B ) LOCATION: 103..139
            ( D ) OTHER INFORMATION: /rpt_type="tandem"
                    / rpt_family="(dC-dA)n.(dG-dT)n"
                    / citation=([2])

( i x ) FEATURE:
            ( A ) NAME/KEY: misc_feature
            ( B ) LOCATION: 72..91
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: complement (144..163)
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: 1..221
            ( C ) IDENTIFICATION METHOD: experimental
            ( D ) OTHER INFORMATION: /evidence=EXPERIMENTAL
                    / standard_name="Only one strand sequenced"

( x ) PUBLICATION INFORMATION:
            ( A ) AUTHORS: Weber, J. L.
                        May, P. E.
            ( B ) TITLE: Dinucleotide repeat polymorphism at the
                        D3S240 locus
            ( C ) JOURNAL: Nucleic Acids Res.
            ( D ) VOLUME: 18
            ( F ) PAGES: 2201-
            ( G ) DATE: 1990

( x ) PUBLICATION INFORMATION:
    ( A ) AUTHORS: Weber, James L.
                 May, Paula E.
    ( B ) TITLE: Abundant Class of Human DNA Polymorphisms
            Which Can Be Typed Using the Polymerase Chain
            Reaction
    ( C ) JOURNAL: Am. J. Hum. Genet.
    ( D ) VOLUME: 44
    ( F ) PAGES: 388-396
    ( G ) DATE: 1989

( x i ) SEQUENCE DESCRIPTION: SEQ ID NO:17:

```
AGCTAAAAGA TGGTAGGTCA GGTGTGGCAA TGTTCTGAAA ATGGAGGCAA GTTCATGGAA      60

ATGTTGGTGT TTGAAATCAC TGATGACAAT GACATATATA ACTGTGTGTG TGTGTGTGTG     120

TGTGTGTGTG TGTGTGTGTA AAATGTAGAG ATATGGGACA TGGGTGCTGG TCCCTATATG     180

AATATTTAAG GATCACTAAC AGTTTCACCT TGCATGAAGC T                         221
```

( 2 ) INFORMATION FOR SEQ ID NO:18:

( i ) SEQUENCE CHARACTERISTICS:
        ( A ) LENGTH: 143 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd32

( v i i i ) POSITION IN GENOME:
        ( A ) CHROMOSOME/SEGMENT: 18

( i x ) FEATURE:
        ( A ) NAME/KEY: repeat_region
        ( B ) LOCATION: 56..80
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 1..21
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (86..104)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..143
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
                  May, P. E.
        ( B ) TITLE: Dinucleotide repeat polymorphism at the
            D18S35 locus
        ( C ) JOURNAL: Nucleic Acids Res.

(D) VOLUME: 18
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:18:

```
AGCTAGATTT TTACTTCTCT GACCAAAACA CAGCAATGTG ATTGAAATAT TATGGACACA      60
CACACACACA CACACACACA GATTAGTCAG GCATGTACAA CCAGGAAGAA AAGAAGTGA     120
AGCAATTTTA GTCAATACAA GCT                                            143
```

(2) INFORMATION FOR SEQ ID NO:19:

(i) SEQUENCE CHARACTERISTICS:
(A) LENGTH: 155 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd33

(viii) POSITION IN GENOME:
(A) CHROMOSOME/SEGMENT: 22

(ix) FEATURE:
(A) NAME/KEY: repeat_region
(B) LOCATION: 82..137
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 50..68
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (136..155)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..155
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, James L.
May, Paula E.
(B) TITLE: Dinucleotide repeat polymorphism at the
D22S156 locus
(C) JOURNAL: Nucleic Acids Res.

(D) VOLUME: 18
            (F) PAGES: 4639-
            (G) DATE: 1990

(x) PUBLICATION INFORMATION:
            (A) AUTHORS: Weber, James L.
                    May, Paula E.
            (B) TITLE: Abundant Class of Human DNA Polymorphisms
                    Which Can Be Typed Using the Polymerase Chain
                    Reaction
            (C) JOURNAL: Am. J. Hum. Genet.
            (D) VOLUME: 44
            (F) PAGES: 388-396
            (G) DATE: 1989

(x i) SEQUENCE DESCRIPTION: SEQ ID NO:19:

AGCTTGGAGG TCGAGGCTGC AGTGAGCCAA AATCTCTCCT CTGCACTCCA GCCTGGGAGT      60

CAGAGTGAGG CCCTGTCTCA AACACACACA CACACACACA CACACACACA TACACACACA    120

CACACACACA CACACACGTC TTTGGATTTG GAGCT                                155

(2) INFORMATION FOR SEQ ID NO:20:

(i) SEQUENCE CHARACTERISTICS:
                (A) LENGTH: 183 base pairs
                (B) TYPE: nucleic acid
                (C) STRANDEDNESS: double
                (D) TOPOLOGY: linear (i i) MOLECULE TYPE: DNA (genomic)

(v i) ORIGINAL SOURCE:
                (A) ORGANISM: Homo sapiens
                (C) INDIVIDUAL ISOLATE: Caucasian
                (F) TISSUE TYPE: Blood (v i i) IMMEDIATE SOURCE:
                (B) CLONE: Mfd34

(v i i i) POSITION IN GENOME:
                (A) CHROMOSOME/SEGMENT: 5

(i x) FEATURE:
                (A) NAME/KEY: repeat_region
                (B) LOCATION: 101..140
                (D) OTHER INFORMATION: /rpt_type="tandem"
                        / rpt_family="(dC-dA)n.(dG-dT)n"
                        / citation=([2])

(i x) FEATURE:
                (A) NAME/KEY: misc_feature
                (B) LOCATION: 77..97
                (C) IDENTIFICATION METHOD: experimental
                (D) OTHER INFORMATION: /evidence=EXPERIMENTAL
                        / standard_name="PCR primer"
                        / citation=([1])

(i x) FEATURE:
                (A) NAME/KEY: misc_feature
                (B) LOCATION: complement (143..164)
                (C) IDENTIFICATION METHOD: experimental
                (D) OTHER INFORMATION: /evidence=EXPERIMENTAL
                        / standard_name="PCR primer"
                        / citation=([1])

(i x) FEATURE:
                (A) NAME/KEY: misc_feature
                (B) LOCATION: 1..183
                (C) IDENTIFICATION METHOD: experimental
                (D) OTHER INFORMATION: /evidence=EXPERIMENTAL
                        / standard_name="Only one strand sequenced"

(x) PUBLICATION INFORMATION:
            (A) AUTHORS: Weber, J. L.
                    Kwitek, A. E.
                    May, P. E.
            (B) TITLE: Dinucleotide repeat polymorphisms at the D5S107, D5S108, D5S111, D5S117, and D5S118 loci
- (C) JOURNAL: Nucleic Acids Res.
- (D) VOLUME: 18
- (F) PAGES: 4035-
- (G) DATE: 1990

(x) PUBLICATION INFORMATION:
- (A) AUTHORS: Weber, James L.
  - May, Paula E.
- (B) TITLE: Abundant Class of Human DNA Polymorphisms Which Can Be Typed Using the Polymerase Chain Reaction
- (C) JOURNAL: Am. J. Hum. Genet.
- (D) VOLUME: 44
- (F) PAGES: 388-396
- (G) DATE: 1989

(xi) SEQUENCE DESCRIPTION: SEQ ID NO:20:

```
AGCTTCTAAC  TTTACTAAGC  TTTTTTCAAC  ACTTACCTGT  GACTATGATA  CATATCAATT     60
CATTAGAGTG  AAGACCTCAT  ATAGCCTTTT  GTTTGCATTC  GTGTGTGTGT  GTGTGTGTGT    120
GTGTGTGTGT  ATGTGTGTGT  ATGAAGAACT  AGAAAAAAGA  AACCCTGAAA  GCAGGAAATA    180
GCT                                                                      183
```

(2) INFORMATION FOR SEQ ID NO:21:

- (i) SEQUENCE CHARACTERISTICS:
  - (A) LENGTH: 191 base pairs
  - (B) TYPE: nucleic acid
  - (C) STRANDEDNESS: double
  - (D) TOPOLOGY: linear

- (ii) MOLECULE TYPE: DNA (genomic)

- (vi) ORIGINAL SOURCE:
  - (A) ORGANISM: Homo sapiens
  - (C) INDIVIDUAL ISOLATE: Caucasian
  - (F) TISSUE TYPE: Blood

- (vii) IMMEDIATE SOURCE:
  - (B) CLONE: Mfd36

- (viii) POSITION IN GENOME:
  - (A) CHROMOSOME/SEGMENT: 2

- (ix) FEATURE:
  - (A) NAME/KEY: repeat_region
  - (B) LOCATION: 59..103
  - (D) OTHER INFORMATION: /rpt_type="tandem"
    / rpt_family="(dC-dA)n.(dG-dT)n"
    / citation=([2])

- (ix) FEATURE:
  - (A) NAME/KEY: misc_feature
  - (B) LOCATION: 1..21
  - (C) IDENTIFICATION METHOD: experimental
  - (D) OTHER INFORMATION: /evidence=EXPERIMENTAL
    / standard_name="PCR primer"
    / citation=([1])

- (ix) FEATURE:
  - (A) NAME/KEY: misc_feature
  - (B) LOCATION: complement (146..165)
  - (C) IDENTIFICATION METHOD: experimental
  - (D) OTHER INFORMATION: /evidence=EXPERIMENTAL
    / standard_name="PCR primer"
    / citation=([1])

- (ix) FEATURE:
  - (A) NAME/KEY: misc_feature
  - (B) LOCATION: 1..191
  - (C) IDENTIFICATION METHOD: experimental
  - (D) OTHER INFORMATION: /evidence=EXPERIMENTAL
    / standard_name="Only one strand sequenced"

- (x) PUBLICATION INFORMATION:

(A) AUTHORS: Weber, J. L.
    May, P. E.
(B) TITLE: Dinucleotide repeat polymorphism at the D2S72
    locus
(C) JOURNAL: Nucleic Acids Res.
(D) VOLUME: 18
(F) PAGES: 2200-
(G) DATE: 1990

(x) PUBLICATION INFORMATION:
    (A) AUTHORS: Weber, James L.
        May, Paula E.
    (B) TITLE: Abundant Class of Human DNA Polymorphisms
        Which Can Be Typed Using the Polymerase Chain
        Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:21:

```
AGCTATAATT GCATCATTGC ACTCTTGTCT GGGTGACAGA GTGAGACCCT GTCTGAAAAC      60
ACACACACAC ACACACACAC ACACACACAT ACACACACAC ACATCCCCAC AACAACAACA     120
CAAAAAACTG CTGCTTGGGT CCCAACATAG ACCAGTTATA GACCAATTGA ATTAGAACCA     180
CCAGTGCTGG G                                                          191
```

(2) INFORMATION FOR SEQ ID NO:22:

(i) SEQUENCE CHARACTERISTICS:
    (A) LENGTH: 211 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian
    (F) TISSUE TYPE: Blood (vii) IMMEDIATE SOURCE:
    (B) CLONE: Mfd37

(viii) POSITION IN GENOME:
    (A) CHROMOSOME/SEGMENT: 19

(ix) FEATURE:
    (A) NAME/KEY: repeat_region
    (B) LOCATION: 92..112
    (D) OTHER INFORMATION: /rpt_type="tandem"
        / rpt_family="(dC-dA)n.(dG-dT)n"
        / citation=([2])

(ix) FEATURE:
    (A) NAME/KEY: misc_feature
    (B) LOCATION: 68..87
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: complement (111..132)
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: 1..211
    (C) IDENTIFICATION METHOD: experimental
    (D) OTHER INFORMATION: /evidence=EXPERIMENTAL / standard_name="Only one strand sequenced"

( x ) PUBLICATION INFORMATION:
            ( A ) AUTHORS: Weber, J. L.
                        May, P. E.
            ( B ) TITLE: Dinucleotide repeat polymorphism at the
                        D19S76 locus
            ( C ) JOURNAL: Nucleic Acids Res.
            ( D ) VOLUME: 18
            ( F ) PAGES: 2835-
            ( G ) DATE: 1990

( x ) PUBLICATION INFORMATION:
            ( A ) AUTHORS: Weber, James L.
                        May, Paula E.
            ( B ) TITLE: Abundant Class of Human DNA Polymorphisms
                        Which Can Be Typed Using the Polymerase Chain
                        Reaction
            ( C ) JOURNAL: Am. J. Hum. Genet.
            ( D ) VOLUME: 44
            ( F ) PAGES: 388-396
            ( G ) DATE: 1989

( x i ) SEQUENCE DESCRIPTION: SEQ ID NO:22:

| | | | | | |
|---|---|---|---|---|---|
| AGCTGACATT | TACATTTGTG | TGAATTTGTG | AATATTTGTG | TGAGTCTGTG | AGCACTTATT | 60 |
| CCTGTTCACA | AGGTGACAAG | GTGCCTATGT | ATGTGTGTGT | GTGTGTGTGT | GTTCTGAAAG | 120 |
| TAACACACTT | TTTTCTTTTC | TTTTTTTTTT | TTTTTGAGA | CAGAGTCTGG | CTCTGTCACC | 180 |
| CAGGCTGGAG | TGCAGTGGCA | AGATCTCAGC | T | | | 211 |

( 2 ) INFORMATION FOR SEQ ID NO:23:

( i ) SEQUENCE CHARACTERISTICS:
            ( A ) LENGTH: 210 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd39

( v i i i ) POSITION IN GENOME:
            ( A ) CHROMOSOME/SEGMENT: 8

( i x ) FEATURE:
            ( A ) NAME/KEY: repeat_region
            ( B ) LOCATION: 148..187
            ( D ) OTHER INFORMATION: /rpt_type="tandem"
                        / rpt_family="(dC-dA)n.(dG-dT)n"
                        / citation=([2])

( i x ) FEATURE:
            ( A ) NAME/KEY: misc_feature
            ( B ) LOCATION: 60..80
            ( C ) IDENTIFICATION METHOD: experimental
            ( D ) OTHER INFORMATION: /evidence=EXPERIMENTAL
                        / standard_name="PCR primer"
                        / citation=([1])

( i x ) FEATURE:
            ( A ) NAME/KEY: misc_feature
            ( B ) LOCATION: complement (190..209)
            ( C ) IDENTIFICATION METHOD: experimental
            ( D ) OTHER INFORMATION: /evidence=EXPERIMENTAL
                        / standard_name="PCR primer"
                        / citation=([1])

( i x ) FEATURE:
            ( A ) NAME/KEY: misc_feature (B) LOCATION: 1..210
(C) IDENTIFICATION METHOD: experimental
(D) OTHER INFORMATION: /evidence=EXPERIMENTAL
 / standard_name="Only one strand sequenced"

(x) PUBLICATION INFORMATION:
(A) AUTHORS: Weber, J. L.
 Kwitek, A. E.
 May, P. E.
 Patterson, D.
 Drabkin, H.
(B) TITLE: Dinucleotide repeat polymorphisms at the
 D8S85, D8S87 and D8S88 loci
(C) JOURNAL: Nucleic Acids Res.
(D) VOLUME: 18
(F) PAGES: 4038-
(G) DATE: 1990

(x) PUBLICATION INFORMATION:
(A) AUTHORS: Weber, James L.
 May, Paula E.
(B) TITLE: Abundant Class of Human DNA Polymorphisms
 Which Can Be Typed Using the Polymerase Chain
 Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:23:

```
AGCTATTATA ATGCTTAGAT TATATGAGAG CAAACCCAAT TCAGACAAGT AATTACCTTG      60

GGTTGGTTGT AAATTAAAAC TCTATTTCTT ACACCATCTC TCTCTCTCTC TCTCTCTCTC     120

TGTTTCTCTC TCTCTCTCTC TCTCTCAC ACACACACAC ACACACAC ACACAACACA         180

CACACACCAC TGTGCTTAAG TATTTGACAG                                       210
```

(2) INFORMATION FOR SEQ ID NO:24:

(i) SEQUENCE CHARACTERISTICS:
(A) LENGTH: 259 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd40

(viii) POSITION IN GENOME:
(A) CHROMOSOME/SEGMENT: 5

(ix) FEATURE:
(A) NAME/KEY: repeat_region
(B) LOCATION: 165..214
(D) OTHER INFORMATION: /rpt_type="tandem"
 / rpt_family="(dC-dA)n.(dG-dT)n"
 / citation=([2])

(ix) FEATURE:
(A) NAME/KEY: misc_feature
(B) LOCATION: 65..85
(C) IDENTIFICATION METHOD: experimental
(D) OTHER INFORMATION: /evidence=EXPERIMENTAL
 / standard_name="PCR primer"
 / citation=([1])

(ix) FEATURE:
(A) NAME/KEY: misc_feature
(B) LOCATION: complement (214..233)
(C) IDENTIFICATION METHOD: experimental (D) OTHER INFORMATION: /evidence=EXPERIMENTAL
    /standard_name="PCR primer"
    /citation=([1])

(ix) FEATURE:
    (A) NAME/KEY: misc_feature
    (B) LOCATION: 1..259
    (C) IDENTIFICATION METHOD: experimental
    (D) OTHER INFORMATION: /evidence=EXPERIMENTAL
        /standard_name="Only one strand sequenced"

(x) PUBLICATION INFORMATION:
    (A) AUTHORS: Weber, J. L.
        Kwitek, A. E.
        May, A. E.
    (B) TITLE: Dinucleotide repeat polymorphisms at the
        D5S107, D5S108, D5S111, D5S117, and D5S118 loci
    (C) JOURNAL: Nucleic Acids Res.
    (D) VOLUME: 18
    (F) PAGES: 4035-
    (G) DATE: 1990

(x) PUBLICATION INFORMATION:
    (A) AUTHORS: Weber, James L.
        May, Paula E.
    (B) TITLE: Abundant Class of Human DNA Polymorphisms
        Which Can Be Typed Using the Polymerase Chain
        Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:24:

| | | | | | |
|---|---|---|---|---|---|
| AGCTGTTAAA | ATCTCAAGGT | CCTATTATAG | GTACTACCAG | CCTTTGGTTA | TCTTTTATAT | 60 |
| GAATGGCATC | ATTTTAGAAG | GAAATAGGTA | GCCGTGGAAG | TGCTGGGATT | TTATAAAACT | 120 |
| AAAAATTATA | CATTAACACT | AATTTTCCAC | TCAAAGTTCC | AAAGCACACA | CACACACACA | 180 |
| CACACACACA | CCACACACAC | ACATACACAC | ACACTTTGGT | CCTGAACAAA | TGTGTTGCCA | 240 |
| TCTGCAGGAC | TCAAAAGCT | | | | | 259 |

(2) INFORMATION FOR SEQ ID NO:25:

(i) SEQUENCE CHARACTERISTICS:
    (A) LENGTH: 240 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian
    (F) TISSUE TYPE: Blood (vii) IMMEDIATE SOURCE:
    (B) CLONE: Mfd41

(viii) POSITION IN GENOME:
    (A) CHROMOSOME/SEGMENT: 17

(ix) FEATURE:
    (A) NAME/KEY: repeat_region
    (B) LOCATION: 114..147
    (D) OTHER INFORMATION: /rpt_type="tandem"
        /rpt_family="(dC-dA)n.(dG-dT)n"
        /citation=([2])

(ix) FEATURE:
    (A) NAME/KEY: misc_feature
    (B) LOCATION: 12..31
    (C) IDENTIFICATION METHOD: experimental
    (D) OTHER INFORMATION: /evidence=EXPERIMENTAL
        /standard_name="PCR primer"

( i x ) FEATURE:
        ( A ) NAME/KEY: misc_feature
        ( B ) LOCATION: complement (151..170)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..240
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            Kwitek, A. E.
            May, P. E.
            Wallace, M. R.
            Collins, F. S.
            Ledbetter, D. H.
        ( B ) TITLE: Dinucleotide repeat polymorphisms at the
            D17S250 and D17S261 loci
        ( C ) JOURNAL: Nucleic Acids Res.
        ( D ) VOLUME: 18
        ( F ) PAGES: 4640-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:25:

```
GATCAAAGTG TCAGGTTCTG TCATAGGACT ATTTTATTCA ACCCTACTAC ATAAACACTG      60

TTTGGACTCC ACCTAGGCAC TGAAGCCAGG AAGATTGCCG CTAATCTTCC TTTACACACA     120

CACACACACA CACACACACA CACACGGC TCAGGAGTAG GTTCCAGAA TCCAACAGCA        180

CGGGGTCTAG AATGGAGTAA GTTTAAGGC CATCACCTGT CACATGCCTG ACTTGGATTT      240
```

( 2 ) INFORMATION FOR SEQ ID NO:26:

( i ) SEQUENCE CHARACTERISTICS:
        ( A ) LENGTH: 179 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd42

( v i i i ) POSITION IN GENOME:
        ( A ) CHROMOSOME/SEGMENT: 14

( i x ) FEATURE:
        ( A ) NAME/KEY: repeat_region
        ( B ) LOCATION: 81..121
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 33..52
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (127..146)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..179
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            Kwitek, A. E.
            May, P. E.
        ( B ) TITLE: Dinucleotide repeat polymorphism at the
            D14S34 locus
        ( C ) JOURNAL: Nucleic Acids Res.
        ( D ) VOLUME: 18
        ( F ) PAGES: 4638-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:26:

```
GATCCCCCCT TGAACAAGTC CTCTTTAACT CAGGCCTCAA AGAATCCTAC AGATAGAGTT      60

CTAACAAATA TGACCTTATT CACACACACA CACACACACA CACACACACA CATACACACA     120

GAGAGAGTAA TAAGCAACTA CGTGTCAGAT TGAGCAGAAA CAACAAAGTA AACCAGATC      179
```

( 2 ) INFORMATION FOR SEQ ID NO:27:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd43

( v i i i ) POSITION IN GENOME:
        ( A ) CHROMOSOME/SEGMENT: 5q ( i x ) FEATURE:
        ( A ) NAME/KEY: repeat_region
        ( B ) LOCATION: 128..160
        ( D ) OTHER INFORMATION: /rpt_type="tandem"

/ rpt_family="(dC-dA)n.(dG-dT)n"
            / citation=([2])

( i x ) FEATURE:
            ( A ) NAME/KEY: misc_feature
            ( B ) LOCATION: 43..62
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: complement (160..181)
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: 1..225
            ( C ) IDENTIFICATION METHOD: experimental
            ( D ) OTHER INFORMATION: /evidence=EXPERIMENTAL
                    / standard_name="Only one strand sequenced"

( x ) PUBLICATION INFORMATION:
            ( A ) AUTHORS: Weber, J. L.
                    Polymeropoulos, M. H.
                    May, P. E.
                    Kwitek, A. E.
                    Xiao, H.
                    McPherson, J. D.
                    Wasmuth, J. J.
            ( B ) TITLE: Mapping of human chromosome 5 microsatellite
                    polymorphisms
            ( C ) JOURNAL: Genomics
            ( G ) DATE: 1991

( x ) PUBLICATION INFORMATION:
            ( A ) AUTHORS: Weber, James L.
                    May, Paula E.
            ( B ) TITLE: Abundant Class of Human DNA Polymorphisms
                    Which Can Be Typed Using the Polymerase Chain
                    Reaction
            ( C ) JOURNAL: Am. J. Hum. Genet.
            ( D ) VOLUME: 44
            ( F ) PAGES: 388-396
            ( G ) DATE: 1989

( x i ) SEQUENCE DESCRIPTION: SEQ ID NO:27:

GATCAGGTAA AAGTATTTCA AAAAATTATC ACCTCACTTA GATTGGAAGC CTTAGGAAGT    60

GCTGTGTTAA CATATTCTCT CAACCTTTAG AATCCACTCT CCTGGACTAC ACACATACGC    120

GCGCACGCAC ACACACACAC ACACACACAC ACACACACAC GGTATTGAAA CTAGAATTCT    180

TTCAATGTTG TATTCCCATA CTTATTTATG TCTCAAAGAC TGATC                    225

( 2 ) INFORMATION FOR SEQ ID NO:28:

( i ) SEQUENCE CHARACTERISTICS:
            ( A ) LENGTH: 249 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd44

( v i i i ) POSITION IN GENOME:

(A) CHROMOSOME/SEGMENT: 13

(ix) FEATURE:
  (A) NAME/KEY: repeat_region
  (B) LOCATION: 27..60
  (D) OTHER INFORMATION: /rpt_type="tandem"
    / rpt_family="(dC-dA)n.(dG-dT)n"
    / citation=([2])

(ix) FEATURE:
  (A) NAME/KEY: misc_feature
  (B) LOCATION: 7..27
  (C) IDENTIFICATION METHOD: experimental
  (D) OTHER INFORMATION: /evidence=EXPERIMENTAL
    / standard_name="PCR primer"
    / citation=([1])

(ix) FEATURE:
  (A) NAME/KEY: misc_feature
  (B) LOCATION: complement (60..81)
  (C) IDENTIFICATION METHOD: experimental
  (D) OTHER INFORMATION: /evidence=EXPERIMENTAL
    / standard_name="PCR primer"
    / citation=([1])

(ix) FEATURE:
  (A) NAME/KEY: misc_feature
  (B) LOCATION: 1..249
  (C) IDENTIFICATION METHOD: experimental
  (D) OTHER INFORMATION: /evidence=EXPERIMENTAL
    / standard_name="Only one strand sequenced"

(x) PUBLICATION INFORMATION:
  (A) AUTHORS: Weber, J. L.
    Kwitek, A. E.
    May, P. E.
  (B) TITLE: Dinucleotide repeat polymorphism at the
    D13S71 locus
  (C) JOURNAL: Nucleic Acids Res.
  (D) VOLUME: 18
  (F) PAGES: 4638-
  (G) DATE: 1990

(x) PUBLICATION INFORMATION:
  (A) AUTHORS: Weber, James L.
    May, Paula E.
  (B) TITLE: Abundant Class of Human DNA Polymorphisms
    Which Can Be Typed Using the Polymerase Chain
    Reaction
  (C) JOURNAL: Am. J. Hum. Genet.
  (D) VOLUME: 44
  (F) PAGES: 388-396
  (G) DATE: 1989

(xi) SEQUENCE DESCRIPTION: SEQ ID NO:28:

```
GATCAGGTAT TTTTGGTATG CTTGTGCACA CACACACACA CACACACACA CACACACACA      60
GGCACATATA TTCCAAAATA GAGAATTATC TTACCTTATT TATCTTCCCT CATCTTGACT     120
CCTCTCCTTT TAAAATAATA GGAGAAACAG AGGCACAAAG TTAAGATTTA TGGCACAAGG     180
ACAGCATATC AGAAGTGCAG AGATAAGGAG CCAGAACAAG ACCTAGGTTT TTTATTTCTG     240
GAACAGAAA                                                              249
```

(2) INFORMATION FOR SEQ ID NO:29:

(i) SEQUENCE CHARACTERISTICS:
    (A) LENGTH: 244 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian ( F ) TISSUE TYPE: Blood ( v i i ) IMMEDIATE SOURCE:
(B) CLONE: Mfd45

( v i i i ) POSITION IN GENOME:
(A) CHROMOSOME/SEGMENT: 8

( i x ) FEATURE:
(A) NAME/KEY: repeat_region
(B) LOCATION: 175..215
(D) OTHER INFORMATION: /rpt_type="tandem"
/ rpt_family="(dC-dA)n.(dG-dT)n"
/ citation=([2])

( i x ) FEATURE:
(A) NAME/KEY: misc_feature
(B) LOCATION: 155..174
(C) IDENTIFICATION METHOD: experimental
(D) OTHER INFORMATION: /evidence=EXPERIMENTAL
/ standard_name="PCR primer"
/ citation=([1])

( i x ) FEATURE:
(A) NAME/KEY: misc_feature
(B) LOCATION: complement (222..241)
(C) IDENTIFICATION METHOD: experimental
(D) OTHER INFORMATION: /evidence=EXPERIMENTAL
/ standard_name="PCR primer"
/ citation=([1])

( i x ) FEATURE:
(A) NAME/KEY: misc_feature
(B) LOCATION: 1..244
(C) IDENTIFICATION METHOD: experimental
(D) OTHER INFORMATION: /evidence=EXPERIMENTAL
/ standard_name="Only one strand sequenced"

( x ) PUBLICATION INFORMATION:
(A) AUTHORS: Weber, J. L.
Kwitek, A. E.
May, P. E.
Patterson, D.
Drabkin, H.
(B) TITLE: Dinucleotide repeat polymorphisms at the
D8S85, D8S87 and D8S88 loci
(C) JOURNAL: Nucleic Acids Res.
(D) VOLUME: 18
(F) PAGES: 4038-
(G) DATE: 1990

( x ) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

( x i ) SEQUENCE DESCRIPTION: SEQ ID NO:29:

```
GATCATAAGC GAGTGCTTTT AATATTAAGT ATGCACCTCC CCCCCACCCA AATTATACTG        60

GTTGAATTTT CATGTTAAAA TAAAGCAAAA ATAAATATTA ATATAAAATA TTTAATCAAA       120

TATTTTAAAA ATTTCAGTAG TAAAGTAAAC CAACTCCAGC AGAGAAAGGG TTATCACACA       180

CACACACACA CACACACACA CACACACACA CACACCCCT ATCTGATGAG TTCTCTTTGC        240

CAAT                                                                    244
```

( 2 ) INFORMATION FOR SEQ ID NO:30:

( i ) SEQUENCE CHARACTERISTICS:
(A) LENGTH: 240 base pairs
(B) TYPE: nucleic acid (C) STRANDEDNESS: double
(D) TOPOLOGY: linear (i i) MOLECULE TYPE: DNA (genomic)

(v i) ORIGINAL SOURCE:
(A) ORGANISM: Homo sapiens
(C) INDIVIDUAL ISOLATE: Caucasian
(F) TISSUE TYPE: Blood (v i i) IMMEDIATE SOURCE:
(B) CLONE: Mfd47

(v i i i) POSITION IN GENOME:
(A) CHROMOSOME/SEGMENT: 6

(i x) FEATURE:
(A) NAME/KEY: repeat_region
(B) LOCATION: 150..184
(D) OTHER INFORMATION: /rpt_type="tandem"
/ rpt_family="(dC-dA)n.(dG-dT)n"
/ citation=([2])

(i x) FEATURE:
(A) NAME/KEY: misc_feature
(B) LOCATION: 75..94
(C) IDENTIFICATION METHOD: experimental
(D) OTHER INFORMATION: /evidence=EXPERIMENTAL
/ standard_name="PCR primer"
/ citation=([1])

(i x) FEATURE:
(A) NAME/KEY: misc_feature
(B) LOCATION: complement (203..222)
(C) IDENTIFICATION METHOD: experimental
(D) OTHER INFORMATION: /evidence=EXPERIMENTAL
/ standard_name="PCR primer"
/ citation=([1])

(i x) FEATURE:
(A) NAME/KEY: misc_feature
(B) LOCATION: 1..240
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
(B) TITLE: Dinucleotide repeat polymorphism at the D6S87
locus
(C) JOURNAL: Nucleic Acids Res.
(D) VOLUME: 18
(F) PAGES: 4636-
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(x i) SEQUENCE DESCRIPTION: SEQ ID NO:30:

```
GATCACTTAA GCCTAGGGAG GCCAAGGCTG CAGTGAGCCG AGATTGCACC ATTGCTCTGC      60
AGCCAGCCTG GGTGACAGAG TGAGACCGTG TAACAAAAAA CAACAAAAAA AAAACAAGAA     120
TATATATATA TACACATATA TGTGTGTATA CACACACACA CACACACACA CACACACACA     180
CACAGAGTAA GACATTTGTT TTACTAAGTG AGATGCTTCT CTGAGCCTTC CTTTGTGTAA     240
```

(2) INFORMATION FOR SEQ ID NO:31:

( i ) SEQUENCE CHARACTERISTICS:
    ( A ) LENGTH: 323 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Homo sapiens
    ( C ) INDIVIDUAL ISOLATE: Caucasian
    ( F ) TISSUE TYPE: Blood ( v i i ) IMMEDIATE SOURCE:
    ( B ) CLONE: Mfd48

( v i i i ) POSITION IN GENOME:
    ( A ) CHROMOSOME/SEGMENT: 5

( i x ) FEATURE:
    ( A ) NAME/KEY: repeat_region
    ( B ) LOCATION: 243..276
    ( D ) OTHER INFORMATION: /rpt_type="tandem"
        / rpt_family="(dC-dA)n.(dG-dT)n"
        / citation=([2])

( i x ) FEATURE:
    ( A ) NAME/KEY: misc_feature
    ( B ) LOCATION: 153..171
    ( C ) IDENTIFICATION METHOD: experimental
    ( D ) OTHER INFORMATION: /evidence=EXPERIMENTAL
        / standard_name="PCR primer"
        / citation=([1])

( i x ) FEATURE:
    ( A ) NAME/KEY: misc_feature
    ( B ) LOCATION: complement (283..303)
    ( C ) IDENTIFICATION METHOD: experimental
    ( D ) OTHER INFORMATION: /evidence=EXPERIMENTAL
        / standard_name="PCR primer"
        / citation=([1])

( i x ) FEATURE:
    ( A ) NAME/KEY: misc_feature
    ( B ) LOCATION: 1..323
    ( C ) IDENTIFICATION METHOD: experimental
    ( D ) OTHER INFORMATION: /evidence=EXPERIMENTAL
        / standard_name="Only one strand sequenced"

( x ) PUBLICATION INFORMATION:
    ( A ) AUTHORS: Weber, J. L.
        Kwitek, A. E.
        May, A. E.
    ( B ) TITLE: Dinucleotide repeat polymorphisms at the
        D5S107, D5S108, D5S111, D5S117, and D5S118 loci
    ( C ) JOURNAL: Nucleic Acids Res.
    ( D ) VOLUME: 18
    ( F ) PAGES: 4035-
    ( G ) DATE: 1990

( x ) PUBLICATION INFORMATION:
    ( A ) AUTHORS: Weber, James L.
        May, Paula E.
    ( B ) TITLE: Abundant Class of Human DNA Polymorphisms
        Which Can Be Typed Using the Polymerase Chain
        Reaction
    ( C ) JOURNAL: Am. J. Hum. Genet.
    ( D ) VOLUME: 44
    ( F ) PAGES: 388-396
    ( G ) DATE: 1989

( x i ) SEQUENCE DESCRIPTION: SEQ ID NO:31:

```
GATCCTTTAG ATACTGAGAT AATATGATAC AAATTATTAC TAGTGAGAGG TTATTTTAAA      60
ATATAGGCAT TGTTCAGCAA GCGAAACTTT CTTCAGCCCC TTGGCCCCTG TCATATTTTT     120
ACAAGAAGTC TCCAAAGCAG GCCTTGCCTT GCTGTCTCCT GCTGAGAATA GAAGGCTTCC     180
```

```
TCCTACCAGG  TTGCTTCCCC  TAGTGCCCCT  GTGTATTGCG  CCCTGTGACG  ATTCCCTTGT        240

GTACACACAC  ACACACACAC  ACACACACAC  ACACACTACT  CTACCTTTGT  GGTTTGGATA        300

TTACTCTACA  GGCATAGCTG  ATC                                                   323
```

( 2 ) INFORMATION FOR SEQ ID NO:32:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd49

( v i i i ) POSITION IN GENOME:
        ( A ) CHROMOSOME/SEGMENT: 15

( i x ) FEATURE:
        ( A ) NAME/KEY: repeat_region
        ( B ) LOCATION: 82..125
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 61..81
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (128..147)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..240
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            Kwitek, A. E.
            May, P. E.
        ( B ) TITLE: Dinucleotide repeat polymorphism at the
            D15S87 locus
        ( C ) JOURNAL: Nucleic Acids Res.
        ( D ) VOLUME: 18
        ( F ) PAGES: 4640-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:32:

| | | | | | |
|---|---|---|---|---|---|
| GATCTTTCAC | ATGGAAATCC | AAATGTCTGG | GGAAATCTAT | CTTGTCTGCA | AGAATTTTCT | 60
| GATAAATGCC | AAACATGTTG | TCACACACAC | ACACACACAC | ACACACACAC | ACACACACAC | 120
| ACACAAATGG | AGGAAATCCT | GAGAGCATCT | CGAATATCAG | GATGCTGAGG | GCCCACCAGT | 180
| CCACAGCCCT | TCCGTGACCC | TCGCTCTGAA | TGACTTCGGG | GGCCAGGTAC | TCGGGTATTC | 240

( 2 ) INFORMATION FOR SEQ ID NO:33:

( i ) SEQUENCE CHARACTERISTICS:
        ( A ) LENGTH: 297 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd50

( v i i i ) POSITION IN GENOME:
        ( A ) CHROMOSOME/SEGMENT: 7

( i x ) FEATURE:
        ( A ) NAME/KEY: repeat_region
        ( B ) LOCATION: 224..261
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 105..125
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (260..279)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..297
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            Kwitek, A. E.
            May, P. E.
        ( B ) TITLE: Dinucleotide repeat polymorphisms at the
            D7S435 and D7S440 loci
        ( C ) JOURNAL: Nucleic Acids Res.
        ( D ) VOLUME: 18
        ( F ) PAGES: 4039-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction
        ( C ) JOURNAL: Am. J. Hum. Genet.

( D ) VOLUME: 44
( F ) PAGES: 388-396
( G ) DATE: 1989

( x i ) SEQUENCE DESCRIPTION: SEQ ID NO:33:

| | | | | | | |
|---|---|---|---|---|---|---|
| GATCAGAAGA | CAATGGTGTG | CAAAATAGGA | AAAATCCAAT | ATGAATGGGG | AGCGCCTTTC | 60 |
| CTTTCAATTT | TTTAAAAGGG | ACATGTCAGA | GATTTTATGA | AAGAACATTC | TAAGACTTTC | 120 |
| CCAATCCTCC | TATAATTCTT | TGGGACAAAA | CCTGCAATGA | ATTTCAGATA | AAAATGAAGT | 180 |
| ACAAACAATA | TCAATGAGTT | CACCAGACAA | CCCCCCCCAC | CTCCACACAC | ACACACACAC | 240 |
| ACACACACAC | ACACACACAC | AATTCAGGGT | GCATGCTCTA | TGTTGCAAAT | ATGTACC | 297 |

( 2 ) INFORMATION FOR SEQ ID NO:34:

( i ) SEQUENCE CHARACTERISTICS:
            ( A ) LENGTH: 365 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd52

( v i i i ) POSITION IN GENOME:
            ( A ) CHROMOSOME/SEGMENT: 1

( i x ) FEATURE:
            ( A ) NAME/KEY: repeat_region
            ( B ) LOCATION: 211..246
            ( D ) OTHER INFORMATION: /rpt_type="tandem"
                    / rpt_family="(dC-dA)n.(dG-dT)n"
                    / citation=([2])

( i x ) FEATURE:
            ( A ) NAME/KEY: misc_feature
            ( B ) LOCATION: 81..100
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: complement (261..280)
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: 1..365
            ( C ) IDENTIFICATION METHOD: experimental
            ( D ) OTHER INFORMATION: /evidence=EXPERIMENTAL
                    / standard_name="Only one strand sequenced"

( x ) PUBLICATION INFORMATION:
            ( A ) AUTHORS: Weber, J. L.
                    Kwitek, A. E.
                    May, P. E.
            ( B ) TITLE: Dinucleotide repeat polymorphism at the
                    D1S102
            ( C ) JOURNAL: Nucleic Acids Res.
            ( D ) VOLUME: 18
            ( F ) PAGES: 2199-
            ( G ) DATE: 1990

( x ) PUBLICATION INFORMATION:

(A) AUTHORS: Weber, James L.
    May, Paula E.
(B) TITLE: Abundant Class of Human DNA Polymorphisms
    Which Can Be Typed Using the Polymerase Chain
    Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:34:

| | | | | | |
|---|---|---|---|---|---|
| GATCCAGGCT | TCTGTGGTTC | TAAAGCAGCT | TCTAGATGAG | GTAGAGATTA | AATCACTTTG | 60
| GCTCAAAACA | TTATCCTTTC | AAATCAGACA | AGTACAGGTG | CCCCATAGTT | TCTCTCTCTG | 120
| TGTCTCTCTC | TCCTCTCTCA | GCCACACACA | CAGACACACA | TGCACACAGG | CACACACACA | 180
| TATGCATGCA | TGAATGTGTG | CACAAGCAAA | ACACACACAC | ACACACACAC | ACACACACAC | 240
| ACACACTTGC | ACACATACAC | TCCTCCCAGA | ACAAGTTCAT | CAGCTATTAT | AAAACTCATG | 300
| TCCACACCAT | CGCCTCTCTA | GAGATTTGGG | TGAGAAAAAG | AGGCATAGAA | GGCTCTGAAA | 360
| TGATC | | | | | | 365

(2) INFORMATION FOR SEQ ID NO:35:

(i) SEQUENCE CHARACTERISTICS:
       (A) LENGTH: 345 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
        (A) ORGANISM: Homo sapiens
        (C) INDIVIDUAL ISOLATE: Caucasian
        (F) TISSUE TYPE: Blood (vii) IMMEDIATE SOURCE:
         (B) CLONE: Mfd58

(viii) POSITION IN GENOME:
          (A) CHROMOSOME/SEGMENT: 11

(ix) FEATURE:
        (A) NAME/KEY: repeat_region
        (B) LOCATION: 98..130
        (D) OTHER INFORMATION: /rpt_type="tandem"
              / rpt_family="(dC-dA)n.(dG-dT)n"
              / citation=([2])

(ix) FEATURE:
        (A) NAME/KEY: misc_feature
        (B) LOCATION: 49..68
        (C) IDENTIFICATION METHOD: experimental
        (D) OTHER INFORMATION: /evidence=EXPERIMENTAL
              / standard_name="PCR primer"
              / citation=([1])

(ix) FEATURE:
        (A) NAME/KEY: misc_feature
        (B) LOCATION: complement (143..161)
        (C) IDENTIFICATION METHOD: experimental
        (D) OTHER INFORMATION: /evidence=EXPERIMENTAL
              / standard_name="PCR primer"
              / citation=([1])

(ix) FEATURE:
        (A) NAME/KEY: misc_feature
        (B) LOCATION: 1..345
        (C) IDENTIFICATION METHOD: experimental
        (D) OTHER INFORMATION: /evidence=EXPERIMENTAL
              / standard_name="Only one strand sequenced"

(x) PUBLICATION INFORMATION:
       (A) AUTHORS: Weber, J. L.

Kwitek, A. E.
                    May, P. E.
            ( B ) TITLE: Dinucleotide repeat polymorphisms at the
                    D11S419 and CD3D loci
            ( C ) JOURNAL: Nucleic Acids Res.
            ( D ) VOLUME: 18
            ( F ) PAGES: 4036-
            ( G ) DATE: 1990

( x ) PUBLICATION INFORMATION:
            ( A ) AUTHORS: Weber, James L.
                    May, Paula E.
            ( B ) TITLE: Abundant Class of Human DNA Polymorphisms
                    Which Can Be Typed Using the Polymerase Chain
                    Reaction
            ( C ) JOURNAL: Am. J. Hum. Genet.
            ( D ) VOLUME: 44
            ( F ) PAGES: 388-396
            ( G ) DATE: 1989

( x i ) SEQUENCE DESCRIPTION: SEQ ID NO:35:

| | | | | | |
|---|---|---|---|---|---|
| GATCCTCCCA | CTGTTCCTGA | AAGGGCCCCA | GCCAGCTACT | GTAAAGTCCT | CATTTGAAGA | 60 |
| CTGCAGCAGA | ATTACAGCTC | TCCTCCCCTC | TCTACACCAC | ACACACACAC | ACACACACAC | 120 |
| ACACACACAC | TTCACATATT | AATAGATGGA | CAGGAAGCCC | TGCCATGGGG | GGAAGAGGGT | 180 |
| TGGATTAGGA | ATCACACACC | CGAGTTCTGG | TCTGGGCTCT | GTCACTTTCA | GAGCTTCATC | 240 |
| TGTAACGCAC | ACTGTGAGGC | TTCTGTGAGC | AGCTAGATGT | GGGGGGATGT | TCTGGCGAAA | 300 |
| GGTAAGAAGA | TGCTTACTGG | CAGCATCGTT | ATCCTCATTC | AGGAC | | 345 |

( 2 ) INFORMATION FOR SEQ ID NO:36:

( i ) SEQUENCE CHARACTERISTICS:
            ( A ) LENGTH: 324 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd59

( v i i i ) POSITION IN GENOME:
            ( A ) CHROMOSOME/SEGMENT: 4

( i x ) FEATURE:
            ( A ) NAME/KEY: repeat_region
            ( B ) LOCATION: 244..290
            ( D ) OTHER INFORMATION: /rpt_type="tandem"
                    / rpt_family="(dC-dA)n.(dG-dT)n"
                    / citation=([2])

( i x ) FEATURE:
            ( A ) NAME/KEY: misc_feature
            ( B ) LOCATION: 132..141
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:
            ( A ) NAME/KEY: misc_feature
            ( B ) LOCATION: complement (301..320)
            ( C ) IDENTIFICATION METHOD: experimental
            ( D ) OTHER INFORMATION: /evidence=EXPERIMENTAL
                    / standard_name="PCR primer"
                    / citation=([1])

( i x ) FEATURE:

(A) NAME/KEY: misc_feature
(B) LOCATION: 1..324
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
(B) TITLE: Dinucleotide repeat polymorphism at the
D4S174 locus
(C) JOURNAL: Nucleic Acids Res.
(D) VOLUME: 18
(F) PAGES: 4636-
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:36:

| | | | | | | |
|---|---|---|---|---|---|---|
| GATCTCAGAG | CGACGGCAGC | GGCGGCACAT | CATTTATTGC | TTGCTGAGAC | ACCTTGGTGA | 60 |
| GCATGCAGCC | GATGTTGGGT | GTTCGCATTT | TTTCTACTGA | TAAAAAGGAT | ACTGACTGTG | 120 |
| ACATTACTTG | GCTTCAAAAG | AACCATGCGA | TACGACTGTA | TTTCTCAATG | TTAACATTGG | 180 |
| AAGACAGCAG | TTCAAAGATG | AAAGTGTTTT | TACACACACA | CATATTTATA | TATTTATTTA | 240 |
| TATACACACA | CACACACACA | CACACACACA | CACACACACA | CACACACACA | TATACACCAA | 300 |
| GCTTTACCCA | TCTAGGAATG | GATC | | | | 324 |

(2) INFORMATION FOR SEQ ID NO:37:

(i) SEQUENCE CHARACTERISTICS:
(A) LENGTH: 214 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd61

(viii) POSITION IN GENOME:
(A) CHROMOSOME/SEGMENT: 6p (ix) FEATURE:
(A) NAME/KEY: repeat_region
(B) LOCATION: 91..136
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 60..81
(C) IDENTIFICATION METHOD: experimental
(D) OTHER INFORMATION: /evidence=EXPERIMENTAL
/ standard_name="PCR primer"
/ citation=([1])

(ix) FEATURE:

( A ) NAME/KEY: misc_feature
( B ) LOCATION: complement (171..190)
( C ) IDENTIFICATION METHOD: experimental
( D ) OTHER INFORMATION: /evidence=EXPERIMENTAL
/ standard_name="PCR primer"
/ citation=([1])

( i x ) FEATURE:
( A ) NAME/KEY: misc_feature
( B ) LOCATION: 1..214
( C ) IDENTIFICATION METHOD: experimental
( D ) OTHER INFORMATION: /evidence=EXPERIMENTAL
/ standard_name="Only one strand sequenced"

( x ) PUBLICATION INFORMATION:
( A ) AUTHORS: Weber, J. L.
Kwitek, A. E.
May, P. E.
Zoghbi, H. Y.
( B ) TITLE: Dinucleotide repeat polymorphism at the
D6S105 locus
( C ) JOURNAL: Nucleic Acids Res.
( G ) DATE: 1991

( x ) PUBLICATION INFORMATION:
( A ) AUTHORS: Weber, James L.
May, Paula E.
( B ) TITLE: Abundant Class of Human DNA Polymorphisms
Which Can Be Typed Using the Polymerase Chain
Reaction
( C ) JOURNAL: Am. J. Hum. Genet.
( D ) VOLUME: 44
( F ) PAGES: 388-396
( G ) DATE: 1989

( x i ) SEQUENCE DESCRIPTION: SEQ ID NO:37:

| | | | | | |
|---|---|---|---|---|---|
| GATCTGCCCA | CCTCGGCCTC | CCAAAGTGCT | GGGATTACAG | GCAGGAGCCA | CCGCGCTTGG | 60 |
| CCCTATAAAA | TCCTAATTAA | CAAAATCATT | CACACACACA | CACACACACA | CACACACACA | 120 |
| CACACACACA | CACACAGATG | TAAGGGCATG | GTCTCTCTTC | CTTGAAGCTA | CGGAATTACA | 180 |
| ATTCTCCTTC | ACAAGACAG | TAAAGGATGT | GATC | | | 214 |

( 2 ) INFORMATION FOR SEQ ID NO:38:

( i ) SEQUENCE CHARACTERISTICS:
( A ) LENGTH: 202 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Homo sapiens
( C ) INDIVIDUAL ISOLATE: Caucasian
( F ) TISSUE TYPE: Blood ( v i i ) IMMEDIATE SOURCE:
( B ) CLONE: Mfd62

( v i i i ) POSITION IN GENOME:
( A ) CHROMOSOME/SEGMENT: 16

( i x ) FEATURE:
( A ) NAME/KEY: repeat_region
( B ) LOCATION: 83..124
( D ) OTHER INFORMATION: /rpt_type="tandem"
/ rpt_family="(dC-dA)n.(dG-dT)n"
/ citation=([2])

( i x ) FEATURE:
( A ) NAME/KEY: misc_feature
( B ) LOCATION: 43..62
( C ) IDENTIFICATION METHOD: experimental
( D ) OTHER INFORMATION: /evidence=EXPERIMENTAL
/ standard_name="PCR primer"

/ citation=([1])

( i x ) FEATURE:
        ( A ) NAME/KEY: misc_feature
        ( B ) LOCATION: complement (124..143)
        ( C ) IDENTIFICATION METHOD: experimental
        ( D ) OTHER INFORMATION: /evidence=EXPERIMENTAL
                / standard_name="PCR primer"
                / citation=([1])

( i x ) FEATURE:
        ( A ) NAME/KEY: misc_feature
        ( B ) LOCATION: 1..202
        ( C ) IDENTIFICATION METHOD: experimental
        ( D ) OTHER INFORMATION: /evidence=EXPERIMENTAL
                / standard_name="Only one strand sequenced"

( x ) PUBLICATION INFORMATION:
        ( A ) AUTHORS: Weber, J. L.
                Kwitek, A. E.
                May, A. E.
        ( B ) TITLE: Dinucleotide repeat polymorphisms at the
                D16S260, D16S261, D16S265, D16S266 and D16S267
                loci
        ( C ) JOURNAL: Nucleic Acids Res.
        ( D ) VOLUME: 18
        ( F ) PAGES: 4034-
        ( G ) DATE: 1990

( x ) PUBLICATION INFORMATION:
        ( A ) AUTHORS: Weber, James L.
                May, Paula E.
        ( B ) TITLE: Abundant Class of Human DNA Polymorphisms
                Which Can Be Typed Using the Polymerase Chain
                Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:38:

| | | | | | |
|---|---|---|---|---|---|
| GATCTGTCAA | ATATTATCTA | TTTCAAAAGT | GTCATTGGGT | CAAGCTTTAC | AGATGAGACC | 60
| AGATTTTCTG | TTTAATGTAC | ATACACACAC | ACACACACAC | ACACACACAC | ACACACACAC | 120
| ACACGGACTC | AAGAAATTGG | CTGGTGGAAA | TACGAAGTAA | AGTTTTAAGA | TAATTGGCAT | 180
| AAAAGTAAAA | CATTCTCGGA | TC | | | | 202

( 2 ) INFORMATION FOR SEQ ID NO:39:

( i ) SEQUENCE CHARACTERISTICS:
            ( A ) LENGTH: 264 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
            ( A ) ORGANISM: Homo sapiens
            ( C ) INDIVIDUAL ISOLATE: Caucasian
            ( F ) TISSUE TYPE: Blood ( v i i ) IMMEDIATE SOURCE:
            ( B ) CLONE: Mfd63

( v i i i ) POSITION IN GENOME:
            ( A ) CHROMOSOME/SEGMENT: 5

( i x ) FEATURE:
            ( A ) NAME/KEY: repeat_region
            ( B ) LOCATION: 183..223
            ( D ) OTHER INFORMATION: /rpt_type="tandem"
                    / rpt_family="(dC-dA)n.(dG-dT)n"
                    / citation=([2])

( i x ) FEATURE:

(A) NAME/KEY: misc_feature
(B) LOCATION: 163..183
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (232..251)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..264
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, A. E.
(B) TITLE: Dinucleotide repeat polymorphisms at the
D5S107, D5S108, D5S111, D5S117, and D5S118 loci
(C) JOURNAL: Nucleic Acids Res.
(D) VOLUME: 18
(F) PAGES: 4035-
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:39:

```
GATCAGGCCA  TATCACCACT  AGGTTTTCTT  CCCAGCATCT  GAAAATCCTA  TCTTAATCAC    60

GAGAAAATAT  GAAACAAACA  CAAATTGAGG  AACATTCTAC  AAAATCACTG  AAGAGTAGTC   120

TTTAAACTGA  AAGGTCACCA  AAATAAAAAA  ACAAAAAAAA  ACCAAAACCA  AAAAACCAAA   180

GGCACACACA  CACACACACA  CACACACACA  CACACACACA  CACGAAAAGA  ATGAGAAACT   240

GTCACAGATT  GGAGAAGACT  AAGG                                            264
```

(2) INFORMATION FOR SEQ ID NO:40:

(i) SEQUENCE CHARACTERISTICS:
(A) LENGTH: 243 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd64

(viii) POSITION IN GENOME:
(A) CHROMOSOME/SEGMENT: 1

(ix) FEATURE:
(A) NAME/KEY: repeat_region ( B ) LOCATION: 54..84
        ( D ) OTHER INFORMATION: /rpt_type="tandem"
                / rpt_family="(dC-dA)n.(dG-dT)n"
                / citation=([2])

( i x ) FEATURE:
        ( A ) NAME/KEY: misc_feature
        ( B ) LOCATION: 31..50
        ( C ) IDENTIFICATION METHOD: experimental
        ( D ) OTHER INFORMATION: /evidence=EXPERIMENTAL
                / standard_name="PCR primer"
                / citation=([1])

( i x ) FEATURE:
        ( A ) NAME/KEY: misc_feature
        ( B ) LOCATION: complement (96..115)
        ( C ) IDENTIFICATION METHOD: experimental
        ( D ) OTHER INFORMATION: /evidence=EXPERIMENTAL
                / standard_name="PCR primer"
                / citation=([1])

( i x ) FEATURE:
        ( A ) NAME/KEY: misc_feature
        ( B ) LOCATION: 1..243
        ( C ) IDENTIFICATION METHOD: experimental
        ( D ) OTHER INFORMATION: /evidence=EXPERIMENTAL
                / standard_name="Only one strand sequenced"

( x ) PUBLICATION INFORMATION:
        ( A ) AUTHORS: Weber, J. L.
                Kwitek, A. E.
                May, P. E.
        ( B ) TITLE: Dinucleotide repeat polymorphism at the
                D1S103 locus
        ( C ) JOURNAL: Nucleic Acids Res.
        ( D ) VOLUME: 18
        ( F ) PAGES: 2199-
        ( G ) DATE: 1990

( x ) PUBLICATION INFORMATION:
        ( A ) AUTHORS: Weber, James L.
                May, Paula E.
        ( B ) TITLE: Abundant Class of Human DNA Polymorphisms
                Which Can Be Typed Using the Polymerase Chain
                Reaction
        ( C ) JOURNAL: Am. J. Hum. Genet.
        ( D ) VOLUME: 44
        ( F ) PAGES: 388-396
        ( G ) DATE: 1989

( x i ) SEQUENCE DESCRIPTION: SEQ ID NO:40:

GATCTCTCAG CTATTACAAG GATACAAAAT ACGAACATTC TACAAGTTAC TTAACACACA        60

CACACACACA CACACACACA CACAAAATTA ATTCCACAGG TCAGTTTCTC TGAAACATTT      120

TTTCACTAAA TTCTAAGTCT TCCTGGAGTT GCAAGTGCCT ATCTCCTAGA CAAGGCAATT      180

ACTCACCAAC TAAAATCACT GTCAATCTGA GATTTCGGCT GGGCATGAGA CCATGGTCAG      240

GGG                                                                    243

( 2 ) INFORMATION FOR SEQ ID NO:41:

( i ) SEQUENCE CHARACTERISTICS:
        ( A ) LENGTH: 208 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd65

(viii) POSITION IN GENOME:
  (A) CHROMOSOME/SEGMENT: 16

(ix) FEATURE:
  (A) NAME/KEY: repeat_region
  (B) LOCATION: 61..89
  (D) OTHER INFORMATION: /rpt_type="tandem"
    / rpt_family="(dC-dA)n.(dG-dT)n"
    / citation=([2])

(ix) FEATURE:
  (A) NAME/KEY: misc_feature
  (B) LOCATION: 9..28
  (C) IDENTIFICATION METHOD: experimental
  (D) OTHER INFORMATION: /evidence=EXPERIMENTAL
    / standard_name="PCR primer"
    / citation=([1])

(ix) FEATURE:
  (A) NAME/KEY: misc_feature
  (B) LOCATION: complement (142..161)
  (C) IDENTIFICATION METHOD: experimental
  (D) OTHER INFORMATION: /evidence=EXPERIMENTAL
    / standard_name="PCR primer"
    / citation=([1])

(ix) FEATURE:
  (A) NAME/KEY: misc_feature
  (B) LOCATION: 1..208
  (C) IDENTIFICATION METHOD: experimental
  (D) OTHER INFORMATION: /evidence=EXPERIMENTAL
    / standard_name="Only one strand sequenced"

(x) PUBLICATION INFORMATION:
  (A) AUTHORS: Weber, J. L.
    Kwitek, A. E.
    May, A. E.
  (B) TITLE: Dinucleotide repeat polymorphisms at the
    D16S260, D16S261, D16S265, D16S266 and D16S267
    loci
  (C) JOURNAL: Nucleic Acids Res.
  (D) VOLUME: 18
  (F) PAGES: 4034-
  (G) DATE: 1990

(x) PUBLICATION INFORMATION:
  (A) AUTHORS: Weber, James L.
    May, Paula E.
  (B) TITLE: Abundant Class of Human DNA Polymorphisms
    Which Can Be Typed Using the Polymerase Chain
    Reaction
  (C) JOURNAL: Am. J. Hum. Genet.
  (D) VOLUME: 44
  (F) PAGES: 388-396
  (G) DATE: 1989

(xi) SEQUENCE DESCRIPTION: SEQ ID NO:41:

| | | | | | | |
|---|---|---|---|---|---|---|
| GATCCTATGC | AAACCACAAT | GGAATGCATT | AAATATAAAA | CCCATCTTCC | TTGTTCTGTT | 60 |
| CACACACACA | CACACACACA | CACACACACT | CTCTCTGAAG | TATGTAAACA | AGATGTCATT | 120 |
| TTCATTTTAT | TAATACACAT | ACTGAGGCAA | AGGAAGTAAA | GTGATAATCA | TGATGATGAT | 180 |
| AACACTAATG | AAAATCTACA | GCCATAAA | | | | 208 |

(2) INFORMATION FOR SEQ ID NO:42:

(i) SEQUENCE CHARACTERISTICS:
    (A) LENGTH: 198 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens (C) INDIVIDUAL ISOLATE: Caucasian
(F) TISSUE TYPE: Blood (vii) IMMEDIATE SOURCE:
(B) CLONE: Mfd66

(viii) POSITION IN GENOME:
(A) CHROMOSOME/SEGMENT: X (ix) FEATURE:
(A) NAME/KEY: repeat_region
(B) LOCATION: 34..77
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 11..30
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (161..180)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..198
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
Polymeropoulos, M. H.
Ledbetter, S.
(B) TITLE: Dinucleotide repeat polymorphisms at the
DXS453, DXS454, and DXS458 loci
(C) JOURNAL: Nucleic Acids Res.
(D) VOLUME: 18
(F) PAGES: 4037-
(G) DATE: 1990

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:42:

```
GATCTTTGCT GCCCCTACCT TGGCTAGTTA TATACACACA CACACACACA CACACACACA      60
CACACACACA CACACACCCT ACAGCATGAA TTCATCCAAT TGTTTTGCAC AAAAACATGT    120
TTAAAATGAA AAGGCAGAAA GCCAGAGCGA GGTAGGGTAA CTTGGGTATA AGCTGAGGTT    180
AGCCAGTGCA CATGCATG                                                  198
```

(2) INFORMATION FOR SEQ ID NO:43:

(i) SEQUENCE CHARACTERISTICS:
(A) LENGTH: 228 base pairs
(B) TYPE: nucleic acid
(C) STRANDEDNESS: double (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian
    (F) TISSUE TYPE: Blood (vii) IMMEDIATE SOURCE:
    (B) CLONE: Mfd67

(viii) POSITION IN GENOME:
    (A) CHROMOSOME/SEGMENT: 1

(ix) FEATURE:
    (A) NAME/KEY: repeat_region
    (B) LOCATION: 50..86
    (D) OTHER INFORMATION: /rpt_type="tandem"
        / rpt_family="(dC-dA)n.(dG-dT)n"
        / citation=([2])

(ix) FEATURE:
    (A) NAME/KEY: misc_feature
    (B) LOCATION: 2..21
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: complement (138..157)
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: 1..228
    (C) IDENTIFICATION METHOD: experimental
    (D) OTHER INFORMATION: /evidence=EXPERIMENTAL
        / standard_name="Only one strand sequenced"

(x) PUBLICATION INFORMATION:
    (A) AUTHORS: Weber, J. L.
        Kwitek, A. E.
        May, P. E.
    (B) TITLE: Dinucleotide repeat polymorphism at the
        D1S104 locus
    (C) JOURNAL: Nucleic Acids Res.
    (D) VOLUME: 18
    (F) PAGES: 2835-
    (G) DATE: 1990

(x) PUBLICATION INFORMATION:
    (A) AUTHORS: Weber, James L.
        May, Paula E.
    (B) TITLE: Abundant Class of Human DNA Polymorphisms
        Which Can Be Typed Using the Polymerase Chain
        Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:43:

```
GATCCTGCCC TTATGGAGTG CTTTCTTCTC TCTCTCTCTC TCTCTCTCTC ACACACACAC      60

ACACACACAC ACACACACAC ACACACGGTT TTTTGGGAGA TACTAAGTAC TAGGAAGTAA     120

AATAAAGCAG GATGATATAC AATGACAGAG GAGTGGGGGA CAGCCTGTAC TACATTTGAT     180

GGAAGGATGA GGGAAGCTCT CTCGATGAAA TGGAATTTGA GTAAAGAA                  228
```

(2) INFORMATION FOR SEQ ID NO:44:

( i ) SEQUENCE CHARACTERISTICS:
      ( A ) LENGTH: 387 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Homo sapiens
      ( C ) INDIVIDUAL ISOLATE: Caucasian
      ( F ) TISSUE TYPE: Blood ( v i i ) IMMEDIATE SOURCE:
      ( B ) CLONE: Mfd72

( v i i i ) POSITION IN GENOME:
      ( A ) CHROMOSOME/SEGMENT: X ( i x ) FEATURE:
      ( A ) NAME/KEY: repeat_region
      ( B ) LOCATION: 314..347
      ( D ) OTHER INFORMATION: /rpt_type="tandem"
          / rpt_family="(dC-dA)n.(dG-dT)n"
          / citation=([2])

( i x ) FEATURE:
      ( A ) NAME/KEY: misc_feature
      ( B ) LOCATION: 243..262
      ( C ) IDENTIFICATION METHOD: experimental
      ( D ) OTHER INFORMATION: /evidence=EXPERIMENTAL
          / standard_name="PCR primer"
          / citation=([1])

( i x ) FEATURE:
      ( A ) NAME/KEY: misc_feature
      ( B ) LOCATION: complement (368..387)
      ( C ) IDENTIFICATION METHOD: experimental
      ( D ) OTHER INFORMATION: /evidence=EXPERIMENTAL
          / standard_name="PCR primer"
          / citation=([1])

( i x ) FEATURE:
      ( A ) NAME/KEY: misc_feature
      ( B ) LOCATION: 1..387
      ( C ) IDENTIFICATION METHOD: experimental
      ( D ) OTHER INFORMATION: /evidence=EXPERIMENTAL
          / standard_name="Only one strand sequenced"

( x ) PUBLICATION INFORMATION:
      ( A ) AUTHORS: Weber, J. L.
          Kwitek, A. E.
          May, P. E.
          Polymeropoulos, M. H.
          Ledbetter, S.
      ( B ) TITLE: Dinucleotide repeat polymorphisms at the
          DXS453, DXS454, and DXS458 loci
      ( C ) JOURNAL: Nucleic Acids Res.
      ( D ) VOLUME: 18
      ( F ) PAGES: 4037-
      ( G ) DATE: 1990

( x ) PUBLICATION INFORMATION:
      ( A ) AUTHORS: Weber, James L.
          May, Paula E.
      ( B ) TITLE: Abundant Class of Human DNA Polymorphisms
          Which Can Be Typed Using the Polymerase Chain
          Reaction
      ( C ) JOURNAL: Am. J. Hum. Genet.
      ( D ) VOLUME: 44
      ( F ) PAGES: 388-396
      ( G ) DATE: 1989

( x i ) SEQUENCE DESCRIPTION: SEQ ID NO:44:

```
GATCCAAAAG ACTGAATATA TCATTCAAAG TTGAGCACAC TTAGAGAATA AGCATAGTCA      60

TATGGTGAGG TCTTTTTTGT TGCCACCTAA TATATATTGC TACAATAAAA GGAAAACATT     120

TTGTTTAAAA CTTTGTAATT GCATTGGCA  AGATTCCCTA TCCTCTTGTC TGTAAGAACT     180
```

| AATCAGAATT | CACAGTGACT | GTTAAACAGA | AACAAATTGA | AAGTGTAAGC | TTACCATTGA | 240 |
| AAAGAAGACA | TAAGGATACT | GCATTATTGC | CAGTGGTGAG | AAGCAAAATA | GGTATAAACA | 300 |
| CACACACACT | CAAACACACA | CACACACACA | CACACACACA | CACACACGGA | GAGAGAGAGA | 360 |
| GAGAAAGAGA | AAGAAATAGT | TGGGATC | | | | 387 |

( 2 ) INFORMATION FOR SEQ ID NO:45:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( C ) INDIVIDUAL ISOLATE: Caucasian
        ( F ) TISSUE TYPE: Blood ( v i i ) IMMEDIATE SOURCE:
        ( B ) CLONE: Mfd79

( v i i i ) POSITION IN GENOME:
        ( A ) CHROMOSOME/SEGMENT: X ( i x ) FEATURE:
        ( A ) NAME/KEY: repeat_region
        ( B ) LOCATION: 98..128
        ( D ) OTHER INFORMATION: /rpt_type="tandem"
            / rpt_family="(dC-dA)n.(dG-dT)n"
            / citation=([2])

( i x ) FEATURE:
        ( A ) NAME/KEY: misc_feature
        ( B ) LOCATION: 67..88
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: complement (233..252)
        ( C ) IDENTIFICATION METHOD: experimental
        ( D ) OTHER INFORMATION: /evidence=EXPERIMENTAL
            / standard_name="PCR primer"
            / citation=([1])

( i x ) FEATURE:
        ( A ) NAME/KEY: misc_feature
        ( B ) LOCATION: 1..300
        ( C ) IDENTIFICATION METHOD: experimental
        ( D ) OTHER INFORMATION: /evidence=EXPERIMENTAL
            / standard_name="Only one strand sequenced"

( x ) PUBLICATION INFORMATION:
        ( A ) AUTHORS: Weber, J. L.
            Kwitek, A. E.
            May, P. E.
            Polymeropoulos, M. H.
            Ledbetter, S.
        ( B ) TITLE: Dinucleotide repeat polymorphisms at the
            DXS453, DXS454, and DXS458 loci
        ( C ) JOURNAL: Nucleic Acids Res.
        ( D ) VOLUME: 18
        ( F ) PAGES: 4037-
        ( G ) DATE: 1990

( x ) PUBLICATION INFORMATION:
        ( A ) AUTHORS: Weber, James L.
            May, Paula E.
        ( B ) TITLE: Abundant Class of Human DNA Polymorphisms
            Which Can Be Typed Using the Polymerase Chain
            Reaction (C) JOURNAL: Am. J. Hum. Genet.
(D) VOLUME: 44
(F) PAGES: 388-396
(G) DATE: 1989

(xi) SEQUENCE DESCRIPTION: SEQ ID NO:45:

| | | | | | |
|---|---|---|---|---|---|
| GATCCTTGTG | GTGATGGAAC | TGTTCCATAT | CTTGATTGTG | GTGTTGGTAT | ACCTGAATTT | 60 |
| ACACATGATA | AAACTGCATA | GAAATGCGTA | TATATATACA | CACACACACA | CACACACACA | 120 |
| CACACACATA | TAAAAATATA | TATACACATG | TATATATACA | CACACACATA | TATAACACAC | 180 |
| AAATAAGTAC | AAATAAAACT | AGGGAAATTT | GAATAAGATA | GATGGGTTTT | ATCAATGTCA | 240 |
| ATATCCCAGT | TGTGATATCA | TAATATAGAT | TACCAGGATG | TTACCATTGG | GGAAAGGATC | 300 |

(2) INFORMATION FOR SEQ ID NO:46:

(i) SEQUENCE CHARACTERISTICS:
(A) LENGTH: 262 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd84

(viii) POSITION IN GENOME:
(A) CHROMOSOME/SEGMENT: 12

(ix) FEATURE:
(A) NAME/KEY: repeat_region
(B) LOCATION: 172..205
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 126..145
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (215..236)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..262
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
(B) TITLE: Dinucleotide repeat polymorphism at the
D12S43 locus
(C) JOURNAL: Nucleic Acids Res.
(D) VOLUME: 18
(F) PAGES: 4637-
(G) DATE: 1990

(x) PUBLICATION INFORMATION:
  (A) AUTHORS: Weber, James L.
       May, Paula E.
  (B) TITLE: Abundant Class of Human DNA Polymorphisms
     Which Can Be Typed Using the Polymerase Chain
     Reaction
  (C) JOURNAL: Am. J. Hum. Genet.
  (D) VOLUME: 44
  (F) PAGES: 388-396
  (G) DATE: 1989

(xi) SEQUENCE DESCRIPTION: SEQ ID NO:46:

| | | | | | | |
|---|---|---|---|---|---|---|
| GATCCTGTAC | ATATAAAGGA | TATTATTGGA | ACAATTAGTG | AAATTTGAAT | GGGGCCTGTT | 60 |
| GATTAGATGG | TAATTTTAAT | CAATGTTAAC | TTCCAGATTT | TGATGATGAT | TTTGTGGTTA | 120 |
| GATAGAATGT | CCTTGTACTT | AGGATACACA | CACACATACA | CAGATACACG | GACACACACA | 180 |
| CACACACACA | CACACACACA | CACACTGTGT | ATATGTATAC | ATTGAGATAT | TAAGTGGGCA | 240 |
| TCATGTCTGA | AACATTCTTA | AA | | | | 262 |

(2) INFORMATION FOR SEQ ID NO:47:

(i) SEQUENCE CHARACTERISTICS:
    (A) LENGTH: 259 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Homo sapiens
    (C) INDIVIDUAL ISOLATE: Caucasian
    (F) TISSUE TYPE: Blood (vii) IMMEDIATE SOURCE:
    (B) CLONE: Mfd88

(viii) POSITION IN GENOME:
    (A) CHROMOSOME/SEGMENT: 5p (ix) FEATURE:
    (A) NAME/KEY: repeat_region
    (B) LOCATION: 116..162
    (D) OTHER INFORMATION: /rpt_type="tandem"
      / rpt_family="(dC-dA)n.(dG-dT)n"
      / citation=([2])

(ix) FEATURE:
    (A) NAME/KEY: misc_feature
    (B) LOCATION: 77..96
    (C) IDENTIFICATION METHOD: experimental
    (D) OTHER INFORMATION: /evidence=EXPERIMENTAL
      / standard_name="PCR primer"
      / citation=([1])

(ix) FEATURE:
    (A) NAME/KEY: misc_feature
    (B) LOCATION: complement (209..228)
    (C) IDENTIFICATION METHOD: experimental
    (D) OTHER INFORMATION: /evidence=EXPERIMENTAL
      / standard_name="PCR primer"
      / citation=([1])

(ix) FEATURE:
    (A) NAME/KEY: misc_feature
    (B) LOCATION: 1..259
    (C) IDENTIFICATION METHOD: experimental
    (D) OTHER INFORMATION: /evidence=EXPERIMENTAL
      / standard_name="Only one strand sequenced"

(x) PUBLICATION INFORMATION:
    (A) AUTHORS: Weber, J. L.
       Polymeropoulos, M. H.
       May, P. E.
       Kwitek, A. E.

Xiao, H.
McPherson, J. D.
Wasmuth, J. J.
( B ) TITLE: Mapping of human chromosome 5 microsatellite
polymorphisms
( C ) JOURNAL: Genomics
( G ) DATE: 1991

( x ) PUBLICATION INFORMATION:
( A ) AUTHORS: Weber, James L.
May, Paula E.
( B ) TITLE: Abundant Class of Human DNA Polymorphisms
Which Can Be Typed Using the Polymerase Chain
Reaction
( C ) JOURNAL: Am. J. Hum. Genet.
( D ) VOLUME: 44
( F ) PAGES: 388-396
( G ) DATE: 1989

( x i ) SEQUENCE DESCRIPTION: SEQ ID NO:47:

| | | | | | |
|---|---|---|---|---|---|
| GATCAGTTTG | TAGAAGAGAC | ATCTGAACTT | TCATGTTCTT | AGTGCCACTC | TTTACATTAG | 60 |
| CCGAGATGTG | GAATCAACCT | GAGTGTTCAT | CAATACATGA | ATAGGTAGTA | AAAATACACA | 120 |
| CACACACACA | CACACACACA | CACACACACA | CACACACACA | CAATGGAATA | CTATTCAGCC | 180 |
| ATAAAAGAA | TGAAACCCTG | TCATTTTGAC | AACATGGATG | ATTCTGGAGG | ACATTATGAT | 240 |
| AACTGAAATA | AGATAAGCC | | | | | 259 |

( 2 ) INFORMATION FOR SEQ ID NO:48:

( i ) SEQUENCE CHARACTERISTICS:
( A ) LENGTH: 244 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Homo sapiens
( C ) INDIVIDUAL ISOLATE: Caucasian
( F ) TISSUE TYPE: Blood ( v i i ) IMMEDIATE SOURCE:
( B ) CLONE: Mfd116

( v i i i ) POSITION IN GENOME:
( A ) CHROMOSOME/SEGMENT: 5q ( i x ) FEATURE:
( A ) NAME/KEY: repeat_region
( B ) LOCATION: 133..172
( D ) OTHER INFORMATION: /rpt_type="tandem"
/ rpt_family="(dC-dA)n.(dG-dT)n"
/ citation=([2])

( i x ) FEATURE:
( A ) NAME/KEY: misc_feature
( B ) LOCATION: 38..57
( C ) IDENTIFICATION METHOD: experimental
( D ) OTHER INFORMATION: /evidence=EXPERIMENTAL
/ standard_name="PCR primer"
/ citation=([1])

( i x ) FEATURE:
( A ) NAME/KEY: misc_feature
( B ) LOCATION: complement (217..236)
( C ) IDENTIFICATION METHOD: experimental
( D ) OTHER INFORMATION: /evidence=EXPERIMENTAL
/ standard_name="PCR primer"
/ citation=([1])

( i x ) FEATURE:
( A ) NAME/KEY: misc_feature
( B ) LOCATION: 1..244
( C ) IDENTIFICATION METHOD: experimental (D) OTHER INFORMATION: /evidence=EXPERIMENTAL
/ standard_name="Only one strand sequenced"

(x) PUBLICATION INFORMATION:
(A) AUTHORS: Weber, J. L.
Polymeropoulos, M. H.
May, P. E.
Kwitek, A. E.
Xiao, H.
McPherson, J. D.
Wasmuth, J. J.
(B) TITLE: Mapping of human chromosome 5 microsatellite polymorphisms
(C) JOURNAL: Genomics
(G) DATE: 1991

(x) PUBLICATION INFORMATION:
(A) AUTHORS: Weber, James L.
May, Paula E.
(B) TITLE: Abundant Class of Human DNA Polymorphisms Which Can Be Typed Using the Polymerase Chain Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:48:

| | | | | | |
|---|---|---|---|---|---|
| GATCTGAAGT | GATAAATCTC | CTGTGACATT | TTGGTCTCTG | CACTAGAAAG | GCAGAGTAAC | 60
| TTCATGTATA | GTCACCAAGA | CATCACACGA | CAGGCAAAAA | ATAACTTCTT | ATACCCACCA | 120
| CGCCCCCACC | CAACACACAC | ACACACACAC | ACACACACAC | ACACACACAC | ACCCTGCAAT | 180
| TAGAAATTAG | AAAGAGGGAT | GCAATTAGAA | AGAGGGACTT | GGTGTTTGGT | GCTGCATAGC | 240
| TCCC | | | | | | 244

(2) INFORMATION FOR SEQ ID NO:49:

(i) SEQUENCE CHARACTERISTICS:
(A) LENGTH: 293 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd122

(viii) POSITION IN GENOME:
(A) CHROMOSOME/SEGMENT: 5q (ix) FEATURE:
(A) NAME/KEY: repeat_region
(B) LOCATION: 41..74
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 4..23
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (204..223)
(C) IDENTIFICATION METHOD: experimental (D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..293
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Polymeropoulos, M. H.
May, P. E.
Kwitek, A. E.
Xiao, H.
McPherson, J. D.
Wasmuth, J. J.
(B) TITLE: Mapping of human chromosome 5 microsatellite
polymorphisms
(C) JOURNAL: Genomics
(G) DATE: 1991

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:49:

```
GATCTTTAAC ATCCTTTAAC AGCTAGCCGT ATTCCTAGGG GTGTGTGTGT GTGTGTGTGT      60

GTGTGTGTGT GTGTCTACTG TAAATGAGAT TACATTCTTA ACTTGGCACT CAGCTTCAAT     120

ATTTTTGATG TATAAATATG CTACTGTTCA TATTCTTTGC CCACTTTTTG ATGGGGTTGT     180

TTTTTCTTG TAAATTTGTT TAAGGTCCTT GTAGATTCTG CATATTAGCC CTTTTTTAGA     240

TGGATAGATT ACAACAGACC CTTCTCAAAA GAAGACATTT ATGTGGCCAA AAA           293
```

(2) INFORMATION FOR SEQ ID NO:50:

(i) SEQUENCE CHARACTERISTICS:
(A) LENGTH: 236 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd134

(viii) POSITION IN GENOME:
(A) CHROMOSOME/SEGMENT: 20

(ix) FEATURE:
(A) NAME/KEY: repeat_region
(B) LOCATION: 48..90
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature
(B) LOCATION: 15..34
(C) IDENTIFICATION METHOD: experimental (D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (105..123)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..236
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
(B) TITLE: Dinucleotide repeat polymorphisms at the
D20SXX and D20SXX loci
(C) JOURNAL: Nucleic Acids Res.
(G) DATE: 1991

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:50:

| | | | | | |
|---|---|---|---|---|---|
| GATCAGTGCC | TGACCAGATG | CCTTTGCCTT | TTACTGGCTG | GTGCTGCCAC | ACACACACAC | 60 |
| ACACACACAC | ACACACACAC | ACACACACAC | CCCTGCTGCT | GTGAGACTTG | GCAGCTACAG | 120 |
| GCTCACTGGG | CATCCTTCCC | TGGAGAACTG | CCCGAGGCTG | GCAGAACCAC | CTGGCTCCAA | 180 |
| AATGCCTGGA | GGCCCAGCTT | CCTCCACTCA | CCCTCAGCTG | ACCCGATGGG | TCCTGC | 236 |

(2) INFORMATION FOR SEQ ID NO:51:

(i) SEQUENCE CHARACTERISTICS:
(A) LENGTH: 270 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd136

(viii) POSITION IN GENOME:
(A) CHROMOSOME/SEGMENT: 20

(ix) FEATURE:
(A) NAME/KEY: repeat_region
(B) LOCATION: 118..169
(D) OTHER INFORMATION: /rpt_type="tandem"
/ rpt_family="(dC-dA)n.(dG-dT)n"
/ citation=([2])

(ix) FEATURE:
(A) NAME/KEY: misc_feature (B) LOCATION: 80..99
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: complement (192..211)
(C) IDENTIFICATION METHOD: experimental
(D) OTHER INFORMATION: /evidence=EXPERIMENTAL
/ standard_name="PCR primer"
/ citation=([1])

(ix) FEATURE:
(A) NAME/KEY: misc_feature
(B) LOCATION: 1..270
(C) IDENTIFICATION METHOD: experimental
(D) OTHER INFORMATION: /evidence=EXPERIMENTAL
/ standard_name="Only one strand sequenced"

(x) PUBLICATION INFORMATION:
(A) AUTHORS: Weber, J. L.
Kwitek, A. E.
May, P. E.
(B) TITLE: Dinucleotide repeat polymorphisms at the
D20SXX and D20SXX loci
(C) JOURNAL: Nucleic Acids Res.
(G) DATE: 1991

(x) PUBLICATION INFORMATION:
(A) AUTHORS: Weber, James L.
May, Paula E.
(B) TITLE: Abundant Class of Human DNA Polymorphisms
Which Can Be Typed Using the Polymerase Chain
Reaction
(C) JOURNAL: Am. J. Hum. Genet.
(D) VOLUME: 44
(F) PAGES: 388-396
(G) DATE: 1989

(xi) SEQUENCE DESCRIPTION: SEQ ID NO:51:

```
GATCTGGTTG GTGGGTGGGT GGGTCCTGAG AATGTACTTG TTAAGTTTCA AGCAGTGTTG      60

ATATGGGTGG CCTGAGGAAT GGATTCTGTG AACTAAACAT TACTTCAAGA AAAAATCTGT    120

GTGTGTGTGT GTGTGTGTGT GTGTGTGTGT GTGTTGTGTG TGTGTGTGTT ATTCATCTTT    180

AAATTCTGCA AGGTCCAATA TAATGCTTTG AATATATTAT CGACTCAATA CATAAGAGTT    240

TGTTTTGAAT CATGTTAGTG GTGTGATTTT                                       270
```

(2) INFORMATION FOR SEQ ID NO:52:

(i) SEQUENCE CHARACTERISTICS:
(A) LENGTH: 278 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Homo sapiens
(C) INDIVIDUAL ISOLATE: Caucasian
(F) TISSUE TYPE: Blood (vii) IMMEDIATE SOURCE:
(B) CLONE: Mfd154

(viii) POSITION IN GENOME:
(A) CHROMOSOME/SEGMENT: 5q (ix) FEATURE:
(A) NAME/KEY: repeat_region
(B) LOCATION: 76..118
(D) OTHER INFORMATION: /rpt_type="tandem"
/ rpt_family="(dC-dA)n.(dG-dT)n"

/ citation=([2])

(ix) FEATURE:
    (A) NAME/KEY: misc_feature
    (B) LOCATION: 20..39
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: complement (198..217)
    (C) IDENTIFICATION METHOD: experimental
    (D) OTHER INFORMATION: /evidence=EXPERIMENTAL
        / standard_name="PCR primer"
        / citation=([1])

(ix) FEATURE:
    (A) NAME/KEY: misc_feature
    (B) LOCATION: 1..278
    (C) IDENTIFICATION METHOD: experimental
    (D) OTHER INFORMATION: /evidence=EXPERIMENTAL
        / standard_name="Only one strand sequenced"

(x) PUBLICATION INFORMATION:
    (A) AUTHORS: Weber, J. L.
        Polymeropoulos, M. H.
        May, P. E.
        Kwitek, A. E.
        Xiao, H.
        McPherson, J. D.
        Wasmuth, J. J.
    (B) TITLE: Mapping of human chromosome 5 microsatellite polymorphisms
    (C) JOURNAL: Genomics
    (G) DATE: 1991

(x) PUBLICATION INFORMATION:
    (A) AUTHORS: Weber, James L.
        May, Paula E.
    (B) TITLE: Abundant Class of Human DNA Polymorphisms Which Can Be Typed Using the Polymerase Chain Reaction
    (C) JOURNAL: Am. J. Hum. Genet.
    (D) VOLUME: 44
    (F) PAGES: 388-396
    (G) DATE: 1989

(xi) SEQUENCE DESCRIPTION: SEQ ID NO:52:

```
GATCCATTTC  TGGGCGCACA  TGTATCTAGC  CATGGTAGCA  CAGGCCGGGA  AGCTCTGTGC     60
TGGAAATTCT  GAGTTTGTGT  GTGTGTGTGT  GTGTGTGTGT  GTGTGTGTGT  GTGTGTGTTA    120
CCTTTCTTCC  TTTCTCTTTAC TCTCCTTTTC  TGCCTTCTGT  CGAGCACAGC  CTGCCTGTGA    180
CCTCACAGCA  ATAAGTTAGG  CCAGTGGTTT  TCAAAGTGCA  GTTCCCAGAA  TAGTAACAGC    240
AGCATCACCT  GGTTCCTGTT  AGAAATGCAA  ATTCTCAG                              278
```

(2) INFORMATION FOR SEQ ID NO:53:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd1rs (xi) SEQUENCE DESCRIPTION: SEQ ID NO:53:

```
CATACACACA  CACACACACA  CACACACACA  CACACACACA  CA                        42
```

( 2 ) INFORMATION FOR SEQ ID NO:54:

( i ) SEQUENCE CHARACTERISTICS:
           ( A ) LENGTH: 20 base pairs
           ( B ) TYPE: nucleic acid
           ( C ) STRANDEDNESS: double
           ( D ) TOPOLOGY: linear ( v i i ) IMMEDIATE SOURCE:
           ( B ) CLONE: mfd1p1

( x i ) SEQUENCE DESCRIPTION: SEQ ID NO:54:

| | |
|---|---:|
| GCTAGCCAGC TGGTGTTATT | 20 |

( 2 ) INFORMATION FOR SEQ ID NO:55:

( i ) SEQUENCE CHARACTERISTICS:
           ( A ) LENGTH: 20 base pairs
           ( B ) TYPE: nucleic acid
           ( C ) STRANDEDNESS: double
           ( D ) TOPOLOGY: linear ( i i ) MOLECULE TYPE: DNA (genomic)

( v i i ) IMMEDIATE SOURCE:
           ( B ) CLONE: mfd1p2

( x i ) SEQUENCE DESCRIPTION: SEQ ID NO:55:

| | |
|---|---:|
| ACCACTCTGG GAGAAGGGTA | 20 |

( 2 ) INFORMATION FOR SEQ ID NO:56:

( i ) SEQUENCE CHARACTERISTICS:
           ( A ) LENGTH: 62 base pairs
           ( B ) TYPE: nucleic acid
           ( C ) STRANDEDNESS: double
           ( D ) TOPOLOGY: linear ( i i ) MOLECULE TYPE: DNA (genomic)

( v i i ) IMMEDIATE SOURCE:
           ( B ) CLONE: mfd2rs ( x i ) SEQUENCE DESCRIPTION: SEQ ID NO:56:

| | |
|---|---:|
| ACACACACAC ACACACACAC ACACACAACA CACACACACA CACACACACA CACACACACA | 60 |
| CA | 62 |

( 2 ) INFORMATION FOR SEQ ID NO:57:

( i ) SEQUENCE CHARACTERISTICS:
           ( A ) LENGTH: 20 base pairs
           ( B ) TYPE: nucleic acid
           ( C ) STRANDEDNESS: double
           ( D ) TOPOLOGY: linear ( i i ) MOLECULE TYPE: DNA (genomic)

( v i i ) IMMEDIATE SOURCE:
           ( B ) CLONE: mfd2p1

( x i ) SEQUENCE DESCRIPTION: SEQ ID NO:57:

| | |
|---|---:|
| CATTAGGATG CATTCTTCTG | 20 |

( 2 ) INFORMATION FOR SEQ ID NO:58:

( i ) SEQUENCE CHARACTERISTICS:
           ( A ) LENGTH: 20 base pairs
           ( B ) TYPE: nucleic acid
           ( C ) STRANDEDNESS: double
           ( D ) TOPOLOGY: linear ( i i ) MOLECULE TYPE: DNA (genomic)

( v i i ) IMMEDIATE SOURCE:
    ( B ) CLONE: mfd2p2

( x i ) SEQUENCE DESCRIPTION: SEQ ID NO:58:

GTCAGGATTG AACTGGGAAC 20

( 2 ) INFORMATION FOR SEQ ID NO:59:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd3rs ( x i ) SEQUENCE DESCRIPTION: SEQ ID NO:59:

CACACACACA CACACACACA CACACACACA CAC 33

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd3p1

( x i ) SEQUENCE DESCRIPTION: SEQ ID NO:60:

GGTCTGGAAG TACTGAGAAA 20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd3p2

( x i ) SEQUENCE DESCRIPTION: SEQ ID NO:61:

GATTCACTGC TGTGGACCCA 20

( 2 ) INFORMATION FOR SEQ ID NO:62:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd4rs ( x i ) SEQUENCE DESCRIPTION: SEQ ID NO:62:

ACACACACAC ACACACACAC ACACGCACAA ACACACACAC ACACACACAC ACACACA 57

( 2 ) INFORMATION FOR SEQ ID NO:63:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd4p1

( x i ) SEQUENCE DESCRIPTION: SEQ ID NO:63:

GCTCAAATGT TTCTGCAACC      20

( 2 ) INFORMATION FOR SEQ ID NO:64:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd4p2

( x i ) SEQUENCE DESCRIPTION: SEQ ID NO:64:

CTTTGTAGCT CGTGATGTGA      20

( 2 ) INFORMATION FOR SEQ ID NO:65:

( i ) SEQUENCE CHARACTERISTICS:
    ( A ) LENGTH: 56 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd5rs ( x i ) SEQUENCE DESCRIPTION: SEQ ID NO:65:

CTCTCTCTCT CACACACACA CACACACACA CACACACACA CACACACACA CACACA      56

( 2 ) INFORMATION FOR SEQ ID NO:66:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd5p1

( x i ) SEQUENCE DESCRIPTION: SEQ ID NO:66:

CATAGCGAGA CTCCATCTCC      20

( 2 ) INFORMATION FOR SEQ ID NO:67:

( i ) SEQUENCE CHARACTERISTICS:
    ( A ) LENGTH: 20 base pairs
    ( B ) TYPE: nucleic acid
    ( C ) STRANDEDNESS: double ( D ) TOPOLOGY: linear ( i i ) MOLECULE TYPE: DNA (genomic)

( v i i ) IMMEDIATE SOURCE:
    ( B ) CLONE: mfd5p2

( x i ) SEQUENCE DESCRIPTION: SEQ ID NO:67:

GGGAGAGGGC AAAGATCGAT     20

( 2 ) INFORMATION FOR SEQ ID NO:68:

( i ) SEQUENCE CHARACTERISTICS:
    ( A ) LENGTH: 38 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd6rs ( x i ) SEQUENCE DESCRIPTION: SEQ ID NO:68:

CACACACACA AACACACACA CACACACACA CACACACA     38

( 2 ) INFORMATION FOR SEQ ID NO:69:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( A ) LIBRARY: mfd6p1

( x i ) SEQUENCE DESCRIPTION: SEQ ID NO:69:

TCCTACCTTA ATTTCTGCCT     20

( 2 ) INFORMATION FOR SEQ ID NO:70:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd6p2

( x i ) SEQUENCE DESCRIPTION: SEQ ID NO:70:

GCAGGTTGTT TAATTTCGGC     20

( 2 ) INFORMATION FOR SEQ ID NO:71:

( i ) SEQUENCE CHARACTERISTICS:
    ( A ) LENGTH: 46 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:71:

CACACACACA CACACACACA CACACACACA CACACACACA TACACA     46

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd7p1

( x i ) SEQUENCE DESCRIPTION: SEQ ID NO:72:

GTTAGCATAA TGCCCTCAAG                                                        20

( 2 ) INFORMATION FOR SEQ ID NO:73:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd7p2

( x i ) SEQUENCE DESCRIPTION: SEQ ID NO:73:

CGATGGAGTT TATGTTGAGA                                                        20

( 2 ) INFORMATION FOR SEQ ID NO:74:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd8rs ( x i ) SEQUENCE DESCRIPTION: SEQ ID NO:74:

ACACACACAC ACACACACAC ACACACACAC ACACACACAC A                        41

( 2 ) INFORMATION FOR SEQ ID NO:75:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd8p1

( x i ) SEQUENCE DESCRIPTION: SEQ ID NO:75:

CGAAAGTTCA GAGATTTGCA                                                        20

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
   ( B ) CLONE: mfd8p2

( x i ) SEQUENCE DESCRIPTION: SEQ ID NO:76:

ACATTAGGAT TAGCTGTGGA  20

( 2 ) INFORMATION FOR SEQ ID NO:77:

( i ) SEQUENCE CHARACTERISTICS:
      ( A ) LENGTH: 35 base pairs
      ( B ) TYPE: nucleic acid
      ( C ) STRANDEDNESS: double
      ( D ) TOPOLOGY: linear ( i i ) MOLECULE TYPE: DNA (genomic)

( v i i ) IMMEDIATE SOURCE:
      ( B ) CLONE: mfd9rs ( x i ) SEQUENCE DESCRIPTION: SEQ ID NO:77:

CACACACACA CACACACACA CACACACACA CACAG  35

( 2 ) INFORMATION FOR SEQ ID NO:78:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: DNA (genomic)

( v i i ) IMMEDIATE SOURCE:
      ( B ) CLONE: mfd9p1

( x i ) SEQUENCE DESCRIPTION: SEQ ID NO:78:

ATGTCTCCTT GGTAAGTTA  19

( 2 ) INFORMATION FOR SEQ ID NO:79:

( i ) SEQUENCE CHARACTERISTICS:
      ( A ) LENGTH: 20 base pairs
      ( B ) TYPE: nucleic acid
      ( C ) STRANDEDNESS: double
      ( D ) TOPOLOGY: linear ( i i ) MOLECULE TYPE: DNA (genomic)

( v i i ) IMMEDIATE SOURCE:
      ( B ) CLONE: mfd9p2

( x i ) SEQUENCE DESCRIPTION: SEQ ID NO:79:

AATACCTAGG AAGGGGAGGG  20

( 2 ) INFORMATION FOR SEQ ID NO:80:

( i ) SEQUENCE CHARACTERISTICS:
      ( A ) LENGTH: 29 base pairs
      ( B ) TYPE: nucleic acid
      ( C ) STRANDEDNESS: double
      ( D ) TOPOLOGY: linear ( i i ) MOLECULE TYPE: DNA (genomic)

( v i i ) IMMEDIATE SOURCE:
      ( B ) CLONE: mfd10rs ( x i ) SEQUENCE DESCRIPTION: SEQ ID NO:80:

ACACACACAC ACACACACAC ACACACACA                                       29

( 2 ) INFORMATION FOR SEQ ID NO:81:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd10p1

( x i ) SEQUENCE DESCRIPTION: SEQ ID NO:81:

CATGCCTGGC CTTACTTGC                                                  19

( 2 ) INFORMATION FOR SEQ ID NO:82:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd10p2

( x i ) SEQUENCE DESCRIPTION: SEQ ID NO:82:

AGTTTGAGAC CAGCCTGCG                                                  19

( 2 ) INFORMATION FOR SEQ ID NO:83:

( i ) SEQUENCE CHARACTERISTICS:
            ( A ) LENGTH: 47 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd11rs ( x i ) SEQUENCE DESCRIPTION: SEQ ID NO:83:

ACACACACAC ACACACACAC ACACACACAC ACACACACAC ACACACA                   47

( 2 ) INFORMATION FOR SEQ ID NO:84:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd11p1

( x i ) SEQUENCE DESCRIPTION: SEQ ID NO:84:

ACTCATGAAG GTGACAGTTC                                                 20

( 2 ) INFORMATION FOR SEQ ID NO:85:

( i ) SEQUENCE CHARACTERISTICS:
            ( A ) LENGTH: 20 base pairs
            ( B ) TYPE: nucleic acid ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd11p2

( x i ) SEQUENCE DESCRIPTION: SEQ ID NO:85:

GTGTTGTTGA CCTATTGCAT                                                                    20

( 2 ) INFORMATION FOR SEQ ID NO:86:

( i ) SEQUENCE CHARACTERISTICS:
            ( A ) LENGTH: 39 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd12rs ( x i ) SEQUENCE DESCRIPTION: SEQ ID NO:86:

ACACACACAC ACACACACAC ATACACACAC ACACACACA                                               39

( 2 ) INFORMATION FOR SEQ ID NO:87:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd12p1

( x i ) SEQUENCE DESCRIPTION: SEQ ID NO:87:

GGTTGAGATG CTGACATGC                                                                     19

( 2 ) INFORMATION FOR SEQ ID NO:88:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd12p2

( x i ) SEQUENCE DESCRIPTION: SEQ ID NO:88:

CAGGGTGGCT GTTATAATG                                                                     19

( 2 ) INFORMATION FOR SEQ ID NO:89:

( i ) SEQUENCE CHARACTERISTICS:
            ( A ) LENGTH: 51 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd13rs ( x i ) SEQUENCE DESCRIPTION: SEQ ID NO:89:

CACACACACG CGCACACACA CACACACACA CACACACACA CACACACACA C  51

( 2 ) INFORMATION FOR SEQ ID NO:90:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd13p1

( x i ) SEQUENCE DESCRIPTION: SEQ ID NO:90:

TTCCCTTTGC TCCCCAAACG  20

( 2 ) INFORMATION FOR SEQ ID NO:91:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd13p2

( x i ) SEQUENCE DESCRIPTION: SEQ ID NO:91:

ATTAATCCAT CTAAAAGCGA A  21

( 2 ) INFORMATION FOR SEQ ID NO:92:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd14rs ( x i ) SEQUENCE DESCRIPTION: SEQ ID NO:92:

ACACACACAC ACACACACAC ACACACACAC ACACACACAC ACACACA  47

( 2 ) INFORMATION FOR SEQ ID NO:93:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd14p1

( x i ) SEQUENCE DESCRIPTION: SEQ ID NO:93:

TTCCCTTTGC TCCCCAAACG  20

( 2 ) INFORMATION FOR SEQ ID NO:94:

( i ) SEQUENCE CHARACTERISTICS:

(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd14p2

(xi) SEQUENCE DESCRIPTION: SEQ ID NO:94:

TTCTGATATC AAAACCTGGC                                                                                                  20

(2) INFORMATION FOR SEQ ID NO:95:

(i) SEQUENCE CHARACTERISTICS:
(A) LENGTH: 50 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd15rs (xi) SEQUENCE DESCRIPTION: SEQ ID NO:95:

ACACACACAC ACACACACAC ACACACACAC ACACACACAC ACACACACAC                                                                 50

(2) INFORMATION FOR SEQ ID NO:96:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd15p1

(xi) SEQUENCE DESCRIPTION: SEQ ID NO:96:

GGAAGAATCA AATAGACAAT                                                                                                  20

(2) INFORMATION FOR SEQ ID NO:97:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd15p2

(xi) SEQUENCE DESCRIPTION: SEQ ID NO:97:

GCTGGCCATA TATATATTTA AACC                                                                                             24

(2) INFORMATION FOR SEQ ID NO:98:

(i) SEQUENCE CHARACTERISTICS:
(A) LENGTH: 89 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:

(B) CLONE: mfd16rs (xi) SEQUENCE DESCRIPTION: SEQ ID NO:98:

GCGCGCGCGC ACACACACAT ACACACATAT ACACACACAC ACACCAACAC ACACACACAC    60

ACACACACAC ACACACACAC ACACACACA    89

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd16p1

(xi) SEQUENCE DESCRIPTION: SEQ ID NO:99:

AGAGATTAAA GGCTAAATTC    20

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd16p2

(xi) SEQUENCE DESCRIPTION: SEQ ID NO:100:

TTCGTAGTTG GTTAAAATTG    20

(2) INFORMATION FOR SEQ ID NO:101:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd17rs (xi) SEQUENCE DESCRIPTION: SEQ ID NO:101:

ACACACACAC ACACACACAC ACACACACAC ACACACACAC ACACAC    46

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd17p1

(xi) SEQUENCE DESCRIPTION: SEQ ID NO:102:

TTTCCACTGG GGAACATGGT    20

( 2 ) INFORMATION FOR SEQ ID NO:103:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd17p2

( x i ) SEQUENCE DESCRIPTION: SEQ ID NO:103:

ACTCTTTGTT GAATTCCCAT                                            20

( 2 ) INFORMATION FOR SEQ ID NO:104:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd18rs ( x i ) SEQUENCE DESCRIPTION: SEQ ID NO:104:

ACACACACAC ACACACACAC ACACACACAC ACACAC                      36

( 2 ) INFORMATION FOR SEQ ID NO:105:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd18p1

( x i ) SEQUENCE DESCRIPTION: SEQ ID NO:105:

AGCTATCATC ACCCTATAAA AT                                        22

( 2 ) INFORMATION FOR SEQ ID NO:106:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd18p2

( x i ) SEQUENCE DESCRIPTION: SEQ ID NO:106:

AGTTTAACCA TGTCTCTCCC G                                         21

( 2 ) INFORMATION FOR SEQ ID NO:107:

( i ) SEQUENCE CHARACTERISTICS:
        ( A ) LENGTH: 91 base pairs
        ( B ) TYPE: nucleic acid
        ( C ) STRANDEDNESS: double
        ( D ) TOPOLOGY: linear (  i i ) MOLECULE TYPE: DNA (genomic)

( v i i ) IMMEDIATE SOURCE:
    ( B ) CLONE: mfd19rs ( x i ) SEQUENCE DESCRIPTION: SEQ ID NO:107:

ACACACACAC ACACACAGAC ACACAGACAC ACACACACAC ACACACACAC ACACACACAC    60

ACACACACAC ACACTCACTC TCTCTCTCTC T    91

( 2 ) INFORMATION FOR SEQ ID NO:108:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd19p1

( x i ) SEQUENCE DESCRIPTION: SEQ ID NO:108:

TCTAACCCTT TGGCCATTTG    20

( 2 ) INFORMATION FOR SEQ ID NO:109:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd19p2

( x i ) SEQUENCE DESCRIPTION: SEQ ID NO:109:

GCTTGTTACA TTGTTGCTTC    20

( 2 ) INFORMATION FOR SEQ ID NO:110:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd20rs ( x i ) SEQUENCE DESCRIPTION: SEQ ID NO:110:

ACACACACAC ACACACACAC ACACACACAC ACAC    34

( 2 ) INFORMATION FOR SEQ ID NO:111:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd20p1

( x i ) SEQUENCE DESCRIPTION: SEQ ID NO:111:

TTTGAGTAGG TGGCATCTCA 20

( 2 ) INFORMATION FOR SEQ ID NO:112:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd20p2

( x i ) SEQUENCE DESCRIPTION: SEQ ID NO:112:

TTAAAATGTT GAAGGCATCT TC 22

( 2 ) INFORMATION FOR SEQ ID NO:113:

( i ) SEQUENCE CHARACTERISTICS:
    ( A ) LENGTH: 82 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd21rs ( x i ) SEQUENCE DESCRIPTION: SEQ ID NO:113:

TATATATATA TATTTATATC TATATATATA TTTATATACA TATATATATA TATACACACA 60
CACACACACA TACATGTATA TA 82

( 2 ) INFORMATION FOR SEQ ID NO:114:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd21p1

( x i ) SEQUENCE DESCRIPTION: SEQ ID NO:114:

GCTCAGGAGT TCGAGATCA 19

( 2 ) INFORMATION FOR SEQ ID NO:115:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd21p2

( x i ) SEQUENCE DESCRIPTION: SEQ ID NO:115:

CACCACACCC GACATTTTA 19

( 2 ) INFORMATION FOR SEQ ID NO:116:

( i ) SEQUENCE CHARACTERISTICS:
    ( A ) LENGTH: 65 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd22rs ( x i ) SEQUENCE DESCRIPTION: SEQ ID NO:116:

```
ACACACACAC ACACACAC ACACACACAC ACACACACAC AGAGACAGAC AGACAGACAG        60
ACAGA                                                                  65
```

( 2 ) INFORMATION FOR SEQ ID NO:117:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd22p1

( x i ) SEQUENCE DESCRIPTION: SEQ ID NO:117:

```
TGGGTAAAGA GTGAGGCTG                                                   19
```

( 2 ) INFORMATION FOR SEQ ID NO:118:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd22p2

( x i ) SEQUENCE DESCRIPTION: SEQ ID NO:118:

```
GGTCCAGTAA GAGGACAGT                                                   19
```

( 2 ) INFORMATION FOR SEQ ID NO:119:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd23rs ( x i ) SEQUENCE DESCRIPTION: SEQ ID NO:119:

```
ACACACACAC ACACACACAC ACACACACAC ACACACACAC                            40
```

( 2 ) INFORMATION FOR SEQ ID NO:120:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
    ( B ) CLONE: mfd23p1

( x i ) SEQUENCE DESCRIPTION: SEQ ID NO:120:

AGTCCTCTGT GCACTTTGT     19

( 2 ) INFORMATION FOR SEQ ID NO:121:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd23p2

( x i ) SEQUENCE DESCRIPTION: SEQ ID NO:121:

CCAGACATGG CAGTCTCTA     19

( 2 ) INFORMATION FOR SEQ ID NO:122:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd24rs ( x i ) SEQUENCE DESCRIPTION: SEQ ID NO:122:

ACACACACAC ACACAGAGAC ACACACACAC ACACACACAC ACACACA     47

( 2 ) INFORMATION FOR SEQ ID NO:123:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd24p1

( x i ) SEQUENCE DESCRIPTION: SEQ ID NO:123:

AAGCTTGTAT CTTTCTCAGG     20

( 2 ) INFORMATION FOR SEQ ID NO:124:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd24p2

( x i ) SEQUENCE DESCRIPTION: SEQ ID NO:124:

ATCTACCTTG GCTGTCATTG 20

( 2 ) INFORMATION FOR SEQ ID NO:125:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd25rs ( x i ) SEQUENCE DESCRIPTION: SEQ ID NO:125:

ACACACACAC ACACACACAC AC 22

( 2 ) INFORMATION FOR SEQ ID NO:126:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd25p1

( x i ) SEQUENCE DESCRIPTION: SEQ ID NO:126:

TTTATGCGAG CGTATGGATA 20

( 2 ) INFORMATION FOR SEQ ID NO:127:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd25p2

( x i ) SEQUENCE DESCRIPTION: SEQ ID NO:127:

CACCACCATT GATCTGGAAG 20

( 2 ) INFORMATION FOR SEQ ID NO:128:

( i ) SEQUENCE CHARACTERISTICS:
    ( A ) LENGTH: 57 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd26rs ( x i ) SEQUENCE DESCRIPTION: SEQ ID NO:128:

ACACACACAC ACACACACAC ACACACACAC ACACACACAC ACACACACAC ACACACA 57

( 2 ) INFORMATION FOR SEQ ID NO:129:

( i ) SEQUENCE CHARACTERISTICS:
    ( A ) LENGTH: 20 base pairs
    ( B ) TYPE: nucleic acid ( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd26p1

( x i ) SEQUENCE DESCRIPTION: SEQ ID NO:129:

CAGAAAATTC TCTCTGGCTA 20

( 2 ) INFORMATION FOR SEQ ID NO:130:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd26p2

( x i ) SEQUENCE DESCRIPTION: SEQ ID NO:130:

CTCATGTTCC TGGCAAGAAT 20

( 2 ) INFORMATION FOR SEQ ID NO:131:

( i ) SEQUENCE CHARACTERISTICS:
( A ) LENGTH: 72 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd27rs ( x i ) SEQUENCE DESCRIPTION: SEQ ID NO:131:

CACACACACA CACACACAAA CACACACACA CACACACACA CACACACACA CACACACAGA 60

GAGAGAGAGA GA 72

( 2 ) INFORMATION FOR SEQ ID NO:132:

( i ) SEQUENCE CHARACTERISTICS:
( A ) LENGTH: 21 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd27p1

( x i ) SEQUENCE DESCRIPTION: SEQ ID NO:132:

GATCCACTTT AACCCAAATA C 21

( 2 ) INFORMATION FOR SEQ ID NO:133:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:

( B ) CLONE: mfd27p2

( x i ) SEQUENCE DESCRIPTION: SEQ ID NO:133:

GGCATCAACT TGAACAGCAT 20

( 2 ) INFORMATION FOR SEQ ID NO:134:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd28rs ( x i ) SEQUENCE DESCRIPTION: SEQ ID NO:134:

ACACACACAC ACACACACAC AGACACACAC ACACACACAC ACACACACAC ACACACACAC 60

ACACA 65

( 2 ) INFORMATION FOR SEQ ID NO:135:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd28p1

( x i ) SEQUENCE DESCRIPTION: SEQ ID NO:135:

AACACTAGTG ACATTATTTT CA 22

( 2 ) INFORMATION FOR SEQ ID NO:136:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd28p2

( x i ) SEQUENCE DESCRIPTION: SEQ ID NO:136:

AGCTAGGCCT GAAGGCTTCT 20

( 2 ) INFORMATION FOR SEQ ID NO:137:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd29rs ( x i ) SEQUENCE DESCRIPTION: SEQ ID NO:137:

ACACACACAC ACACACACAC ACACACACAC ACACACA 39

( 2 ) INFORMATION FOR SEQ ID NO:138:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd29p1

( x i ) SEQUENCE DESCRIPTION: SEQ ID NO:138:

AGCTCCCTCG AGATGCACT                         19

( 2 ) INFORMATION FOR SEQ ID NO:139:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd29p2

( x i ) SEQUENCE DESCRIPTION: SEQ ID NO:139:

TTCTTTGCTT TACATGTGGC                        20

( 2 ) INFORMATION FOR SEQ ID NO:140:

( i ) SEQUENCE CHARACTERISTICS:
    ( A ) LENGTH: 37 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd30rs ( x i ) SEQUENCE DESCRIPTION: SEQ ID NO:140:

ACACACACAC ACACACACAC ACACACACAC ACACACA             37

( 2 ) INFORMATION FOR SEQ ID NO:141:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd30p1

( x i ) SEQUENCE DESCRIPTION: SEQ ID NO:141:

CCATGTCCCA TATCTCTACA                        20

( 2 ) INFORMATION FOR SEQ ID NO:142:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd30p2

( x i ) SEQUENCE DESCRIPTION: SEQ ID NO:142:

TGAAATCACT GATGACAATG　　　　　　　　　　　　　　　　　　　　　　　　　　　　20

( 2 ) INFORMATION FOR SEQ ID NO:143:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd31rs ( x i ) SEQUENCE DESCRIPTION: SEQ ID NO:143:

ACACACACAC ACACACACAC ACACACA　　　　　　　　　　　　　　　　　　　　　27

( 2 ) INFORMATION FOR SEQ ID NO:144:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd31p1

( x i ) SEQUENCE DESCRIPTION: SEQ ID NO:144:

TAATAAAGGA GCCAGCTATG　　　　　　　　　　　　　　　　　　　　　　　　　　　　20

( 2 ) INFORMATION FOR SEQ ID NO:145:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd31p2

( x i ) SEQUENCE DESCRIPTION: SEQ ID NO:145:

ACATCTGATG TAAATGCAAG T　　　　　　　　　　　　　　　　　　　　　　　　　　　21

( 2 ) INFORMATION FOR SEQ ID NO:146:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd32rs ( x i ) SEQUENCE DESCRIPTION: SEQ ID NO:146:

ACACACACAC ACACACACAC ACACA                                                                                        25

( 2 ) INFORMATION FOR SEQ ID NO:147:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd32p1

( x i ) SEQUENCE DESCRIPTION: SEQ ID NO:147:

AGCTAGATTT TTACTTCTCT G                                                                                             21

( 2 ) INFORMATION FOR SEQ ID NO:148:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd32p2

( x i ) SEQUENCE DESCRIPTION: SEQ ID NO:148:

CTGGTTGTAC ATGCCTGAC                                                                                                19

( 2 ) INFORMATION FOR SEQ ID NO:149:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd33rs ( x i ) SEQUENCE DESCRIPTION: SEQ ID NO:149:

ACACACACAC ACACACACAC ACACACACAT ACACACACAC ACACACACAC ACACAC                                                       56

( 2 ) INFORMATION FOR SEQ ID NO:150:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd33p1

( x i ) SEQUENCE DESCRIPTION: SEQ ID NO:150:

AGCCTGGGAG TCAGAGTGA                                                                                                19

( 2 ) INFORMATION FOR SEQ ID NO:151:

( i ) SEQUENCE CHARACTERISTICS:
        ( A ) LENGTH: 20 base pairs
        ( B ) TYPE: nucleic acid ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd33p2

( x i ) SEQUENCE DESCRIPTION: SEQ ID NO:151:

AGCTCCAAAT CCAAAGACGT 20

( 2 ) INFORMATION FOR SEQ ID NO:152:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd34rs ( x i ) SEQUENCE DESCRIPTION: SEQ ID NO:152:

ACACACACAT ACACACACAC ACACACACAC ACACACACAC 40

( 2 ) INFORMATION FOR SEQ ID NO:153:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd34p1

( x i ) SEQUENCE DESCRIPTION: SEQ ID NO:153:

GGTTTCTTTT TTCTAGTTCT TC 22

( 2 ) INFORMATION FOR SEQ ID NO:154:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd34p2

( x i ) SEQUENCE DESCRIPTION: SEQ ID NO:154:

TCATATAGCC TTTTGTTTGC A 21

( 2 ) INFORMATION FOR SEQ ID NO:155:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd35p1

( x i ) SEQUENCE DESCRIPTION: SEQ ID NO:155:

GTGGAGAGTA AGACTCTGTC 20

( 2 ) INFORMATION FOR SEQ ID NO:156:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd35p2

( x i ) SEQUENCE DESCRIPTION: SEQ ID NO:156:

TGATGCAACA CAGGAGACCT 20

( 2 ) INFORMATION FOR SEQ ID NO:157:

( i ) SEQUENCE CHARACTERISTICS:
    ( A ) LENGTH: 45 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd36rs ( x i ) SEQUENCE DESCRIPTION: SEQ ID NO:157:

ACACACACAC ACACACACAC ACACACACAC ATACACACAC ACACA 45

( 2 ) INFORMATION FOR SEQ ID NO:158:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd36p1

( x i ) SEQUENCE DESCRIPTION: SEQ ID NO:158:

AGCTATAATT GCATCATTGC A 21

( 2 ) INFORMATION FOR SEQ ID NO:159:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd36p2

( x i ) SEQUENCE DESCRIPTION: SEQ ID NO:159:

TGGTCTATAA CTGGTCTATG 20

( 2 ) INFORMATION FOR SEQ ID NO:160:

( i ) SEQUENCE CHARACTERISTICS:

(A) LENGTH: 21 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd37rs (xi) SEQUENCE DESCRIPTION: SEQ ID NO:160:

ACACACACAC ACACACACAC A 21

(2) INFORMATION FOR SEQ ID NO:161:

(i) SEQUENCE CHARACTERISTICS:
(A) LENGTH: 22 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd37p1

(xi) SEQUENCE DESCRIPTION: SEQ ID NO:161:

AAAAGTGTGT TACTTTCAGA AC 22

(2) INFORMATION FOR SEQ ID NO:162:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd37p2

(xi) SEQUENCE DESCRIPTION: SEQ ID NO:162:

ACAAGGTGAC AAGGTGCCTA 20

(2) INFORMATION FOR SEQ ID NO:163:

(i) SEQUENCE CHARACTERISTICS:
(A) LENGTH: 57 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd38rs (xi) SEQUENCE DESCRIPTION: SEQ ID NO:163:

ATATATATAT ATATATATAT ATATATATAC ACACACACAC ACACACACAC ACACACA 57

(2) INFORMATION FOR SEQ ID NO:164:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:

(B) CLONE: mfd38p1

(x i) SEQUENCE DESCRIPTION: SEQ ID NO:164:

ATCTCTGTTC CCTCCCTGTT 20

(2) INFORMATION FOR SEQ ID NO:165:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd38p2

(x i) SEQUENCE DESCRIPTION: SEQ ID NO:165:

CTTATTGGCC TTGAAGGTAG 20

(2) INFORMATION FOR SEQ ID NO:166:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd39rs (x i) SEQUENCE DESCRIPTION: SEQ ID NO:166:

TCTCTCTCTC TCTCTCTCTC TCTCTGTTTC TCTCTCTCTC TCTCTCTCTC TCACACACAC 60

ACACACACAC ACACACACAA CACACACACA C 91

(2) INFORMATION FOR SEQ ID NO:167:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: mfd39p1

(x i) SEQUENCE DESCRIPTION: SEQ ID NO:167:

GGGTTGGTTG TAAATTAAAA C 21

(2) INFORMATION FOR SEQ ID NO:168:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd39p2

(x i) SEQUENCE DESCRIPTION: SEQ ID NO:168:

TGTCAAATAC TTAAGCACAG 20

( 2 ) INFORMATION FOR SEQ ID NO:169:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd40rs ( x i ) SEQUENCE DESCRIPTION: SEQ ID NO:169:

CACACACACA CACACACACA CACACACCAC ACACACACAT ACACACACAC      50

( 2 ) INFORMATION FOR SEQ ID NO:170:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd40p1

( x i ) SEQUENCE DESCRIPTION: SEQ ID NO:170:

GGCATCATTT TAGAAGGAAA T      21

( 2 ) INFORMATION FOR SEQ ID NO:171:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: mfd40p2

( x i ) SEQUENCE DESCRIPTION: SEQ ID NO:171:

GGCATCATTT TAGAAGGAAA T      21

( 2 ) INFORMATION FOR SEQ ID NO:172:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd41rs ( x i ) SEQUENCE DESCRIPTION: SEQ ID NO:172:

ACACACACAC ACACACACAC ACACACACAC ACAC      34

( 2 ) INFORMATION FOR SEQ ID NO:173:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear (i i) MOLECULE TYPE: DNA (genomic)

(v i i) IMMEDIATE SOURCE:
    (B) CLONE: mfd41p1

(x i) SEQUENCE DESCRIPTION: SEQ ID NO:173:

CAGGTTCTGT CATAGGACTA 20

(2) INFORMATION FOR SEQ ID NO:174:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd41p2

(x i) SEQUENCE DESCRIPTION: SEQ ID NO:174:

TTCTGGAAAC CTACTCCTGA 20

(2) INFORMATION FOR SEQ ID NO:175:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd42rs (x i) SEQUENCE DESCRIPTION: SEQ ID NO:175:

CACACACACA CACACACACA CACACACACA CATACACACA 40

(2) INFORMATION FOR SEQ ID NO:176:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd42p1

(x i) SEQUENCE DESCRIPTION: SEQ ID NO:176:

GGCCTCAAAG AATCCTACAG 20

(2) INFORMATION FOR SEQ ID NO:177:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd42p2

(x i) SEQUENCE DESCRIPTION: SEQ ID NO:177:

GACACGTAGT TGCTTATTAC 20

( 2 ) INFORMATION FOR SEQ ID NO:178:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd43p1

( x i ) SEQUENCE DESCRIPTION: SEQ ID NO:178:

TTGGAAGCCT TAGGAAGTGC 20

( 2 ) INFORMATION FOR SEQ ID NO:179:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd43p2

( x i ) SEQUENCE DESCRIPTION: SEQ ID NO:179:

AAGAATTCTA GTTTCAATAC CG 22

( 2 ) INFORMATION FOR SEQ ID NO:180:

( i ) SEQUENCE CHARACTERISTICS:
    ( A ) LENGTH: 34 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd44rs ( x i ) SEQUENCE DESCRIPTION: SEQ ID NO:180:

CACACACACA CACACACACA CACACACACA CACA 34

( 2 ) INFORMATION FOR SEQ ID NO:181:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd44p1

( x i ) SEQUENCE DESCRIPTION: SEQ ID NO:181:

GTATTTTTGG TATGCTTGTG C 21

( 2 ) INFORMATION FOR SEQ ID NO:182:

( i ) SEQUENCE CHARACTERISTICS:
    ( A ) LENGTH: 22 base pairs
    ( B ) TYPE: nucleic acid ( C ) STRANDEDNESS: double
( D ) TOPOLOGY: linear ( i i ) MOLECULE TYPE: DNA (genomic)

( v i i ) IMMEDIATE SOURCE:
    ( B ) CLONE: mfd44p2

( x i ) SEQUENCE DESCRIPTION: SEQ ID NO:182:

CTATTTTGGA ATATATGTGC CT  22

( 2 ) INFORMATION FOR SEQ ID NO:183:

( i ) SEQUENCE CHARACTERISTICS:
       ( A ) LENGTH: 41 base pairs
       ( B ) TYPE: nucleic acid
       ( C ) STRANDEDNESS: double
       ( D ) TOPOLOGY: linear ( i i ) MOLECULE TYPE: DNA (genomic)

( v i i ) IMMEDIATE SOURCE:
       ( B ) CLONE: mfd45rs ( x i ) SEQUENCE DESCRIPTION: SEQ ID NO:183:

CACACACACA CACACACACA CACACACACA CACACACACA C  41

( 2 ) INFORMATION FOR SEQ ID NO:184:

( i ) SEQUENCE CHARACTERISTICS:
       ( A ) LENGTH: 20 base pairs
       ( B ) TYPE: nucleic acid
       ( C ) STRANDEDNESS: double
       ( D ) TOPOLOGY: linear ( i i ) MOLECULE TYPE: DNA (genomic)

( v i i ) IMMEDIATE SOURCE:
       ( B ) CLONE: mfd45p1

( x i ) SEQUENCE DESCRIPTION: SEQ ID NO:184:

TCCAGCAGAG AAAGGGTTAT  20

( 2 ) INFORMATION FOR SEQ ID NO:185:

( i ) SEQUENCE CHARACTERISTICS:
       ( A ) LENGTH: 20 base pairs
       ( B ) TYPE: nucleic acid
       ( C ) STRANDEDNESS: double
       ( D ) TOPOLOGY: linear ( i i ) MOLECULE TYPE: DNA (genomic)

( v i i ) IMMEDIATE SOURCE:
       ( B ) CLONE: mfd45p2

( x i ) SEQUENCE DESCRIPTION: SEQ ID NO:185:

GGCAAAGAGA ACTCATCAGA  20

( 2 ) INFORMATION FOR SEQ ID NO:186:

( i ) SEQUENCE CHARACTERISTICS:
       ( A ) LENGTH: 50 base pairs
       ( B ) TYPE: nucleic acid
       ( C ) STRANDEDNESS: double
       ( D ) TOPOLOGY: linear ( i i ) MOLECULE TYPE: DNA (genomic)

( v i i ) IMMEDIATE SOURCE:
       ( B ) CLONE: mfd46rs ( x i ) SEQUENCE DESCRIPTION: SEQ ID NO:186:

ACACACACAC ACACACACAC ACACACACAC ACACACACAC ACACACACAC　　　　　　50

( 2 ) INFORMATION FOR SEQ ID NO:187:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd46p1

( x i ) SEQUENCE DESCRIPTION: SEQ ID NO:187:

AAAAGGAAGA ATCAAATAGA C　　　　　　21

( 2 ) INFORMATION FOR SEQ ID NO:188:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd46p2

( x i ) SEQUENCE DESCRIPTION: SEQ ID NO:188:

ATATATTTAA ACCATTTGAA AG　　　　　　22

( 2 ) INFORMATION FOR SEQ ID NO:189:

( i ) SEQUENCE CHARACTERISTICS:
    ( A ) LENGTH: 35 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd47rs ( x i ) SEQUENCE DESCRIPTION: SEQ ID NO:189:

ACACACACAC ACACACACAC ACACACACAC ACACA　　　　　　35

( 2 ) INFORMATION FOR SEQ ID NO:190:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd47p1

( x i ) SEQUENCE DESCRIPTION: SEQ ID NO:190:

ACAGAGTGAG ACCGTGTAAC　　　　　　20

( 2 ) INFORMATION FOR SEQ ID NO:191:

( i ) SEQUENCE CHARACTERISTICS:

5,582,979

235                                   236
-continued ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd47p2

( x i ) SEQUENCE DESCRIPTION: SEQ ID NO:191:

AGAGAAGCAT CTCACTTAGT                                                                20

( 2 ) INFORMATION FOR SEQ ID NO:192:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd48rs ( x i ) SEQUENCE DESCRIPTION: SEQ ID NO:192:

ACACACACAC ACACACACAC ACACACACAC ACAC                                                34

( 2 ) INFORMATION FOR SEQ ID NO:193:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd48p1

( x i ) SEQUENCE DESCRIPTION: SEQ ID NO:193:

TGTCTCCTGC TGAGAATAG                                                                 19

( 2 ) INFORMATION FOR SEQ ID NO:194:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd48p2

( x i ) SEQUENCE DESCRIPTION: SEQ ID NO:194:

TAATATCCAA ACCACAAAGG T                                                              21

( 2 ) INFORMATION FOR SEQ ID NO:195:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:

( B ) CLONE: mfd49rs ( x i ) SEQUENCE DESCRIPTION: SEQ ID NO:195:

CACACACACA CACACACACA CACACACACA CACACACACA CACA                                44

( 2 ) INFORMATION FOR SEQ ID NO:196:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: DNA (genomic)

( v i i ) IMMEDIATE SOURCE:
                ( B ) CLONE: mfd49p1

( x i ) SEQUENCE DESCRIPTION: SEQ ID NO:196:

GATAAATGCC AAACATGTTG T                                                         21

( 2 ) INFORMATION FOR SEQ ID NO:197:

( i ) SEQUENCE CHARACTERISTICS:
                ( A ) LENGTH: 20 base pairs
                ( B ) TYPE: nucleic acid
                ( C ) STRANDEDNESS: double
                ( D ) TOPOLOGY: linear ( i i ) MOLECULE TYPE: DNA (genomic)

( v i i ) IMMEDIATE SOURCE:
                ( B ) CLONE: mfd49p2

( x i ) SEQUENCE DESCRIPTION: SEQ ID NO:197:

TGCTCTCAGG ATTTCCTCCA                                                           20

( 2 ) INFORMATION FOR SEQ ID NO:198:

( i ) SEQUENCE CHARACTERISTICS:
                ( A ) LENGTH: 38 base pairs
                ( B ) TYPE: nucleic acid
                ( C ) STRANDEDNESS: double
                ( D ) TOPOLOGY: linear ( i i ) MOLECULE TYPE: DNA (genomic)

( v i i ) IMMEDIATE SOURCE:
                ( B ) CLONE: mfd50rs ( x i ) SEQUENCE DESCRIPTION: SEQ ID NO:198:

CACACACACA CACACACACA CACACACACA CACACACA                                       38

( 2 ) INFORMATION FOR SEQ ID NO:199:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: DNA (genomic)

( v i i ) IMMEDIATE SOURCE:
                ( B ) CLONE: mfd50p1

( x i ) SEQUENCE DESCRIPTION: SEQ ID NO:199:

ACATTCTAAG ACTTTCCCAA T                                                         21

( 2 ) INFORMATION FOR SEQ ID NO:200:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd50p2

( x i ) SEQUENCE DESCRIPTION: SEQ ID NO:200:

AGAGCATGCA CCCTGAATTG 20

( 2 ) INFORMATION FOR SEQ ID NO:201:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd51p1

( x i ) SEQUENCE DESCRIPTION: SEQ ID NO:201:

AGCTGATACA CCACTTCTGA 20

( 2 ) INFORMATION FOR SEQ ID NO:202:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd51p2

( x i ) SEQUENCE DESCRIPTION: SEQ ID NO:202:

GACAGAAATA TCCTTCCCAT 20

( 2 ) INFORMATION FOR SEQ ID NO:203:

( i ) SEQUENCE CHARACTERISTICS:
    ( A ) LENGTH: 45 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd52rs ( x i ) SEQUENCE DESCRIPTION: SEQ ID NO:203:

ACACACACAC ACACACACAC ACACACACAC ACACACTTGC ACACA 45

( 2 ) INFORMATION FOR SEQ ID NO:204:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
         ( B ) CLONE: mfd52p1

( x i ) SEQUENCE DESCRIPTION: SEQ ID NO:204:

AAATCAGACA AGTACAGGTG                                                              20

( 2 ) INFORMATION FOR SEQ ID NO:205:

( i ) SEQUENCE CHARACTERISTICS:
         ( A ) LENGTH: 20 base pairs
         ( B ) TYPE: nucleic acid
         ( C ) STRANDEDNESS: double
         ( D ) TOPOLOGY: linear ( i i ) MOLECULE TYPE: DNA (genomic)

( v i i ) IMMEDIATE SOURCE:
         ( B ) CLONE: mfd52p2

( x i ) SEQUENCE DESCRIPTION: SEQ ID NO:205:

ATGAACTTGT TCTGGGAGGA                                                              20

( 2 ) INFORMATION FOR SEQ ID NO:206:

( i ) SEQUENCE CHARACTERISTICS:
         ( A ) LENGTH: 19 base pairs
         ( B ) TYPE: nucleic acid
         ( C ) STRANDEDNESS: double
         ( D ) TOPOLOGY: linear ( i i ) MOLECULE TYPE: DNA (genomic)

( v i i ) IMMEDIATE SOURCE:
         ( B ) CLONE: mfd53p1

( x i ) SEQUENCE DESCRIPTION: SEQ ID NO:206:

TGCCCCTGCA CTCTAGCCT                                                               19

( 2 ) INFORMATION FOR SEQ ID NO:207:

( i ) SEQUENCE CHARACTERISTICS:
         ( A ) LENGTH: 20 base pairs
         ( B ) TYPE: nucleic acid
         ( C ) STRANDEDNESS: double
         ( D ) TOPOLOGY: linear ( i i ) MOLECULE TYPE: DNA (genomic)

( v i i ) IMMEDIATE SOURCE:
         ( B ) CLONE: mfd53p2

( x i ) SEQUENCE DESCRIPTION: SEQ ID NO:207:

GCTATCAACA AGCTTTAGGT                                                              20

( 2 ) INFORMATION FOR SEQ ID NO:208:

( i ) SEQUENCE CHARACTERISTICS:
         ( A ) LENGTH: 19 base pairs
         ( B ) TYPE: nucleic acid
         ( C ) STRANDEDNESS: double
         ( D ) TOPOLOGY: linear ( i i ) MOLECULE TYPE: DNA (genomic)

( v i i ) IMMEDIATE SOURCE:
         ( B ) CLONE: mfd54p1

( x i ) SEQUENCE DESCRIPTION: SEQ ID NO:208:

CTGACAGGTT GAGGCTGCA                                                               19

( 2 ) INFORMATION FOR SEQ ID NO:209:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd54p2

( x i ) SEQUENCE DESCRIPTION: SEQ ID NO:209:

```
CAGTTTGTAT GTATGTTTGG A                                              21
```

( 2 ) INFORMATION FOR SEQ ID NO:210:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd55rs ( x i ) SEQUENCE DESCRIPTION: SEQ ID NO:210:

```
ACACACACAC ACACACACAC ACACACACAC AC                                  32
```

( 2 ) INFORMATION FOR SEQ ID NO:211:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd55p1

( x i ) SEQUENCE DESCRIPTION: SEQ ID NO:211:

```
GTCAACATAG TGAGACCCCA                                                20
```

( 2 ) INFORMATION FOR SEQ ID NO:212:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd55p2

( x i ) SEQUENCE DESCRIPTION: SEQ ID NO:212:

```
ATCCAGCCTG TAACACATTC                                                20
```

( 2 ) INFORMATION FOR SEQ ID NO:213:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
 ( B ) CLONE: mfd56p1

( x i ) SEQUENCE DESCRIPTION: SEQ ID NO:213:

CTGGTGAATT CAAACAACCT 20

( 2 ) INFORMATION FOR SEQ ID NO:214:

( i ) SEQUENCE CHARACTERISTICS:
 ( A ) LENGTH: 20 base pairs
 ( B ) TYPE: nucleic acid
 ( C ) STRANDEDNESS: double
 ( D ) TOPOLOGY: linear ( i i ) MOLECULE TYPE: DNA (genomic)

( v i i ) IMMEDIATE SOURCE:
 ( B ) CLONE: mfd56p2

( x i ) SEQUENCE DESCRIPTION: SEQ ID NO:214:

TTTTCTCTGA CACCTCAACT 20

( 2 ) INFORMATION FOR SEQ ID NO:215:

( i ) SEQUENCE CHARACTERISTICS:
 ( A ) LENGTH: 31 base pairs
 ( B ) TYPE: nucleic acid
 ( C ) STRANDEDNESS: double
 ( D ) TOPOLOGY: linear ( i i ) MOLECULE TYPE: DNA (genomic)

( v i i ) IMMEDIATE SOURCE:
 ( B ) CLONE: mfd57rs ( x i ) SEQUENCE DESCRIPTION: SEQ ID NO:215:

CACACACACA CACACACACA CACACACACA C 31

( 2 ) INFORMATION FOR SEQ ID NO:216:

( i ) SEQUENCE CHARACTERISTICS:
 ( A ) LENGTH: 20 base pairs
 ( B ) TYPE: nucleic acid
 ( C ) STRANDEDNESS: double
 ( D ) TOPOLOGY: linear ( i i ) MOLECULE TYPE: DNA (genomic)

( v i i ) IMMEDIATE SOURCE:
 ( B ) CLONE: mfd57p1

( x i ) SEQUENCE DESCRIPTION: SEQ ID NO:216:

GATCTATCCC CTCACTTACG 20

( 2 ) INFORMATION FOR SEQ ID NO:217:

( i ) SEQUENCE CHARACTERISTICS:
 ( A ) LENGTH: 20 base pairs
 ( B ) TYPE: nucleic acid
 ( C ) STRANDEDNESS: double
 ( D ) TOPOLOGY: linear ( i i ) MOLECULE TYPE: DNA (genomic)

( v i i ) IMMEDIATE SOURCE:
 ( B ) CLONE: mfd57p2

( x i ) SEQUENCE DESCRIPTION: SEQ ID NO:217:

TATGAACAGA ACAGTGGAGC 20

(2) INFORMATION FOR SEQ ID NO:218:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd58rs (xi) SEQUENCE DESCRIPTION: SEQ ID NO:218:

CACACACACA CACACACACA CACACACACA CAC 33

(2) INFORMATION FOR SEQ ID NO:219:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd58p1

(xi) SEQUENCE DESCRIPTION: SEQ ID NO:219:

CTCATTTGAA GACTGCAGCA 20

(2) INFORMATION FOR SEQ ID NO:220:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd58p2

(xi) SEQUENCE DESCRIPTION: SEQ ID NO:220:

AGGGCTTCCT GTCCATCTA 19

(2) INFORMATION FOR SEQ ID NO:221:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd59rs (xi) SEQUENCE DESCRIPTION: SEQ ID NO:221:

ACACACACAC ACACACACAC ACACACACAC ACACACACAC ACACACA 47

(2) INFORMATION FOR SEQ ID NO:222:

(i) SEQUENCE CHARACTERISTICS:
        (A) LENGTH: 20 base pairs
        (B) TYPE: nucleic acid ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd59p1

( x i ) SEQUENCE DESCRIPTION: SEQ ID NO:222:

AAGAACCATG CGATACGACT 20

( 2 ) INFORMATION FOR SEQ ID NO:223:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd59p2

( x i ) SEQUENCE DESCRIPTION: SEQ ID NO:223:

CATTCCTAGA TGGGTAAAGC 20

( 2 ) INFORMATION FOR SEQ ID NO:224:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd60p1

( x i ) SEQUENCE DESCRIPTION: SEQ ID NO:224:

GTCCCTAGCC TCCCAGCAT 19

( 2 ) INFORMATION FOR SEQ ID NO:225:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd60p2

( x i ) SEQUENCE DESCRIPTION: SEQ ID NO:225:

CAAGAGCGAA AGTCCGTCTC 20

( 2 ) INFORMATION FOR SEQ ID NO:226:

( i ) SEQUENCE CHARACTERISTICS:
            ( A ) LENGTH: 46 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd61rs ( x i ) SEQUENCE DESCRIPTION: SEQ ID NO:226:

CACACACACA CACACACACA CACACACACA CACACACACA CACACA  46

( 2 ) INFORMATION FOR SEQ ID NO:227:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd61p1

( x i ) SEQUENCE DESCRIPTION: SEQ ID NO:227:

GCCCTATAAA ATCCTAATTA AC  22

( 2 ) INFORMATION FOR SEQ ID NO:228:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd61p2

( x i ) SEQUENCE DESCRIPTION: SEQ ID NO:228:

GAAGGAGAAT TGTAATTCCG  20

( 2 ) INFORMATION FOR SEQ ID NO:229:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd62rs ( x i ) SEQUENCE DESCRIPTION: SEQ ID NO:229:

ACACACACAC ACACACACAC ACACACACAC ACACACACAC AC  42

( 2 ) INFORMATION FOR SEQ ID NO:230:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd62p1

( x i ) SEQUENCE DESCRIPTION: SEQ ID NO:230:

AGCTTTACAG ATGAGACCAG  20

( 2 ) INFORMATION FOR SEQ ID NO:231:

( i ) SEQUENCE CHARACTERISTICS:

(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd62p2

(xi) SEQUENCE DESCRIPTION: SEQ ID NO:231:

CAGCCAATTT CTTGAGTCCG 20

(2) INFORMATION FOR SEQ ID NO:232:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd63rs (xi) SEQUENCE DESCRIPTION: SEQ ID NO:232:

CACACACACA CACACACACA CACACACACA CACACACACA C 41

(2) INFORMATION FOR SEQ ID NO:233:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd63p1

(xi) SEQUENCE DESCRIPTION: SEQ ID NO:233:

CAAAACCAAA AAACCAAAGG C 21

(2) INFORMATION FOR SEQ ID NO:234:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: mfd63p2

(xi) SEQUENCE DESCRIPTION: SEQ ID NO:234:

CAATCTGTGA CAGTTTCTCA 20

(2) INFORMATION FOR SEQ ID NO:235:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:

( B ) CLONE: mfd64rs ( x i ) SEQUENCE DESCRIPTION: SEQ ID NO:235:

ACACACACAC ACACACACAC ACACACACAC A                31

( 2 ) INFORMATION FOR SEQ ID NO:236:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd64p1

( x i ) SEQUENCE DESCRIPTION: SEQ ID NO:236:

ACGAACATTC TACAAGTTAC                20

( 2 ) INFORMATION FOR SEQ ID NO:237:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd64p2

( x i ) SEQUENCE DESCRIPTION: SEQ ID NO:237:

TTTCAGAGAA ACTGACCTGT                20

( 2 ) INFORMATION FOR SEQ ID NO:238:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd65rs ( x i ) SEQUENCE DESCRIPTION: SEQ ID NO:238:

CACACACACA CACACACACA CACACACAC                29

( 2 ) INFORMATION FOR SEQ ID NO:239:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd65p1

( x i ) SEQUENCE DESCRIPTION: SEQ ID NO:239:

GCAAACCACA ATGGAATGCA                20

( 2 ) INFORMATION FOR SEQ ID NO:240:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( v i i ) IMMEDIATE SOURCE:
  ( B ) CLONE: mfd65p2

( x i ) SEQUENCE DESCRIPTION: SEQ ID NO:240:

CTTTACTTCC TTTGCCTCAG 20

( 2 ) INFORMATION FOR SEQ ID NO:241:

( i ) SEQUENCE CHARACTERISTICS:
  ( A ) LENGTH: 44 base pairs
  ( B ) TYPE: nucleic acid
  ( C ) STRANDEDNESS: double
  ( D ) TOPOLOGY: linear ( i i ) MOLECULE TYPE: DNA (genomic)

( v i i ) IMMEDIATE SOURCE:
  ( B ) CLONE: mfd66rs ( x i ) SEQUENCE DESCRIPTION: SEQ ID NO:241:

ACACACACAC ACACACACAC ACACACACAC ACACACACAC ACAC 44

( 2 ) INFORMATION FOR SEQ ID NO:242:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( v i i ) IMMEDIATE SOURCE:
  ( B ) CLONE: mfd66p1

( x i ) SEQUENCE DESCRIPTION: SEQ ID NO:242:

GCCCCTACCT TGGCTAGTTA 20

( 2 ) INFORMATION FOR SEQ ID NO:243:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( v i i ) IMMEDIATE SOURCE:
  ( B ) CLONE: mfd66p2

( x i ) SEQUENCE DESCRIPTION: SEQ ID NO:243:

AACCTCAGCT TATACCCAAG 20

( 2 ) INFORMATION FOR SEQ ID NO:244:

( i ) SEQUENCE CHARACTERISTICS:
  ( A ) LENGTH: 60 base pairs
  ( B ) TYPE: nucleic acid
  ( C ) STRANDEDNESS: double
  ( D ) TOPOLOGY: linear ( i i ) MOLECULE TYPE: DNA (genomic)

( v i i ) IMMEDIATE SOURCE:
    ( B ) CLONE: mfd67rs ( x i ) SEQUENCE DESCRIPTION: SEQ ID NO:244:

TCTCTCTCTC TCTCTCTCTC TCTCACACAC ACACACACAC ACACACACAC ACACACACAC     60

( 2 ) INFORMATION FOR SEQ ID NO:245:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd67p1

( x i ) SEQUENCE DESCRIPTION: SEQ ID NO:245:

ATCCTGCCCT TATGGAGTGC     20

( 2 ) INFORMATION FOR SEQ ID NO:246:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd67p2

( x i ) SEQUENCE DESCRIPTION: SEQ ID NO:246:

CCCACTCCTC TGTCATTGTA     20

( 2 ) INFORMATION FOR SEQ ID NO:247:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd68p1

( x i ) SEQUENCE DESCRIPTION: SEQ ID NO:247:

ATGTATAGAA TTCCATTCCT G     21

( 2 ) INFORMATION FOR SEQ ID NO:248:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd68p2

( x i ) SEQUENCE DESCRIPTION: SEQ ID NO:248:

TAAAATCAAG TGTTGATGTA G     21

( 2 ) INFORMATION FOR SEQ ID NO:249:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd69rs ( x i ) SEQUENCE DESCRIPTION: SEQ ID NO:249:

ACACACACAC ACACACACAC ACACACACAC ACACACAAAC ACAC        44

( 2 ) INFORMATION FOR SEQ ID NO:250:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd69p1

( x i ) SEQUENCE DESCRIPTION: SEQ ID NO:250:

TAGCTGGTGC ATAAGCTCAC        20

( 2 ) INFORMATION FOR SEQ ID NO:251:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd69p2

( x i ) SEQUENCE DESCRIPTION: SEQ ID NO:251:

GTTAGTGGAA GAGCAGAGC        19

( 2 ) INFORMATION FOR SEQ ID NO:252:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd70p1

( x i ) SEQUENCE DESCRIPTION: SEQ ID NO:252:

AACATAGTGA AACCCCATCT        20

( 2 ) INFORMATION FOR SEQ ID NO:253:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear (i i) MOLECULE TYPE: DNA (genomic)

(v i i) IMMEDIATE SOURCE:
    (B) CLONE: mfd70p2

(x i) SEQUENCE DESCRIPTION: SEQ ID NO:253:

GTGCCACTAC ATGCAGCTA 19

(2) INFORMATION FOR SEQ ID NO:254:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd71p1

(x i) SEQUENCE DESCRIPTION: SEQ ID NO:254:

CCAAACTACA ATACCAGCTA 20

(2) INFORMATION FOR SEQ ID NO:255:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd71p2

(x i) SEQUENCE DESCRIPTION: SEQ ID NO:255:

CTTGATTTGA GTATAACCAA TA 22

(2) INFORMATION FOR SEQ ID NO:256:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd72rs (x i) SEQUENCE DESCRIPTION: SEQ ID NO:256:

ACACACACAC ACACACACAC ACACACACAC ACACGGAGAG AGAGAGAGAG A 51

(2) INFORMATION FOR SEQ ID NO:257:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd72p1

(x i) SEQUENCE DESCRIPTION: SEQ ID NO:257:

```
AGAAGACATA AGGATACTGC                                                    20
```

( 2 ) INFORMATION FOR SEQ ID NO:258:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd72p2

( x i ) SEQUENCE DESCRIPTION: SEQ ID NO:258:

```
GATCCCAACT ATTTCTTTCT                                                    20
```

( 2 ) INFORMATION FOR SEQ ID NO:259:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd73p1

( x i ) SEQUENCE DESCRIPTION: SEQ ID NO:259:

```
CCTGGAAAAA TGGCTCACC                                                     19
```

( 2 ) INFORMATION FOR SEQ ID NO:260:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd73p2

( x i ) SEQUENCE DESCRIPTION: SEQ ID NO:260:

```
GGAAAATCAG TCTCTAGTTG                                                    20
```

( 2 ) INFORMATION FOR SEQ ID NO:261:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd74p1

( x i ) SEQUENCE DESCRIPTION: SEQ ID NO:261:

```
TTTCACCTCC TTGGCTTTGT                                                    20
```

( 2 ) INFORMATION FOR SEQ ID NO:262:

( i ) SEQUENCE CHARACTERISTICS:
        ( A ) LENGTH: 20 base pairs
        ( B ) TYPE: nucleic acid ( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd74p2

( x i ) SEQUENCE DESCRIPTION: SEQ ID NO:262:

ATCCCTTTTA CAACAACTGC 20

( 2 ) INFORMATION FOR SEQ ID NO:263:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd75p1

( x i ) SEQUENCE DESCRIPTION: SEQ ID NO:263:

CTCACTCATG CTTGTTTTGA 20

( 2 ) INFORMATION FOR SEQ ID NO:264:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd75p2

( x i ) SEQUENCE DESCRIPTION: SEQ ID NO:264:

GATCACGTCA GACTGGGCT 19

( 2 ) INFORMATION FOR SEQ ID NO:265:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd76p1

( x i ) SEQUENCE DESCRIPTION: SEQ ID NO:265:

CCTGTGAGAC AAAGCAAGAC 20

( 2 ) INFORMATION FOR SEQ ID NO:266:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd76p2

( x i ) SEQUENCE DESCRIPTION: SEQ ID NO:266:

GACATTAGGC ACAGGGCTAA 20

( 2 ) INFORMATION FOR SEQ ID NO:267:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd77p1

( x i ) SEQUENCE DESCRIPTION: SEQ ID NO:267:

ATAGACTTCC AGACAGATAG 20

( 2 ) INFORMATION FOR SEQ ID NO:268:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd77p2

( x i ) SEQUENCE DESCRIPTION: SEQ ID NO:268:

CCTCTCTCAT TCCTGGTACT 20

( 2 ) INFORMATION FOR SEQ ID NO:269:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd78p1

( x i ) SEQUENCE DESCRIPTION: SEQ ID NO:269:

GAATCCATAG CTGTACTCCA 20

( 2 ) INFORMATION FOR SEQ ID NO:270:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd78p2

( x i ) SEQUENCE DESCRIPTION: SEQ ID NO:270:

AATTGTCTAT GGTCCCAGCA 20

( 2 ) INFORMATION FOR SEQ ID NO:271:

( i ) SEQUENCE CHARACTERISTICS:

(A) LENGTH: 31 base pairs
(B) TYPE: nucleic acid
(C) STRANDEDNESS: double
(D) TOPOLOGY: linear (i i) MOLECULE TYPE: DNA (genomic)

(v i i) IMMEDIATE SOURCE:
(B) CLONE: mfd79rs (x i) SEQUENCE DESCRIPTION: SEQ ID NO:271:

ACACACACAC ACACACACAC ACACACACAC A  31

(2) INFORMATION FOR SEQ ID NO:272:

(i) SEQUENCE CHARACTERISTICS:
(A) LENGTH: 22 base pairs
(B) TYPE: nucleic acid
(C) STRANDEDNESS: double
(D) TOPOLOGY: linear (i i) MOLECULE TYPE: DNA (genomic)

(v i i) IMMEDIATE SOURCE:
(B) CLONE: mfd79p1

(x i) SEQUENCE DESCRIPTION: SEQ ID NO:272:

GATAAAACTG CATAGAAATG CG  22

(2) INFORMATION FOR SEQ ID NO:273:

(i) SEQUENCE CHARACTERISTICS:
(A) LENGTH: 20 base pairs
(B) TYPE: nucleic acid
(C) STRANDEDNESS: double
(D) TOPOLOGY: linear (i i) MOLECULE TYPE: DNA (genomic)

(v i i) IMMEDIATE SOURCE:
(B) CLONE: mfd79p2

(x i) SEQUENCE DESCRIPTION: SEQ ID NO:273:

CAACTGGGAT ATTGACATTG  20

(2) INFORMATION FOR SEQ ID NO:274:

(i) SEQUENCE CHARACTERISTICS:
(A) LENGTH: 20 base pairs
(B) TYPE: nucleic acid
(C) STRANDEDNESS: double
(D) TOPOLOGY: linear (i i) MOLECULE TYPE: DNA (genomic)

(v i i) IMMEDIATE SOURCE:
(B) CLONE: mfd80p1

(x i) SEQUENCE DESCRIPTION: SEQ ID NO:274:

TTGAGGCTGC AGTGAGCTAT  20

(2) INFORMATION FOR SEQ ID NO:275:

(i) SEQUENCE CHARACTERISTICS:
(A) LENGTH: 20 base pairs
(B) TYPE: nucleic acid
(C) STRANDEDNESS: double
(D) TOPOLOGY: linear (i i) MOLECULE TYPE: DNA (genomic)

(v i i) IMMEDIATE SOURCE:

(B) CLONE: mfd80p2

(x i) SEQUENCE DESCRIPTION: SEQ ID NO:275:

ATGTTGTGTT TTCACAGCAG 20

(2) INFORMATION FOR SEQ ID NO:276:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd81p1

(x i) SEQUENCE DESCRIPTION: SEQ ID NO:276:

GCACTCATGT CACCAATTCT 20

(2) INFORMATION FOR SEQ ID NO:277:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd81p2

(x i) SEQUENCE DESCRIPTION: SEQ ID NO:277:

ATAGTCAATG GTTAATGCTC 20

(2) INFORMATION FOR SEQ ID NO:278:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd82p1

(x i) SEQUENCE DESCRIPTION: SEQ ID NO:278:

AGCTTGGGTG CAAGAAGAG 19

(2) INFORMATION FOR SEQ ID NO:279:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: DNA (genomic)

(v i i) IMMEDIATE SOURCE:
        (B) CLONE: mfd82p2

(x i) SEQUENCE DESCRIPTION: SEQ ID NO:279:

GATCCCATTA TTTAAAAGTG TA 22

(2) INFORMATION FOR SEQ ID NO:280:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd83p1

( x i ) SEQUENCE DESCRIPTION: SEQ ID NO:280:

GATCTCATGT GCTCAGTTTA    20

( 2 ) INFORMATION FOR SEQ ID NO:281:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd83p2

( x i ) SEQUENCE DESCRIPTION: SEQ ID NO:281:

CCAAAAAAGT GCAAATTTAG AGT    23

( 2 ) INFORMATION FOR SEQ ID NO:282:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd84rs ( x i ) SEQUENCE DESCRIPTION: SEQ ID NO:282:

ACACACACAC ATACACAGAT TACACGGACA CACACACACA CACACACACA CACACACACA    60
C    61

( 2 ) INFORMATION FOR SEQ ID NO:283:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd84p1

( x i ) SEQUENCE DESCRIPTION: SEQ ID NO:283:

AATGTCCTTG TACTTAGGAT    20

( 2 ) INFORMATION FOR SEQ ID NO:284:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
    ( B ) CLONE: mfd84p2

( x i ) SEQUENCE DESCRIPTION: SEQ ID NO:284:

CACTTAATAT CTCAATGTAT AC                                                                                                      22

( 2 ) INFORMATION FOR SEQ ID NO:285:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd85p1

( x i ) SEQUENCE DESCRIPTION: SEQ ID NO:285:

GATCCTTTTC ATCTTCTGAC                                                                                                          20

( 2 ) INFORMATION FOR SEQ ID NO:286:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd85p2

( x i ) SEQUENCE DESCRIPTION: SEQ ID NO:286:

GAGGGACGGA GCAACTGAT                                                                                      19

( 2 ) INFORMATION FOR SEQ ID NO:287:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd86p1

( x i ) SEQUENCE DESCRIPTION: SEQ ID NO:287:

CAACATAGCA AGACCCTGTC                                                                              20

( 2 ) INFORMATION FOR SEQ ID NO:288:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd86p2

( x i ) SEQUENCE DESCRIPTION: SEQ ID NO:288:

GCACATGCCA CCAAGACAAG                                                                                                   20

( 2 ) INFORMATION FOR SEQ ID NO:289:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd87p1

( x i ) SEQUENCE DESCRIPTION: SEQ ID NO:289:

TCAAAAGCTT GTAATTGGAG                                                                                                   20

( 2 ) INFORMATION FOR SEQ ID NO:290:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd87p2

( x i ) SEQUENCE DESCRIPTION: SEQ ID NO:290:

TGCAATCTGT AAGCATTCCT                                                                                                   20

( 2 ) INFORMATION FOR SEQ ID NO:291:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd88p1

( x i ) SEQUENCE DESCRIPTION: SEQ ID NO:291:

ACCTGAGTGT TCATCAATAC                                                                                                   20

( 2 ) INFORMATION FOR SEQ ID NO:292:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd88p2

( x i ) SEQUENCE DESCRIPTION: SEQ ID NO:292:

TCCAGAATCA TCCATGTTGT                                                                                                   20

( 2 ) INFORMATION FOR SEQ ID NO:293:

( i ) SEQUENCE CHARACTERISTICS:
        ( A ) LENGTH: 19 base pairs
        ( B ) TYPE: nucleic acid (C) STRANDEDNESS: double
(D) TOPOLOGY: linear ( i i ) MOLECULE TYPE: DNA (genomic)

( v i i ) IMMEDIATE SOURCE:
(B) CLONE: mfd89p1

( x i ) SEQUENCE DESCRIPTION: SEQ ID NO:293:

GTCTTGTTTG CTGGCTCCA 19

( 2 ) INFORMATION FOR SEQ ID NO:294:

( i ) SEQUENCE CHARACTERISTICS:
(A) LENGTH: 20 base pairs
(B) TYPE: nucleic acid
(C) STRANDEDNESS: double
(D) TOPOLOGY: linear ( i i ) MOLECULE TYPE: DNA (genomic)

( v i i ) IMMEDIATE SOURCE:
(B) CLONE: mfd89p2

( x i ) SEQUENCE DESCRIPTION: SEQ ID NO:294:

AGCTATGAAG TGGGAGTTCA 20

( 2 ) INFORMATION FOR SEQ ID NO:295:

( i ) SEQUENCE CHARACTERISTICS:
(A) LENGTH: 20 base pairs
(B) TYPE: nucleic acid
(C) STRANDEDNESS: double
(D) TOPOLOGY: linear ( i i ) MOLECULE TYPE: DNA (genomic)

( v i i ) IMMEDIATE SOURCE:
(B) CLONE: mfd90p1

( x i ) SEQUENCE DESCRIPTION: SEQ ID NO:295:

ATTTTGGATG AGCCAAGCCT 20

( 2 ) INFORMATION FOR SEQ ID NO:296:

( i ) SEQUENCE CHARACTERISTICS:
(A) LENGTH: 21 base pairs
(B) TYPE: nucleic acid
(C) STRANDEDNESS: double
(D) TOPOLOGY: linear ( i i ) MOLECULE TYPE: DNA (genomic)

( v i i ) IMMEDIATE SOURCE:
(B) CLONE: mfd90p2

( x i ) SEQUENCE DESCRIPTION: SEQ ID NO:296:

ATCTGTATAT ATGTGTACCT G 21

( 2 ) INFORMATION FOR SEQ ID NO:297:

( i ) SEQUENCE CHARACTERISTICS:
(A) LENGTH: 22 base pairs
(B) TYPE: nucleic acid
(C) STRANDEDNESS: double
(D) TOPOLOGY: linear ( i i ) MOLECULE TYPE: DNA (genomic)

( v i i ) IMMEDIATE SOURCE:
(B) CLONE: mfd91p1

( x i ) SEQUENCE DESCRIPTION: SEQ ID NO:297:

CTACATATTT CTAAATACAT GC 22

( 2 ) INFORMATION FOR SEQ ID NO:298:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd91p2

( x i ) SEQUENCE DESCRIPTION: SEQ ID NO:298:

ACTTAGTAGT TTTAAGCAGG A 21

( 2 ) INFORMATION FOR SEQ ID NO:299:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd92p1

( x i ) SEQUENCE DESCRIPTION: SEQ ID NO:299:

ATTTCCACCC ACTTCTGGT 19

( 2 ) INFORMATION FOR SEQ ID NO:300:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd92p2

( x i ) SEQUENCE DESCRIPTION: SEQ ID NO:300:

GATGGTGTTG AGAATTAGGC 20

( 2 ) INFORMATION FOR SEQ ID NO:301:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd93rs ( x i ) SEQUENCE DESCRIPTION: SEQ ID NO:301:

AAATAAATAA ATAAATAAAT AAATTTTATA TATATATATA CACACACACA CACACACACA 60

CACACA 66

( 2 ) INFORMATION FOR SEQ ID NO:302:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd93p1

( x i ) SEQUENCE DESCRIPTION: SEQ ID NO:302:

GACAGAGTGA GACTCCATCT     20

( 2 ) INFORMATION FOR SEQ ID NO:303:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd93p2

( x i ) SEQUENCE DESCRIPTION: SEQ ID NO:303:

CTTCCCATTT TCAATCCCTA G     21

( 2 ) INFORMATION FOR SEQ ID NO:304:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd94rs ( x i ) SEQUENCE DESCRIPTION: SEQ ID NO:304:

AAACGCACAG ACACACACAC ACACACACAC ACACACACAC ACACACACAC ACA     53

( 2 ) INFORMATION FOR SEQ ID NO:305:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd94p1

( x i ) SEQUENCE DESCRIPTION: SEQ ID NO:305:

AGTCTTTCTC CTGTTGTGCT     20

( 2 ) INFORMATION FOR SEQ ID NO:306:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

-continued ( v i i ) IMMEDIATE SOURCE:
    ( B ) CLONE: mfd94p2

( x i ) SEQUENCE DESCRIPTION: SEQ ID NO:306:

CCCTAAGGAC AGAACAAGTG     20

( 2 ) INFORMATION FOR SEQ ID NO:307:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd95rs ( x i ) SEQUENCE DESCRIPTION: SEQ ID NO:307:

GGAGATTTGG ACACACAC ACACACAC ACACACAC ACACACAC ACACAC     56

( 2 ) INFORMATION FOR SEQ ID NO:308:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd95p1

( x i ) SEQUENCE DESCRIPTION: SEQ ID NO:308:

TAGGCCCTAC TGCAATAATG     20

( 2 ) INFORMATION FOR SEQ ID NO:309:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd95p2

( x i ) SEQUENCE DESCRIPTION: SEQ ID NO:309:

CTTTATCTTC ACACAGCTTC     20

( 2 ) INFORMATION FOR SEQ ID NO:310:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd96p1

( x i ) SEQUENCE DESCRIPTION: SEQ ID NO:310:

TCAACAATGG CCGAGGTTA     19

( 2 ) INFORMATION FOR SEQ ID NO:311:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd96p2

( x i ) SEQUENCE DESCRIPTION: SEQ ID NO:311:

```
AACCTGACAC CATGCTCCT                                                    19
```

( 2 ) INFORMATION FOR SEQ ID NO:312:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd97rs ( x i ) SEQUENCE DESCRIPTION: SEQ ID NO:312:

```
CTCTCTCTCT CACACACACA CACACACACA CAC                                    33
```

( 2 ) INFORMATION FOR SEQ ID NO:313:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd97p1

( x i ) SEQUENCE DESCRIPTION: SEQ ID NO:313:

```
TTCTATTTCT GAAGGTGAAC TA                                                22
```

( 2 ) INFORMATION FOR SEQ ID NO:314:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd97p2

( x i ) SEQUENCE DESCRIPTION: SEQ ID NO:314:

```
ATAGTTACCA TCAGTCACTG                                                   20
```

( 2 ) INFORMATION FOR SEQ ID NO:315:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear 5,582,979

291                                                                                                                292
                                              -continued ( i i ) MOLECULE TYPE: DNA (genomic)

( v i i ) IMMEDIATE SOURCE:
                     ( B ) CLONE: mfd98p1

( x i ) SEQUENCE DESCRIPTION: SEQ ID NO:315:

TCTGGAGACC ACTAACTGTA                                                                                                    20

( 2 ) INFORMATION FOR SEQ ID NO:316:

( i ) SEQUENCE CHARACTERISTICS:
                     ( A ) LENGTH: 20 base pairs
                     ( B ) TYPE: nucleic acid
                     ( C ) STRANDEDNESS: double
                     ( D ) TOPOLOGY: linear ( i i ) MOLECULE TYPE: DNA (genomic)

( v i i ) IMMEDIATE SOURCE:
                     ( B ) CLONE: mfd98p2

( x i ) SEQUENCE DESCRIPTION: SEQ ID NO:316:

ACTCTCCATG AGTCCTGATG                                                                                                    20

( 2 ) INFORMATION FOR SEQ ID NO:317:

( i ) SEQUENCE CHARACTERISTICS:
                     ( A ) LENGTH: 51 base pairs
                     ( B ) TYPE: nucleic acid
                     ( C ) STRANDEDNESS: double
                     ( D ) TOPOLOGY: linear ( i i ) MOLECULE TYPE: DNA (genomic)

( v i i ) IMMEDIATE SOURCE:
                     ( B ) CLONE: mfd99rs ( x i ) SEQUENCE DESCRIPTION: SEQ ID NO:317:

TCTCTATCTT CACACACACA CACACACACA CACACACACA CACACACACA C                                                                 51

( 2 ) INFORMATION FOR SEQ ID NO:318:

( i ) SEQUENCE CHARACTERISTICS:
                     ( A ) LENGTH: 21 base pairs
                     ( B ) TYPE: nucleic acid
                     ( C ) STRANDEDNESS: double
                     ( D ) TOPOLOGY: linear ( i i ) MOLECULE TYPE: DNA (genomic)

( v i i ) IMMEDIATE SOURCE:
                     ( B ) CLONE: mfd99p1

( x i ) SEQUENCE DESCRIPTION: SEQ ID NO:318:

ATGAGCTAAT TCTCTATCTT C                                                                                                  21

( 2 ) INFORMATION FOR SEQ ID NO:319:

( i ) SEQUENCE CHARACTERISTICS:
                     ( A ) LENGTH: 20 base pairs
                     ( B ) TYPE: nucleic acid
                     ( C ) STRANDEDNESS: double
                     ( D ) TOPOLOGY: linear ( i i ) MOLECULE TYPE: DNA (genomic)

( v i i ) IMMEDIATE SOURCE:
                     ( B ) CLONE: mfd99p2

( x i ) SEQUENCE DESCRIPTION: SEQ ID NO:319:

TAGCCTACAT AAAGGAGGGT                                                                              20

( 2 ) INFORMATION FOR SEQ ID NO:320:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd100p1

( x i ) SEQUENCE DESCRIPTION: SEQ ID NO:320:

GGAGCCAAAT ACTAAATTCT                                                                              20

( 2 ) INFORMATION FOR SEQ ID NO:321:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd100p2

( x i ) SEQUENCE DESCRIPTION: SEQ ID NO:321:

TTAGGCACTT TAATCAGGCT                                                                              20

( 2 ) INFORMATION FOR SEQ ID NO:322:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd101rs ( x i ) SEQUENCE DESCRIPTION: SEQ ID NO:322:

ACACACACAC ACACACACAC ACACACACAC ACAC                                                              34

( 2 ) INFORMATION FOR SEQ ID NO:323:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd101p1

( x i ) SEQUENCE DESCRIPTION: SEQ ID NO:323:

CATAAAAGGC TTATTGGTTT G                                                                            21

( 2 ) INFORMATION FOR SEQ ID NO:324:

( i ) SEQUENCE CHARACTERISTICS:
        ( A ) LENGTH: 20 base pairs
        ( B ) TYPE: nucleic acid ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd101p2

( x i ) SEQUENCE DESCRIPTION: SEQ ID NO:324:

CAAAACAGAG AACAGAGTAG                                                                        20

( 2 ) INFORMATION FOR SEQ ID NO:325:

( i ) SEQUENCE CHARACTERISTICS:
            ( A ) LENGTH: 51 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd102rs ( x i ) SEQUENCE DESCRIPTION: SEQ ID NO:325:

ACACACACAC ACACACACAC ACACACACAC ACACACACAA ACACACACAC A                                     51

( 2 ) INFORMATION FOR SEQ ID NO:326:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd102p1

( x i ) SEQUENCE DESCRIPTION: SEQ ID NO:326:

AGGAGAGCTA GAGCTTCTAT                                                                        20

( 2 ) INFORMATION FOR SEQ ID NO:327:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd102p2

( x i ) SEQUENCE DESCRIPTION: SEQ ID NO:327:

GTTTCAACAT GAGTTTCAGA                                                                        20

( 2 ) INFORMATION FOR SEQ ID NO:328:

( i ) SEQUENCE CHARACTERISTICS:
            ( A ) LENGTH: 50 base pairs
            ( B ) TYPE: nucleic acid
            ( C ) STRANDEDNESS: double
            ( D ) TOPOLOGY: linear ( i i ) MOLECULE TYPE: DNA (genomic)

( v i i ) IMMEDIATE SOURCE:
            ( B ) CLONE: mfd103rs ( x i ) SEQUENCE DESCRIPTION: SEQ ID NO:328:

GCAGTAAAAG CACACACACA CACACACACA CACACACACA CACACACACA  50

( 2 ) INFORMATION FOR SEQ ID NO:329:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd103p1

( x i ) SEQUENCE DESCRIPTION: SEQ ID NO:329:

CAGATAAACT AATACAAGCA G  21

( 2 ) INFORMATION FOR SEQ ID NO:330:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd103p2

( x i ) SEQUENCE DESCRIPTION: SEQ ID NO:330:

CTCTGCCTCC CAAAGTGCT  19

( 2 ) INFORMATION FOR SEQ ID NO:331:

( i ) SEQUENCE CHARACTERISTICS:
    ( A ) LENGTH: 39 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd104rs ( x i ) SEQUENCE DESCRIPTION: SEQ ID NO:331:

TTATATATAT ACACACACAC ACACACACAC ACACACACA  39

( 2 ) INFORMATION FOR SEQ ID NO:332:

( i ) SEQUENCE CHARACTERISTICS:
    ( A ) LENGTH: 23 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd104p1

( x i ) SEQUENCE DESCRIPTION: SEQ ID NO:332:

GATCATGTGA GTTAATACTT AAT  23

( 2 ) INFORMATION FOR SEQ ID NO:333:

( i ) SEQUENCE CHARACTERISTICS:

(A) LENGTH: 20 base pairs
            (B) TYPE: nucleic acid
            (C) STRANDEDNESS: double
            (D) TOPOLOGY: linear (ii) MOLECULE TYPE: DNA (genomic)

(vii) IMMEDIATE SOURCE:
            (B) CLONE: mfd104p2

(xi) SEQUENCE DESCRIPTION: SEQ ID NO:333:

TCAGCTGCCT GTATTACTCA                                                           20

(2) INFORMATION FOR SEQ ID NO:334:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (ii) MOLECULE TYPE: DNA (genomic)

(vii) IMMEDIATE SOURCE:
            (B) CLONE: mfd105rs (xi) SEQUENCE DESCRIPTION: SEQ ID NO:334:

TCAAACACAA ACACACACAC ACACACACAC ACACACACAC AC                                  42

(2) INFORMATION FOR SEQ ID NO:335:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(vii) IMMEDIATE SOURCE:
            (B) CLONE: mfd105p1

(xi) SEQUENCE DESCRIPTION: SEQ ID NO:335:

GATCCTGTCT CAAACACAAA C                                                         21

(2) INFORMATION FOR SEQ ID NO:336:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(vii) IMMEDIATE SOURCE:
            (B) CLONE: mfd105p2

(xi) SEQUENCE DESCRIPTION: SEQ ID NO:336:

AAGTCTTCAG CTTTATCAAC                                                           20

(2) INFORMATION FOR SEQ ID NO:337:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(vii) IMMEDIATE SOURCE:

(B) CLONE: mfd106rs (xi) SEQUENCE DESCRIPTION: SEQ ID NO:337:

TCTTCCCCCA ACACACACAC ACACACACAC ACACACACAC ACACACACAC A    51

(2) INFORMATION FOR SEQ ID NO:338:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd106p1

(xi) SEQUENCE DESCRIPTION: SEQ ID NO:338:

GATCTGTCTT CCCCCAAC    18

(2) INFORMATION FOR SEQ ID NO:339:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd106p2

(xi) SEQUENCE DESCRIPTION: SEQ ID NO:339:

TTTCATGTTG CAGTCAGAGC    20

(2) INFORMATION FOR SEQ ID NO:340:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd107rs (xi) SEQUENCE DESCRIPTION: SEQ ID NO:340:

TGCCCGGCCT ACACACACAC ACACACACAC ACACACACAC AC    42

(2) INFORMATION FOR SEQ ID NO:341:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd107p1

(xi) SEQUENCE DESCRIPTION: SEQ ID NO:341:

CCCAAAGTAC TGGGATTACA    20

(2) INFORMATION FOR SEQ ID NO:342:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd107p2

( x i ) SEQUENCE DESCRIPTION: SEQ ID NO:342:

TTCAAGTGTT ACTGTACTGC      20

( 2 ) INFORMATION FOR SEQ ID NO:343:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd108rs ( x i ) SEQUENCE DESCRIPTION: SEQ ID NO:343:

GTGGCTAAAT ACACACACAC ACACACACAC ACACACACAC AC      42

( 2 ) INFORMATION FOR SEQ ID NO:344:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd108p1

( x i ) SEQUENCE DESCRIPTION: SEQ ID NO:344:

GCCTCTGAAG TGGCTAAATA      20

( 2 ) INFORMATION FOR SEQ ID NO:345:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd108p2

( x i ) SEQUENCE DESCRIPTION: SEQ ID NO:345:

CCCCTCACCA CATCACTTG      19

( 2 ) INFORMATION FOR SEQ ID NO:346:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
   ( B ) CLONE: mfd109rs ( x i ) SEQUENCE DESCRIPTION: SEQ ID NO:346:

GGGAAATAGG CACACACACA CACACACACA CACACACACA CACACA    46

( 2 ) INFORMATION FOR SEQ ID NO:347:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd109p1

( x i ) SEQUENCE DESCRIPTION: SEQ ID NO:347:

GACACAGAGA AGGGAAATAG    20

( 2 ) INFORMATION FOR SEQ ID NO:348:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd109p2

( x i ) SEQUENCE DESCRIPTION: SEQ ID NO:348:

TCCCATATCC TATGTAGAAG    20

( 2 ) INFORMATION FOR SEQ ID NO:349:

( i ) SEQUENCE CHARACTERISTICS:
    ( A ) LENGTH: 46 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd110rs ( x i ) SEQUENCE DESCRIPTION: SEQ ID NO:349:

ATTTATTTAT TTATTTATTT ATTTATTTAT TTATTTATTT ATTTAT    46

( 2 ) INFORMATION FOR SEQ ID NO:350:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( v i i ) IMMEDIATE SOURCE:
    ( B ) CLONE: mfd110p1

( x i ) SEQUENCE DESCRIPTION: SEQ ID NO:350:

GCTAGAGGGA GGTTTAATTG    20

( 2 ) INFORMATION FOR SEQ ID NO:351:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd110p2

( x i ) SEQUENCE DESCRIPTION: SEQ ID NO:351:

AATTAGCCAG GTGTTGTGGT 20

( 2 ) INFORMATION FOR SEQ ID NO:352:

( i ) SEQUENCE CHARACTERISTICS:
( A ) LENGTH: 41 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd111rs ( x i ) SEQUENCE DESCRIPTION: SEQ ID NO:352:

TGAGACCCTG ACACACACAC ACACACACAC ACACACACAC A 41

( 2 ) INFORMATION FOR SEQ ID NO:353:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd111p1

( x i ) SEQUENCE DESCRIPTION: SEQ ID NO:353:

AACCAAGATT GTGCCACTG 19

( 2 ) INFORMATION FOR SEQ ID NO:354:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd111p2

( x i ) SEQUENCE DESCRIPTION: SEQ ID NO:354:

GATCATGACT CTTTTGTG 18

( 2 ) INFORMATION FOR SEQ ID NO:355:

( i ) SEQUENCE CHARACTERISTICS:
( A ) LENGTH: 41 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
    ( B ) CLONE: mfd111rs ( x i ) SEQUENCE DESCRIPTION: SEQ ID NO:355:

TGAGACCCTG ACACACACAC ACACACACAC ACACACACAC A          41

( 2 ) INFORMATION FOR SEQ ID NO:356:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd112p1

( x i ) SEQUENCE DESCRIPTION: SEQ ID NO:356:

GATCCATGCC CACCCCCA          18

( 2 ) INFORMATION FOR SEQ ID NO:357:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd112p2

( x i ) SEQUENCE DESCRIPTION: SEQ ID NO:357:

CCTCTCAGAC TCATCCCAC          19

( 2 ) INFORMATION FOR SEQ ID NO:358:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd113rs ( x i ) SEQUENCE DESCRIPTION: SEQ ID NO:358:

ACACACACAC ACACACACAC ACACACACAC ACACAC          36

( 2 ) INFORMATION FOR SEQ ID NO:359:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd113p1

( x i ) SEQUENCE DESCRIPTION: SEQ ID NO:359:

CTGCTGACTT TGACTCAGTA 20

( 2 ) INFORMATION FOR SEQ ID NO:360:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd113p2

( x i ) SEQUENCE DESCRIPTION: SEQ ID NO:360:

GGTCCTGAGC AGGTCTCTTC 20

( 2 ) INFORMATION FOR SEQ ID NO:361:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd114rs ( x i ) SEQUENCE DESCRIPTION: SEQ ID NO:361:

GTTATCCATT ACACACACAC ACACACACAC ACACACACAC ACACACACA 49

( 2 ) INFORMATION FOR SEQ ID NO:362:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd114p1

( x i ) SEQUENCE DESCRIPTION: SEQ ID NO:362:

TGGCATCTCT AATCATACTG 20

( 2 ) INFORMATION FOR SEQ ID NO:363:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd114p2

( x i ) SEQUENCE DESCRIPTION: SEQ ID NO:363:

GACTAAAACA TTGCAGAATA C 21

( 2 ) INFORMATION FOR SEQ ID NO:364:

( i ) SEQUENCE CHARACTERISTICS:
        ( A ) LENGTH: 45 base pairs
        ( B ) TYPE: nucleic acid ( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd115rs ( x i ) SEQUENCE DESCRIPTION: SEQ ID NO:364:

ATAGAGAAGG ACACACACAC ACACACACAC ACACACACAC ACACA     45

( 2 ) INFORMATION FOR SEQ ID NO:365:

( i ) SEQUENCE CHARACTERISTICS:
( A ) LENGTH: 21 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd115p1

( x i ) SEQUENCE DESCRIPTION: SEQ ID NO:365:

AGAAAATAAG AATAGAGAAG G     21

( 2 ) INFORMATION FOR SEQ ID NO:366:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd115p2

( x i ) SEQUENCE DESCRIPTION: SEQ ID NO:366:

CAAGAACTAT GTTATTGGGA     20

( 2 ) INFORMATION FOR SEQ ID NO:367:

( i ) SEQUENCE CHARACTERISTICS:
( A ) LENGTH: 50 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd116rs ( x i ) SEQUENCE DESCRIPTION: SEQ ID NO:367:

CCCCCACCCA ACACACACAC ACACACACAC ACACACACAC ACACACACAC     50

( 2 ) INFORMATION FOR SEQ ID NO:368:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( v i i ) IMMEDIATE SOURCE:
( B ) CLONE: mfd116p1

( x i ) SEQUENCE DESCRIPTION: SEQ ID NO:368:

CTGCACTAGA AAGGCAGAGT 20

( 2 ) INFORMATION FOR SEQ ID NO:369:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd116p2

( x i ) SEQUENCE DESCRIPTION: SEQ ID NO:369:

TGCAGCACCA AACACCAAGT 20

( 2 ) INFORMATION FOR SEQ ID NO:370:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd117rs ( x i ) SEQUENCE DESCRIPTION: SEQ ID NO:370:

GCAGCAACAT ACACACACAC ACACACACAC ACACACACAC ACA 43

( 2 ) INFORMATION FOR SEQ ID NO:371:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd117p1

( x i ) SEQUENCE DESCRIPTION: SEQ ID NO:371:

ACAAGAGCAC ATTTAGTCAG 20

( 2 ) INFORMATION FOR SEQ ID NO:372:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd117p2

( x i ) SEQUENCE DESCRIPTION: SEQ ID NO:372:

AGCTTCATTT TTCCCTCTAG 20

( 2 ) INFORMATION FOR SEQ ID NO:373:

( i ) SEQUENCE CHARACTERISTICS:

(A) LENGTH: 30 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd118rs (xi) SEQUENCE DESCRIPTION: SEQ ID NO:373:

ACACACACAC ACACACACAC ACACACACAC 30

(2) INFORMATION FOR SEQ ID NO:374:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd118p1

(xi) SEQUENCE DESCRIPTION: SEQ ID NO:374:

CTTTCTTATA GTTAAGGTTA GC 22

(2) INFORMATION FOR SEQ ID NO:375:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd118p2

(xi) SEQUENCE DESCRIPTION: SEQ ID NO:375:

TAGCATCAGA AGACCTGGC 19

(2) INFORMATION FOR SEQ ID NO:376:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: mfd119rs (xi) SEQUENCE DESCRIPTION: SEQ ID NO:376:

ACACACACAC ACACACACAC ACACACACAC AC 32

(2) INFORMATION FOR SEQ ID NO:377:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:

(B) CLONE: mfd119p1

(xi) SEQUENCE DESCRIPTION: SEQ ID NO:377:

GAATCTTAAG TAGTTATCCC TC                                                                    22

(2) INFORMATION FOR SEQ ID NO:378:

(i) SEQUENCE CHARACTERISTICS:
                (A) LENGTH: 21 base pairs
                (B) TYPE: nucleic acid
                (C) STRANDEDNESS: double
                (D) TOPOLOGY: linear (ii) MOLECULE TYPE: DNA (genomic)

(vii) IMMEDIATE SOURCE:
                (B) CLONE: mfd119p2

(xi) SEQUENCE DESCRIPTION: SEQ ID NO:378:

TCTACAAAAA GTCAGATACC T                                                                     21

(2) INFORMATION FOR SEQ ID NO:379:

(i) SEQUENCE CHARACTERISTICS:
                (A) LENGTH: 50 base pairs
                (B) TYPE: nucleic acid
                (C) STRANDEDNESS: double
                (D) TOPOLOGY: linear (ii) MOLECULE TYPE: DNA (genomic)

(vii) IMMEDIATE SOURCE:
                (B) CLONE: mfd120rs (xi) SEQUENCE DESCRIPTION: SEQ ID NO:379:

TCTCTCTCTC ACACACACAC ACACACACAC ACACACACAC ACACACACAC                                      50

(2) INFORMATION FOR SEQ ID NO:380:

(i) SEQUENCE CHARACTERISTICS:
                (A) LENGTH: 20 base pairs
                (B) TYPE: nucleic acid
                (C) STRANDEDNESS: double
                (D) TOPOLOGY: linear (ii) MOLECULE TYPE: DNA (genomic)

(vii) IMMEDIATE SOURCE:
                (B) CLONE: mfd120p1

(xi) SEQUENCE DESCRIPTION: SEQ ID NO:380:

CAATGACTTC AAGCACTAAG                                                                       20

(2) INFORMATION FOR SEQ ID NO:381:

(i) SEQUENCE CHARACTERISTICS:
                (A) LENGTH: 19 base pairs
                (B) TYPE: nucleic acid
                (C) STRANDEDNESS: double
                (D) TOPOLOGY: linear (ii) MOLECULE TYPE: DNA (genomic)

(vii) IMMEDIATE SOURCE:
                (B) CLONE: mfd120p2

(xi) SEQUENCE DESCRIPTION: SEQ ID NO:381:

TCAGAGGTTG AGGCTGAAG                                                                        19

(2) INFORMATION FOR SEQ ID NO:382:

( i ) SEQUENCE CHARACTERISTICS:
   ( A ) LENGTH: 57 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
   ( B ) CLONE: mfd121rs ( x i ) SEQUENCE DESCRIPTION: SEQ ID NO:382:

```
TCTCTCTCTC CACACACACA CACACACACA CACACACACA CACACACACA CACACAC            57
```

( 2 ) INFORMATION FOR SEQ ID NO:383:

( i ) SEQUENCE CHARACTERISTICS:
   ( A ) LENGTH: 20 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
   ( B ) CLONE: mfd121p1

( x i ) SEQUENCE DESCRIPTION: SEQ ID NO:383:

```
GATCTGGGTA TGTCTTTCTG                                                      20
```

( 2 ) INFORMATION FOR SEQ ID NO:384:

( i ) SEQUENCE CHARACTERISTICS:
   ( A ) LENGTH: 20 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
   ( B ) CLONE: mfd121p2

( x i ) SEQUENCE DESCRIPTION: SEQ ID NO:384:

```
ACTGGGACTC TAACTAATGT                                                      20
```

( 2 ) INFORMATION FOR SEQ ID NO:385:

( i ) SEQUENCE CHARACTERISTICS:
   ( A ) LENGTH: 44 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
   ( B ) CLONE: mfd122rs ( x i ) SEQUENCE DESCRIPTION: SEQ ID NO:385:

```
TTTACAGTAG CAGAGAGAGA GAGAGAGAGA GAGAGAGAGA GAGA                           44
```

( 2 ) INFORMATION FOR SEQ ID NO:386:

( i ) SEQUENCE CHARACTERISTICS:
   ( A ) LENGTH: 20 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
    ( B ) CLONE: mfd122p1

( x i ) SEQUENCE DESCRIPTION: SEQ ID NO:386:

ATGCAGAATC TACAAGGACC                    20

( 2 ) INFORMATION FOR SEQ ID NO:387:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd122p2

( x i ) SEQUENCE DESCRIPTION: SEQ ID NO:387:

CTTTAACATC CTTTAACAGC                    20

( 2 ) INFORMATION FOR SEQ ID NO:388:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd123rs ( x i ) SEQUENCE DESCRIPTION: SEQ ID NO:388:

ACACACACAC ACACACACAC ACACACACAC ACACACACAC ACA                    43

( 2 ) INFORMATION FOR SEQ ID NO:389:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd123p1

( x i ) SEQUENCE DESCRIPTION: SEQ ID NO:389:

AGCAGCTATT ATGGAATTGC                    20

( 2 ) INFORMATION FOR SEQ ID NO:390:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd123p2

( x i ) SEQUENCE DESCRIPTION: SEQ ID NO:390:

CAACATATGC AAGGTGCCTA                    20

( 2 ) INFORMATION FOR SEQ ID NO:391:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd124rs ( x i ) SEQUENCE DESCRIPTION: SEQ ID NO:391:

```
ATTTAGCATA ACACACACAC ACACACACAC ACACACACAC ACACACACAC A                51
```

( 2 ) INFORMATION FOR SEQ ID NO:392:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd124p1

( x i ) SEQUENCE DESCRIPTION: SEQ ID NO:392:

```
TGCTTAAACA GAAAAGTAGC                                                   20
```

( 2 ) INFORMATION FOR SEQ ID NO:393:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd124p2

( x i ) SEQUENCE DESCRIPTION: SEQ ID NO:393:

```
TAAAACAGTA CCCAGTACCT                                                   20
```

( 2 ) INFORMATION FOR SEQ ID NO:394:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: mfd125rs ( x i ) SEQUENCE DESCRIPTION: SEQ ID NO:394:

```
CTGAAACAAA ACACACACAC ACACACACAC ACACACACAC ACACACACAC ACACAC           56
```

( 2 ) INFORMATION FOR SEQ ID NO:395:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear (ii) MOLECULE TYPE: DNA (genomic)

(vii) IMMEDIATE SOURCE:
  (B) CLONE: mfd125p1

(xi) SEQUENCE DESCRIPTION: SEQ ID NO:395:

TGAGACCCTG TCTCTGAAAC    20

(2) INFORMATION FOR SEQ ID NO:396:

(i) SEQUENCE CHARACTERISTICS:
  (A) LENGTH: 20 base pairs
  (B) TYPE: nucleic acid
  (C) STRANDEDNESS: double
  (D) TOPOLOGY: linear (ii) MOLECULE TYPE: DNA (genomic)

(vii) IMMEDIATE SOURCE:
  (B) CLONE: mfd125p2

(xi) SEQUENCE DESCRIPTION: SEQ ID NO:396:

TGTATGGGCT CTTGAAATTG    20

(2) INFORMATION FOR SEQ ID NO:397:

(i) SEQUENCE CHARACTERISTICS:
  (A) LENGTH: 38 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:397:

ACACACACAC ACACACACAC ACACACACAC ACACACAC    38

(2) INFORMATION FOR SEQ ID NO:398:

(i) SEQUENCE CHARACTERISTICS:
  (A) LENGTH: 10 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:398:

TTTAGAAAAA    10

(2) INFORMATION FOR SEQ ID NO:399:

(i) SEQUENCE CHARACTERISTICS:
  (A) LENGTH: 10 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:399:

CCCCAAAGCT    10

(2) INFORMATION FOR SEQ ID NO:400:

(i) SEQUENCE CHARACTERISTICS:
  (A) LENGTH: 40 base pairs
  (B) TYPE: nucleic acid
  (C) STRANDEDNESS: double (D) TOPOLOGY: linear (ii) MOLECULE TYPE: DNA (genomic)

(xi) SEQUENCE DESCRIPTION: SEQ ID NO:400:

ACACACACAC ACACACACAC ACACACACAC ACACACACAC 40

(2) INFORMATION FOR SEQ ID NO:401:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:401:

ACAGGCATCA 10

(2) INFORMATION FOR SEQ ID NO:402:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:402:

CACAAAGTGC 10

(2) INFORMATION FOR SEQ ID NO:403:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:403:

CACACACACA CACACACACA CACACACACA CACACACACA 40

(2) INFORMATION FOR SEQ ID NO:404:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:404:

CATGCACGTG 10

(2) INFORMATION FOR SEQ ID NO:405:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:405:

TACACCAGCT 10

(2) INFORMATION FOR SEQ ID NO:406:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:406:

CACACACACA CACACACACA CACTCACACA CA 32

(2) INFORMATION FOR SEQ ID NO:407:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:407:

TTGTTGATTT 10

(2) INFORMATION FOR SEQ ID NO:408:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:408:

TACTGATGTG 10

(2) INFORMATION FOR SEQ ID NO:409:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:409:

ACACACACAC ACACAGAGAC ACACACACAC ACACACACAC ACACACA 47

(2) INFORMATION FOR SEQ ID NO:410:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:410:

CTTTCTCAGG 10

(2) INFORMATION FOR SEQ ID NO:411:

( i ) SEQUENCE CHARACTERISTICS:
   ( A ) LENGTH: 10 base pairs
   ( B ) TYPE: nucleic acid
   ( C ) STRANDEDNESS: double
   ( D ) TOPOLOGY: linear ( i i ) MOLECULE TYPE: DNA (genomic)

( x i ) SEQUENCE DESCRIPTION: SEQ ID NO:411:

GGCAATGACA 10

( 2 ) INFORMATION FOR SEQ ID NO:412:

( i ) SEQUENCE CHARACTERISTICS:
      ( A ) LENGTH: 56 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:412:

CACACACACA CACACAGACA CACACAGACA CACATACACA CACACACACA CACACA 56

( 2 ) INFORMATION FOR SEQ ID NO:413:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:413:

CAGTCCAAGC 10

( 2 ) INFORMATION FOR SEQ ID NO:414:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:414:

ATTTTCATTC 10

( 2 ) INFORMATION FOR SEQ ID NO:415:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:415:

CACACACACA GACAGACACA CACACACACA 30

( 2 ) INFORMATION FOR SEQ ID NO:416:

( i ) SEQUENCE CHARACTERISTICS:
      ( A ) LENGTH: 10 base pairs
      ( B ) TYPE: nucleic acid
      ( C ) STRANDEDNESS: double ( D ) TOPOLOGY: linear ( i i ) MOLECULE TYPE: DNA (genomic)

( x i ) SEQUENCE DESCRIPTION: SEQ ID NO:416:

ATATAAACAT                                                                                                    10

( 2 ) INFORMATION FOR SEQ ID NO:417:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:417:

ACAATTAACA                                                                                                    10

( 2 ) INFORMATION FOR SEQ ID NO:418:

( i ) SEQUENCE CHARACTERISTICS:
        ( A ) LENGTH: 52 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:418:

ACACACACAC ACACACACAC ACACACACAC ACTCTCTCTC TCTCTCTCTC TC                          52

( 2 ) INFORMATION FOR SEQ ID NO:419:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:419:

CCTTGTCTC                                                                                                      9

( 2 ) INFORMATION FOR SEQ ID NO:420:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:420:

AGCCAGGCAC                                                                                                    10

( 2 ) INFORMATION FOR SEQ ID NO:421:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:421:

ACACACACAC ACACACACAC ACACACACAC ACACACACAC AGAGACAGAC AGACAGACAG        60

ACAGA        65

( 2 ) INFORMATION FOR SEQ ID NO:422:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:422:

ATACATACAT        10

( 2 ) INFORMATION FOR SEQ ID NO:423:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:423:

ATACTGTCCT        10

( 2 ) INFORMATION FOR SEQ ID NO:424:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:424:

AAAAAAAAAA AAAAAAGCA CACACACACA CACACACACA CACACACACA C        51

( 2 ) INFORMATION FOR SEQ ID NO:425:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:425:

ACTCCATCTC        10

( 2 ) INFORMATION FOR SEQ ID NO:426:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:426:

TCACTACATT        10

( 2 ) INFORMATION FOR SEQ ID NO:427:

( i ) SEQUENCE CHARACTERISTICS:
    ( A ) LENGTH: 72 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:427:

CACACACACA CACACACAAA CACACACACA CACACACACA CACACACACA CACACACAGA        60

GAGAGAGAGA GA        72

( 2 ) INFORMATION FOR SEQ ID NO:428:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:428:

GGCATGCATG        10

( 2 ) INFORMATION FOR SEQ ID NO:429:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:429:

CATGCTGTTC        10

( 2 ) INFORMATION FOR SEQ ID NO:430:

( i ) SEQUENCE CHARACTERISTICS:
    ( A ) LENGTH: 92 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:430:

TCTCTCTCTC TCTCTCTCTC TCTCTGTTTC TCTCTCTCTC TCTCTCTCTC TCACACACAC        60

ACACACACAC ACACACACAA ACACACACAC AC        92

( 2 ) INFORMATION FOR SEQ ID NO:431:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:431:

TCTTACACCA        10

( 2 ) INFORMATION FOR SEQ ID NO:432:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:432:

CCACTGTGCT                                                           10

( 2 ) INFORMATION FOR SEQ ID NO:433:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:433:

ACACACACAC AC                                                 12

( 2 ) INFORMATION FOR SEQ ID NO:434:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:434:

AGGAGTTAGG AGCTGGAGGT                                 20

( 2 ) INFORMATION FOR SEQ ID NO:435:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:435:

CAACCCCACC TCACATTTGT                                 20

( 2 ) INFORMATION FOR SEQ ID NO:436:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:436:

ACACACACAC ACAC                                         14

( 2 ) INFORMATION FOR SEQ ID NO:437:

( i ) SEQUENCE CHARACTERISTICS:
        ( A ) LENGTH: 20 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:437:

CTCACAGCCA GAAATTAGCA                            20

(2) INFORMATION FOR SEQ ID NO:438:

(i) SEQUENCE CHARACTERISTICS:
    (A) LENGTH: 20 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:438:

ACAGAGAATA TGGAATTGGT                            20

(2) INFORMATION FOR SEQ ID NO:439:

(i) SEQUENCE CHARACTERISTICS:
    (A) LENGTH: 16 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:439:

CACACACACA CACACA                                16

(2) INFORMATION FOR SEQ ID NO:440:

(i) SEQUENCE CHARACTERISTICS:
    (A) LENGTH: 20 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:440:

CGAGCTCAAG AAGGTGATCT                            20

(2) INFORMATION FOR SEQ ID NO:441:

(i) SEQUENCE CHARACTERISTICS:
    (A) LENGTH: 20 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:441:

GAGGATTCTA CGTGGTTCTC                            20

(2) INFORMATION FOR SEQ ID NO:442:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: DNA (genomic)

( x i ) SEQUENCE DESCRIPTION: SEQ ID NO:442:

ACACACACAC ACACACACA                                                                19

( 2 ) INFORMATION FOR SEQ ID NO:443:

( i ) SEQUENCE CHARACTERISTICS:
      ( A ) LENGTH: 21 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:443:

AGATTTAGAT ATTGCCAATT C                                                             21

( 2 ) INFORMATION FOR SEQ ID NO:444:

( i ) SEQUENCE CHARACTERISTICS:
      ( A ) LENGTH: 21 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:444:

TTAAAAATCT TGTCATGCAG A                                                             21

( 2 ) INFORMATION FOR SEQ ID NO:445:

( i ) SEQUENCE CHARACTERISTICS:
      ( A ) LENGTH: 24 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:445:

CACACACACA CACACACACA CACA                                                          24

( 2 ) INFORMATION FOR SEQ ID NO:446:

( i ) SEQUENCE CHARACTERISTICS:
      ( A ) LENGTH: 22 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:446:

CAAAATCTAA GAAAATAAAC TG                                                            22

( 2 ) INFORMATION FOR SEQ ID NO:447:

( i ) SEQUENCE CHARACTERISTICS:
      ( A ) LENGTH: 22 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:447:

CTACTTTTAT TGATGCAATA CT                                                            22

( 2 ) INFORMATION FOR SEQ ID NO:448:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:448:

ACACACACAC ACACACA 17

( 2 ) INFORMATION FOR SEQ ID NO:449:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:449:

CCAAGTACCA ACATACCAAC 20

( 2 ) INFORMATION FOR SEQ ID NO:450:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:450:

AAAGGTGGCT ACCCTGAATG 20

( 2 ) INFORMATION FOR SEQ ID NO:451:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:451:

ACACACAC ACACACAC ACACACAC 28

( 2 ) INFORMATION FOR SEQ ID NO:452:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:452:

GTGCTCAGTG ACTTTCCCT 19

( 2 ) INFORMATION FOR SEQ ID NO:453:

( i ) SEQUENCE CHARACTERISTICS:
        ( A ) LENGTH: 20 base pairs
        ( B ) TYPE: nucleic acid ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:453:

CGAGGACCAT TTTTTATTCA 20

( 2 ) INFORMATION FOR SEQ ID NO:454:

( i ) SEQUENCE CHARACTERISTICS:
            ( A ) LENGTH: 23 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:454:

ACACACACAC ACACACACAC ACA 23

( 2 ) INFORMATION FOR SEQ ID NO:455:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:455:

TCGACCAGCC CCTATAATCA 20

( 2 ) INFORMATION FOR SEQ ID NO:456:

( i ) SEQUENCE CHARACTERISTICS:
            ( A ) LENGTH: 19 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:456:

ATGCCCTAAG CCCTGTGTC 19

( 2 ) INFORMATION FOR SEQ ID NO:457:

( i ) SEQUENCE CHARACTERISTICS:
            ( A ) LENGTH: 52 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:457:

ACACACACAC ACACACACAC ACACGTACAT AAACACACAC ACACACACAC AC 52

( 2 ) INFORMATION FOR SEQ ID NO:458:

( i ) SEQUENCE CHARACTERISTICS:
            ( A ) LENGTH: 47 base pairs
            ( B ) TYPE: nucleic acid
            ( C ) STRANDEDNESS: double
            ( D ) TOPOLOGY: linear ( i i ) MOLECULE TYPE: DNA (genomic)

(x i) SEQUENCE DESCRIPTION: SEQ ID NO:458:

ACACACACAC ACACACAC ACACACAC ATACGCACAC ACACACA    47

(2) INFORMATION FOR SEQ ID NO:459:

(i) SEQUENCE CHARACTERISTICS:
      (A) LENGTH: 29 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:459:

AGGCTGCAGG ATTCACTGCT GTGGACCCA    29

(2) INFORMATION FOR SEQ ID NO:460:

(i) SEQUENCE CHARACTERISTICS:
      (A) LENGTH: 29 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:460:

GTCGGTACCG GTCTGGAAGT ACTGAGAAA    29